United States Patent
Kosuri et al.

(10) Patent No.: US 12,129,523 B2
(45) Date of Patent: Oct. 29, 2024

(54) PATHOGEN DIAGNOSTIC TEST

(71) Applicant: Octant, Inc., Emeryville, CA (US)

(72) Inventors: Sriram Kosuri, Berkeley, CA (US);
Eric Matthew Jones, Oakland, CA (US); Aaron Cooper, Berkeley, CA (US); Molly Jeanette Gasperini, Oakland, CA (US)

(73) Assignee: Octant, Inc., Emeryville, CA (US)

( * ) Notice: Subject to any disclaimer, the term of this patent is extended or adjusted under 35 U.S.C. 154(b) by 598 days.

(21) Appl. No.: 17/222,807

(22) Filed: Apr. 5, 2021

(65) Prior Publication Data

US 2022/0356535 A1 Nov. 10, 2022

Related U.S. Application Data

(60) Provisional application No. 63/154,571, filed on Feb. 26, 2021, provisional application No. 63/136,449, filed on Jan. 12, 2021, provisional application No. 63/062,406, filed on Aug. 6, 2020, provisional application No. 63/005,996, filed on Apr. 6, 2020.

(51) Int. Cl.
*C12Q 1/68* (2018.01)
*C12Q 1/70* (2006.01)

(52) U.S. Cl.
CPC ....... *C12Q 1/701* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2004/0265796 A1 | 12/2004 | Briese et al. |
| 2016/0281131 A1 | 9/2016 | Young et al. |
| 2021/0285061 A1* | 9/2021 | Manohar ............ C12Q 1/701 |

FOREIGN PATENT DOCUMENTS

| | | |
|---|---|---|
| JP | 2017209036 A | 11/2017 |
| WO | WO-2007100397 A2 | 9/2007 |
| WO | WO-2009085733 A1 | 7/2009 |
| WO | WO-2012009711 A2 | 1/2012 |
| WO | WO-2018198682 A1 | 11/2018 |

OTHER PUBLICATIONS

Bloom et al., Swab-Seq: A high-throughput platform for massively scaled up SARS-CoV-2 testing. Preprint medRxiv. (2021). 58 pages.
Karlin et al.: Methods for assessing the statistical significance of molecular sequence features by using general scoring schemes. Proc. Natl. Acad. Sci. 87: 2264-2268 (1990).
Karlin, et al. Applications and statistics for multiple high-scoring segments in molecular sequences. PNAS USA 90:5873-5877 (1993).
Altschul et al. Basic local alignment search tool. J Mol Biol 215(3):403-410 (1990).
EP23201494.4 European Search Report dated Feb. 16, 2024.

* cited by examiner

*Primary Examiner* — M Franco G Salvoza
(74) *Attorney, Agent, or Firm* — Wilson Sonsini Goodrich & Rosati

(57) ABSTRACT

Described herein are methods useful for detecting and diagnosing pathogen infection using PCR and sequencing.

16 Claims, 30 Drawing Sheets

Specification includes a Sequence Listing.

RT-PCR with 400nM primers
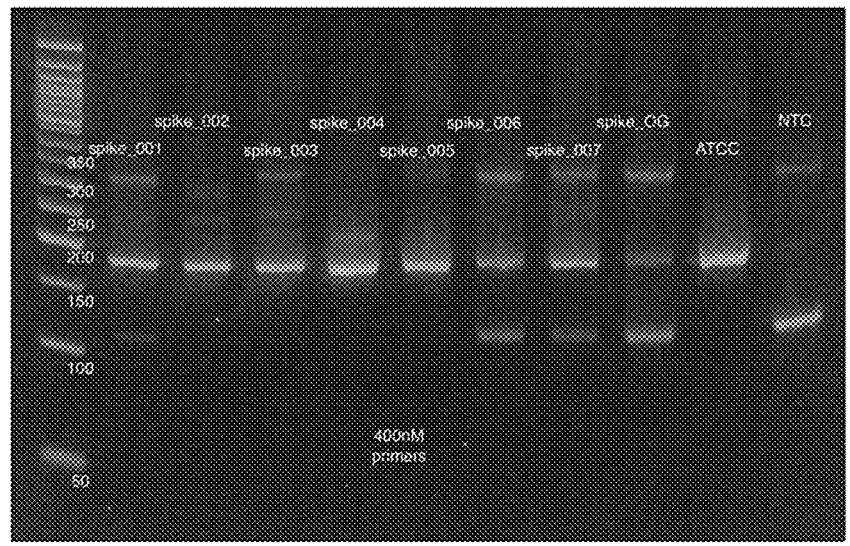
RT-PCR with 100nM primers
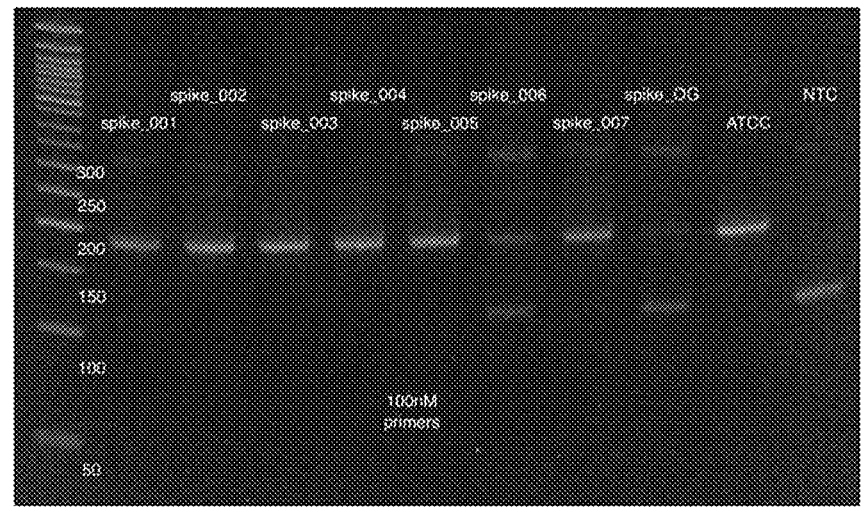
FIG. 22

> SARS-CoV2 S2
-----S2_F_prime_site-----          -------Read1-------         -----S2_R_prime_site-----
GCTGGTGCTGCCAGCTTATTATGTGGGT TATCTTCAACCTAGGACTTTTCTATT AAAAATATAATGAAAAATGGAACCATTACAGATGCTG TAGACTGTGCACTTGACCCT > Original S2 spikein
-----S2_F_prime_site-----          -------Read1-------         -----S2_R_prime_site-----
GCTGGTGCTGCCAGCTTATTATGTGGGT ATAGAACAACCTAGGACTTTTCTATT AAAAATATAATGAAAAATGGAACCATTACAGATGCTG TAGACTGTGCACTTGACCCT > Diversified spike-in Set 1
-----S2_F_prime_site-----          -------Read1-------         -----S2_R_prime_site-----
GCTGGTGCTGCCAGCTTATTATGTGGGT GTGTATCTCACGAAGCGACCCCTTGG  AAAAATATAATGAAAAATGGAACCATTACAGATGCTG TAGACTGTGCACTTGACCCT
GCTGGTGCTGCCAGCTTATTATGTGGGT CCTCGCTAGGACGTCGCTAGTGACGCC AAAAATATAATGAAAAATGGAACCATTACAGATGCTG TAGACTGTGCACTTGACCCT
GCTGGTGCTGCCAGCTTATTATGTGGGT AGCACGACTTGATCTAACTGACACTA AAAAATATAATGAAAAATGGAACCATTACAGATGCTG TAGACTGTGCACTTGACCCT
GCTGGTGCTGCCAGCTTATTATGTGGGT TAAGTAGGACTTCGATTGGATGGAAT AAAAATATAATGAAAAATGGAACCATTACAGATGCTG TAGACTGTGCACTTGACCCT

Diversified spike-in Set 2
-----S2_F_prime_site-----          -------Read1-------         -----S2_R_prime_site-----
GCTGGTGCTGCCAGCTTATTATGTGGGT ataggaCAACCTAGGACTTTTCTATT AAAAATATAATGAAAAATGGAACCATTACAGATGCTG TAGACTGTGCACTTGACCCT
GCTGGTGCTGCCAGCTTATTATGTGGGT tggaCTACCTAGGACTGCGCGACTAA AAAAATATAATGAAAAATGGAACCATTACAGATGCTG TAGACTGTGCACTTGACCCT
GCTGGTGCTGCCAGCTTATTATGTGGGT caCCTCGTGGATCTCAGAAATAGCC  AAAAATATAATGAAAAATGGAACCATTACAGATGCTG TAGACTGTGCACTTGACCCT
GCTGGTGCTGCCAGCTTATTATGTGGGT GCTTGGTGGATCTCAGAACGCGGCGG AAAAATATAATGAAAAATGGAACCATTACAGATGCTG TAGACTGTGCACTTGACCCT

FIG. 23

PATHOGEN DIAGNOSTIC TEST

CROSS REFERENCE TO RELATED APPLICATIONS

This application claims the benefit of U.S. Provisional App. Ser. No. 63/005,996 filed Apr. 6, 2020; U.S. Provisional App. Ser. No. 63/062,406 filed Aug. 6, 2020 U.S. Provisional App. Ser. No. 63/136,449 filed Jan. 12, 2021 U.S. Provisional App. Ser. No. 63/154,571 filed Feb. 26, 2021; each of which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Jun. 21, 2021, is named 52652-707.201-SL and is 153,339 bytes in size.

BACKGROUND

The inventors and the Applicant intend to freely license certain subject matter described herein to entities advancing the shared cause of ending the COVID-19 Pandemic consistent with the Open Covid Pledge dated Mar. 31, 2020.

Viral diseases and outbreaks of viral diseases have plagued mankind for millennia. An important part of identifying, monitoring, and guiding the response to viral disease is the ability to efficiently and accurately test individuals for viral infection. The novel coronavirus SARS-Cov-2, which causes COVID-19, emerged in late 2019 in Wuhan province of China, from there, and throughout the first part of 2020 the virus quickly spread around the world overwhelming medical systems and paralyzing commerce. There exists a need for tests that are quick, sensitive, and cost-effective.

SUMMARY

Described herein is a method of diagnosing an individual with a pathogen infection. The method uses PCR and sequencing to achieve highly specific and sensitive detection of viral genomes from biological samples. Features of the methods described herein that allow for such detection include: 1) reverse transcription and/or amplification directly in a lysis agent or after lysis conditions without purification or isolation; 2) the presence of a synthetic nucleic acid that is able to amplified by oligonucleotide primers that target a viral sequence of interest, but that comprises a different distinguishable intervening sequence, spiked into the reverse transpiration amplification mixture; and allowing for more accurate quantification and lower thresholds of detection; 3) indexes to allow multiplexing by next generation sequencing. In certain embodiments, the pathogen is a viral infection (e.g., SARS-COV-2). The methods herein can also be multiplexed to allow more than one viral pathogen to be detected (e.g., SARS-COV-2 and influenza A or B or both).

Described herein in one aspect is a method of diagnosing an individual with a pathogen infection, the method comprising: a) providing a biological sample from said individual; a) contacting said biological sample from said individual with a lysis agent, to obtain a lysed biological sample; b) performing a polymerase chain reaction (PCR) on said lysed biological sample to obtain a PCR amplified lysed biological sample, wherein said PCR reaction on said lysed biological sample is performed with a first set of PCR primers, wherein said first set of PCR primers amplifies a pathogen nucleic acid sequence; c) sequencing said PCR amplified lysed biological sample using next generation sequencing; and d) providing a positive diagnosis for said pathogen infection if a pathogen sequence is detected by said PCR or by said sequencing or providing a negative diagnosis for said individual if a pathogen sequence is not detected by said PCR or by said sequencing. In certain embodiments, said individual is a human individual. In certain embodiments, said pathogen infection comprises a bacterial infection, a viral infection, a fungal infection, and combinations thereof. In certain embodiments, said bacterial infection is an infection by the genera *Streptococcus, Pseudomonas, Shigella, Campylobacter, Salmonella, Clostridium,* or *Escherichia*, and combinations thereof. In certain embodiments, said fungal infection is an infection by *Candida, Blastomyces, Cryptococcus, Coccidoides, Histoplasma, Paracoccidioides, Sporothrix,* or *Pneumocystis*, and combinations thereof. In certain embodiments, the viral infection is an infection by a DNA virus. In certain embodiments, said DNA virus comprises Hepatitis A, Hepatitis B, Hepatitis C, papillomavirus, Epstein-Barr virus, varicella, or variola, and combinations thereof. In certain embodiments, said viral infection is an infection by an RNA virus. In certain embodiments, said RNA virus comprises an influenza virus, a coronavirus, a polio virus, a measles virus, an Ebola virus, a retrovirus, or an Orthomyxovirus. In certain embodiments, said viral infection is a coronavirus infection. In certain embodiments, said coronavirus infection is SARS-COV-2 infection. In certain embodiments, said biological sample from said individual is from a blood sample, a plasma sample, a serum sample, a cheek swab, a urine sample, a semen sample, a vaginal swab, a stool sample, a nasopharyngeal swab, mid-turbinate swab, or any combination thereof. In certain embodiments, said biological sample from said individual is from a nasopharyngeal swab, a mid-turbinate swab, or any combination thereof. In certain embodiments, the method comprises adding a synthetic nucleic acid to said lysis agent or said lysed biological sample. In certain embodiments, said synthetic nucleic acid is an RNA. In certain embodiments, said synthetic nucleic acid is a DNA. In certain embodiments, said synthetic nucleic acid comprises a set of sequences configured to be bound by said first set of PCR primers. In certain embodiments, said first set of primers amplifies both said pathogen nucleic acid sequence and said synthetic nucleic acid. In certain embodiments, said synthetic nucleic acid sequence comprises a nucleotide sequence that is not identical to said pathogen nucleic acid sequence. In certain embodiments, the method comprises performing a reverse transcription reaction on said lysed biological sample. In certain embodiments, said reverse transcription reaction is performed before said performing said polymerase chain reaction. In certain embodiments, said reverse transcription reaction is performed without further purification of said lysed biological sample. In certain embodiments, said reverse transcription reaction on said lysed biological sample produces viral cDNA. In certain embodiments, said viral cDNA is coronavirus cDNA. In certain embodiments, said coronavirus cDNA is SARS-COV-2 cDNA. In certain embodiments, said reverse transcription reaction and said PCR is a single-step reaction In certain embodiments, said PCR is an end-point analysis. In certain embodiments, said PCR is not a real-time PCR reaction. In certain embodiments, said first set of PCR primers amplifies a coronavirus nucleic acid sequence. In certain embodiments, said coronavirus nucleic acid sequence is a SARS-COV-2 nucleic acid sequence. In certain embodiments, said SARS-COV-2 nucleic acid sequence comprises the N1 or S2 gene. In certain embodiments, the method comprises a second set of primers. In certain embodiments, said second set of PCR primers amplifies a human nucleic acid sequence. In certain embodiments, said second set of PCR primers amplifies a human nucleic acid sequence selected from GAPDH, ACTB, RPP30, and combinations thereof. In certain embodiments, said second set of PCR primers amplifies human RPP30. In certain embodiments, the second set of PCR primer comprises a mixture of primers with sequencing adaptor sequences and primers without sequencing adaptor sequences. In certain embodiments, a ratio of primers with sequencing adaptor sequences to primers without sequencing adaptor sequences is about 1:1, about 1:2, about 1:3 or about 1:4. In certain embodiments, said PCR comprises from 30 to 45 amplification cycles. In certain embodiments, said PCR comprises from 35 to 45 amplification cycles. In certain embodiments, said PCR comprises from 39 to 42 amplification cycles. In certain embodiments, said first set of PCR primers, said second set of PCR primers, or both said first set of PCR primers and said second set of PCR primers comprises a nucleic acid sequence comprising a variable nucleotide sequence. In certain embodiments, said variable nucleotide sequence is a sample ID unique for said individual. In certain embodiments, said first set of PCR primers, said second set of PCR primers, or both said first set of PCR primers and said second set of PCR primers comprises an adapter sequence for a next-generation sequencing reaction. In certain embodiments, said method can detect less than 10 copies of pathogen genome. In certain embodiments, said method can detect less than 5 copies of pathogen genome. In certain embodiments, said pathogen genome is a coronavirus genome. In certain embodiments, said coronavirus genome is a SARS-COV-2 genome. In certain embodiments, said positive diagnosis for coronavirus if a coronavirus sequence is detected by said PCR is a SARS-COV-2 diagnosis. In certain embodiments, the method determines a strain of coronavirus. In certain embodiments, the method determines a strain of COVD-19.

Also described herein is a method of diagnosing an individual with a pathogen infection, the method comprising: (a) providing a biological sample from said individual; (c) performing a polymerase chain reaction (PCR) on said biological sample to obtain a PCR amplified biological sample, wherein said PCR reaction on said biological sample is performed with a first set of PCR primers, wherein said first set of PCR primers amplifies a pathogen nucleic acid sequence; (d) sequencing said PCR amplified biological sample using next generation sequencing; and (e) providing a positive diagnosis for said pathogen infection if a pathogen sequence is detected by said PCR or by said sequencing or providing a negative diagnosis for said individual if a pathogen sequence is not detected by said PCR or by said sequencing. In certain embodiments, said individual is a human individual. In certain embodiments, said pathogen infection comprises a bacterial infection, a viral infection, a fungal infection, and combinations thereof. In certain embodiments, said bacterial infection is an infection by the genera *Streptococcus, Pseudomonas, Shigella, Campylobacter, Salmonella, Clostridium,* or *Escherichia,* and combinations thereof. In certain embodiments, said fungal infection is an infection by *Candida, Blastomyces, Cryptococcus, Coccidoides, Histoplasma, Paracoccidioides, Sporothrix,* or *Pneumocystis,* and combinations thereof. In certain embodiments, the viral infection is an infection by a DNA virus. In certain embodiments, said DNA virus comprises Hepatitis A, Hepatitis B, Hepatitis C, papillomavirus, Epstein-Barr virus, varicella, or variola, and combinations thereof. In certain embodiments, said viral infection is an infection by an RNA virus. In certain embodiments, said RNA virus comprises an influenza virus, a coronavirus, a polio virus, a measles virus, an Ebola virus, a retrovirus, or an Orthomyxovirus. In certain embodiments, said viral infection is a coronavirus infection. In certain embodiments, said coronavirus infection is SARS-COV-2 infection. In certain embodiments, said biological sample from said individual is from a blood sample, a plasma sample, a serum sample, a cheek swab, a urine sample, a semen sample, a vaginal swab, a stool sample, a nasopharyngeal swab, mid-turbinate swab, or any combination thereof. In certain embodiments, said biological sample from said individual is from a nasopharyngeal swab, a mid-turbinate swab, or any combination thereof. In certain embodiments, the method comprises adding a synthetic nucleic acid to a lysis agent or said biological sample. In certain embodiments, said synthetic nucleic acid is an RNA. In certain embodiments, said synthetic nucleic acid is a DNA. In certain embodiments, said synthetic nucleic acid comprises a set of sequences configured to be bound by said first set of PCR primers. In certain embodiments, said first set of primers amplifies both said pathogen nucleic acid sequence and said synthetic nucleic acid. In certain embodiments, said synthetic nucleic acid sequence comprises a nucleotide sequence that is not identical to said pathogen nucleic acid sequence. In certain embodiments, the method comprises performing a reverse transcription reaction on said biological sample. In certain embodiments, said reverse transcription reaction is performed before said performing said polymerase chain reaction. In certain embodiments, said reverse transcription reaction is performed without further purification of said biological sample. In certain embodiments, said reverse transcription reaction on said biological sample produces viral cDNA. In certain embodiments, said viral cDNA is coronavirus cDNA. In certain embodiments, said coronavirus cDNA is SARS-COV-2 cDNA. In certain embodiments, said reverse transcription reaction and said PCR is a single-step reaction In certain embodiments, said PCR is an end-point analysis. In certain embodiments, said PCR is not a real-time PCR reaction. In certain embodiments, said first set of PCR primers amplifies a coronavirus nucleic acid sequence. In certain embodiments, said coronavirus nucleic acid sequence is a SARS-COV-2 nucleic acid sequence. In certain embodiments, said SARS-COV-2 nucleic acid sequence comprises the N1 or S2 gene. In certain embodiments, the method comprises a second set of primers. In certain embodiments, said second set of PCR primers amplifies a human nucleic acid sequence. In certain embodiments, said second set of PCR primers amplifies a human nucleic acid sequence selected from GAPDH, ACTB, RPP30, and combinations thereof. In certain embodiments, said second set of PCR primers amplifies human RPP30. In certain embodiments, the second set of PCR primer comprises a mixture of primers with sequencing adaptor sequences and primers without sequencing adaptor sequences. In certain embodiments, a ratio of primers with sequencing adaptor sequences to primers without sequencing adaptor sequences is about 1:1, about 1:2, about 1:3 or about 1:4. In certain embodiments, said PCR comprises from 30 to 45 amplification cycles. In certain embodiments, said PCR comprises from 35 to 45 amplification cycles. In certain embodiments, said PCR comprises from 39 to 42 amplification cycles. In certain embodiments, said first set of PCR primers, said second set of PCR primers, or both said first set of PCR primers and said second set of PCR primers comprises a nucleic acid sequence comprising a variable nucleotide sequence. In certain embodiments, said variable nucleotide sequence is a sample ID unique for said individual. In certain embodiments, said first set of PCR primers, said second set of PCR primers, or both said first set of PCR primers and said second set of PCR primers comprises an adapter sequence for a next-generation sequencing reaction. In certain embodiments, said method can detect less than 10 copies of pathogen genome. In certain embodiments, said method can detect less than 5 copies of pathogen genome. In certain embodiments, said pathogen genome is a coronavirus genome. In certain embodiments, said coronavirus genome is a SARS-COV-2 genome. In certain embodiments, said positive diagnosis for coronavirus if a coronavirus sequence is detected by said PCR is a SARS-COV-2 diagnosis. In certain embodiments, the method determines a strain of coronavirus. In certain embodiments, the method determines a strain of COVD-19.

Described herein in another aspect is a method of diagnosing an individual with a pathogen infection, the method comprising amplifying nucleic acids from a biological sample from said individual using a first set of PCR primers thereby obtaining amplified nucleic acids, wherein said first set of PCR primers amplifies a pathogen nucleic acid sequence and a synthetic nucleic acid sequence from said biological sample, wherein said synthetic nucleic acid sequence differs from said pathogen nucleic acid sequence by at least one nucleotide. In certain embodiments, said individual is a human individual. In certain embodiments, said pathogen infection comprises a bacterial infection, a viral infection, or a fungal infection. In certain embodiments, said bacterial infection is an infection by the genera *Streptococcus, Pseudomonas, Shigella, Campylobacter, Salmonella, Clostridium*, or *Escherichia*, and combinations thereof. In certain embodiments, said fungal infection is an infection by *Candida, Blastomyces, Cryptococcus, Coccidoides, Histoplasma, Paracoccidioides, Sporothrix*, or *Pneumocystis*, and combinations thereof. In certain embodiments, the viral infection is an infection by a DNA virus. In certain embodiments, said DNA virus comprises hepatitis B, Hepatitis C, papillomavirus, Epstein-Barr virus, varicella, variola, or any combination thereof. In certain embodiments, said viral infection is an infection by an RNA virus. In certain embodiments, said RNA virus comprises an influenza virus, a coronavirus, a polio virus, a measles virus, an Ebola virus, a retrovirus, or an Orthomyxovirus. In certain embodiments, said viral infection is a coronavirus infection. In certain embodiments, said coronavirus infection is SARS-COV-2 infection. In certain embodiments, said biological sample from said individual is from a blood sample, a plasma sample, a serum sample, a cheek swab, a urine sample, a semen sample, a vaginal swab, a stool sample, a nasopharyngeal swab, mid-turbinate swab, or any combination thereof. In certain embodiments, said biological sample from said individual is from a nasopharyngeal swab, a mid-turbinate swab, or any combination thereof. In certain embodiments, said synthetic nucleic acid is an RNA. In certain embodiments, said synthetic nucleic acid is a DNA. In certain embodiments, said synthetic nucleic acid comprises a set of sequences configured to be bound by said first set of PCR primers. In certain embodiments, said synthetic nucleic acid sequence differs from said pathogen nucleic acid sequence by at least 5 nucleotides. In certain embodiments, said pathogen infection is diagnosed based upon the ratio of synthetic nucleic acid sequence to pathogen nucleic acid sequence. In certain embodiments, the method comprises performing a reverse transcription reaction on said nucleic acids from said biological sample. In certain embodiments, said reverse transcription reaction on said nucleic acids from said biological sample produces coronavirus cDNA. In certain embodiments, said coronavirus cDNA is SARS-COV-2 cDNA. In certain embodiments, said amplifying nucleic acids comprises a PCR reaction In certain embodiments, said PCR reaction is an end-point analysis. In certain embodiments, said PCR reaction is not a real-time PCR reaction. In certain embodiments, said first set of PCR primers amplifies a coronavirus nucleic acid sequence. In certain embodiments, said coronavirus nucleic acid sequence is a SARS-COV-2 nucleic acid sequence. In certain embodiments, said SARS-COV-2 nucleic acid sequence comprises the N1 or S2 gene. In certain embodiments, said first set of PCR primers comprises a nucleic acid sequence comprising a variable nucleotide sequence. In certain embodiments, said variable nucleotide sequence is a sample ID unique for said individual. In certain embodiments, said first set of PCR primers comprises an adapter sequence for a next-generation sequencing reaction. In certain embodiments, the method comprises amplifying nucleic acids from said biological sample using a second set of PCR primers, wherein said second set of PCR primers amplifies a human nucleic acid sequence. In certain embodiments, said second set of PCR primers amplifies a nucleic acid sequence selected from GAPDH, ACTB, RPP30, and combinations thereof. In certain embodiments, said second set of PCR primers amplifies human RPP30. In certain embodiments, the second set of PCR primer comprises a mixture of primers with sequencing adaptor sequences and primers without sequencing adaptor sequences. In certain embodiments, a ratio of primers with sequencing adaptor sequences to primers without sequencing adaptor sequences is about 1:1, about 1:2, about 1:3 or about 1:4. In certain embodiments, said PCR comprises from 30 to 45 amplification cycles. In certain embodiments, said PCR comprises from 35 to 45 amplification cycles. In certain embodiments, said PCR comprises from 39 to 42 amplification cycles. In certain embodiments, said second set of PCR primers comprises a nucleic acid sequence comprising a variable nucleotide sequence. In certain embodiments, said variable nucleotide sequence is a sample ID unique for said individual. In certain embodiments, said second set of PCR primers comprises an adapter sequence a next-generation sequencing reaction. In certain embodiments, sequencing said amplified nucleic acids from said biological sample using a next-generation sequencing technology. In certain embodiments, said method can detect less than 10 copies of pathogen genome. In certain embodiments, said method can detect less than 5 copies of pathogen genome. In certain embodiments, said pathogen genome is coronavirus genome. In certain embodiments, said pathogen genome is SARS-COV-2 genome. In certain embodiments, the method determines a strain of coronavirus. In certain embodiments, the method determines a strain of SARS-COV-2.

Also described herein in another aspect is a synthetic nucleic acid comprising a 5' proximal region, a 3' proximal region and an intervening nucleic acid sequence. In certain embodiments, said synthetic nucleic acid comprises RNA. In certain embodiments, said synthetic nucleic acid comprises DNA. In certain embodiments, said 5' proximal region comprises a viral nucleic acid sequence. In certain embodiments, said viral nucleic acid sequence comprises a coronavirus sequence. In certain embodiments, said viral nucleic acid sequence comprises a SARS-COV-2 sequence. In certain embodiments, said 3' proximal region comprises a viral nucleic acid sequence. In certain embodiments, said viral nucleic acid sequence comprises a coronavirus sequence. In certain embodiments, said viral nucleic acid sequence comprises a SARS-COV-2 sequence. In certain embodiments, said 5' proximal region, said 3' proximal region, or both said 5' proximal region and said 3' proximal region are less than about 30 nucleotides in length. In certain embodiments, said 5' proximal region, said 3' proximal region, or both said 5' proximal region and said 3' proximal region are less than about 25 nucleotides in length. In certain embodiments, said 5' proximal region, said 3' proximal region, or both said 5' proximal region and said 3' proximal region are less than about 20 nucleotides in length. In certain embodiments, said 5' proximal region is at the 5' terminus of said synthetic nucleic acid. In certain embodiments, said 3' proximal region is at the 3' terminus of said synthetic nucleic acid. In certain embodiments, said intervening nucleic acid sequence is less than about 99%, 98%, 97%, 95%, 90%, 85%, 80%, or 75%, identical to a viral nucleic acid sequence. In certain embodiments, said synthetic nucleic acid sequence is a coronavirus sequence. In certain embodiments, said synthetic nucleic acid sequence is a SARS-COV-2 sequence. In certain embodiments the synthetic nucleic acid is for use in a method to detect pathogen infection in said individual. In certain embodiments, said pathogen infection is a coronavirus infection. In certain embodiments, said viral infection is a SARS-COV-2 infection.

In another aspect described herein is a composition, comprising a synthetic nucleic acid molecule comprising a first nucleic acid sequence and a second nucleic sequence, wherein (1) the first nucleic acid sequence is identical to a sequence from a pathogen nucleic acid molecule, and (2) the second nucleic acid sequence is not identical to a sequence the pathogen nucleic acid molecule. In certain embodiments, the first nucleic acid sequence is located to the 3' the second nucleic acid sequence. In certain embodiments, the synthetic nucleic acid molecule further comprises a third nucleic acid sequence, wherein the third nucleic acid sequence is identical to a second sequence from the pathogen nucleic acid molecule. In certain embodiments, the third nucleic acid sequence is 5' to the second nucleic acid sequence. In certain embodiments, the first nucleic acid sequence or the third nucleic acid sequence is less than 5, 10, 15, 20, 25, or 30 nucleotides. In certain embodiments, the second nucleic acid sequence comprises a total number of nucleotides less than 25, 50, 100, 150, 200, or 500 nucleotides. In certain embodiments, the second nucleic acid sequence comprises a total number of nucleotides greater than 25, 50, 100, 150, 200, or 500 nucleotides. In certain embodiments, the synthetic nucleic acid molecule is a ribonucleic acid (RNA) molecule, a deoxyribonucleic acid (DNA) molecule, or an RNA-DNA hybrid molecule. In certain embodiments, the first nucleic acid sequence, the third nucleic acid sequence, or both the first nucleic acid sequence and the third nucleic acid sequence comprise a primer binding site. In certain embodiments, the composition further comprises the pathogen nucleic acid molecule. In certain embodiments, the pathogen nucleic molecule is from a pathogen, wherein the pathogen comprises a bacterium, a virus, a fungus, or combinations thereof. In certain embodiments, the bacterium is from the genera *Streptococcus, Pseudomonas, Shigella, Campylobacter, Salmonella, Clostridium*, or *Escherichia*, and combinations thereof. In certain embodiments, the fungus is *Candida, Blastomyces, Cryptococcus, Coccidoides, Histoplasma, Paracoccidioides, Sporothrix*, or *Pneumocystis*, and combinations thereof. In certain embodiments, the virus is a DNA virus. In certain embodiments, the DNA virus comprises hepatitis B, Hepatitis C, papillomavirus, Epstein-Barr virus, varicella, or variola, and combinations thereof. In certain embodiments, the virus is an RNA virus. In certain embodiments, the RNA virus comprises an influenza virus, a coronavirus, a polio virus, a measles virus, an Ebola virus, a retrovirus, or an Orthomyxovirus. In certain embodiments, the virus is a coronavirus. In certain embodiments, the coronavirus is a SARS-COV-2 virus. In certain embodiments, the composition further comprises a plurality of primers, wherein a primer of the plurality of primers is configured to hybridize to a sequence of the synthetic nucleic acid molecule or a sequence of the pathogen nucleic acid molecule. In certain embodiments, a sequence of the synthetic nucleic acid molecule and the sequence the pathogen nucleic acid molecule are identical. In certain embodiments, the synthetic nucleic acid molecule is amplified with the same efficiency as the pathogen nucleic acid molecule. In certain embodiments, the synthetic nucleic acid molecule is configured to create an amplification produce the same size or within 10 base pairs in size as an amplification product of the pathogen nucleic acid molecule.

In another aspect described herein is a method of diagnosing an individual with a pathogen infection, the method comprising: (a) providing a biological sample from said individual; (b) contacting said biological sample from said individual with a lysis agent, to obtain a lysed biological sample; (c) performing a polymerase chain reaction (PCR) on said lysed biological sample to obtain a PCR amplified lysed biological sample, wherein said PCR reaction on said lysed biological sample is performed with a first set of PCR primers, wherein said first set of PCR primers amplifies a pathogen nucleic acid sequence; (d) sequencing said PCR amplified lysed biological sample using next generation sequencing; and (e) providing a positive diagnosis for said pathogen infection if a pathogen sequence is detected by said PCR or by said sequencing or providing a negative diagnosis for said individual if a pathogen sequence is not detected by said PCR or by said sequencing.

In another aspect described herein is a composition comprising a plurality of synthetic nucleic acids with a distinct nucleic acid sequence, said plurality of synthetic nucleic acids with a distinct nucleic acid sequence composing a common 5' sequence identical to a pathogen nucleic acid sequence, a common 3' sequence identical to a pathogen nucleic acid sequence, and an intervening sequence that differs among the plurality of sequences. In certain embodiments, said plurality of synthetic nucleic acids with a distinct nucleic acid sequence are single-stranded. In certain embodiments, said plurality of synthetic nucleic acids with a distinct nucleic acid sequence are double-stranded. In certain embodiments, said plurality of synthetic nucleic acids with a distinct nucleic acid sequences consist of or comprise RNA. In certain embodiments, said plurality of synthetic nucleic acids with a distinct nucleic acid sequences consist of or comprise DNA. In certain embodiments, said common 5' sequence identical to a pathogen nucleic acid sequence is 30 nucleotides or less. In certain embodiments, said common 3' sequence identical to a pathogen nucleic acid sequence is 30 nucleotides or less. In certain embodiments, said intervening sequence is 50 nucleotides or less. In certain embodiments, said intervening sequence is 30 nucleotides or less. In certain embodiments, the pathogen nucleic acid sequence is from a bacterial pathogen, a fungal pathogen, or a viral pathogen. In certain embodiments, said bacterial pathogen is of the genera *Streptococcus, Pseudomonas, Shigella, Campylobacter, Salmonella,*

*Clostridium*, or *Escherichia*, and combinations thereof. In certain embodiments, said fungal pathogen is ('andida, *Blastomyces, Cryptococcus, Coccidoides, Histoplasma, Paracoccidioides, Sporothrix*, or *Pneumocystis*, and combinations thereof. In certain embodiments, said viral pathogen is a DNA virus. In certain embodiments, said DNA virus comprises hepatitis B, Hepatitis C, papillomavirus, Epstein-Barr virus, varicella, or variola, and combinations thereof. In certain embodiments, said viral pathogen is an RNA virus. In certain embodiments, said RNA virus comprises an influenza virus, a coronavirus, a polio virus, a measles virus, an Ebola virus, a retrovirus, an Orthomyxovirus, or combinations thereof. In certain embodiments, said viral pathogen is a coronavirus. In certain embodiments, said coronavirus is SARS-COV-2. In certain embodiments, said pathogen nucleic acid sequence is a nucleic acid sequence that encodes a coronavirus spike protein. In certain embodiments, said plurality of synthetic nucleic acids with a distinct nucleic acid sequence comprise or consist of a sequence selected from any one or more of S2_001, S2_002, S2_003, and S2_004. In certain embodiments, the composition is for use in a method of diagnosing or detecting infection with a pathogen. In certain embodiments, the composition is for use in a method of normalizing pathogen next-generation sequence reads.

Described herein is a method of detecting a Coronavirus infection in an individual, the method comprising: (a) providing a biological sample from said individual, wherein said biological sample comprises a Coronavirus synthetic RNA, wherein a sequence of said Coronavirus synthetic RNA differs from a naturally occurring Coronavirus nucleic acid sequence; (b) lysing said biological sample thereby producing a lysed biological sample; (c) performing a reverse transcription reaction on said lysed biological sample to obtain a lysed, reverse transcribed biological sample; (d) performing an amplification reaction on said lysed, reverse transcribed biological sample to obtain an amplified biological sample, wherein said amplification reaction on said lysed, reverse transcribed biological sample is performed with a set of Coronavirus primers specific for a Coronavirus nucleic acid sequence, wherein said set of Coronavirus primers amplifies said Coronavirus nucleic acid sequence and said Coronavirus synthetic RNA; and (e) sequencing said amplified biological sample using next generation sequencing. In certain embodiments, the method further comprises providing a positive diagnosis for Coronavirus infection if sequence reads from said Coronavirus nucleic acid sequence are detected.

In certain embodiments, said Coronavirus infection is a SARS-Cov-2 infection. In certain embodiments, providing said positive diagnosis for said Coronavirus infection or SARS-Cov-2 infection is provided if a ratio or a mathematical equivalent thereof of said sequence reads from said Coronavirus nucleic acid sequence to sequence reads of said Coronavirus synthetic RNA exceed a ratio of about 0.1. In certain embodiments, providing said positive diagnosis for Coronavirus infection is provided if said sequence reads from said Coronavirus nucleic acid and said sequence reads of Coronavirus synthetic RNA exceed about 100. In certain embodiments, said lysed biological sample is not isolated or purified before performing said reverse transcription reaction. In certain embodiments, lysing said biological sample and performing said reverse transcription reaction on said lysed biological sample occur in the same well, tube, or reaction vessel. In certain embodiments, lysing said biological sample comprises thermal lysis. In certain embodiments, said thermal lysis comprises heating said biological sample to a temperature of at least about 50° C. In certain embodiments, said biological sample from said individual, comprises a plurality of Coronavirus synthetic RNA sequences, wherein said plurality of Coronavirus synthetic RNA sequences comprise at least two distinct synthetic Coronavirus RNA sequences. In certain embodiments, said plurality of synthetic Coronavirus RNA sequences comprise at least four distinct synthetic Coronavirus RNA nucleic acid sequences. In certain embodiments, the synthetic RNA nucleic acid or the plurality of synthetic nucleic acids comprises an amount of guanine nucleotide that is from about 20% to about 30%, an amount of adenine nucleotide that is from about 20% to about 30%, an amount of cytosine nucleotide that is from about 20% to about 30%, an amount of uracil nucleotide that is from about 20% to about 30%. In certain embodiments, said synthetic Coronavirus RNA nucleic acid or said plurality of synthetic Coronavirus RNA nucleic acids comprise a ratio of guanine to cytosine to adenine to uracil that is about equal. In certain embodiments, said synthetic Coronavirus RNA nucleic acid or said plurality of synthetic Coronavirus RNA nucleic acids comprise a synthetic SARS-Cov-2 RNA nucleic acid or a plurality of synthetic SARS-Cov-2 RNA nucleic acids. In certain embodiments, the method further comprises detecting an Influenza A infection, an Influenza B infection, or a combination thereof. In certain embodiments, said amplification reaction on said lysed biological sample is performed with a set of influenza A primers specific for an influenza A nucleic acid sequence or a set of influenza B primers specific for an influenza B nucleic acid sequence. In certain embodiments, said set of influenza A primers specific for said influenza A nucleic acid sequence comprises the sequences set forth in SEQ ID NO: 24 or 25 and SEQ ID NO: 26, or SEQ ID NO: 27 and SEQ ID NO: 28. In certain embodiments, said set of influenza B primers specific for said influenza B nucleic acid sequence comprises the sequences set forth in SEQ ID NO: 29 or 30. In certain embodiments, said amplification reaction on said lysed biological sample is performed with a set of Influenza A primers specific for an influenza A nucleic acid sequence and a set of influenza B primers specific for an influenza B nucleic acid sequence. In certain embodiments, said biological sample from said individual further comprises an influenza A synthetic RNA, an influenza B synthetic RNA, or a combination thereof wherein said influenza A synthetic RNA, said influenza B synthetic RNA, or said combination thereof differs from a naturally occurring influenza A or influenza B nucleic acid sequence. In certain embodiments, the method further comprises providing a positive diagnosis for influenza A infection if a ratio or a mathematical equivalent thereof of sequence reads from influenza A to sequence reads of said influenza A synthetic RNA exceed a ratio of about 0.1. In certain embodiments, the method further comprises providing a positive diagnosis for influenza B infection if a ratio or a mathematical equivalent thereof of sequence reads from influenza A to sequence reads of said influenza B synthetic RNA exceed a ratio of about 0.1. In certain embodiments, said Coronavirus nucleic acid sequence is an N1 sequence, an S2 sequence, or a combination thereof. In certain embodiments, said Coronavirus nucleic acid sequence is a SARS-Cov-2 N1 sequence, a SARS-Cov-2 S2 sequence, or a combination thereof. In certain embodiments, said set of Coronavirus primers comprise the sequences set forth in SEQ ID NO: 13 and SEQ ID NO: 14, or SEQ ID NO: 18 and SEQ ID NO: 19. In certain embodiments, said set of Coronavirus primers comprise the sequences set forth in SEQ ID NO: 20 and SEQ ID NO: 21, or SEQ ID NO: 22 and SEQ ID NO: 23. In certain embodiments, said set of Coronavirus primers are present at a concentration from about 50 nanomolar to about 250 nanomolar. In certain embodiments, said set of Coronavirus primers are present at a concentration of about 100 nanomolar. In certain embodiments, said influenza A nucleic acid sequence is an influenza A matrix sequence, an influenza A non-structural protein 1 sequence, an influenza A hemagglutinin sequence, an influenza A neuraminidase sequence, an influenza A nucleoprotein sequence, and a combination thereof. In certain embodiments, said influenza B nucleic acid sequence is an influenza B matrix sequence, an influenza B non-structural protein 1 sequence, an influenza B hemagglutinin sequence, an influenza B neuraminidase sequence, an influenza B nucleoprotein sequence, and a combination thereof. In certain embodiments, any one or more of said set of Coronavirus primers, said set of influenza A primers, or said set of influenza B primers comprises one or more index sequences allowing sample multiplexing. In certain embodiments, the Coronavirus synthetic RNA comprises a nucleic acid sequence at least about 90% homologous to any one or more of the sequences set forth in any one of SEQ ID NOs: 1 to 12. In certain embodiments, said Coronavirus synthetic RNA comprises a plurality of distinct nucleic acid sequences at least about 90% homologous to any one or more of the sequences set forth in any one of SEQ ID NOs: 1 to 12. In certain embodiments, said Influenza A synthetic RNA comprises an RNA sequence at least about 90% homologous to any one or more of the sequences set forth in any one of SEQ ID NOs: 31 or 32. In certain embodiments, said Influenza B synthetic RNA comprises an RNA sequence at least about 90% homologous to the sequence set forth in SEQ ID NO: 33. In certain embodiments, said Coronavirus synthetic RNA comprises a plurality of four distinct nucleic acid sequences at least about 90% homologous to the four the sequences set forth in SEQ ID NOs: 1 to 4. In certain embodiments, said Coronavirus synthetic RNA, said influenza A synthetic RNA, or said influenza B synthetic RNA is present at a concentration from about 10 copies per/reaction to about 500 copies per reaction. In certain embodiments, said Coronavirus synthetic RNA is present at a concentration from about 10 copies per/reaction to about 500 copies per reaction. In certain embodiments, said Coronavirus synthetic RNA, said Influenza A synthetic RNA, or said Influenza B synthetic RNA is present at a concentration of about 200 copies per reaction. In certain embodiments, said Coronavirus synthetic RNA is present at a concentration of about 200 copies per/reaction. In certain embodiments, said biological sample comprises a nasal swab or a saliva sample. In certain embodiments, said biological sample comprises less than about 10 microliters of saliva of the individual or less than about 10 microliters of a buffer that has been inoculated with a nasal swab of the individual. In certain embodiments, said biological sample comprises less than about 10 microliters of a buffer that has been inoculated with a nasal swab. In certain embodiments, said amplification reaction on said lysed biological sample is performed with a primer pair specific for a sample control. In certain embodiments, said sample control is a housekeeping gene. In certain embodiments, said primer pair specific for said sample control is specific for RPP30. In certain embodiments, said primer pair specific for said sample control comprises a sequence set forth in SEQ ID NO: 15 or 16, and SEQ ID NO: 17.

Also described herein is a synthetic nucleic acid comprising: a 5' proximal region comprising a first nucleotide sequence from a virus; a 3' proximal region comprising a second nucleotide sequence from said virus; and an intervening nucleotide sequence, wherein said intervening nucleotide sequence comprises a percentage of guanine nucleotide that is from about 20% to about 30%, an amount of adenine nucleotide that is from about 20% to about 30%, an amount of cytosine nucleotide that is from about 20% to about 30%, an amount of uracil or thymidine nucleotide that is from about 20% to about 30%, and said intervening sequence differs from a naturally occurring sequence of the virus. In certain embodiments, said synthetic nucleic acid comprises DNA. In certain embodiments, said synthetic nucleic acid consists of DNA. In certain embodiments, said synthetic nucleic acid comprises RNA. In certain embodiments, said synthetic nucleic acid consists of RNA. In certain embodiments, said virus is an influenza A virus, an influenza B virus, or a coronavirus. In certain embodiments, said virus is a coronavirus. In certain embodiments, said coronavirus is SARS-Cov-2. In certain embodiments, said intervening nucleotide sequence nucleic acids comprise an about equal ratio of guanine to cytosine to adenine to uracil or thymidine nucleotides. In certain embodiments, said 3' proximal region and said 5' proximal region comprise a nucleotide sequence at least 90% homologous to a coronavirus S2 gene sequence. In certain embodiments, said 5' proximal region and said 3' proximal region comprise a nucleotide sequence at least 95% homologous to a coronavirus S2 gene sequence. In certain embodiments, said 5' proximal region and said 3' proximal region comprise a nucleotide sequence identical to a coronavirus S2 gene sequence. In certain embodiments, said 5' proximal region and said 3' proximal region comprise a nucleotide sequence at least 90% homologous to a coronavirus N1 gene sequence. In certain embodiments, said 5' proximal region and said 3' proximal region comprise a nucleotide sequence at least 95% homologous to a coronavirus N1 gene sequence. In certain embodiments, said 5' proximal region and said 3' proximal region comprise a nucleotide sequence identical to a coronavirus N1 gene sequence. In certain embodiments, said coronavirus N1 gene sequence or said coronavirus S2 gene sequence is a SARS-COV-2 gene sequence. In certain embodiments, said sequence nucleic acid comprises a sequence that is at least 90% homologous to any one or more sequences set forth in any one of SEQ ID NOs: 1 to 12. In certain embodiments, said sequence nucleic acid comprises a sequence that is at least 95% homologous to any one or more sequences set forth in any one of SEQ ID NOs: 1 to 12. In certain embodiments, said sequence nucleic acid comprises a sequence that is identical to any one or more sequences set forth in any one of SEQ ID NOs: 1 to 12. In certain embodiments, described herein is a plurality of synthetic nucleic acids, wherein said plurality comprises synthetic nucleic acids comprising at least two distinct nucleotide sequences. In certain embodiments, said plurality comprises synthetic nucleic acids comprising at least two distinct nucleotide sequences. In certain embodiments, said plurality comprises at least four distinct nucleotide sequences. In certain embodiments, said four distinct nucleotide sequences are those set forth in SEQ ID NOs: 1 to 4. In certain embodiments, said four distinct nucleotide sequences are selected from those set forth in SEQ ID NOs: 5 to 12.

Also described herein is a reaction mixture for determining the presence or absence of a viral nucleic acid in a biological sample comprising a synthetic nucleic acid described herein or a plurality of synthetic nucleic acids described herein, at least a portion of said biological sample, and one or more enzyme or reagents sufficient to amplify said viral nucleic acid in said biological sample, if present.

In certain embodiments, said biological sample is a human biological sample. In certain embodiments, said biological sample comprises saliva, a cheek swab, a nasopharyngeal swab, or a mid-turbinate swab. In certain embodiments, said biological sample comprises saliva or a nasopharyngeal swab. In certain embodiments, said viral nucleic acid is an influenza A, influenza B, or a coronavirus nucleic acid. In certain embodiments, said coronavirus nucleic acid is a is a Sars-Cov-2 nucleic acid. In certain embodiments, In certain embodiments, said one or more reagents are selected from the list consisting of a reverse transcriptase enzyme, dNTPs, a primer pair specific for said viral nucleotide sequence, a primer pair specific for a sample control nucleotide sequence, a magnesium salt, and combinations thereof. In certain embodiments, said primer pair specific for said sample control nucleotide sequence is specific for a human nucleotide sequence. In certain embodiments, said primer pair specific for said sample control nucleotide sequence is specific for a housekeeping gene. In certain embodiments, said primer pair specific for said sample control is specific for RPP30. In certain embodiments, said primer pair specific for said sample control comprises a sequence set forth in SEQ ID NO: 15 or 16, and SEQ ID NO: 17. In certain embodiments, said primer pair specific for said viral nucleotide sequence is specific for an influenza A nucleotide sequence, an influenza B nucleotide sequence and a coronavirus nucleotide sequence. In certain embodiments, said primer pair specific for said viral nucleotide sequence is specific for a coronavirus S1 or N2 sequence. In certain embodiments, said coronavirus S1 or N2 sequence is a CORONAVIRUS S1 or N2 nucleic acid sequence. In certain embodiments, said primer pair specific for said viral nucleotide sequence or said primer pair specific for said sample control nucleotide sequence comprises the sequence set forth in any one of SEQ ID NOs: 13 to 30 or 100 to 605. In certain embodiments, said primer pair specific for said viral nucleotide sequence or said primer pair specific for said sample control nucleotide sequence comprise the sequences set forth in SEQ ID NO: 13 and SEQ ID NO: 14; SEQ ID NO: 18 and SEQ ID NO: 19; SEQ ID NO: 20 and SEQ ID NO: 21; SEQ ID NO: 24 or 25 and SEQ ID NO: 26; SEQ ID NO: 29 and SEQ ID NO: 30. In certain embodiments, said primer pair specific for said viral nucleotide sequence or said primer pair specific for said sample control nucleotide sequence is present at a concentration from about 50 micromolar to about 250 micromolar. In certain embodiments, said primer pair specific for said viral nucleotide sequence or said primer pair specific for said sample control nucleotide sequence is present at a concentration of about 100 micromolar. In certain embodiments, said primer pair specific for said viral nucleotide sequence or said primer pair specific for said sample control nucleotide sequence is present at a concentration of about 200 micromolar. In certain embodiments, said Coronavirus synthetic RNA is present at a concentration from about 10 copies per/reaction to about 500 copies per reaction mixture. In certain embodiments, said Coronavirus synthetic RNA is present at a concentration of about 200 copies per reaction mixture. In certain embodiments, the volume of said reaction mixture is from about 10 microliters to about 100 microliters. In certain embodiments, the volume of said reaction mixture is about 20 microliters.

Also described herein is a kit for determining the presence or absence of a viral nucleic acid in a biological sample comprising a synthetic nucleic acid described herein or a plurality of synthetic nucleic acids described herein and one or more enzyme or reagents sufficient to amplify said viral nucleic acid from said biological sample. In certain embodiments, the viral nucleic acid is an influenza A, influenza B, or a coronavirus nucleic acid. In certain embodiments, said coronavirus nucleic acid is a Coronavirus nucleic acid. In certain embodiments, said one or more reagents are selected from the list consisting of a reverse transcriptase enzyme, dNTPs, a primer pair specific for said viral nucleotide sequence, a primer pair specific for a sample control nucleotide sequence, a magnesium salt, and combinations thereof. In certain embodiments, said primer pair specific for said sample control nucleotide sequence is specific for a human nucleotide sequence. In certain embodiments, said primer pair specific for said sample control nucleotide sequence is specific for a housekeeping gene. In certain embodiments, said primer pair specific for said sample control is specific for RPP30. In certain embodiments, said primer pair specific for said sample control comprises a sequence set forth in SEQ ID NO: 15 or 16, and SEQ ID NO: 17. In certain embodiments, said primer pair specific for said viral nucleotide sequence is specific for an influenza A nucleotide sequence, an influenza B nucleotide sequence and a coronavirus nucleotide sequence. In certain embodiments, said primer pair specific for said viral nucleotide sequence is specific for a coronavirus S1 or N2 sequence. In certain embodiments, said coronavirus S1 or N2 sequence is a CORONAVIRUS S1 or N2 nucleic acid sequence. In certain embodiments, said primer pair specific for said viral nucleotide sequence or said primer pair specific for said sample control nucleotide sequence comprises the sequence set forth in any one of SEQ ID NOs: 13 to 30 or 100 to 605. In certain embodiments, said primer pair specific for said viral nucleotide sequence or said primer pair specific for said sample control nucleotide sequence comprise the sequences set forth in SEQ ID NO: 13 and SEQ ID NO: 14; SEQ ID NO: 18 and SEQ ID NO: 19; SEQ ID NO: 20 and SEQ ID NO: 21; SEQ ID NO: 24 or 25 and SEQ ID NO: 26; SEQ ID NO: 29 and SEQ ID NO: 30.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 22 shows the effects of lowered primer concentration on primer dimers and non-specific amplification products.

FIG. 23 shows diversified synthetic nucleic acid spike-in sequences.

DETAILED DESCRIPTION

Figure 1:
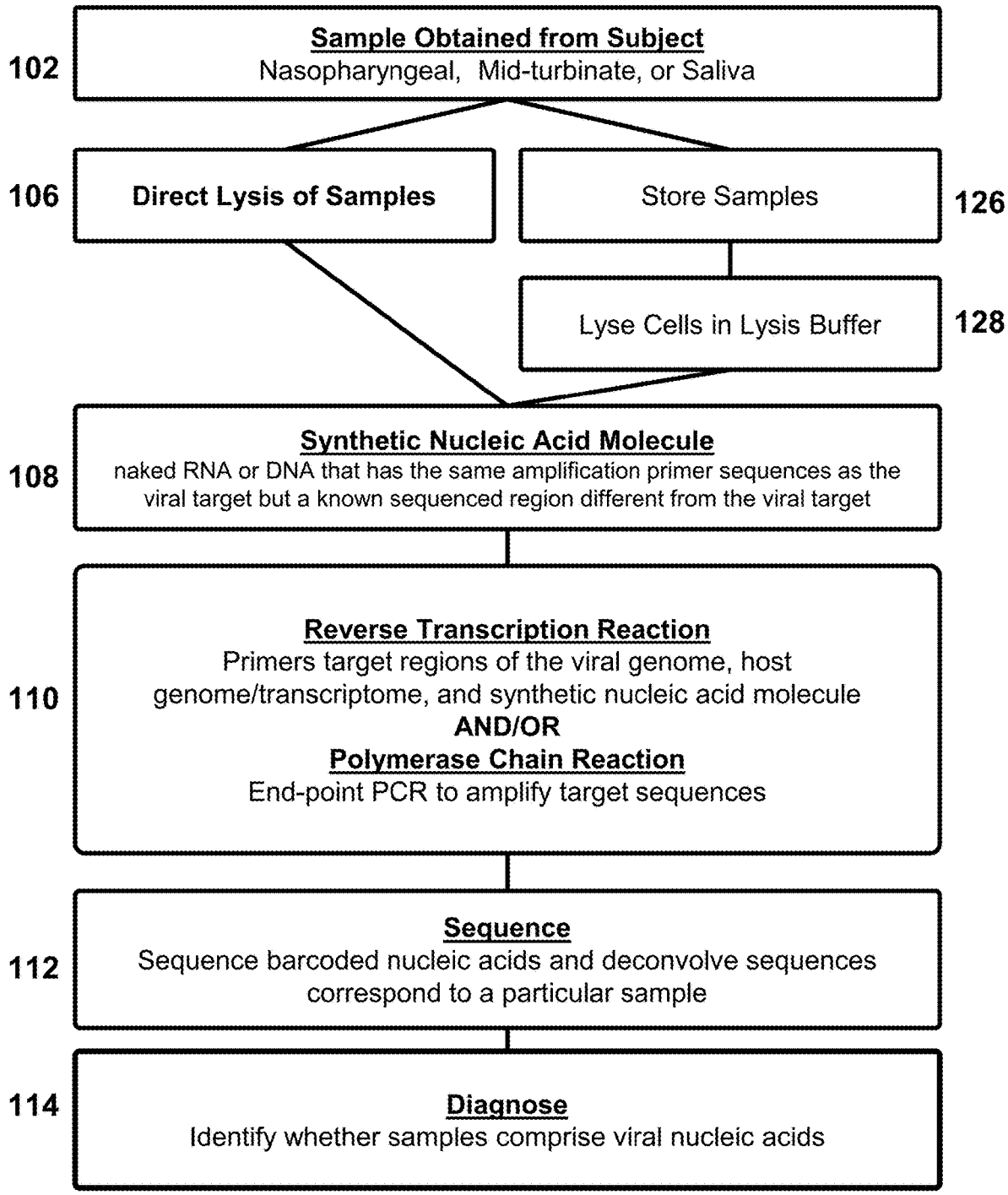
FIG. 1 illustrates an exemplary schematic of the diagnosis of viral infections.

The frequency of outbreaks of highly contagious or highly pathogenic diseases is increasing. One third of worldwide deaths are attributable to infectious diseases, which are the second cause of mortality and disability worldwide. Obtaining a rapid, accurate readout for the identifying and diagnosing the infectious diseases that cause human illness is a critical component of diagnostic medicine, particularly in the case of viral infections, in order to implement effective public health responses and improve the delivery of human healthcare. Numerous methods for detecting viral infections have been developed for clinical diagnostic purposes, however most of these tests do not provide sufficiently rapid or high throughput readouts and/or are not feasible due to the resource burden associated with rapidly testing a rapidly increasing number of subjects.

Additionally, provided herein are methods and systems of diagnosing an individual with a viral infection. Such methods and systems, as describe herein, leverage polymerase chain reaction (PCR), library preparation strategies, and next generation sequencing to yield readouts or information that accurately identifies a viral infection and can be effectively scaled to meet the challenges associated with the need to efficiently test an increasing number of subjects. To facilitate the identification and diagnosis of a viral infection within a sample, the methods provide advances in or solutions for (1) the effective and efficient isolation of a nucleic acid sequence from a virus, (2) the effective and efficient processing of nucleic acid molecules corresponding to or derived from the virus, and (3) the effective and efficient multiplexing of samples that allow for the testing of multiple samples in parallel and reduces the overall resource burden of testing.

Described herein, is a method of detecting pathogen genome in a sample, the method comprising amplifying nucleic acids from a sample using a first set of PCR primers obtaining amplified nucleic acids, wherein said first set of PCR primers amplifies a viral nucleic acid sequence and a synthetic nucleic acid sequence. The synthetic nucleic acid sequence provides a sample and amplification control in the assay allowing for a lower limit of detection compared to amplification without the synthetic nucleic acid. The synthetic nucleic acid can be added ("spiked") into a lysate that has been contacted to the biological sample or it can be present in the lysis buffer before the lysis buffer is contacted to the biological sample. The sample can be a biological sample. The biological sample can be from an individual. The synthetic nucleic acid can be added at any step along the way. More than one synthetic nucleic acid can be used in the method described herein. For example, one synthetic nucleic acid can serve as a control for one or more viral nucleic acids, and one synthetic nucleic acid can serve as a control for one or more human nucleic acids (e.g. a house keeping control), or for example a plurality of synthetic nucleic acids can be added to serve as a control for a plurality of pathogen sequences.

Also described herein is a synthetic nucleic acid comprising a 5' proximal region, a 3' proximal region, and an intervening nucleic acid sequence. The synthetic nucleic acid can comprise any sequence at the 5' and 3' ends that allows amplification of a pathogen sequence, provided that the sequence between the 5' and 3' ends is distinguishable by sequencing. In certain embodiments the sequence between the 5' and 3' ends is identical to the pathogen sequence except for a sequence of 1, 2, 3, 4, 5, 6, 7, 8, 9, or 10 nucleotides that differs from the pathogen sequence.

Also described herein is a synthetic nucleic acid comprising a 5' proximal region, a 3' proximal region, and an intervening nucleic acid sequence. The synthetic nucleic acid can comprise any sequence at the 5' and 3' ends that allows amplification of a pathogen sequence, provided that the sequence between the 5' and 3' ends is distinguishable by sequencing. In certain embodiments the sequence between the 5' and 3' ends is identical to the pathogen sequence except for a sequence of 1, 2, 3, 4, 5, 6, 7, 8, 9, or 10 nucleotides that differs from the pathogen sequence.

Also described herein is a method of detecting a Coronavirus infection in an individual, the method comprising: (a) providing a biological sample from said individual, wherein said biological sample comprises a Coronavirus synthetic RNA, wherein a sequence of said Coronavirus synthetic RNA differs from a naturally occurring Coronavirus nucleic acid sequence; (b) lysing said biological sample thereby producing a lysed biological sample; (c) performing a reverse transcription reaction on said lysed biological sample to obtain a lysed, reverse transcribed biological sample; (d) performing an amplification reaction on said lysed, reverse transcribed biological sample to obtain an amplified biological sample, wherein said amplification reaction on said lysed, reverse transcribed biological sample is performed with a set of Coronavirus primers specific for a Coronavirus nucleic acid sequence, wherein said set of Coronavirus primers amplifies said Coronavirus nucleic acid sequence and said Coronavirus synthetic RNA; and (e) sequencing said amplified biological sample using next generation sequencing. In certain embodiments, the method further comprising providing a positive diagnosis for Coronavirus infection if sequence reads from said Coronavirus nucleic acid sequence are detected. In certain embodiments, said Coronavirus infection is a SARS-Cov-2 infection. In certain embodiments, providing said positive diagnosis for said Coronavirus infection or SARS-Cov-2 infection is provided if a ratio or a mathematical equivalent thereof of said sequence reads from said Coronavirus nucleic acid sequence to sequence reads of said Coronavirus synthetic RNA exceed a ratio of about 0.1. In certain embodiments, providing said positive diagnosis for Coronavirus infection is provided if said sequence reads from said Coronavirus nucleic acid and said sequence reads of Coronavirus synthetic RNA exceed about 100.

Also described herein is a method of detecting a Coronavirus infection in an individual, the method comprising: (a) providing a biological sample from said individual, wherein said biological sample comprises a Coronavirus synthetic RNA, wherein a sequence of said Coronavirus synthetic RNA differs from a naturally occurring Coronavirus nucleic acid sequence; (b) lysing said biological sample thereby producing a lysed biological sample; (c) performing a reverse transcription reaction on said lysed biological sample to obtain a lysed, reverse transcribed biological sample; (d) performing an amplification reaction on said lysed, reverse transcribed biological sample to obtain an amplified biological sample, wherein said amplification reaction on said lysed, reverse transcribed biological sample is performed with a set of Coronavirus primers specific for a Coronavirus nucleic acid sequence, wherein said set of Coronavirus primers amplifies said Coronavirus nucleic acid sequence and said Coronavirus synthetic RNA. In certain embodiments, said Coronavirus infection is a SARS-Cov-2 infection.

Also described herein is a method of detecting a Coronavirus infection in an individual, the method comprising: (a) providing a biological sample from said individual, wherein said biological sample comprises a Coronavirus synthetic RNA, wherein a sequence of said Coronavirus synthetic RNA differs from a naturally occurring Coronavirus nucleic acid sequence; (b) lysing said biological sample thereby producing a lysed biological sample; (c) performing a reverse transcription reaction on said lysed biological sample to obtain a lysed, reverse transcribed biological sample. In certain embodiments, said Coronavirus infection is a SARS-Cov-2 infection.

Compositions comprising a synthetic nucleic acid molecule are also provided and useful in the method disclosed herein. The synthetic nucleotide is, generally, an in vitro transcribed or synthetic control RNA that is identical to the viral sequence targeted for amplification, except for a short, altered stretch that allows for distinguishing sequencing reads corresponding to the synthetic control from those corresponding to the pathogen sequence. For example, compositions are disclosed comprising a synthetic nucleic acid molecule comprising a first nucleic acid sequence and a second nucleic acid sequence, wherein the first nucleic acid sequence is identical to a sequence from a pathogen nucleic acid molecule, and the second nucleic acid sequence is not identical to a sequence the pathogen nucleic acid sequence. In some embodiments, the first nucleic acid sequence is located at the 3' region of the synthetic nucleic acid molecule. In some embodiments, the synthetic nucleic acid molecule further comprises a third nucleic acid sequence, wherein the first nucleic acid sequence is identical to a first sequence from a pathogen nucleic acid molecule and wherein the third nucleic acid sequence is identical to a second sequence from a pathogen nucleic acid molecule. In some embodiments, the first nucleic acid sequence is located at a region 3' of the second nucleic acid molecule, and the third nucleic acid sequence is located at a region 5' of the second nucleic acid molecule In some embodiments, the second nucleic acid sequence is less than 5, 10, 15, 20, 25, or 30 nucleotides. In some embodiments, the second nucleic synthetic nucleic acid molecule comprises a total number of nucleotides less than 25, 50, 100, 150, 200, or 500 nucleotides. In some embodiments, the second nucleic synthetic nucleic acid molecule comprises a total number of nucleotides greater than 25, 50, 100, 150, 200, or 500 nucleotides. In some embodiments, the synthetic nucleic acid mole is a ribonucleic acid (RNA) molecule, a deoxyribonucleic acid (DNA) molecule, or an RNA-DNA hybrid molecule. In certain embodiments, the synthetic nucleic acid molecule is PCR amplified with an efficiency within about 10% of the corresponding pathogen sequence. In certain embodiments, the synthetic nucleic acid molecule is PCR amplified with an efficiency within about 5% of the corresponding pathogen sequence. In certain embodiments, the synthetic nucleic acid molecule is PCR amplified with the same efficiency of the corresponding pathogen sequence.

A plurality of synthetic nucleic acids can be used according to the methods described herein to further increase sensitivity, reduce false positives, or improve the accuracy and or precision of quantification of nucleic acid sequences. The plurality may comprise 2, 3, 4, 5, 6, 7, 8, 9 or more distinct sequences capable of co-amplification with a set of primers specific for the pathogen sequence to be detected. The plurality may have certain characteristics that are desirable for the plurality. In certain embodiments, the melting temperature of the distinct sequences of the plurality may be substantially the same or within about 0.5° 1°, 2°, 3°, 4°, or 5° Celsius of an average melting temperature of the plurality. In certain embodiments, the nucleotide make-up of the plurality targeted to be between about 30% and about 20% A, about 30% and about 20% G, about 30% and about 20% C, about 30% and 20% about T. In certain embodiments, the nucleotide make-up of the plurality targeted to be about 25% A, about 25% G, about 25% C, about 25% about T. In certain embodiments, the nucleotide make-up of the plurality targeted to be one or more of between about 30% and about 20% A, about 30% and about 20% G, about 30% and about 20% C, about 30% and 20% about T. In certain embodiments, the nucleotide make-up of the plurality targeted to be one or more of about 25% A, about 25% G, about 25% C, about 25% about T. In certain embodiments, the plurality of synthetic nucleic acids is selected or designed to minimize secondary structure or dimerization amongst the distinct sequences of the plurality.

Also described herein is a method of diagnosing an individual with a viral infection, the method comprising: (a) providing a biological sample from said individual; (b)

contacting said biological sample from said individual with a lysis agent, to obtain a lysed biological sample; (c) performing a reverse transcription reaction on said lysed biological sample; (d) performing a polymerase chain reaction (PCR) on said lysed biological sample to obtain a PCR amplified lysed biological sample, wherein said PCR reaction on said lysed biological sample is performed with a first set of PCR primers and a second set of PCR primers, wherein said first set of PCR primers amplifies a viral nucleic acid sequence, wherein said second set of primers amplifies a genomic sequence of a species to which said individual belongs; (e) sequencing said PCR amplified lysed biological sample using next generation sequencing; and (f) optionally, providing a positive diagnosis for said viral infection if a viral sequence is detected by said PCR or by said sequencing or providing a negative diagnosis for said human individual if a viral sequence is not detected by said PCR or by said sequencing. In certain embodiments, said first set of PCR primers can amplify a synthetic nucleic acid sequence present in the lysed biological sample. The synthetic nucleic acid sequence comprises the same primer binding sites as the viral nucleic acid sequence, except the intervening nucleic acid sequence is different, such that it can be discriminated by sequencing. In certain embodiments, the synthetic nucleic acid sequence is an RNA.

Also described herein is a method of diagnosing an individual with a pathogen infection, the method comprising: (a) providing a biological sample from said individual; (b) contacting said biological sample from said individual with a lysis agent, to obtain a lysed biological sample; (c) performing a polymerase chain reaction (PCR) on said lysed biological sample to obtain a PCR amplified lysed biological sample, wherein said PCR reaction on said lysed biological sample is performed with a first set of PCR primers and a second set of PCR primers, wherein said first set of PCR primers amplifies a pathogen nucleic acid sequence, wherein said second set of primers amplifies a nucleic acid sequence of said individual; (d) sequencing said PCR amplified lysed biological sample using next generation sequencing; and (e) optionally, providing a positive diagnosis for said pathogen infection if a pathogen sequence is detected by said PCR or by said sequencing or providing a negative diagnosis for said human individual if a pathogen sequence is not detected by said PCR or by said sequencing. In certain embodiments, said first set of PCR primers can amplify a synthetic nucleic acid sequence present in the lysed biological sample. The synthetic nucleic acid sequence comprises the same primer binding sites as the viral nucleic acid sequence, except the intervening nucleic acid sequence is different, such that it can be discriminated by sequencing. In certain embodiments, the synthetic nucleic acid sequence is an RNA.

The methods described herein can be used to surveil pathogen presence in any number of samples, including non-human samples. Surveillance can comprise monitoring a herd of domesticated or wild animals, a wild-animal population, or enclosed live animals (e.g., zoos, wild-animal parks, or live animal markets where the animals are sold for food or as pets).

Also described herein is a method of surveilling for the presence of pathogen in a sample, the method comprising: (a) providing a sample; (b) contacting said sample with an extraction agent, to obtain an extracted sample; (c) performing a polymerase chain reaction (PCR) on said extracted sample to obtain a PCR amplified extracted sample, wherein said PCR reaction on said extracted sample is performed with a first set of PCR primers; (d) sequencing said PCR amplified lysed biological sample using next generation sequencing; and (e) optionally, providing a positive readout for said pathogen if a pathogen sequence is detected by said PCR or by said sequencing or providing a negative readout if a pathogen sequence is not detected by said PCR or by said sequencing. In certain embodiments, said first set of PCR primers can amplify a synthetic nucleic acid sequence present in the extracted biological sample. The synthetic nucleic acid sequence comprises the same primer binding sites as the pathogen nucleic acid sequence, except the intervening nucleic acid sequence is different, such that it can be discriminated by sequencing. In certain embodiments, the synthetic nucleic acid sequence is an RNA. In certain embodiments, the synthetic nucleic acid sequence is a DNA.

To achieve the identification, detection, and/or diagnosis of a viral infection, the methods and systems disclosed herein comprise (a) providing a biological sample from said individual; (b) contacting said biological sample from said individual with a lysis agent to obtain a lysed biological sample; (c) performing an initial nucleic acid extension reaction on said lysed biological sample; (d) performing a polymerase chain reaction (PCR) on said lysed biological sample to obtain a PCR amplified lysed biological sample, wherein said PCR reaction on said lysed biological sample is performed with a first set of PCR primers and a second set of PCR primers, wherein said first set of PCR primers amplifies a viral nucleic acid sequence, wherein said second set of primers amplifies a genomic sequence of a species to which said individual belongs; (e) sequencing said PCR amplified lysed biological sample using next generation sequencing; and (f) providing a positive diagnosis for viral infection if a viral sequence, or derivative thereof, is detected by said PCR or by said sequencing, or providing a negative diagnosis for said human individual if a coronavirus sequence is not detected by said PCR or by said sequencing.

Disclosed herein are also method of nucleic acid processing for the detection of a viral infection. Such methods comprise (a) providing a sample comprising a viral nucleic acid molecule and a host nucleic acid molecule; (b) generating a barcoded viral nucleic acid molecule by performing a nucleic acid extension reaction on said viral nucleic acid molecule using a first primer comprising a barcode sequence; (c) generating a barcoded host nucleic acid molecule by performing a nucleic acid extension reaction on said host nucleic acid molecule using a second primer comprising said barcode sequence; (d) sequencing said barcoded viral nucleic acid molecule and said barcoded host nucleic acid molecule to identify (i) said barcode sequence and (ii) a sequence corresponding to said viral nucleic acid molecule, or a derivative thereof, and said host nucleic acid molecule; and (e) providing a positive diagnosis for a viral infection if said sequence corresponding to said viral nucleic acid molecule is identified in (d).

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real-time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection, or identification.

The term "genome," as used herein, refers to genomic information from a plant, animal, bacteria, fungi, or virus, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). "Next-generation sequencing" refers to method of high throughput sequencing that is not Sanger sequencing. Sequencing can be performed by various systems currently available, such as, without limitation, a sequencing system by Illumina® (e.g., iSeq 100, MiniSeq, MiSeq or NextSeq series of machines) Pacific Biosciences (PacBio®), Oxford Nanopore®, or Life Technologies (Ion Torrent®). Alternatively, or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, is used broadly and can refer to environmental samples (e.g., water samples, sewage samples), samples of raw or prepared food, samples generated from a population of non-human individuals (e.g., wild- or domesticated animals), or biological samples from human or non-human animals. The sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a nasopharyngeal swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, host cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

As used herein the term "pathogen" includes any organism or virus capable of causing disease in a population of individuals, such population could include animals or plants. This also encompasses pathogens that reside in a carrier individual or species, where the pathogen does not cause disease in the carrier individual or species, but can be transmitted to another induvial or species to cause disease. As used herein, pathogens include, but are not limited to bacteria, protozoa, fungi, nematodes, viroids and viruses, or any combination thereof, wherein each pathogen is capable, either by itself or in concert with another pathogen, of eliciting disease in vertebrates including but not limited to mammals, and including but not limited to humans. As used herein the term "host" refers to an organism that can be infected by a pathogen and includes plants, animals, vertebrates, mammals, rodents, cows, horses, pigs, fowl, chickens, geese, ducks, fish, shellfish and the like.

As used herein, the term "Bacteria," or "Eubacteria", refers to a domain of prokaryotic organisms. Bacteria include at least 11 distinct groups as follows: (1) Gram-positive (gram+) bacteria, of which there are two major subdivisions: (i) high G+C group (Actinomycetes, Mycobacteria, *Micrococcus*, others) (ii) low G+C group (*Bacillus, Clostridia, Lactobacillus,* Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and Thermosipho thermophiles. "Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium*. "Gram-positive bacteria" include cocci, nonsporulating rods, and sporulating rods. The genera of Grampositive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces*. "Pathogenic bacteria" or "pathogenic bacterium" are bacterial species that cause disease(s) in another host organism (e.g., animals and plants) by directly infecting the other organism, or by producing agents that causes disease(s) in another organism (e.g., bacteria that produce pathogenic toxins and the like).

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "housekeeping gene," "housekeeping control," or similar such term as used herein, generally, refers to a gene expressed in an organism under both normal and patho-physiological conditions or that is expressed by different tissue and cell types. In some cases, the housekeeping gene is a constitutive gene that is required for the maintenance of basic cellular function. The housekeeping gene is generally expressed at a relatively constant rate in most normal and patho-physiological conditions. Specific examples of housekeeping genes include, without limitation, RPP30, Beta actin, and/or GAPDH.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values.

For example, less than or equal to 3, 2, or 1 is equivalent to less than or equal to 3, less than or equal to 2, or less than or equal to 1.

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by 10% or less.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

As used herein the term "individual," "patient," or "subject" refers to individuals diagnosed with, suspected of being afflicted with, or at-risk of developing at least one disease for which the described compositions and method are useful for detecting. In certain embodiments the individual is a mammal. In certain embodiments, the mammal is a mouse, rat, rabbit, dog, cat, horse, cow, sheep, pig, goat, llama, alpaca, or yak. In certain embodiments, the individual is a human.

Pathogenic Infections

The methods described herein can allow the detection of many different pathogens including bacteria, viruses, fungi, protists, nematodes, and viroids.

For example, pathogens that can be detected or diagnosed include, but are not limited to, *Bacillus anthracis* (anthrax), *Clostridium botulinum* toxin (botulism), *Yersinia pestis* (plague). Variola major (smallpox) and other related pox viruses, *Francisella tularensis* (tularemia), Viral hemorrhagic fevers, Arenaviruses, (e.g., Junin, Machupo, Guanarito, Chapare, Lassa, and/or Lujo), Bunyaviruses (e.g. Hantaviruses causing Hanta Pulmonary syndrome, Rift Valley Fever, and/or Crimean Congo Hemorrhagic Fever), Flaviviruses, Dengue, Filoviruses (e.g. Ebola and Marburg viruses), *Burkholderia pseudomallei* (melioidosis), *Coxiella burnetii* (Q fever), *Brucella* species (brucellosis), *Burkholderia mallei* (glanders), *Chlamydia psittaci* (Psittacosis), Ricin toxin (*Ricinus communis*), Epsilon toxin (*Clostridium perfringens*), *Staphylococcus* enterotoxin B (SEB), Typhus fever (*Rickettsia prowazekii*), Food—and waterborne pathogens, Diarrheagenic *E. coli*, Pathogenic Vibrios, *Shigella* species, *Salmonella, Listeria monocytogenes, Campylobacter jejuni, Yersinia enterocolitica*, Caliciviruses, Hepatitis A, *Cryptosporidium parvum, Cyclospora cayatanensis, Giardia lamblia, Entamoeba histolytica, Toxoplasma gondii, Naegleria fowleri, Balamuthia mandrillaris*, Fungi, Microsporidia, Mosquito-borne viruses (e.g. West Nile virus (WNV), LaCrosse encephalitis (LACV), California encephalitis, Venezuelan equine encephalitis (VEE), Eastern equine encephalitis (EEE), Western equine encephalitis (WEE), Japanese encephalitis virus (JE), St. Louis encephalitis virus (SLEV), Yellow fever virus (YFV), Chikungunya virus, Zika virus, Nipah and Hendra viruses, Additional hantaviruses, Tickborne hemorrhagic fever viruses, Bunyaviruses, Severe Fever with Thrombocytopenia Syndrome virus (SFTSV), Heartland virus, Flaviviruses (e.g. Omsk Hemorrhagic Fever virus, Alkhurma virus, Kyasanur Forest virus), Tickborne encephalitis complex flaviviruses, Tickborne encephalitis viruses, Powassan/Deer Tick virus, Tuberculosis, including drug-resistant TB, Influenza virus, Rabies virus, Prions, *Streptococcus, Pseudomonas, Shigella, Campylobacter, Salmonella, Clostridium, Escherichia*, Hepatitis B, Hepatitis C, papillomavirus, Epstein-Barr virus, varicella, variola, Orthomyxovirus, Severe acute respiratory syndrome associated coronavirus (SARS-COV), SARS-COV-2 (COVID-19), MERS-COV, other highly pathogenic human coronaviruses, or any combination thereof.

The methods described herein can also be used to detect diagnoses viruses. In certain embodiments, the virus comprises a DNA virus. In certain embodiments, the virus comprises an RNA virus.

Detection of viral nucleic acids is the basis of the method described herein to detect and diagnose viral infection. For the detection and diagnosis of a viral infection, the viral nucleic acid molecule is part of a genome of a virus being tested. In some embodiments, said virus is a coronavirus. In some embodiments, said coronavirus is selected from the group consisting of severe acute respiratory syndrome coronavirus 2 (COVID-19), severe acute respiratory syndrome coronavirus (SARS-COV), and Middle East respiratory syndrome coronavirus (MERS-COV). In some embodiments, said coronavirus is COVID-19. The methods disclosed are useful in the classification of other RNA and DNA genome viruses. In some embodiments, said virus is an RNA virus. In some embodiments, said RNA virus comprises a double-stranded RNA genome. In some embodiments, said RNA virus comprises a single-stranded RNA genome. In some embodiments, said RNA virus is selected from the group consisting of coronavirus, influenza, human immunodeficiency virus, and Ebola virus. In some embodiments, said virus is a DNA virus. In some embodiments, the viral infection is COVID-19

For example, the methods herein are useful for the detection of coronaviruses. The methods for diagnosing a coronavirus infection are applicable to other viruses. Coronaviruses are members of the subfamily Coronavirinae in the family Coronaviridae and the order Nidovirales (International Committee on Taxonomy of Viruses). The coronavirus subfamily consists of four genera: Alphacoronavirus, Betacoronavirus, Gammacoronavirus and Deltacoronavirus. These genera are distinguished on the basis of phylogenetic relationships and genomic structures. Generally, alphacoronaviruses and betacoronaviruses infect mammals. Also, generally, the gammacoronaviruses and deltacoronaviruses infect birds, can also infect mammals.

Alphacoronaviruses and betacoronaviruses can be associated with and the cause of respiratory illness and gastroenteritis in humans. Highly pathogenic viruses (e.g. severe acute respiratory syndrome coronavirus (SARS-COV) and Middle East respiratory syndrome coronavirus (MERS-COV), can cause severe respiratory syndrome in humans.

Other four coronaviruses (e.g. HCoV-NL63, HCoV-229E, HCoV-OC43 and HKU1) generally induce mild upper respiratory diseases in immunocompetent hosts, infants, young children, and elderly individuals. Alphacoronaviruses and betacoronaviruses can pose a heavy disease burden not only to humans but also to livestock; these viruses include porcine transmissible gastroenteritis virus, porcine enteric diarrhea virus (PEDV), and swine acute diarrhea syndrome coronavirus (SADS-COV). On the basis of current sequence databases, all human coronaviruses have zoonotic origins. For example, SARS-COV, MERS—COV, HCoV-NL63 and HCoV-229E are considered to have originated in bats. Domestic animals may have important roles as intermediate hosts that enable virus transmission from natural hosts to humans. In addition, domestic animals themselves can suffer disease caused by coronaviruses.

Biological Samples

Provided herein are methods that use and process biological samples from individuals to diagnose viral infection. Such biological samples can be from individuals previously exposed to the virus, previously diagnosed as positive for the virus, or individuals deemed to be at risk of viral exposure. The methods described herein may also be useful for population surveillance, that is using samples provided by a plurality of individuals with the goal of providing information on the amount of viral infection in a given population. The biological samples can be oral or nasal mucosa. The samples can be blood, serum, or plasma. The biological samples, in certain embodiments, comprise a nasal swab, nasopharyngeal swab, buccal swab, oral fluid swab, mid-turbinate swab, or any combination thereof, wherein the swab has been used to collect a sample from an individual.

In practice, biological samples are collected using a myriad of collection devices, all of which can be used with the apparatus of the invention. The collection devices will generally be commercially available but can also be specifically designed and manufactured for a given application. For clinical samples, a variety of commercial swab types are available including nasal, nasopharyngeal, buccal, oral fluid, stool, tonsil, vaginal, cervical, and wound swabs. The dimensions and materials of the sample collection devices vary, and the devices may contain specialized handles, caps, scores to facilitate and direct breakage, and collection matrices.

Blood samples are collected in a wide variety of commercially available tubes of varying volumes, some of which contain additives (including anticoagulants such as heparin, citrate, and EDTA), a vacuum to facilitate sample entry, a stopper to facilitate needle insertion, and coverings to protect the operator from exposure to the sample. Tissue and bodily fluids (e.g. sputum, purulent material, aspirates) are also collected in tubes, generally distinct from blood tubes. These clinical sample collection devices are generally sent to sophisticated hospital or commercial clinical laboratories for testing (although certain testing such as the evaluation of throat/tonsillar swabs for rapid streptococcal tests can be performed at the point of care). Environmental samples may be present as filters or filter cartridges (e.g. from air breathers, aerosols or water filtration devices), swabs, powders, or fluids.

Processing of Samples

After collection biological samples are contacted with a lysis agent in order to release viral nucleic acids that are present in cells that are obtained from the sample. Such lysis also releases genomic DNA of the individual being tested. Such genomic DNA can serve as a sample/amplification control. Sample collection and lysing can be performed before the method described herein for the amplification of viral sequences, or at the site of amplification and sequencing of viral sequences.

In accordance with methods and systems disclosed, a sample may be collected or partitioned along with lysis reagents in order to release the contents of the sample within the partition. Partitions include vials, tubes, and/or wells in a plate. In such embodiments, the lysis agents can be contacted with the sample suspension concurrently with, or prior to, the addition of reagents used in the extension and amplification of nucleic acid molecules. In some embodiments, the processing (e.g. amplification, primer extension, reverse transcriptase, etc.) of nucleic acids within the sample occurs in the same conditions used for cellular lysis. A discrete partition may include an individual sample and/or one or more reagents. In some embodiments, a discrete partition generated may include a primer and enzymes for the amplification of nucleic acids (e.g. reverse transcriptase and/or a polymerase). In some embodiments, a discrete partition generated can include a barcoded oligonucleotide (e.g. primer comprising a barcode sequence). In some embodiments, a discrete partition generated can include a barcode carrying bead. In some embodiments, a discrete partition may be unoccupied (e.g., no reagents, no samples).

Beneficially, when lysis reagents and samples are co-partitioned, the lysis reagents can facilitate the release of the contents of the samples within the partition. The contents released in a partition may remain discrete from the contents of other partitions.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lytiembodiment, and a variety of other lysis enzymes available from, e.g., Sigma-Aldrich, Inc. (St Louis, Mo.), as well as other commercially available lysis enzymes. Other lysis agents may additionally or alternatively be co-partitioned with the samples to cause the release of the sample's contents into the partitions. For example, in some embodiments, surfactant-based lysis solutions may be used to lyse cells, although these may be less desirable for emulsion-based systems where the surfactants can interfere with stable emulsions. In some embodiments, lysis solutions may include non-ionic surfactants such as, for example, TritonX-100 and/or Tween 20. In some embodiments, lysis solutions may include ionic surfactants such as, for example, sarcosyl and sodium dodecyl sulfate (SDS). Lysis agents described herein may comprise one or more proteinases (e.g. proteinase K). Electroporation, thermal, acoustic or mechanical cellular disruption may also be used in certain embodiments, e.g., non-emulsion based partitioning such as encapsulation of samples that may be in addition to or in place of partition partitioning, where any pore size of the encapsulate is sufficiently small to retain nucleic acid fragments of a given size, following cellular disruption.

Lysis agents may also comprise high temperature water or reaction buffers that are heated before or after addition of the sample. For example, a lysis agent can be a heated PCR or reverse transcriptase reaction mix that is heated to at least about 50, 55, 60, 65, 70, 75, 80, 85, 90, or 95° C. For an amount of time that is about 1, 2, 3, 4, 5, 6, 7, 8, 9, 10 minutes or more.

Alternatively or in addition to the lysis agents co-partitioned with the samples described above, other reagents can also be co-partitioned with the samples, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the embodiment of encapsulated samples, the samples may be exposed to an appropriate stimulus to release the samples or their contents from a co-partitioned microcapsule. For example, in some embodiments, a chemical stimulus may be co-partitioned along with an encapsulated sample to allow for the degradation of the microcapsule and release of the cell or its contents into the larger partition. In some embodiments, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated sample to be released into a partition at a different time from the release of nucleic acid molecules into the same partition.

A partition may comprise species (e.g., reagents) for conducting one or more reactions. Species may include, for example, reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for reverse transcription (e.g., reverse transcriptase enzymes), reagents for nucleic acid modification reactions such as polymerization, ligation, or digestion, and/or reagents for template preparation. In some cases, primers may be attached to the precursors. Primers may be used for reverse transcription. Primers may comprise a poly-T sequence or be specific for a target nucleic acid molecule (i.e. complementary to a sequence of the target nucleic acid). In some embodiments, the primers hybridize to specific target nucleic acid sequences (e.g. a viral nucleic acid sequence).

Additional reagents may also be co-partitioned with the samples, such as endonucleases to fragment a sample's DNA, DNA polymerase enzymes and dNTPs used to amplify the sample's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes if the lysed sample comprises an RNA based virus.

One advantage of the methods described herein is the ability to use saliva samples for detection of one or more of influenza A/B, coronavirus, or other pathogen sequences. The saliva sample for use in the methods described herein may comprise less than about 100, 50, 25, 10, 9, 8, 7, 6, 5, 4, 3, or 2 microliters of saliva. In certain embodiments, the saliva sample is less than about 20 microliters. In certain embodiments, the saliva sample is less than about 10 microliters. In certain embodiments, the saliva sample is less than about 8 microliters. In certain embodiments, the saliva sample is less than about 7 microliters. In certain embodiments, the saliva sample is less than about 6 microliters. In certain embodiments, the saliva sample is less than about 5 microliters.

One advantage of the methods described herein is the ability to use small amounts of nasal swab samples for detection of one or more of influenza A/B, coronavirus, or other pathogen sequences. Nasal swabs may be inoculated into about 1 milliliter of buffer such as PBS or saline, and then a small amount of that sample may be used to detect viral infection. The nasal swab sample for use in the methods described herein may comprise less than about 100, 50, 25, 10, 9, 8, 7, 6, 5, 4, 3, or 2 microliters of inoculated nasal swab. In certain embodiments, the inoculated nasal swab sample is less than about 20 microliters. In certain embodiments, the inoculated nasal swab sample is less than about 10 microliters. In certain embodiments, the inoculated nasal swab sample is less than about 8 microliters. In certain embodiments, the inoculated nasal swab sample is less than about 7 microliters. In certain embodiments, the inoculated nasal swab sample is less than about 6 microliters. In certain embodiments, the inoculated nasal swab sample is less than about 5 microliters.

Detection of Pathogen Sequences

Viruses generally comprise a genomic structure comprising deoxyribonucleic acid (DNA) or ribonucleic acid (RNA). Such genomes can consist single-stranded or double-stranded nucleic acids. The genomes of viruses also generally comprise nucleic acid sequence that are different than the host they infect. Therefore, the differential nucleic acid sequences within a viral genome provide a target for detection using molecular and genetic amplification and sequencing technologies. Furthermore, differences in the genetic sequences and structures among viruses allows for the distinguishing classes, subclasses, and individual strains of viruses apart from one another. Accordingly, primers (e.g. probes) that recognize nucleic acid sequences, elements, templates, or loci specific to a virus can be used in the identification and detection of a viral infection.

Figure 3:
FIG. 3 illustrates an exemplary priming scheme according to the current disclosure.

Described herein the detection of viral sequences comprises amplifying viral nucleic acid using a PCR reaction and sequencing the results of the PCR amplification. In instances where the virus being detected is an RNA based virus amplification also includes a reverse transcription reaction. The reverse transcription reaction can be a distinct step before PCT amplification or a one-step reaction that occurs in the presence of PCR enzymes and primers. PCR amplification is carried out via oligonucleotide primer pairs. Such primers in addition to comprising a target specific portion, may also comprise index sequences and/or sequencing adaptor sequences as shown in FIG. 3.

Amplification of viral and host nucleic acid molecules can be achieved through the use of enzymes that extend or amplify a primer hybridized to the viral and host nucleic acid molecules. Particularly, reverse transcriptase enzymes are used to generate cDNA corresponding to the host and viral nucleic acids. For example, for viruses having a genome comprising RNA, said nucleic acid extension reaction is a reverse transcription reaction. RNA nucleic acid products of DNA transcription in a host cell can also be processed using a reverse transcriptase enzyme. Known reverse transcriptase enzymes are readily available for use. Avian Myeloblastosis Virus (AMV) Reverse Transcriptase and Moloney Murine Leukemia Virus (M-MuLV, MMLV) Reverse Transcriptase are RTs that are commonly used in molecular biology workflows. M-MuL V Reverse Transcriptase lacks 3'->5' exonuclease activity. ProtoScript II Reverse Transcriptase is a recombinant M-MuL V reverse transcriptase with reduced RNase H activity and increased thermostability. It can be used to synthesize first strand cDNA at higher temperatures than the wild-type M-MuLV. The enzyme is active up to 50° C., providing higher specificity, higher yield of cDNA and more full-length cDNA product, up to 12 kb in length. The use of engineered RTs improves the efficiency of full-length product formation, ensuring the copying of the 5' end of the mRNA transcript is complete, and enabling the propagation and characterization of a faithful DNA copy of an RNA sequence. The use of the more thermostable RTs, where reactions are performed at higher temperatures, can be helpful when dealing with RNA that contains high amounts of secondary structure. In some embodiments, said nucleic acid extension reaction comprises a reverse transcriptase reaction, a polymerase chain reaction, or a combination thereof. In certain embodiments, said nucleic acid extension reaction comprises (i) hybridizing a primer to a viral nucleic acid molecule; and (ii) using a reverse transcriptase enzyme; extending said primer.

After or during reverse transcription (if applicable) the samples are subjected to an amplification reaction. In certain embodiments, the amplification reaction is a PCR reaction. In certain embodiments, the PCR reaction is not a real-time PCR reaction. In certain embodiments the PCR is carried out for a set number of cycles sufficient to amplify viral nucleic acid sequences. The lysed and reverse transcribed sample can be amplified for N cycles. In certain embodiments, N is greater than 30, 35, 40, or 45 cycles. In certain embodiments, N is between 30 and 50 cycles, between 40 and 50 cycles, between 35 and 45 cycles, between 36 and 44 cycles, between 37 and 43 cycles, between 38 and 42 cycles, between 39 and 41 cycles, or between 40 and 45 cycles. In certain embodiments, the lysed and reverse transcribed sample can be amplified for 40 cycles.

Primer pairs can be added to the amplification PCR reaction at an optimized concentration. In certain embodiments, the concentration of the primer sets that amplify the viral nucleic acid/synthetic nucleic acid and/or the host control is Primer pairs can be added to the PCR reaction at a concentration below 1 micromolar. In certain embodiments, the concentration is about 800 nM, 400 nM, 200 nM, 100 nM, 150 nM, or 50 nM.

Polymerase chain reaction amplification can be used to further incorporate functional sequences such as a variable nucleotide sequence (barcode). In some embodiments, said polymerase chains reaction incorporates one or more additional sequences into one or both of said barcoded viral nucleic acid molecule and barcoded host nucleic acid molecule, selected from the group consisting of a sample index sequence, an adapter sequence, primer sequence, a primer binding sequence, a sequence configured to couple to the flow cell of a sequencer, and an additional barcode sequence.

The method described herein includes a synthetic nucleic acid that is co-reverse transcribed and/or amplified with viral nucleic acid. In a certain embodiment a set of oligonucleotide primers that amplify a viral sequence also amplifies the synthetic nucleic acid. A sample can be "spiked" with a synthetic nucleic acid molecule that provides information regarding the processing of nucleic acids in a sample. In certain embodiments, the synthetic nucleic acid molecule is added to the biological sample prior to processing or amplification. In certain embodiments, the synthetic nucleic acid is spiked into the biological sample at a known concentration or amount. In certain embodiments, the known amount is $1\times10^4$, $1\times10^3$, $1\times10^2$, 10, 5, 4, 3, 2, or 1 copies of synthetic nucleic acid. In certain embodiments, the synthetic control nucleic acid is an RNA. Ideally, the length of the amplified portion of the synthetic nucleic acid matches the length of viral nucleic acid target to be amplified, and produces an amplicon that is the same length as the viral nucleic acid target or within about 1, 2, 3, 4, 5, 6, 7, 8, 9, 10, 15, 20, 30, 40, or 50 nucleotides. Also, the sequence of the synthetic nucleic acid should be highly homologous to the viral sequence but vary by at least one nucleotide such that the synthetic nucleic acid can be discriminated by sequencing. In certain embodiments, the synthetic nucleic acid varies by at least about 1, 2, 3, 4, 5, 6, 7, 8, 9, 10, 11, 12, 13 14 or 15 nucleotides compared to the sequence of the viral nucleic acid to be amplified.

The synthetic nucleic acid sequence may be used to normalize sequence reads and account for losses during sample preparation or inefficiencies/bias introduced during amplification or sequencing.

The synthetic nucleic acid may comprise a plurality of nucleic acids with distinct sequences to further improve the performance of the "spiked" synthetic nucleic acid for downstream processing and analysis. The plurality may comprise 2, 3, 4, 5, 6, 7, 8, 9, 10, or more distinct sequences. The plurality may comprise 2, 3, 4, 5 distinct sequences. The plurality may comprise 4 distinct sequences. The plurality may be for use with primers that amplify the S2 spike sequence, the N1 nucleoprotein sequence, or a combination thereof. Exemplary sequences are shown in the table below (as the synthetic nucleic acids are RNA all Ts are Us in the RNA version of the sequence). Any one or more of the synthetic nucleic acids or the plurality of synthetic nucleic acids can possess at least about 90%, 95%, 97%, 98%, 99% or identical homology to any of SEQ ID NOs. 1 to 12 shown below.

Exemplary sequences for COVID 19 S2 and N1 synthetic spike sequences

| | | |
|---|---|---|
| S2_001 SEQ ID NO: 1 | | GCUGGUGCUGCAGCUUAUUAUGUGGGUGUGUAUCUCACGAAGCG ACCCUUUGGAAAAUAUAAUGAAAAUGGAACCAUUACAGAUGCUG UAGACUGUGCACUUGACCCU |
| S2_002 SEQ ID NO: 2 | | GCUGGUGCUGCAGCUUAUUAUGUGGGUCCUCGCUAGGACGUCGC UAUgacgccAAAAUAUAAUGAAAAUGGAACCAUUACAGAUGCUGUA GACUGUGCACUUGACCCU |
| S2_003 SEQ ID NO: 3 | | GCUGGUGCUGCAGCUUAUUAUGUGGGUAGCACGACUUGAUCUAA CUgacacuaAAAAUAUAAUGAAAAUGGAACCAUUACAGAUGCUGUA GACUGUGCACUUGACCCU |
| S2_004 SEQ ID NO: 4 | | GCUGGUGCUGCAGCUUAUUAUGUGGGUUAAGUAGGACUUCGAUU ggaUggaauAAAAUAUAAUGAAAAUGGAACCAUUACAGAUGCUGUA GACUGUGCACUUGACCCU |
| N1_001 SEQ ID NO: 5 | | UCUGGUUACUGCCAGUUGAAUCUGAGGGUCCGGACGGAUAUCGC ACUAAGUGUACCUGGUGCAUUUCGCUGAUUUUGGGGUC |
| N1_002 SEQ ID NO: 6 | | UCUGGUUACUGCCAGUUGAAUCUGAGGGUCCCAUGACCAUGUCA CUGGCUACACUGAGGUGCAUUUCGCUGAUUUUGGGGUC |

-continued

| Exemplary sequences for COVID 19 S2 and N1 synthetic spike sequences | |
|---|---|
| N1_003<br>SEQ ID NO: 7 | UCUGGUUACUGCCAGUUGAAUCUGAGGGUCCUUGACAUGGCAUG<br>UGACUCCACUGUCGGUGCAUUUCGCUGAUUUUGGGGUC |
| N1_004<br>SEQ ID NO: 8 | UCUGGUUACUGCCAGUUGAAUCUGAGGGUCCACCUUUGCCAGAU<br>GACUGAGUGGAAGGGUGCAUUUCGCUGAUUUUGGGGUC |
| N1_005<br>SEQ ID NO: 9 | UCUGGUUACUGCCAGUUGAAUCUGAGGGUCCAGCUUGAAGCGUU<br>CGCGACAAGUGUCGGUGCAUUUCGCUGAUUUUGGGGUC |
| N1_006<br>SEQ ID NO: 10 | UCUGGUUACUGCCAGUUGAAUCUGAGGGUCCUCACGUCCUGAGA<br>UCAACUGCUACAUGGUGCAUUUCGCUGAUUUUGGGGUC |
| N1_007<br>SEQ ID NO: 11 | UCUGGUUACUGCCAGUUGAAUCUGAGGGUCCGUUGACUGAUCAC<br>AUGCUGCUCCACGGGUGCAUUUCGCUGAUUUUGGGGUC |
| N1_008<br>SEQ ID NO: 12 | UCUGGUUACUGCCAGUUGAAUCUGAGGGUCCAGACAGUCAUCG<br>GAUUGAUGAGUGAGGUGCAUUUCGCUGAUUUUGGGGUC |

The synthetic nucleic acid comprises 5' and 3' proximal sequences that can be bound by the same primers that amplify the viral nucleic acid sequence being tested for, but that comprise a distinct intervening sequence distinguishable from the viral nucleic acid sequence being tested for by sequencing. In some embodiments, the method described herein further comprises providing a synthetic nucleic acid molecule. In some embodiments, the method described herein further comprises providing a synthetic nucleic acid molecule compromising 5' and 3' proximal sequences that can be bound by the same primers that amplify the viral nucleic acid. In certain embodiments, the 5' proximal region, said 3' proximal region, or both said 5' proximal region and said 3' proximal region are less than about 30 nucleotides in length. In certain embodiments, the 5' proximal region, the 3' proximal region, or both the 5' proximal region and the 3' proximal region are less than about 25 nucleotides in length. In certain embodiments, the 5' proximal region, the 3' proximal region, or both the 5' proximal region and said 3' proximal region are less than about 20 nucleotides in length. In certain embodiments, the 5' proximal region is at the 5' terminus of the synthetic nucleic acid. In certain embodiments, the 3' proximal region is at the 3' terminus of the synthetic nucleic acid. In certain embodiments, the intervening nucleic acid sequence is less than about 99%, 98%, 97%, 95%, 90%, 85%, 80%, or 75%, identical to a viral nucleic acid sequence. In some embodiments, the synthetic nucleic acid molecule comprises a synthetic sequence that is different from said viral nucleic acid molecule and said human nucleic acid molecule. In some embodiments, the synthetic nucleic acid molecule comprises a nucleotide sequence identity to a host and/or viral sequence no greater than 10%, 25%, 50%, 75%, 90%, 95%, or 98%.

In certain embodiments, the synthetic nucleic acid is added to a lysate to achieve a concentration in the method of about 1 copy/well to about 1,000,000 copies/well. In certain embodiments, the synthetic nucleic acid is added at about 1 copy/well to about 50 copies/well, about 1 copy/well to about 100 copies/well, about 1 copy/well to about 500 copies/well, about 1 copy/well to about 1,000 copies/well, about 1 copy/well to about 5,000 copies/well, about 1 copy/well to about 10,000 copies/well, about 1 copy/well to about 100,000 copies/well, about 1 copy/well to about 1,000,000 copies/well, about 50 copies/well to about 100 copies/well, about 50 copies/well to about 500 copies/well, about 50 copies/well to about 1,000 copies/well, about 50 copies/well to about 5,000 copies/well, about 50 copies/well to about 10,000 copies/well, about 50 copies/well to about 100,000 copies/well, about 50 copies/well to about 1,000,000 copies/well, about 100 copies/well to about 500 copies/well, about 100 copies/well to about 1,000 copies/well, about 100 copies/well to about 5,000 copies/well, about 100 copies/well to about 10,000 copies/well, about 100 copies/well to about 100,000 copies/well, about 100 copies/well to about 1,000,000 copies/well, about 500 copies/well to about 1,000 copies/well, about 500 copies/well to about 5,000 copies/well, about 500 copies/well to about 10,000 copies/well, about 500 copies/well to about 100,000 copies/well, about 500 copies/well to about 1,000,000 copies/well, about 1,000 copies/well to about 5,000 copies/well, about 1,000 copies/well to about 10,000 copies/well, about 1,000 copies/well to about 100,000 copies/well, about 1,000 copies/well to about 1,000,000 copies/well, about 5,000 copies/well to about 10,000 copies/well, about 5,000 copies/well to about 100,000 copies/well, about 5,000 copies/well to about 1,000,000 copies/well, about 10,000 copies/well to about 100,000 copies/well, about 10,000 copies/well to about 1,000,000 copies/well, or about 100,000 copies/well to about 1,000,000 copies/well. In certain embodiments, the synthetic nucleic acid is added at about 1 copy/well, about 50 copies/well, about 100 copies/well, about 500 copies/well, about 1,000 copies/well, about 5,000 copies/well, about 10,000 copies/well, about 100,000 copies/well, or about 1,000,000 copies/well. In certain embodiments, the synthetic nucleic acid is added at least about 1 copy/well, about 50 copies/well, about 100 copies/well, about 500 copies/well, about 1,000 copies/well, about 5,000 copies/well, about 10,000 copies/well, or about 100,000 copies/well. In certain embodiments, the synthetic nucleic acid is added at most about 50 copies/well, about 100 copies/well, about 500 copies/well, about 1,000 copies/well, about 5,000 copies/well, about 10,000 copies/well, about 100,000 copies/well, or about 1,000,000 copies/well.

After amplification and/or sequencing the resulting ratio of detected pathogen nucleic acid molecule and synthetic oligonucleotide is useful in detecting and diagnosing a pathogenic infection. The components of the ratio used in the detection and diagnosis of an infectious pathogen can be based on the number of reads for a specific sequence or set of sequences, the copy number of a specific sequence or set of sequences (e.g. the number of different unique molecular identifier sequences associated with a specific sequence), an number or amount derived from the sequencing information, or any combination thereof. In some embodiments, the ratio of pathogen nucleic acids to synthetic nucleic acids is greater than 1. In some embodiments, the ratio of pathogen nucleic acids to synthetic nucleic acids is equal to or about 1. In some embodiments, the ratio of pathogen nucleic acids to synthetic nucleic acids is less than 1.

In certain embodiments, the ratio of pathogen nucleic acids to synthetic nucleic acids is about 0.00001:1 to about 0.5:1. In certain embodiments, the ratio of pathogen nucleic acids to synthetic nucleic acids is about 0.00001:1 to about 0.00005:1, about 0.00001: 1 to about 0.0001:1, about 0.00001:1 to about 0.0002:1, about 0.00001:1 to about 0.0003:1, about 0.00001:1 to about 0.0004:1, about 0.00001:1 to about 0.0005:1, about 0.00001:1 to about 0.001:1, about 0.00001:1 to about 0.005:1, about 0.00001:1 to about 0.01:1, about 0.00001:1 to about 0.1:1, about 0.00001:1 to about 0.5:1, about 0.00005:1 to about 0.0001:1, about 0.00005:1 to about 0.0002:1, about 0.00005:1 to about 0.0003:1, about 0.00005:1 to about 0.0004:1, about 0.00005:1 to about 0.0005:1, about 0.00005:1 to about 0.001:1, about 0.00005:1 to about 0.005:1, about 0.00005:1 to about 0.01:1, about 0.00005:1 to about 0.1:1, about 0.00005:1 to about 0.5:1, about 0.0001:1 to about 0.0002:1, about 0.0001:1 to about 0.0003:1, about 0.0001:1 to about 0.0004:1, about 0.0001:1 to about 0.0005:1, about 0.0001:1 to about 0.001:1, about 0.0001:1 to about 0.005:1, about 0.0001:1 to about 0.01:1, about 0.0001:1 to about 0.1:1, about 0.0001:1 to about 0.5:1, about 0.0002:1 to about 0.0003:1, about 0.0002:1 to about 0.0004:1, about 0.0002:1 to about 0.0005:1, about 0.0002:1 to about 0.001:1, about 0.0002:1 to about 0.005:1, about 0.0002:1 to about 0.01:1, about 0.0002:1 to about 0.1:1, about 0.0002:1 to about 0.5:1, about 0.0003:1 to about 0.0004:1, about 0.0003:1 to about 0.0005:1, about 0.0003:1 to about 0.001:1, about 0.0003:1 to about 0.005:1, about 0.0003:1 to about 0.01:1, about 0.0003:1 to about 0.1:1, about 0.0003:1 to about 0.5:1, about 0.0004:1 to about 0.0005:1, about 0.0004:1 to about 0.001:1, about 0.0004:1 to about 0.005:1, about 0.0004:1 to about 0.01:1, about 0.0004:1 to about 0.1:1, about 0.0004:1 to about 0.5:1, about 0.0005:1 to about 0.001:1, about 0.0005:1 to about 0.005:1, about 0.0005:1 to about 0.01:1, about 0.0005:1 to about 0.1:1, about 0.0005:1 to about 0.5:1, about 0.001:1 to about 0.005:1, about 0.001:1 to about 0.01:1, about 0.001:1 to about 0.1:1, about 0.001:1 to about 0.5:1, about 0.005:1 to about 0.01:1, about 0.005:1 to about 0.1:1, about 0.005:1 to about 0.5:1, about 0.01:1 to about 0.1:1, about 0.01:1 to about 0.5:1, or about 0.1:1 to about 0.5:1. In certain embodiments, the ratio of pathogen nucleic acids to synthetic nucleic acids is about 0.00001:1, about 0.00005:1, about 0.0001:1, about 0.0002:1, about 0.0003:1, about 0.0004:1, about 0.0005:1, about 0.001:1, about 0.005:1, about 0.01:1, about 0.1:1, or about 0.5:1. In certain embodiments, the ratio of pathogen nucleic acids to synthetic nucleic acids is at least about 0.00001:1, about 0.00005:1, about 0.0001:1, about 0.0002:1, about 0.0003:1, about 0.0004:1, about 0.0005:1, about 0.001:1, about 0.005:1, about 0.01:1, or about 0.1:1.

In certain embodiments, the ratio of pathogen nucleic acids to synthetic nucleic acids is about 1:1 to about 1:100. In certain embodiments, the ratio of pathogen nucleic acids to synthetic nucleic acids is about 1:100 to about 1:50, about 1:100 to about 1:25, about 1:100 to about 1:10, about 1:100 to about 1:5, about 1:100 to about 1:4, about 1:100 to about 1:3, about 1:100 to about 1:2, about 1:100 to about 1:1, about 1:100 to about 1:1, about 1:50 to about 1:25, about 1:50 to about 1:10, about 1:50 to about 1:5, about 1:50 to about 1:4, about 1:50 to about 1:3, about 1:50 to about 1:2, about 1:50 to about 1:1, about 1:50 to about 1:1, about 1:25 to about 1:10, about 1:25 to about 1:5, about 1:25 to about 1:4, about 1:25 to about 1:3, about 1:25 to about 1:2, about 1:25 to about 1:1, about 1:25 to about 1:1, about 1:10 to about 1:5, about 1: 10 to about 1:4, about 1:10 to about 1:3, about 1: 10 to about 1:2, about 1:10 to about 1:1, about 1:10 to about 1:1, about 1:5 to about 1:4, about 1:5 to about 1:3, about 1:5 to about 1:2, about 1:5 to about 1:1, about 1:5 to about 1:1, about 1:4 to about 1:3, about 1:4 to about 1:2, about 1:4 to about 1:1, about 1:4 to about 1:1, about 1:3 to about 1:2, about 1:3 to about 1:1, about 1:3 to about 1:1, about 1:2 to about 1:1, about 1:2 to about 1:1, or about 1:1 to about 1:1. In certain embodiments, the ratio of pathogen nucleic acids to synthetic nucleic acids is about 1:100, about 1:50, about 1:25, about 1:10, about 1:5, about 1:4, about 1:3, about 1:2, about 1:1, or about 1:1. In certain embodiments, the ratio of pathogen nucleic acids to synthetic nucleic acids is at least about 1:100, about 1:50, about 1:25, about 1:10, about 1:5, about 1:4, about 1:3, about 1:2, or about 1:1. In certain embodiments, the ratio of pathogen nucleic acids to synthetic nucleic acids is at most about 1:50, about 1:25, about 1:10, about 1:5, about 1:4, about 1:3, about 1:2, about 1:1, or about 1:1.

In certain embodiments, the ratio of synthetic nucleic acids to pathogen nucleic acids is about 1:100 to about 1:50, about 1:100 to about 1:25, about 1:100 to about 1:10, about 1:100 to about 1:5, about 1:100 to about 1:4, about 1:100 to about 1:3, about 1:100 to about 1:2, about 1:100 to about 1:1, about 1:100 to about 1:1, about 1:50 to about 1:25, about 1:50 to about 1:10, about 1:50 to about 1:5, about 1:50 to about 1:4, about 1:50 to about 1:3, about 1:50 to about 1:2, about 1:50 to about 1:1, about 1:50 to about 1:1, about 1:25 to about 1:10, about 1:25 to about 1:5, about 1:25 to about 1:4, about 1:25 to about 1:3, about 1:25 to about 1:2, about 1:25 to about 1:1, about 1:25 to about 1:1, about 1:10 to about 1:5, about 1:10 to about 1:4, about 1:10 to about 1:3, about 1:10 to about 1:2, about 1:10 to about 1:1, about 1:10 to about 1:1, about 1:5 to about 1:4, about 1:5 to about 1:3, about 1:5 to about 1:2, about 1:5 to about 1:1, about 1:5 to about 1:1, about 1:4 to about 1:3, about 1:4 to about 1:2, about 1:4 to about 1:1, about 1:4 to about 1:1, about 1:3 to about 1:2, about 1:3 to about 1:1, about 1:3 to about 1:1, about 1:2 to about 1:1, about 1:2 to about 1:1, or about 1:1 to about 1:1. In certain embodiments, the ratio of pathogen nucleic acids to synthetic nucleic acids is about 1:100, about 1:50, about 1:25, about 1:10, about 1:5, about 1:4, about 1:3, about 1:2, about 1:1, or about 1:1. In certain embodiments, the ratio of pathogen nucleic acids to synthetic nucleic acids is at least about 1:100, about 1:50, about 1:25, about 1:10, about 1:5, about 1:4, about 1:3, about 1:2, or about 1:1. In certain embodiments, the ratio of pathogen nucleic acids to synthetic nucleic acids is at most about 1:50, about 1:25, about 1:10, about 1:5, about 1:4, about 1:3, about 1:2, about 1:1, or about 1:1.

The ratio of pathogen reads to pathogen synthetic nucleic acid (with sequence distinguishable from pathogen read) can be used to indicate positive diagnosis with a particular pathogen (e.g., coronavirus, Influenza A, Influenza B). Alternatively, a negative diagnosis is made if the ratio does not exceed a threshold for positivity. In some embodiments, a positive diagnosis for the pathogen is made if the sequence reads from pathogen nucleic acids to synthetic nucleic acids exceeds a ratio of from about 0.01 to about 0.5. In some embodiments, a positive diagnosis for the pathogen is made if the sequence reads from pathogen nucleic acids to synthetic nucleic acids exceeds a ratio of from about 0.01 to about 0.4, from about 0.01 to about 0.3, from about 0.01 to about 0.2, from about 0.02 to about 0.5, from about 0.02 to about 0.2, from about 0.03 to about 0.5, from about 0.03 to about 0.2, from about 0.04 to about 0.5, from about 0.04 to about 0.2, from about 0.05 to about 0.5, from about 0.05 to about 0.2, from about 0.06 to about 0.5, from about 0.06 to about 0.2, from about 0.07 to about 0.5, from about 0.07 to about 0.2, from about 0.08 to about 0.5, from about 0.08 to about 0.2. In some embodiments, a positive diagnosis for the pathogen is made if the sequence reads from pathogen nucleic acids to synthetic nucleic acids exceeds a ratio of about 0.01, about 0.02, about 0.03, about 0.04, about 0.05, about 0.06, about 0.07, about 0.08, about 0.09, or about 0.1.

The total amount of pathogen reads plus pathogen synthetic nucleic acid (with sequence distinguishable from pathogen read) can be used to indicate if enough sequence data is present to attempt a positive or negative diagnosis for the presence of the pathogen (e.g., coronavirus, Influenza A, Influenza B). In some embodiments, the positive or negative diagnosis can only be made if the combined number of sequence reads of the pathogen nucleic acids together with the synthetic nucleic acids exceeds a minimum threshold, or else the result is inconclusive. In some embodiments, the minimum threshold is at least about 10 reads, at least about 20 reads, at least about 30 reads, at least about 40 reads, at least about 50 reads, at least about 60 reads, at least about 70 reads, at least about 80 reads, at least about 90 reads, at least about 100, at least about 150 reads, at least about 200 reads, or at least about 250 reads.

In some cases, a sample control can be used to verify that enough genetic material was present in the sample to reliably call a positive or negative diagnosis. The amount of reads can be counted for the sample control. This sample control is usually a housekeeping gene of the species of individual that the test is being performed on. In certain embodiments, when the individual being tested is human the sample control is beta actin, GAPDH, or RPP30. In certain embodiments, when the individual being tested is human the sample control is RPP30. In certain embodiments, the amount of reads from a sample control present in order to deliver a positive or negative diagnosis exceeds 5, 6, 7, 8, 9, 10, 11, 12, 13, 14, 15, 16, 17, 128, 19, 20, 25, or 30 reads. In certain embodiments, the amount of reads from a sample control present in order to deliver a positive or negative diagnosis equals or exceeds 10 reads.

The methods disclosed can also be combined with multiplexing strategies to effectively and efficiently allow for the testing of multiple samples in parallel. As used herein, "multiplex" refers to simultaneously conducting a plurality of assays on one or more samples. Multiplexing can further include simultaneously conducting a plurality of assays in each of a plurality of separate samples. For example, the number of reaction mixtures analyzed can be based on the number of partitions and the number of assays conducted in each partition can be based on the number of probes that contact the contents of each well. Multiplexing design and strategies can be effectively employed in the application of the method disclosed. For example, one or more unique barcode or adapter nucleic acid molecules can be coupled to a target nucleic acid molecule, wherein the unique barcode or adapter nucleic acid molecule identifies or barcodes the target nucleic acid molecule. Once barcoded, samples can be combined or pooled into a single sequencing library, wherein a barcoded target nucleic acid (e.g. a pathogen nucleic acid molecule and/or a synthetic nucleic acid molecule) can be distinguished from other barcoded samples. Accordingly, sample multiplexing and the use of nucleic acid barcodes can be used to identify sequencing reads from a first individual from a group or plurality of individuals. In some embodiments, the samples are pooled prior to sequencing. In certain embodiments, greater than 10, 25, 50, 75, 100, or 500 samples are pooled and analyzed in in a single sequencing library.

Furthermore, one or more pathogens may be tested in a single assay. For example, multiple respiratory viruses (or viral subtypes) can be analyzed in a single assay. Accordingly, the method disclosed for a single pathogen can be combined for the detection and analysis of multiple pathogens in a single reaction. (e.g. using multiple primers specific for multiple pathogen nucleic acid molecules and multiple synthetic nucleic acid molecule can be added to a sample). By way of further example, in some embodiments, a first pathogen is a coronavirus and a second pathogen is an influenza virus. Examples of multiple pathogens also include different subtypes or clades of viruses (e.g. influenza A H1N1 and influenza A H3N2).

The method and reaction mixtures described herein may make use of amplification and sequencing of a plurality of coronavirus sequences. In certain embodiments, the plurality of coronavirus sequences that are amplified and sequenced comprises an S2 sequence. In certain embodiments, the plurality of coronavirus sequences that are amplified and sequenced comprises an N1 sequence. In certain embodiments, the plurality of coronavirus sequences that are amplified and sequenced comprises an S2 and N1 sequence. Such tests may make use of a plurality of synthetic nucleic acid spike-ion controls, for each viral target.

The methods, reaction mixtures, and kits described herein can be used to test for a coronavirus (e.g., SARS-COV2) and Influenza A and/or Influenza B. Such tests would be useful for healthcare providers and health agencies in monitoring outbreaks of different common respiratory pathogens simultaneously. The methods described herein can be used in a triplex test to simultaneously detect coronavirus and Influenzas A and B. Such tests may make use of three different synthetic nucleic acid spike-ion controls, one for each viral target.

The methods described herein may also comprise a second set of oligonucleotide primers that targets a nucleic acid sequence of the viral host (e.g., the individual being tested) such a primer set provides a positive control for the sample and for amplification. In certain embodiments, said second set of PCR primers amplifies a human nucleic acid sequence selected from GAPDH, ACTB, RPP30, and combinations thereof. In certain embodiments, said second set of PCR primers amplifies a human RPP30 sequence. In certain embodiments, the second set of PCR primer comprises a mixture of primers with sequencing adaptor sequences and primers without sequencing adaptor sequences. In certain embodiments, a ratio of primers with sequencing adaptor sequences to primers without sequencing adaptor sequences is about 1:1, about 1:2, about 1:3 or about 1:4. A mixture of primers with and without adaptors allows for detection of the viral host nucleic acid, but allows more sequencing reads to be devoted to viral sequences.

In some embodiments, a result of a diagnosis of infection of a pathogen is inconclusive if a minimum predetermined number of reads of the human nucleic acid sequence is not detected. In some embodiments, the minimum predetermined number of reads of the human nucleic acid sequence must exceed at least about 2, at least about 3, at least about 4, at least about 5, at least about 6, at least about 7, at least about 8, at least about 9, at least about 10 reads, at least about 15 reads, at least about 20 reads, or at least about 25 reads of the human nucleic acid sequence. In some embodiments, the minimum predetermined number of reads of the human nucleic acid sequence must exceed at least about 10 reads.

Coronaviruses form enveloped viral particles of 100-160 nm in diameter. Coronaviruses are single-stranded ribonucleic acid (ssRNA) viruses, comprising a positive-sense RNA genome of 27-32 kb in size. The 5' region of the coronavirus the genome encodes a polyprotein, pp1ab, which is further cleaved into 16 non-structural proteins that are involved in genome transcription and replication. The 3' region encodes structural proteins, including envelope glycoproteins spike (e.g. viral spike), envelope, membrane, and nucleocapsid. The genes encoding structural proteins can also function as accessory genes that are species-specific and can be dispensable for virus replication.

COVID-19 (also referred to as HCOV-19 or SARS-COV-2) is a betacoronoavirus and the seventh coronavirus known to infect humans. The COVID-19 coronavirus can cause severe disease (as also observed with SARS-COV, MERS-COV). COVID-19 demonstrates efficient targeting of the human receptor ACE2. The receptor-binding domain (RBD) in the spike protein is the most variable part of the coronavirus genome. Six receptor-binding domain (RBD) amino acids have been shown to be critical for binding to ACE2 receptors and for determining the host range of SARS-COV-like viruses. Based on the SARS-COV protein sequence, the residues that participate in ACE2 binding, and contribute to receptor targeting, are Y442, L472, N479, D480, T487 and Y4911 (these residues also correspond to L455, F486, Q493, S494, N501 and Y505 in SARS-COV-2). In COVID-19, five of these six residues differ between COVID-19 and SARS-COV, corresponding to L455, F486, Q493, S494, and N501 of the COVID-19 receptor-binding domain (RBD) protein. Such sequence properties of COVID-19 can be used to identify, detect, and/or diagnose COVID-19. For example, the unique sequence of the sequence of the COVID-19 receptor-binding domain (RBD) can be used to identify, detect, or diagnose COVID-19.

COVID-19 also comprises a functional polybasic (furin) cleavage site within the S1 subunit and S2 subunit of the viral spike protein boundary through the insertion of 12 nucleotides. The inserted sequence also potentiates the acquisition of three O-linked glycans. Both the polybasic cleavage site and the three adjacent predicted O-linked glycans are unique to COVID-19 and have not previously identified in alpha- or betacoronaviruses. Accordingly, the viral spike sequence properties of COVID-19 can be used to identify, detect, and/or diagnose COVID-19. For example, the unique sequence of the sequence of the COVID-19 viral spike insertion can be used to identify, detect, or diagnose COVID-19.

The methods described herein are useful for the detection and diagnosis of viral infections in individuals. In certain embodiments, the viral infection is influenza. In certain embodiments, the viral infection is a coronavirus. In certain embodiments, the viral infection is COVID-19. In certain embodiments, the viral infection is MERS-COV. In certain embodiments, the viral infection is SARS-COV-2.

In principle any suitable viral nucleic acid sequence can be targeted by an oligo nucleotide primer pair. Such targets include nucleic acid sequences that encode the viral nucleocapsid protein, viral spike protein, viral envelop protein, or viral membrane protein. Such targets include non-structural proteins.

If the viral infection to be detected is SARS-COV-2 the viral nucleic acid detected can be one that encodes one or more of the viral nucleocapsid protein (N1), viral spike protein (S2), viral envelop protein, or viral membrane protein. In certain embodiments, the nucleic acid detected is one that encodes any one or more of the 16 SARS-COV-2 non-structural proteins; NSP1, NSP2, NSP3, NSP4, NSP5, NSP6, NSP7, NSP8, NSP9, NSP10, NSP111, NSP12, NSP13, NSP14, NSP15, or NSP16.

Exemplary primer pairs that can be used in the methods described herein can bind to sequences described in the sequence Appendix following this disclosure. In certain embodiments, any of the primers listed in the appendix can be used in the methods described herein.

Primers comprising barcoded oligos are useful in sample analysis (e.g. sample identification, tracing, quantification, etc.). For examples, primers within a partition comprising barcoded oligonucleotides that further comprise a common barcode sequence and a unique molecular identifier sequence can be used to (1) identify sequences belong to a partition through the use of the common barcode and (2) identify transcript copy number through the use of unique molecular identifiers. In some embodiments, said first primer set further comprises one or more additional functional sequences selected from the group consisting of primer sequences, adapter sequences, primer annealing sequences, a unique molecular identifier sequence, and capture sequences. In some embodiments, said second primer further comprises one or more additional functional sequences selected from the group consisting of primer sequences, adapter sequences, primer annealing sequences, a unique molecular identifier sequence, and capture sequences. Generally, the primers are specific for (i.e. complementary to or comprising a sequence complementary to) a target sequence of a viral, host or synthetic nucleic acid molecule.

FIG. 4-FIG. 21 further demonstrate and/or exemplify the methods and compositions disclosed herein, and the advantages of their use and/or application. FIG. 4 exemplifies the SwabSeq Diagnostic Testing Platform for COVID19. In (A) the workflow for Swab Seq is a five-step process that takes approximately 12 hours from start to finish. In (B) each well, perform RT-PCR on clinical samples is performed. Each well has two sets of indexed primers that generate cDNA and amplicons for SARS-COV-2 S2 gene and the human RPP30 gene. Each primer is synthesized with the P5 and P7 adaptors for Illumina sequencing, a unique i7 and i5 molecular barcodes, and the unique primer pair. Importantly, every well has a synthetic in vitro S2 standard that is key to allowing the method to work at scale. In (C) the in vitro S2 standard (abbreviated as S2-Spike) differs from the virus S2 gene by 6 base pairs that are complemented (underlined). In (D) read count at various viral concentrations. In (E) ratiometric normalization allow for in-well normalization for each amplicon. In (F) every well has two internal well controls for amplification, the in vitro S2 standard and the human RPP30. The RPP30 amplicon serves as a control for specimen collection. The in vitro S2 standard is critical to SwabSeq's ability to distinguish true negatives.

FIG. 5 shows that validation in clinical specimens demonstrate a limit of detection equivalent to sensitive RT-qPCR reactions. In (A) Limit of Detection (LOD) in nasal swab samples with no SARS-COV2 were pooled and ATCC inactivated virus was added at different concentrations. Nasal Swab sample was RNA purified and using SwabSeq showed a limit of detection of 250 genome copy equivalents (GCE) per mL. In (B) RNA-purified clinical nasal swab specimens obtained through the UCLA Health Clinical Microbiology Laboratory were tested based on clinical protocols using FDA authorized platforms and then also tested using SwabSeq. 100% agreement with samples that tested positive for SARS-COV-2 (n=31) and negative for SARS-COV-2 (n=35) is shown. In (C) tested RNA purified samples from extraction-free nasopharyngeal swab were tested and showed a limit of detection of 558 GCE/mL and in (D) clinical samples, 100% agreement between tests run in the UCLA Health Clinical Microbiology Laboratory is shown, negative (n=20) and positive (n=20). In (E) extraction free processing of saliva specimens show a limit or detection down to 1000 GCE per mL.

Figure 6:
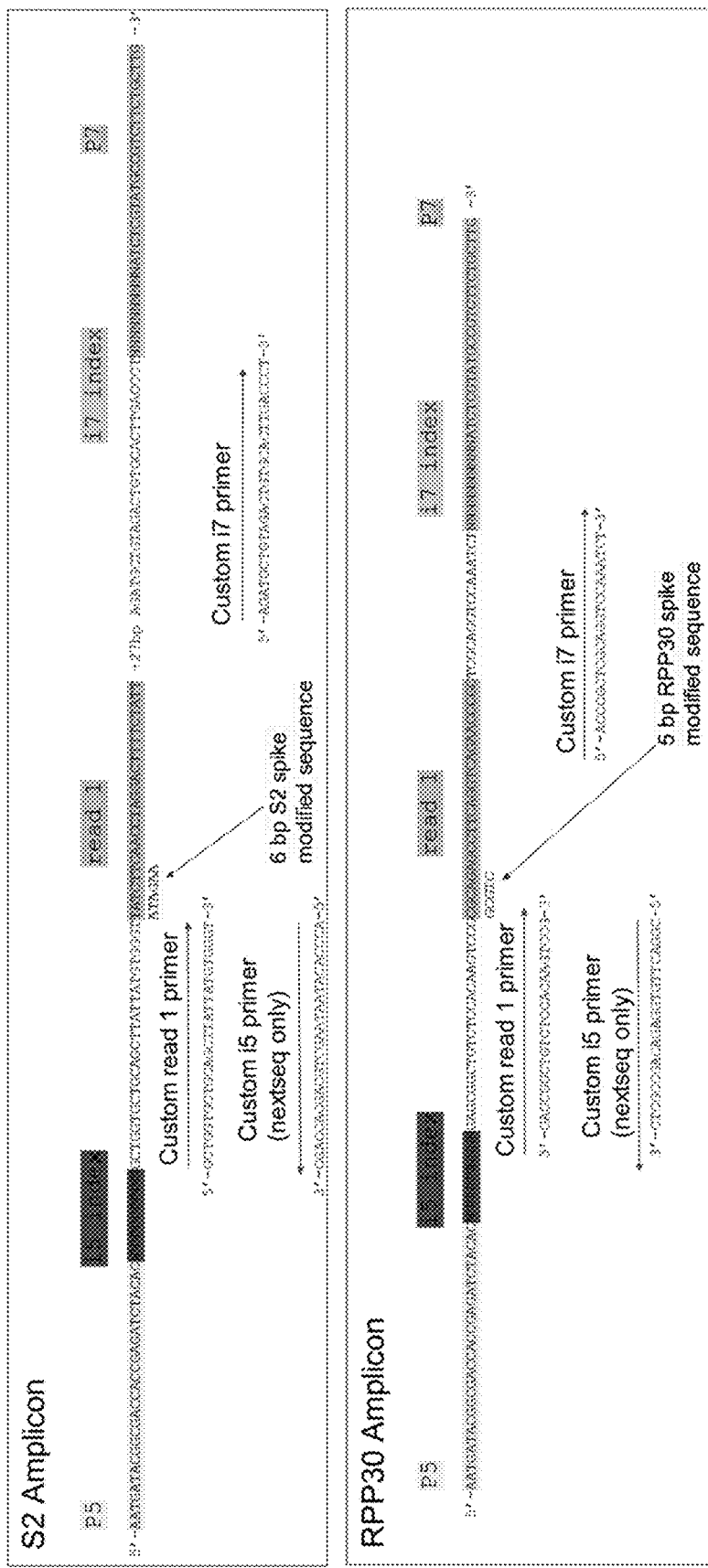
FIG. 6 shows a sequencing library design.
Figure 7:
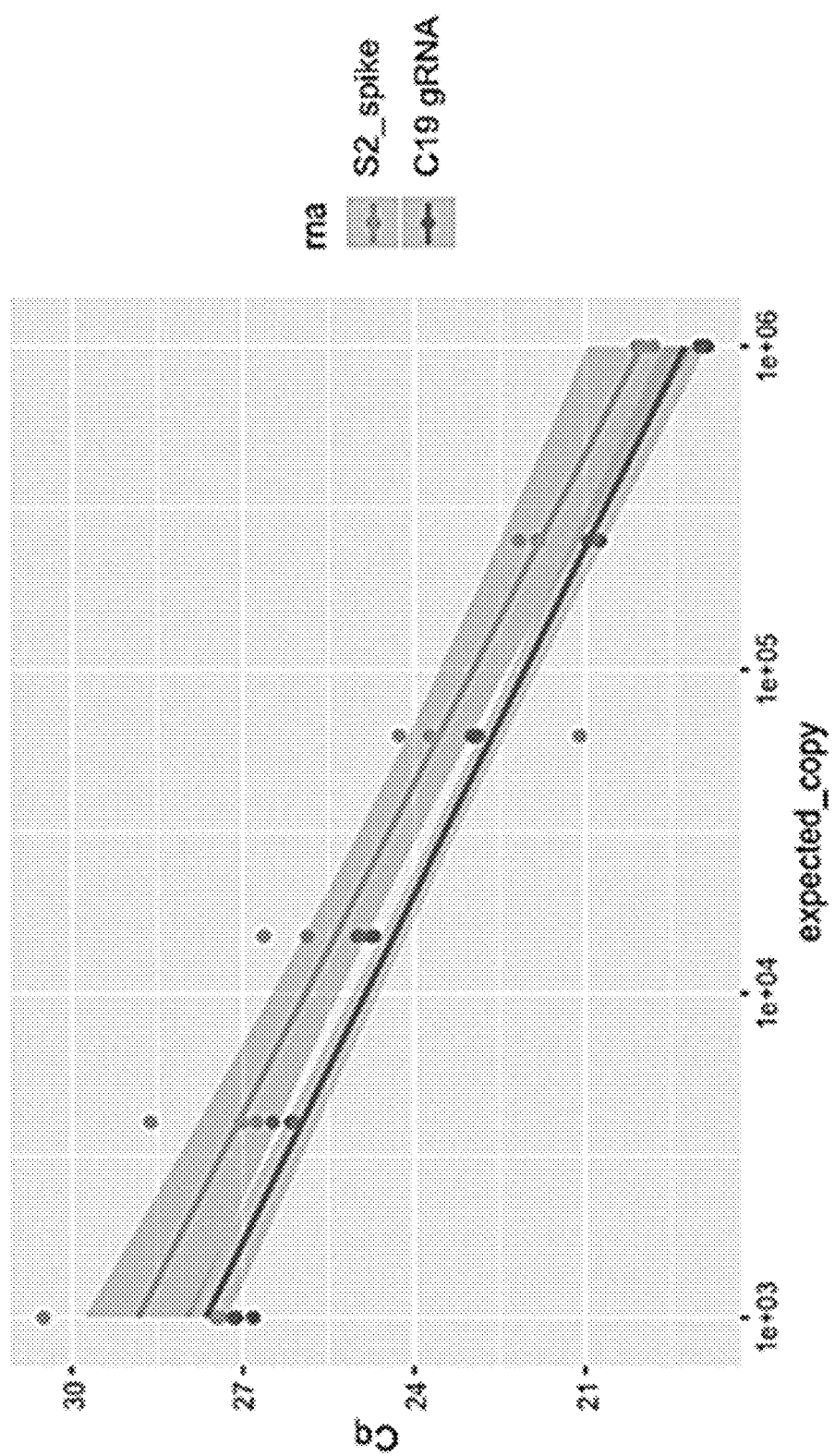
FIG. 7 shows that S2 primers show equivalent PCR efficiency when amplifying the COVID-19 amplicon and the synthetic S2 spike.

FIG. 6 shows sequencing library design. The amplicon designs are shown for the S2 (top) and RPP30 (bottom) amplicons. Amplicons were designed such that the i5 and i7 molecular indexes uniquely identify each sample. SwabSeq was designed to be compatible with all Illumina platforms. FIG. 7 shows that S2 primers show equivalent PCR efficiency when amplifying the COVID-19 amplicon and the synthetic S2 spike. Slope of PCR efficiency of the primers with either the S2_spike or the SARS-COV-2 viral (labeled in green as C19gRNA) input are as follows: S2_spike slope=−6.68e-6 and C19gRNA(Twist Control) slope=−6.74e-6. The slopes are expected to equivalent (parallel) if the primers do not show preferential amplification of the S2 spike RNA versus the C19gRNA. This shows that the S2 spike and C19gRNA have equivalent amplification efficiencies using the S2 primer pair. The bands represent 95% confidence intervals for predicted values, are non-overlapping due to different intercepts, and are not relevant for this analysis of slopes.

Figure 8:
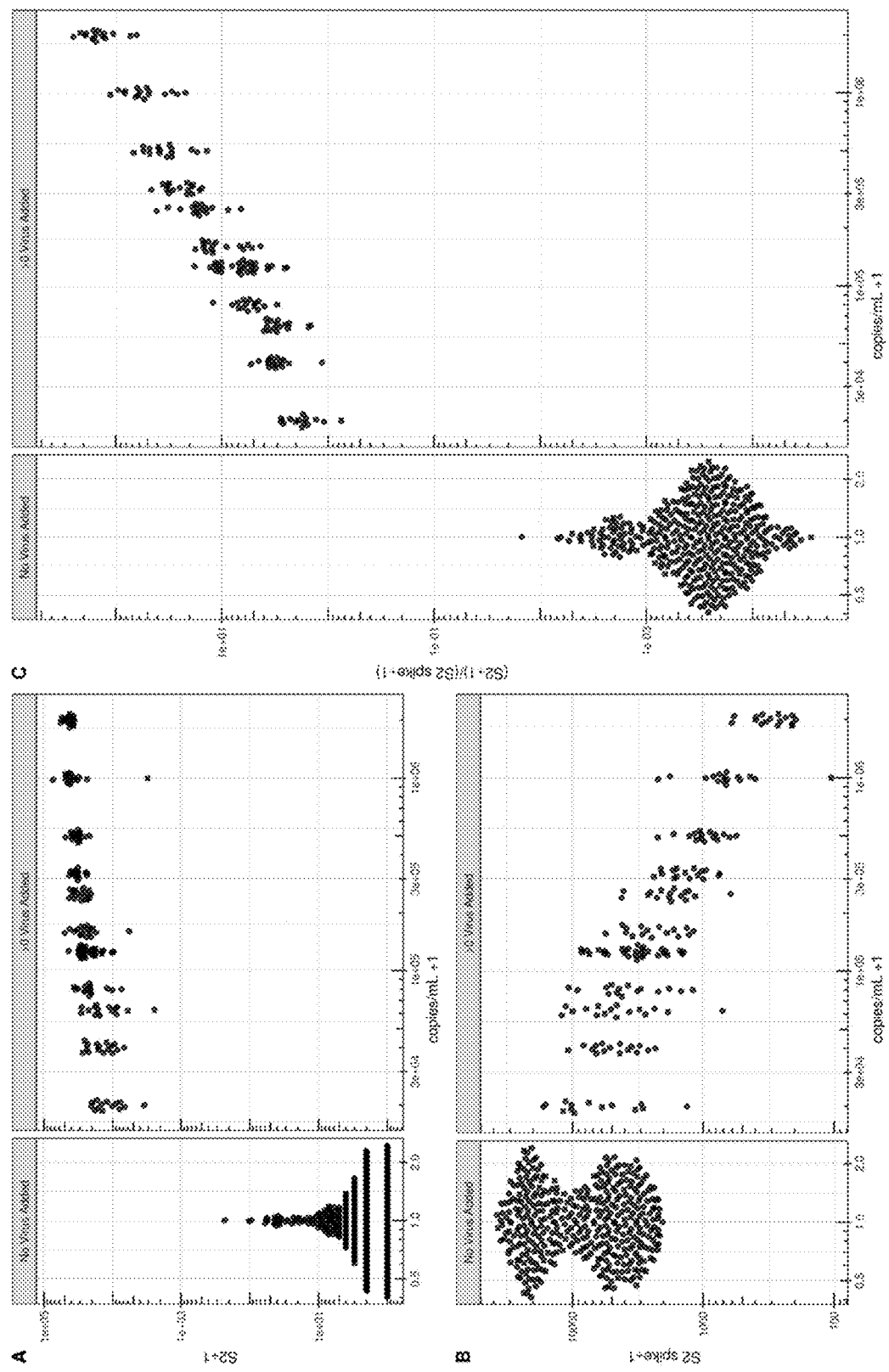
FIG. 8 shows that at very high viral concentrations SwabSeq maintains linearity.

FIG. 8 shows that at very high viral concentrations SwabSeq maintains linearity. An internal well control is included, the S2 Spike, to enable calling negative samples, even in the presence of heterogeneous sample types and PCR inhibition. In (A) as virus concentration increases, increased reads attributed to S2 are observed and, in (B), decreased reads attributed to the S2 Spike. In (C), The ratio between the S2 and S2 Spike provides an additional level of ratiometric normalization and exhibits linearity up to at least 2 million copies/mL of lysate. Note that ticks on both axes are spaced on a log 10 scale.

Figure 9:
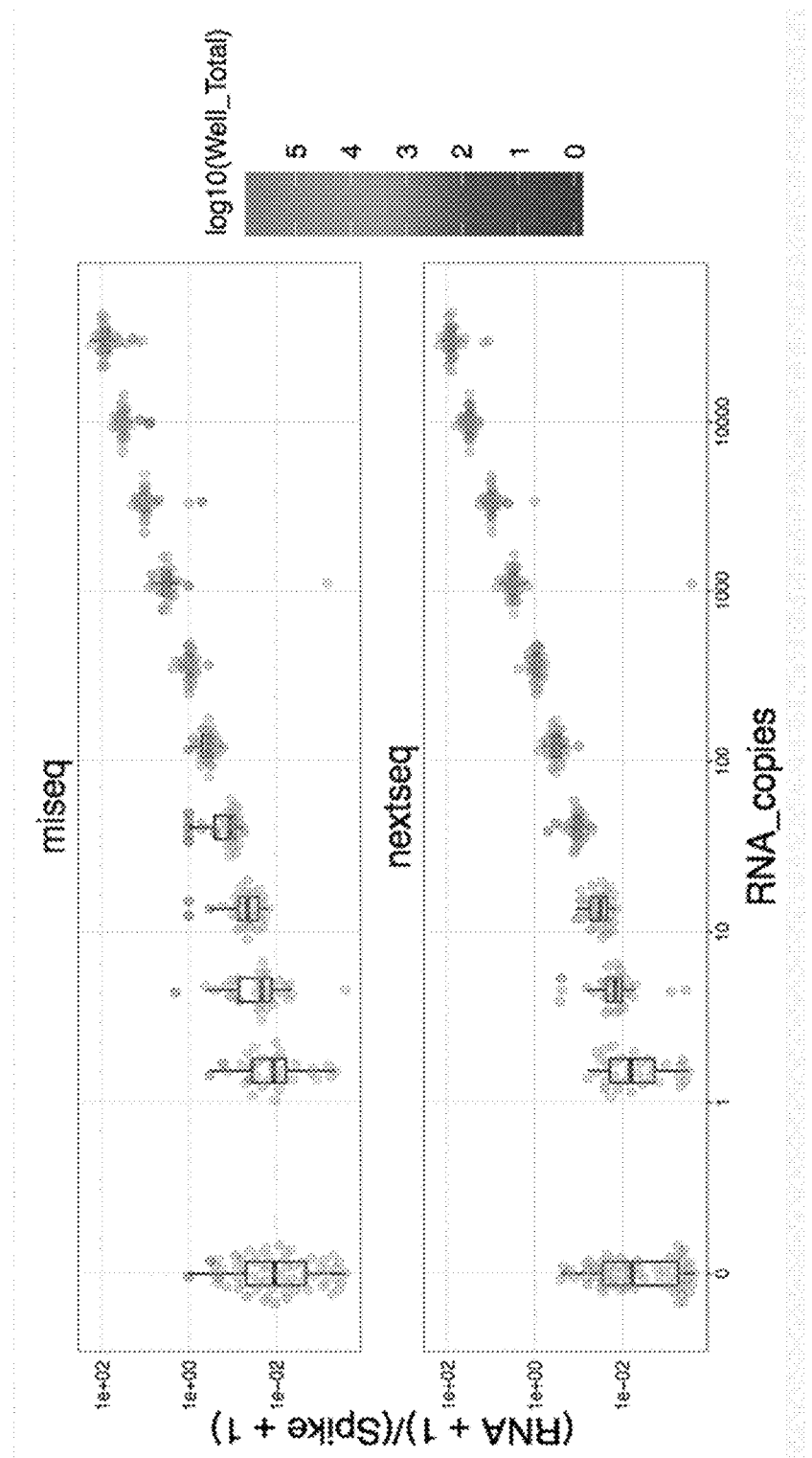
FIG. 9 shows sequencing performed on MiSeq or NextSeq Machine exhibits similar sensitivity.
Figure 10:
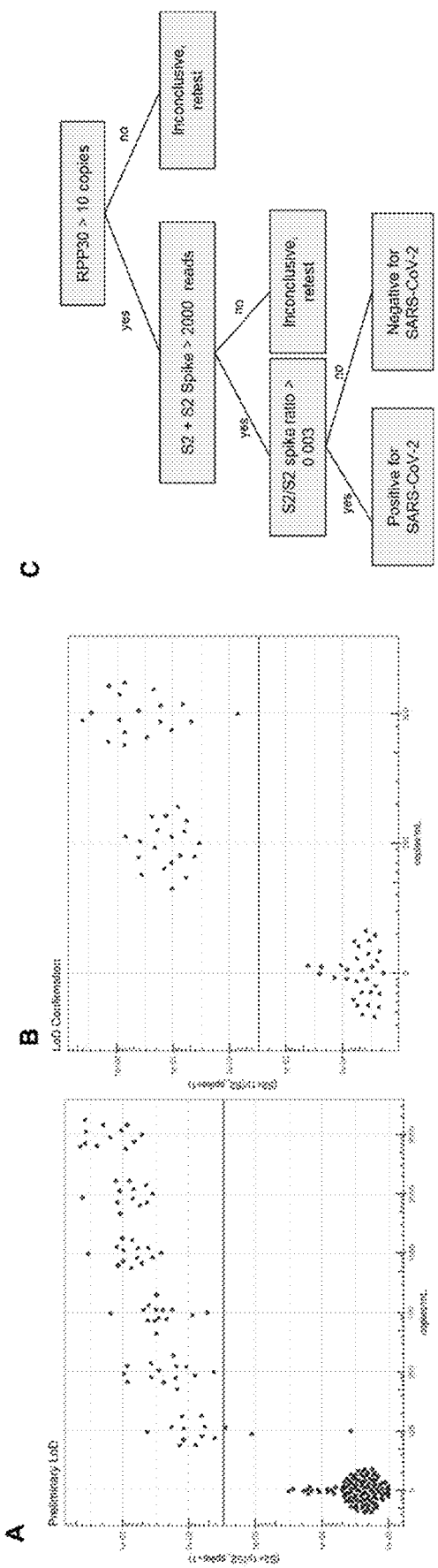
FIG. 10 show preliminary and Confirmatory Limit of Detection Data for RNA purified Samples using the NextSeq550.

FIG. 9 shows sequencing performed on MiSeq or NextSeq Machine exhibits similar sensitivity. Multiplexed libraries run on both MiSeq and NextSeq showed linearity across a wide range of SARS-COV2 virus copies in a purified RNA background. FIG. 10 shows preliminary and Confirmatory Limit of Detection Data for RNA purified Samples using the NextSeq550. In (A) the preliminary LOD data identified a LOD of 250 copies/mL, and in (B), confirmatory studies showed an LOD of 250 copies/mL. In (C) exemplary result interpretation guidelines are shown for purified RNA.

Figure 11:
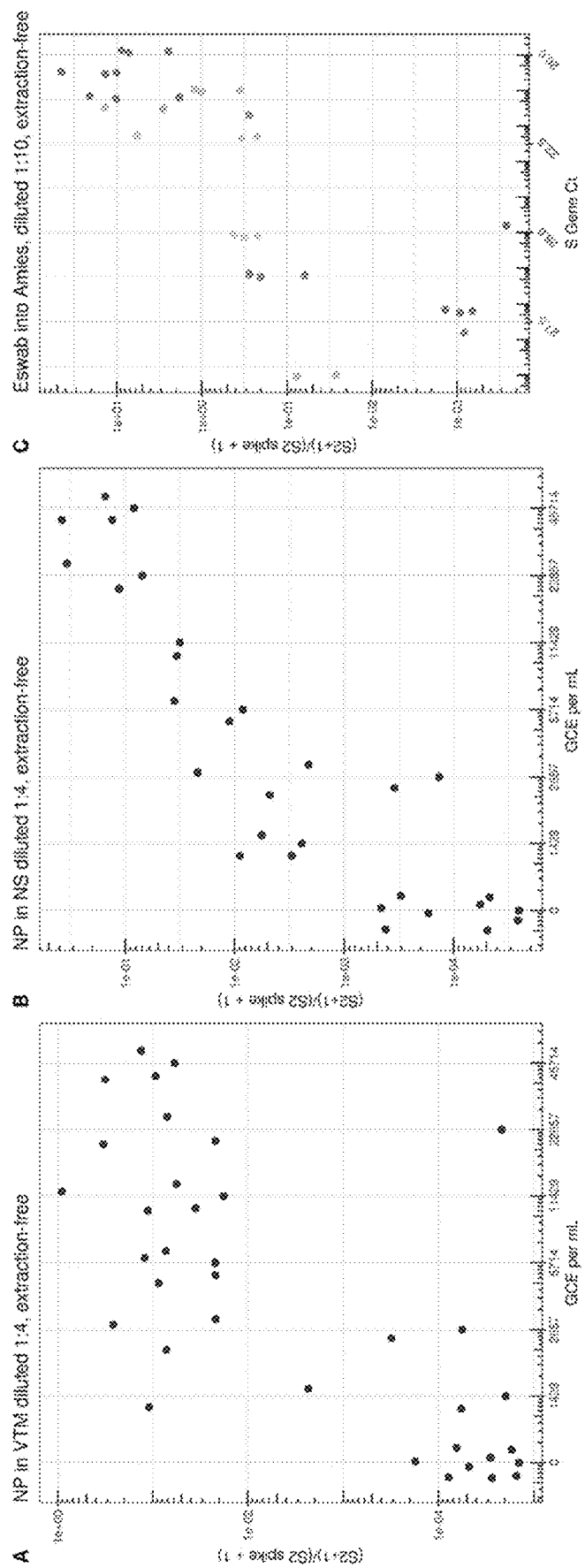
FIG. 11 shows extraction-Free protocols into traditional collection medias and buffers require dilution to overcome effects of RT and PCR inhibition.

FIG. 11 shows extraction-Free protocols into traditional collection medias and buffers require dilution to overcome effects of RT and PCR inhibition. In (A) tested extraction free protocols for nasopharyngeal (NP) swabs that were placed into viral transport media (VTM). ATCC live inactivated virus were spiked at varying concentrations into pooled VTM and then diluted samples 1:4 with water before adding to the RT-PCR reaction. Limit of detection of 5714 copies per mL was observed. In (B) tested nasopharyngeal (NP) swabs that were collected in normal saline (NS), pooled and then spiked with ATCC live inactivated virus at varying concentrations. Contrived samples were diluted 1:4 in water. Here, the early studies show a similar limit of detection between 2857 and 5714 copies per mL. In (C) tested natural clinical samples that were collected into Amies Buffer (ESwab). S gene Ct count (x-axis) from positive samples were compared to the SwabSeq S2 to S2 spike ratio (y-axis). Samples were run in triplicate (colors). High concordance for Ct counts of 27 and lower but more variability for Ct counts greater than 27 was observed suggesting that RT and PCR inhibition were affecting the limit of detection.

Figure 12:
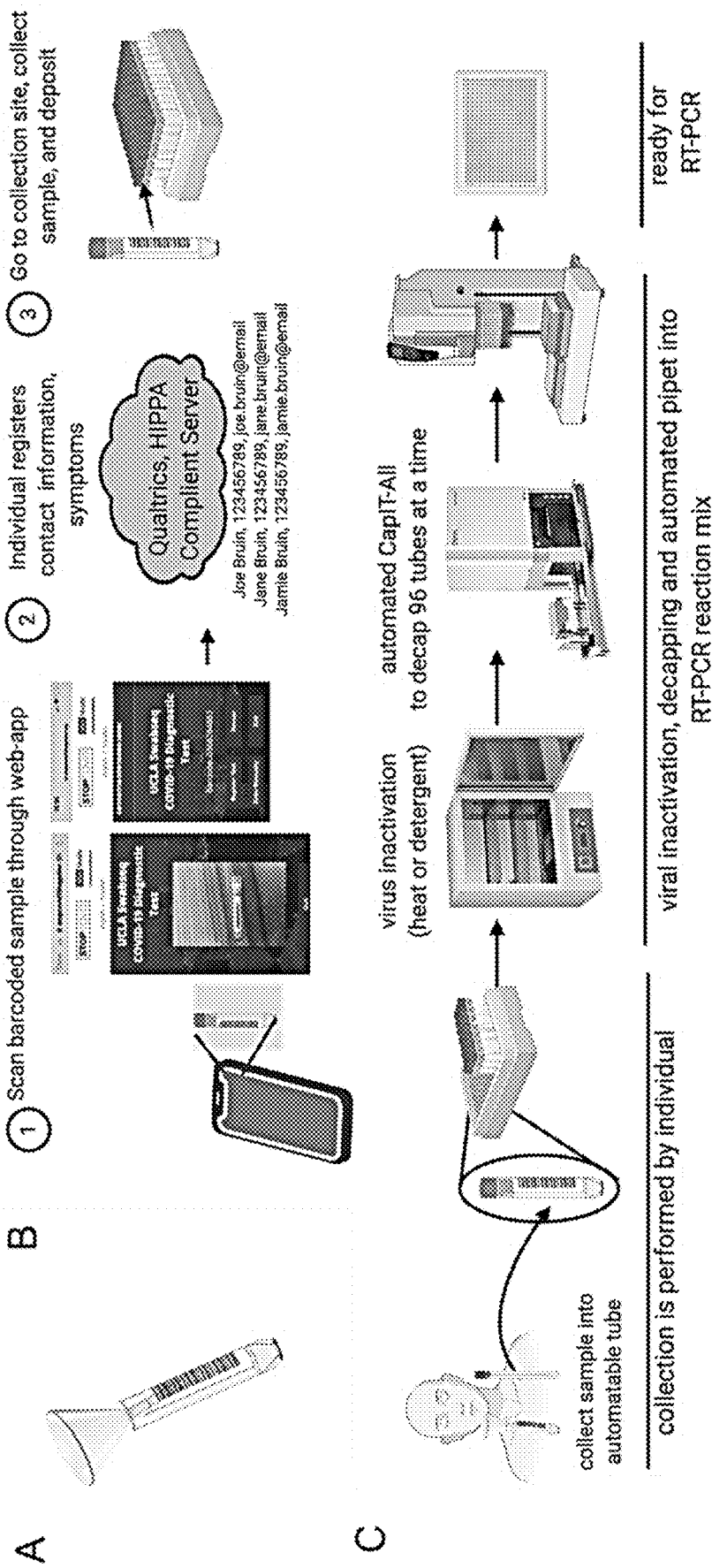
FIG. 12 shows exemplary development of a lightweight sample accessioning, collection and processing system to allow for scalable testing into the thousands of samples per day.

FIG. 12 shows developing a lightweight sample accessioning, collection and processing to allow for scalable testing into the thousands of samples per day. In (A) to address the challenge of sample collection, lightweight collection methods were developed that collect sample directly into an automatable tube. Here a funnel is used for an individual to deposit a small sample of saliva (0.25 mL into the funnel and tube). This setup can accommodate multiple sample types. In (B) to facilitate the sample accessioning and collection, a web-based app was developed for individuals to register their sample tube using a barcode reader and send their identifying information into a secure instance of Qualtrics. Individuals then collect their sample and then place the tube in the rack. This low-touch preanalytic process allows for thousands of samples a day without heavy administrative burden. In (C) The overall workflow streamlines processing in the lab. First, individuals collect samples into an automatable tube and place them into a 96-tube rack. Samples arrive in the lab in a 96-rack format allowing for efficient inactivation and processing of the samples, drastically increasing the flow of samples through the platform.

Figure 13:
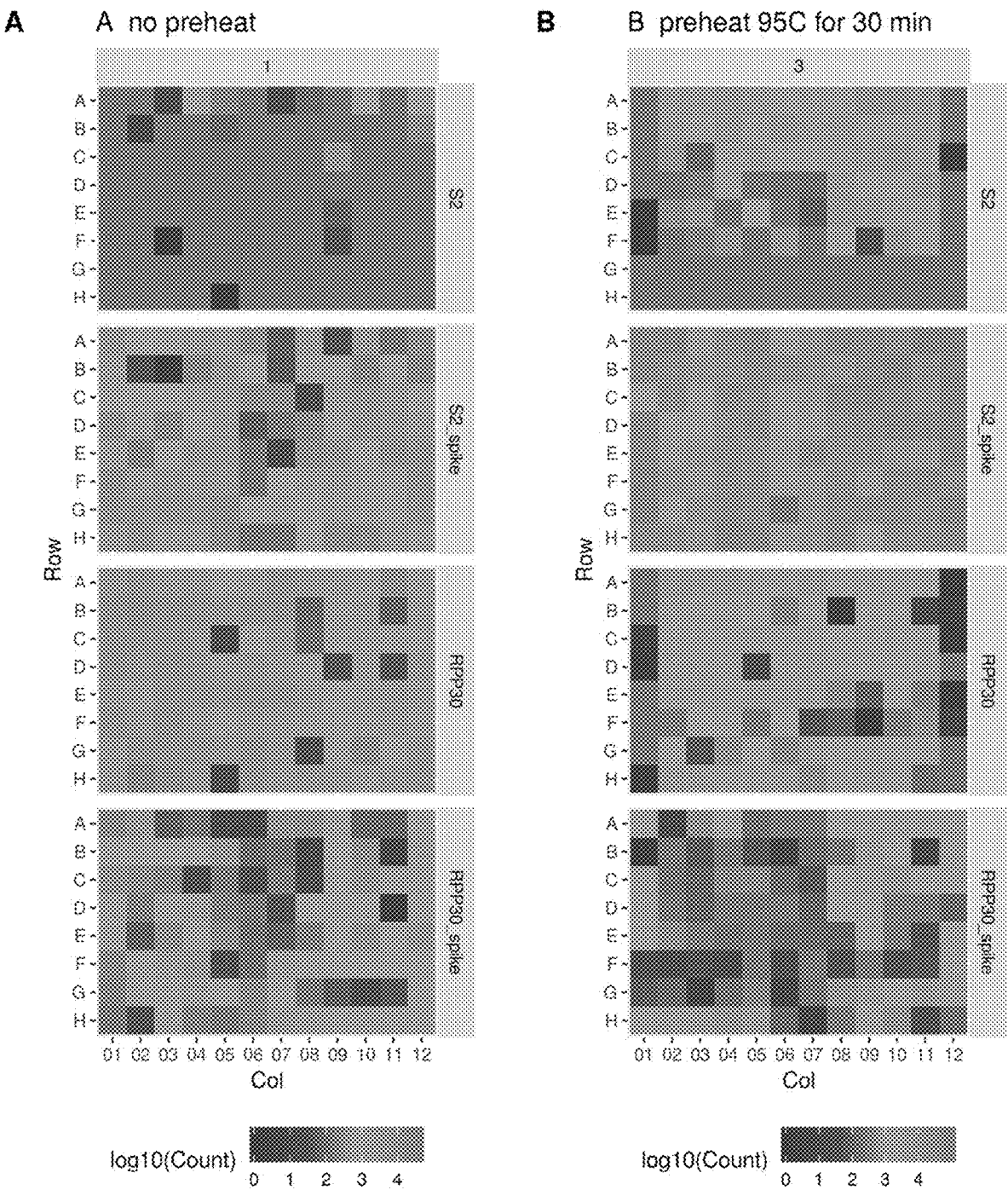
FIG. 13 show that preheating Saliva to 95C for 30 minutes improves RT-PCR.
Figure 14:
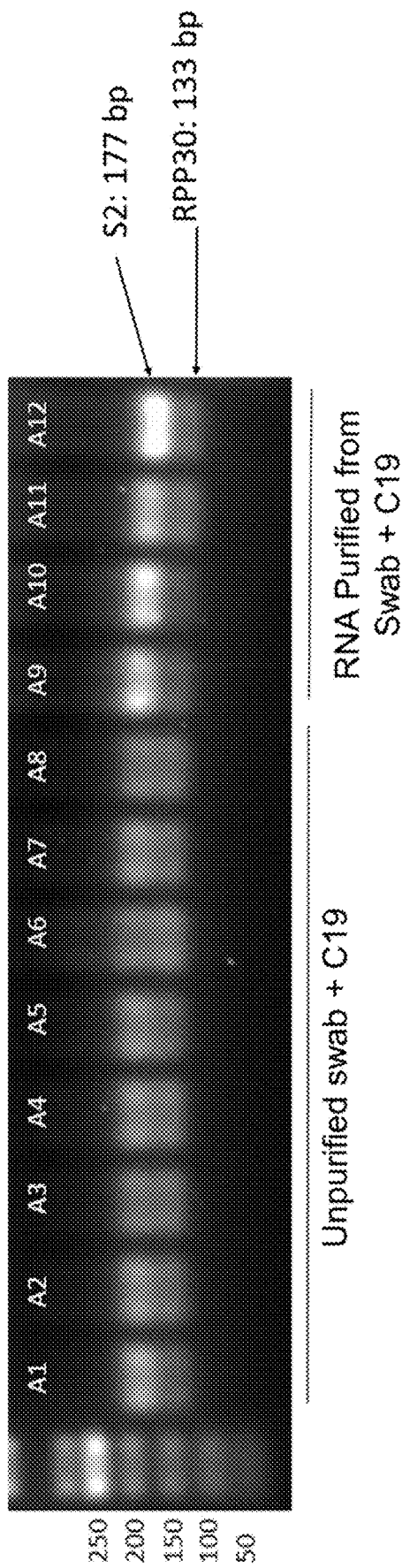
FIG. 14 shows that PCR inhibition has significant effect on amplification products.
Figure 15:
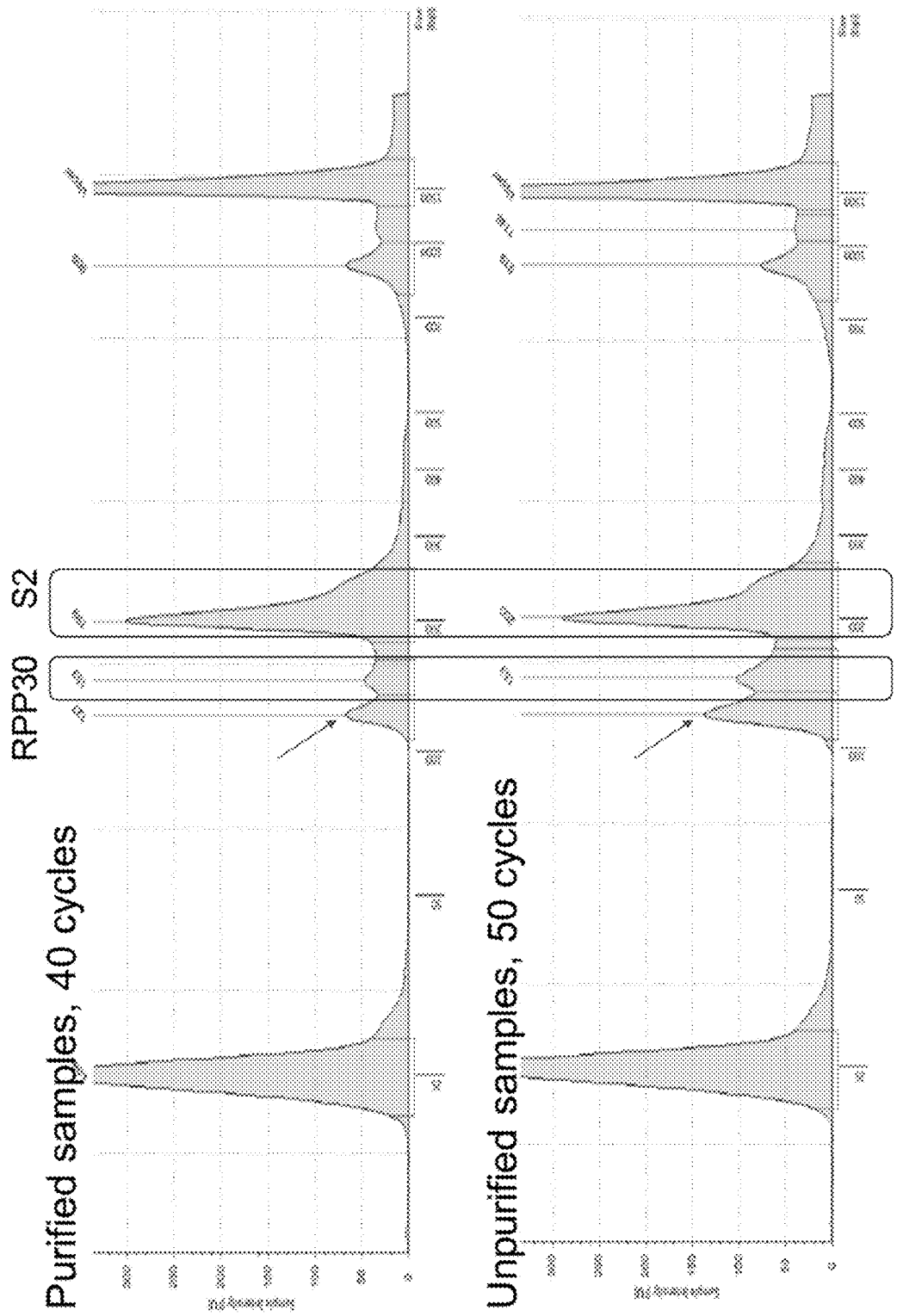
FIG. 15 shows that tapestation increasing the number of PCR cycles and working with unpurified or inhibitory samples types (e.g. Saliva) was seen to increase the size of a nonspecific peak in the library preparation.

FIG. 13 show that preheating Saliva to 95° C. for 30 minutes drastically improves RT-PCR. Detection of viral genome and shows improved robustness in detection of the controls. In (A) Without preheating, detection of S2 spike is minimal and there are lower counts for the control amplicons. In (B) with a 95° C. preheating step for 30 minutes, robust detection of the S2 amplicon and synthetic S2 Spike was observed. FIG. 14 shows that PCR inhibition has a significant effect on amplification products 2% Agarose gene was run for a subset of wells from the Rt-PCR reactions. RT-PCR inhibition from swabs in unpurified lysate (A1-A8) as compared to purified RNA (A9-A12) was observed. Two bands were observed in this subset of wells representing 2 amplicons for the S2 or S2 spike (177 bp) and RPP30 (133 bp) primer pairs. FIG. 15 shows that tapestation increasing the number of PCR cycles and working with unpurified or inhibitory samples types (e.g. Saliva) was seen to increase the size of a nonspecific peak in the library preparation. Representative result from Agilent TapeStation for the purified amplicon libraries. It was observed that a nonspecific peak slightly above 100 bp (arrow) in both library traces, but this peak increases in size with unpurified samples and an increased number of PCR cycles. Importantly, it was observed that that an increase in the size of this nonspecific peak leads to inaccurate library quantification. Therefore, in order to optimize cluster density on Illumina sequencers, it is suggested that quantifying the loading concentration of the final library based on the proportion of the desired peaks (RPP30 and S2).

Figure 16:
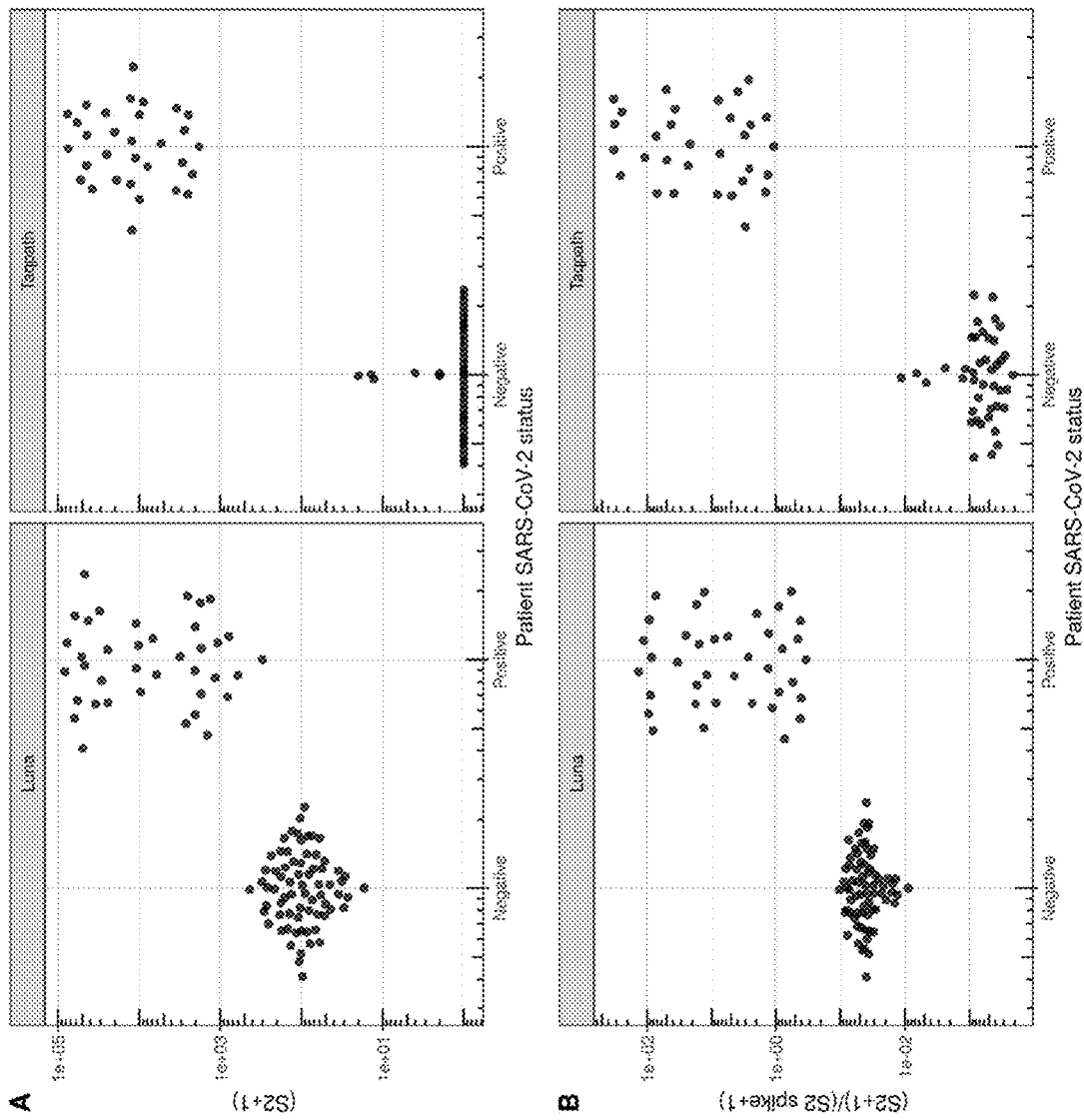
FIG. 16 shows that TaqPath™ decreases the number of S2 reads in SARS-COV2-negative samples relative to NEB Luna®.

FIG. 16 shows that TaqPath™ decreases the number of S2 reads in SARS-COV2-negative samples relative to NEB Luna®. In (A) and (B) Luna® One Step RT-PCR Mix (New England Biosciences) to TaqPath™ 1-Step RT-qPCR Master Mix (Thermofisher Scientific) was compared. It is likely that the presence of UNG in the TaqPath™ Mastermix significantly reduced the number of S2 reads in the SARS-COV-2-negative samples allowing a more accurate diagnosis of SARS-COV-2-positive and SARS-COV-2-negative samples.

Figure 17:
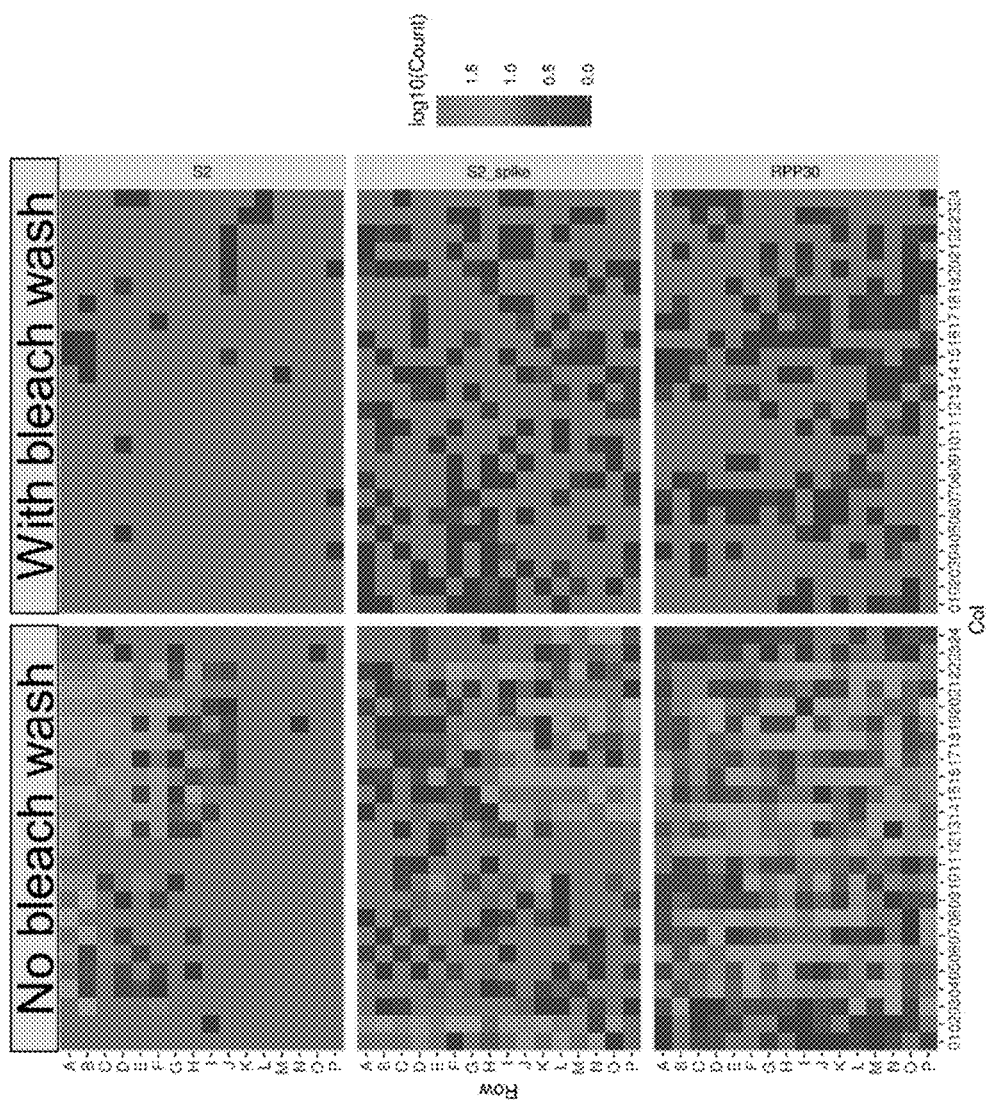
FIG. 17 shows carryover contamination from template line in a MiSeq contributes to cross contamination.
Figure 18:
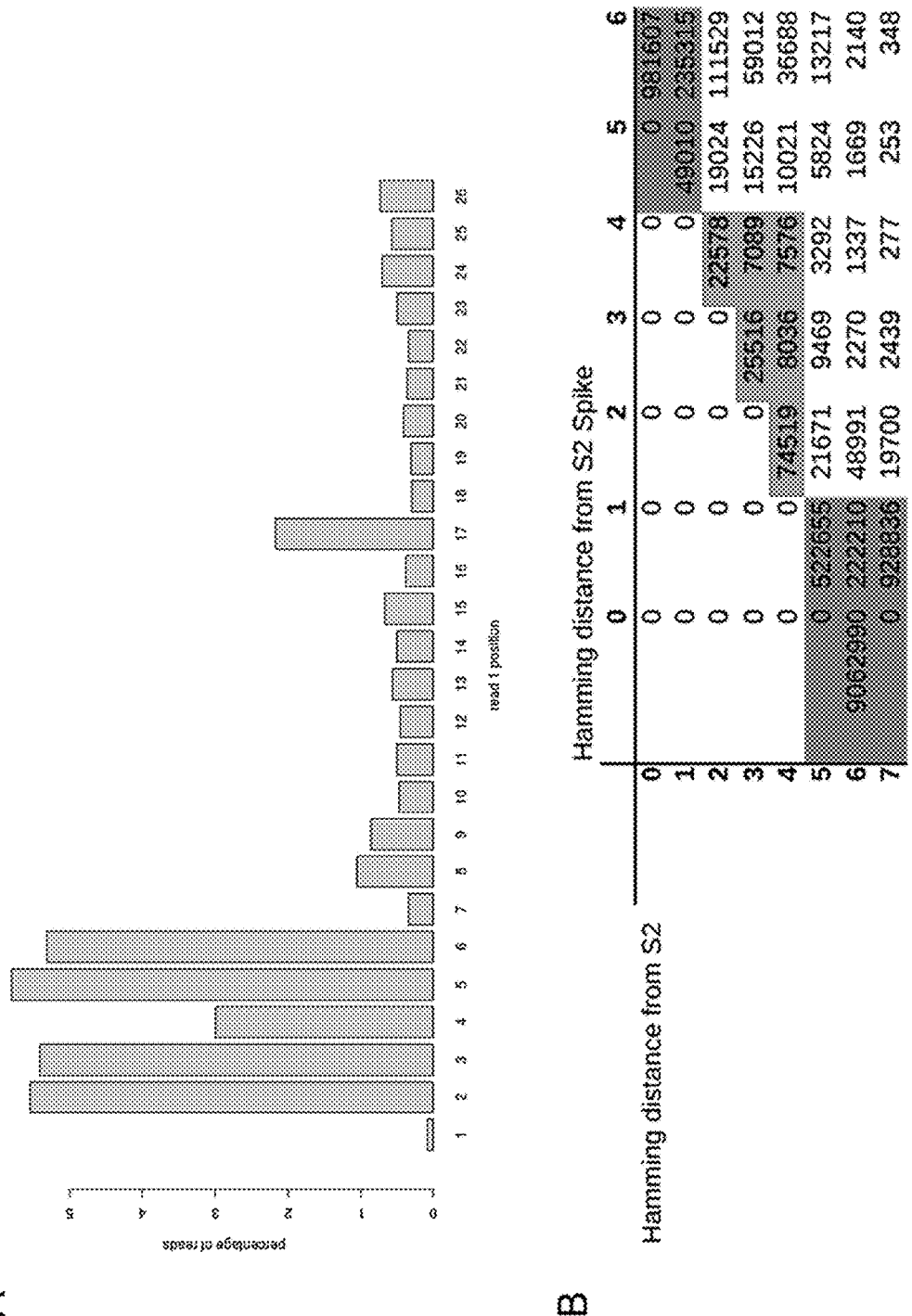
FIG. 18 shows sequencing errors in amplicon read and potential amplicon mis-assignment.

FIG. 17 shows carryover contamination from template line in a MiSeq contributes to cross contamination. In this experiment RT-PCR was performed on four 384-well plates but only pooled three plates. On the left are observed counts of each of the amplicons for each sample for the 384-well plate not included in the run (but for which the indices were used in the previous run). Amplicon reads for indices used in the previous run are present at a low level (0-150 reads). A bleach wash in addition to regular wash was performed prior to the subsequent run. In this subsequent run, three different plates were pooled and left out the fourth 384 well plate. On the right are observed counts of each of the amplicons for sample indices corresponding to the left-out plate (again, for which the indices were used in the previous run). A remarkable decrease in the amount of carryover contamination was observed, where carryover reads are <10 per sample. Alternatively, in some embodiments, in order to reduce contamination and confounding of results therefrom, different combinations of reverse and forward primers are used on subsequent runs on the same instrument. Rotating the primers on the sequences allows for a determination to be made if the reads are true reads from samples or crossover contamination from a previous run. FIG. 18 shows sequencing errors in amplicon read and potential amplicon mis-assignment. In experiment v18 less PhiX was loaded than usual (11%) and the overall quality of reads was lower. Trends noticed here persist in other runs but this run more clearly highlights issues that can occur due to sequencing errors and overly tolerant error-correction. In (A) The percentage of reads with base quality scores less than 12 for each position in read 1. Note that the first 6 bases of read1 distinguish S2 from S2 spike and have the highest percentage of low-quality base calls. In (B) The hamming distance between each read1 sequence and either the expected S2 sequence (rows) or S2 spike sequence (columns), In yellow are perfect match and edit distance 1 sequences that can be clearly identified as S2 or S2 spike. In red are sequences with errors that may be mis-assigned (S2 spike assigned as S2 is most problematic for this assay.)

Figure 19:
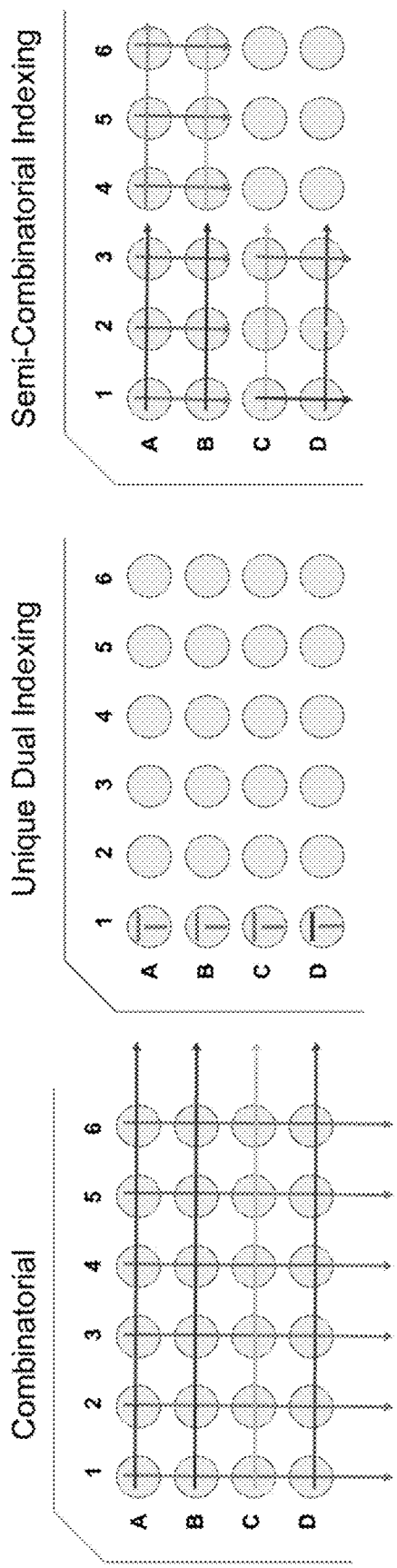
FIG. 19 shows a visualization of different indexing strategies.

FIG. 19 shows visualization of different indexing strategies. Here i5 indices are depicted as horizontal lines, i7 indices are depicted as vertical lines, and colors represent unique indices. In combinatorial (or fully-combinatorial) indexing, the i5 and i7 indices are combined to make unique combinations, but each i5 and i7 index may be used multiple times within a plate, and all possible i5 and i7. For unique dual indexing, each i5 and i7 index are only used 1 time per plate. This requires many more oligos to be synthesized. For Semi-combinatorial indexing, the combinations used are more limited, such that indices are only repeated for a subset of wells and many possible combinations are not used. In practice (not depicted here), a design where the i7 index is unique but the i5 index can be repeated up to four times across a 384-well plate was used. For the majority of the Swabseq development, either semi-combinatorial indexing (384×96) that allowed for 1536 combinations or samples to be run or unique dual indexing (384 UDI) was used.

Figure 20:
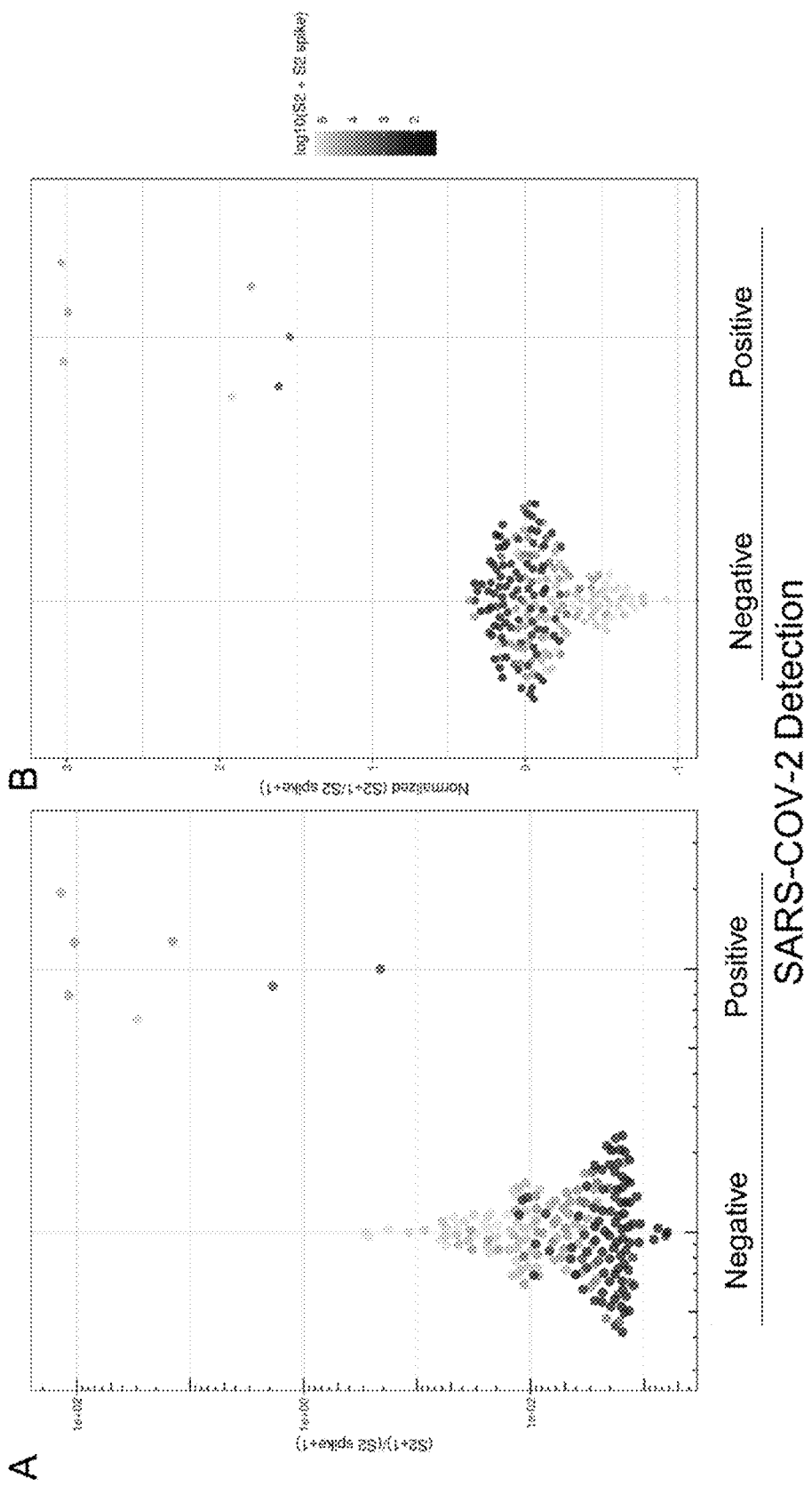
FIG. 20 shows computational correction for index mis-assignment using a mixed-model.

FIG. 20 shows computational correction for index mis-assignment using a mixed-model. To expand the number of samples capable of testing, a combinatorial indexing strategy can be used. In this experiment a single index on i5 was used to uniquely identify a plate and 96 i7 indices to identify wells. In (A) the ratio of S2 to S2 spike (y-axis) is plotted for clinical samples based on whether Covid was detected by RT-qPCR (x-axis). SARS-COV-2 positive samples were filtered to have Ct<32. The effects of index mis-assignment across plates can be observed as i7 indices that have high a sum of S2 and S2 spike across all samples that share the same i7 barcode across plates (colors). In (B) best linear unbiased predictor residuals are plotted (y-axis) for data in A, after computational correction of the log 10(S2+1/ S2_spike+1) ratio by treating the identity of the i7 barcode as a random effect.

Figure 21:
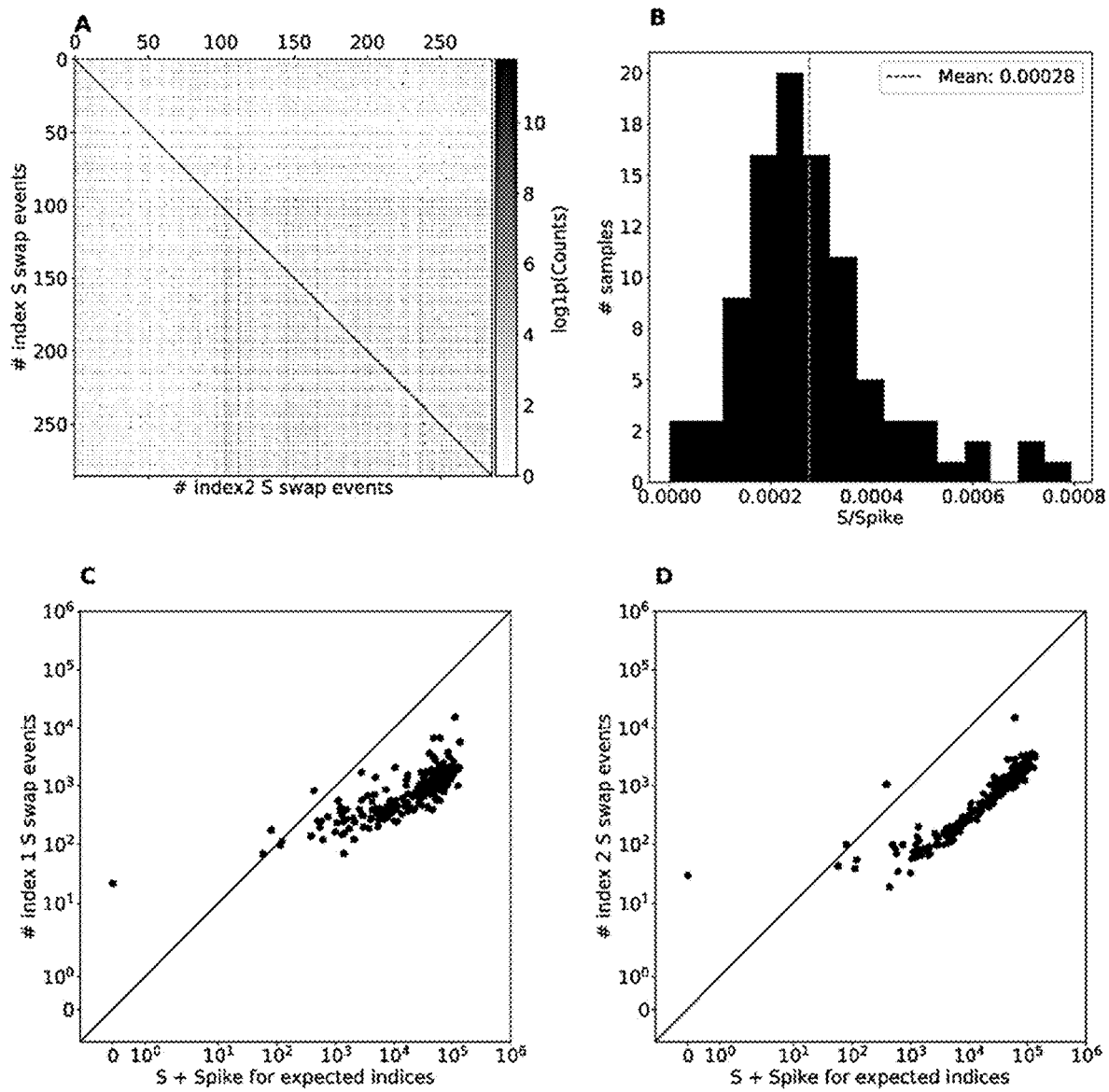
FIG. 21 shows quantifying the role of index mis-assignment as a source of noise in the S2 reads.

FIG. 21 shows quantifying the role of index mis-assignment as a source of noise in the S2 reads. In (A) a matching matrix for the viral S2+S2 spike count for each pair of i5 and i7 index pairs from run v19 that used a unique dual index design. The index pairs along the diagonal correspond to expected index pairs for samples present in the experiment (expected matching indices) and the index pairs off of the diagonal correspond to index mis-assignment events. In (B) the distribution of ratios of viral S counts to Spike counts for samples with known zero amount of viral RNA. The mean ratio is 0.00028. In (C) the number of i7 mis-assignment events vs the number of viral S2+S2 Spike counts for each sample. In (D) the number of i5 mis-assignment events vs the number of viral S2+S2 Spike counts for each sample.

Barcodes

Variable nucleotide sequences (barcodes) that serve as an index can be included on any of the first or second set of PCR primers described herein. Additionally, barcodes may be added in a separate library preparation reaction. The variable nucleotide sequences described herein can be used as a sample index in order to deconvolve results obtained from a sequencing reaction used herein.

Once the contents of the cells are released into their respective partitions by a lysis agent, the macromolecular components (e.g., macromolecular constituents of samples, such as RNA, DNA, or proteins) contained therein may be further processed within the partitions. In accordance with the methods and systems described herein, the macromolecular component contents of individual samples can be provided with unique identifiers such that, upon characterization of those macromolecular components they may be attributed as having been derived from the same sample or particles. The ability to attribute characteristics to individual samples or groups of samples is provided by the assignment of unique identifiers specifically to an individual sample or groups of samples. Unique identifiers, e.g., in the form of nucleic acid barcodes can be assigned or associated with individual samples or populations of samples, in order to tag or label the sample's macromolecular components (and as a result, its characteristics) with the unique identifiers. These unique identifiers can then be used to attribute the sample's components and characteristics to an individual sample or group of samples.

In some aspects, this is performed by co-partitioning the individual sample or groups of samples with the unique identifiers or barcodes comprising an unique molecular identifier sequence (UMI). In some aspects, the unique identifiers are provided in the form of nucleic acid molecules (e.g., oligonucleotides) that comprise nucleic acid barcode sequences that may be attached to or otherwise associated with the nucleic acid contents of individual sample, or to other components of the sample, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some embodiments, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some embodiments, the length of a barcode sequence may be about 6, 7, 8, 9, 10, 11, 12, 13, 14, 15, 16, 17, 18, 19, 20 nucleotides or longer. In some embodiments, the length of a barcode sequence may be at least about 6, 7, 8, 9, 10, 11, 12, 13, 14, 15, 16, 17, 18, 19, 20 nucleotides or longer. In some embodiments, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some embodiments, separated barcode subsequences can be from about 4 to about 16 nucleotides in length. In some embodiments, the barcode subsequence may be about 4, 5, 6, 7, 8, 9, 10, 11, 12, 13, 14, 15, 16 nucleotides or longer. In some embodiments, the barcode subsequence may be at least about 4, 5, 6, 7, 8, 9, 10, 11, 12, 13, 14, 15, 16 nucleotides or longer. In some embodiments, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned samples. These sequences include, e.g., targeted or random/universal amplification primer sequences for amplifying the genomic DNA from the individual samples within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more partitions, where one partition contains oligonucleotides, or microdispensing of oligonucleotides into partitions, e.g., partitions within microfluidic systems. In some embodiments, a primer comprises a barcode oligonucleotide. In some embodiments the primer sequence is a targeted primer sequence complementary to a sequence in the template nucleic acid molecule. In some embodiments, the first nucleic acid molecule further comprises one or more functional sequences and wherein the second nucleic acid molecule comprises the one or more functional sequences. In some embodiments, the one or more functional sequences are selected from the group consisting of an adapter sequence, an additional primer sequence, a primer annealing sequence, a sequencing primer sequence, a sequence configured to attach to a flow cell of a sequencer, and a unique molecular identifier sequence.

For example, the above described barcoded nucleic acid molecules (e.g., barcoded oligonucleotides) are added to a sample. In some embodiments, a partition comprises barcoded oligonucleotides having the same barcode sequence. In some embodiments, a partition among a plurality of partitions comprises barcoded oligonucleotides having an identical barcode sequence, wherein each partition among within the plurality of partitions comprises a unique barcode sequence. In some embodiments, the population of barcoded oligonucleotides provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each barcoded oligonucleotide can be provided with large numbers of nucleic acid (e.g., oligonucleotide) molecules attached. In particular, the number of molecules of nucleic acid molecules including the barcode sequence on an individual barcoded oligonucleotide can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some embodiments at least about 1 billion nucleic acid molecules, or more. Nucleic acid molecules of a given barcoded oligonucleotide can include identical (or common) barcode sequences, different barcode sequences, or a combination of both. Nucleic acid molecules of a given barcoded oligonucleotide can include multiple sets of nucleic acid molecules. Nucleic acid molecules of a given set can include identical barcode sequences. The identical barcode sequences can be different from barcode sequences of nucleic acid molecules of another set Moreover, when the population of barcoded oligonucleotides is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some embodiments at least about 1 billion nucleic acid molecules.

In some embodiments, it may be desirable to incorporate multiple different barcodes within a given partition. For example, in some embodiments, a barcoded oligonucleotide within a partition can comprise (1) a common barcode sequence shared by all barcoded oligonucleotides within the partition and (2) a unique molecular identifier or additional barcode sequence that is different among each barcoded oligonucleotide. The common barcode sequences may provide greater assurance of identification in the subsequent processing, e.g., by providing a stronger address or attribution of the barcodes to a given partition, as a duplicate or independent confirmation of the output from a given partition.

In some embodiments, the barcoded oligonucleotides are attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein.

The nucleic acid molecules (e.g., oligonucleotides) can be releasable from the beads upon the application of a particular stimulus to the beads. In some embodiments, the stimulus may be a photo-stimulus, e.g., through cleavage of a photolabile linkage that releases the nucleic acid molecules. In other embodiments, a thermal stimulus may be used, where elevation of the temperature of the beads environment will result in cleavage of a linkage or other release of the nucleic acid molecules form the beads. In still other embodiments, a chemical stimulus can be used that cleaves a linkage of the nucleic acid molecules to the beads, or otherwise results in release of the nucleic acid molecules from the beads. In one embodiment, such compositions include the polyacrylamide matrices described above for encapsulation of samples, and may be degraded for release of the attached nucleic acid molecules through exposure to a reducing agent, such as DTT.

A support can be contemplated for use in a method of the present disclosure may be, for example, a well, matrix, rod, container, or bead(s). A support may have any useful features and characteristics, such as any useful size, surface chemistry, fluidity, solidity, density, porosity, and composition. In some embodiments, a support is a surface of a well on a plate. In some embodiments, a support may be a bead such as a gel bead. A bead may be solid or semi-solid. Additional details of beads are provided elsewhere herein.

A support (e.g., a bead) may comprise an anchor sequence functionalized thereto (e.g., as described herein). An anchor sequence may be attached to the support via, for example, a disulfide linkage. An anchor sequence may comprise a partial read sequence and/or flow cell functional sequence. Such a sequence may permit sequencing of nucleic acid molecules attached to the sequence by a sequencer (e.g., an Illumina sequencer). Different anchor sequences may be useful for different sequencing applications. An anchor sequence may comprise, for example, a TruSeq or Nextera sequence. An anchor sequence may have any useful characteristics such as any useful length and nucleotide composition. For example, an anchor sequence may comprise 2, 3, 4, 5, 6, 7, 8, 9, 10, 11, 12, 13, 14, 15, 16, 17, 18, 19, 20, or more nucleotides. In some embodiments, an anchor sequence may comprise 15 nucleotides. Nucleotides of an anchor sequence may be naturally occurring or non-naturally occurring (e.g., as described herein). A bead may comprise a plurality of anchor sequences attached thereto. For example, a bead may comprise a plurality of first anchor sequences attached thereto. In some embodiments, a bead may comprise two or more different anchor sequences attached thereto. For example, a bead may comprise both a plurality of first anchor sequences (e.g., Nextera sequences) and a plurality of second anchor sequences (e.g., TruSeq sequences) attached thereto. For a bead comprising two or more different anchor sequences attached thereto, the sequence of each different anchor sequence may be distinguishable from the sequence of each other anchor sequence at an end distal to the bead. For example, the different anchor sequences may comprise one or more nucleotide differences in the 2, 3, 4, 5, 6, 7, 8, 9, 10, or more nucleotides furthest from the bead.

In some embodiments, multiple different barcode molecules (e.g., nucleic acid barcode molecules) may be generated on the same support (e.g., bead). For example, two different barcode molecules may be generated on the same support. Alternatively, three or more different barcode molecules may be generated on the same support. Different barcode molecules attached to the same support may comprise one or more different sequences. For example, different barcode molecules may comprise one or more different barcode sequences, and/or other sequences (e.g., starter sequences). In some embodiments, different barcode molecules attached to the same support may comprise the same barcode sequences. Different barcode molecules attached to the same support may comprise barcode sequences that are the same or different. Similarly, different barcode molecules may comprise unique molecular identifiers (UMIs) that are the same or different.

Next Generation Sequencing

As described in the methods disclosed herein, the sequencing of nucleic acid molecules is used and is useful for the detection and diagnosis of a pathogenic infection. Generally, sequencing refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina, Pacific Biosciences, Oxford Nanopore, or Life Technologies (Ion Torrent). Such devices may provide a plurality of raw genetic data corresponding to the genetic information of a subject (e.g., human), as generated by the device from a sample provided by the subject. In some situations, systems and methods provided herein may be used with proteomic information. Alternatively, or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

Next generation sequencing includes many technologies capable of generating large amounts of sequence information and excluding Sanger sequencing or Maxam-Gilbert sequencing. Generally, next generation sequencing encompasses single molecule real-time sequencing, sequencing-by-synthesis, ion semiconductor sequencing and the like. Exemplary next-generation sequencing machines may comprise the MiniSeq, the iSeq 100, the NextSeq 1000, the NextSeq 2000, the NovaSeq 6000, the NextSeq 550 series and the like from Illumina, Inc; Ion Torrent machines from Thermo Fisher Scientific; or the Sequel systems from Pacific Biosciences.

Next generation sequencing machines used with the method herein can generate at least 1, 5, 10, 15, 25, 50, 75, 100, 200, 300 gigabases of data or more in a 24 hour period from a single machine.

Next generation sequencing machines used with the method herein can generate at least 1, 1, 4, 10, 15, 25, 50, 75, 100, 200, 300, 500, or 1,000 million sequence reads of data or more in a 24 hour period from a single machine.

Also included is a computer program, computing device, or analysis platform/system to receive and analyze sequencing data, and output one or more reports that can be transmitted or accessed electronically via a server, an analysis portal, or by e-mail. The computing device or analysis platform can operate according to the algorithms and methods described herein.

Reaction Mixtures

Also provided herein are reaction mixtures for determining the presence or absence of a viral nucleic acid in a biological sample. In some embodiments, the reaction mixture comprises a synthetic nucleic acid provided herein, at least a portion of said biological sample, and one or more enzyme or reagents sufficient to amplify said viral nucleic acid in said biological sample, if present.

The biological sample may be any of the biological samples provided herein. In some embodiments, the biological sample is a human biological sample. In some embodiments, said biological sample comprises saliva, a cheek swab, a nasopharyngeal swab, or a mid-turbinate swab. In some embodiments, said biological sample comprises saliva or a nasopharyngeal swab. In some embodiments, said biological sample comprises saliva. In some embodiments, said biological sample comprises a nasopharyngeal swab.

The synthetic nucleic acid may be any of the synthetic nucleic acids provided herein. In some embodiments, the synthetic nucleic acid is a SARS-COV-2 synthetic RNA nucleic acid provided herein. In some embodiments, said SARS-COV-2 synthetic RNA nucleic acid is present at a concentration from about 10 copies per reaction mixture to about 500 copies per reaction mixture. In some embodiments, said SARS-COV-2 synthetic RNA nucleic acid is present at a concentration of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, or 500 copies per reaction mixture.

The viral nucleic acid may be any of the viral nucleic acids provided herein. In some embodiments, said viral nucleic acid is an influenza A, influenza B, or a coronavirus nucleic acid. In some embodiments, said coronavirus nucleic acid is a is SARS-COV-2 nucleic acid.

In some embodiments, the enzymes or reagents comprise a reverse transcriptase enzyme, dNTPs, a primer pair specific for said viral nucleotide sequence, a primer pair specific for a sample control nucleotide sequence, a magnesium salt, or combinations thereof.

In some embodiments, the reaction mixture comprises one or more enzymes which can be used to amplify the viral nucleic acid. In some embodiments, the enzyme is a reverse transcriptase. Non-limiting examples of reverse-transcriptase enzymes include Avian Myeloblastosis Virus (AMV) Reverse Transcriptase and Moloney Murine Leukemia Virus (M-MuLV, MMLV), and variants thereof.

In some embodiments, the reaction comprises deoxynucleotide triphosphates (dNTPs). In some embodiments, the kit comprises a mixture of each of the dNTPs necessary for amplification of the viral nucleic acid, as well as any other desired nucleic acids (e.g., dATG, dCTP, dTTP, dGTP).

In some embodiments, the reaction mixture comprises a primer pair specific for the viral nucleotide sequence. The primer pair specific for the viral nucleotide sequence can be any of the primer pairs provided herein. said primer pair specific for said viral nucleotide sequence is specific for an influenza A nucleotide sequence, an influenza B nucleotide sequence and a coronavirus nucleotide sequence. In some embodiments, said primer pair specific for said viral nucleotide sequence is specific for a coronavirus S1 or N2 sequence.

In some embodiments, the reaction mixture comprises a primer pair specific for a sample control nucleotide sequence. In some embodiments, the primer pair specific for the sample control nucleotide sequence is specific for an endogenous nucleotide sequence expressed by the organism from which the biological sample is derived. In some embodiments, the primer pair specific for the sample control nucleotide is specific for a housekeeping gene. In some embodiments, the primer pair specific for the sample control nucleotide sequence is specific for GAPDH, RPP30, or ACTB. In some embodiments, the primer pair specific for the sample control nucleotide is specific for RPP30.

In some embodiments, said primer pair specific for said viral nucleotide sequence or said primer pair specific for said sample control nucleotide sequence is present at a concentration from about 50 micromolar to about 250 micromolar. In some embodiments, said primer pair specific for said viral nucleotide sequence or said primer pair specific for said sample control nucleotide sequence is present at a concentration of about 50, 60, 70, 80, 90, 100, 110, 120, 130, 140, 150, 160, 170, 180, 190, 200, 210, 220, 230, 240, or 250 micromolar. In some embodiments, said primer pair specific for said viral nucleotide sequence or said primer pair specific for said sample control nucleotide sequence is present at a concentration of about 100 micromolar. In some embodiments, said primer pair specific for said viral nucleotide sequence or said primer pair specific for said sample control nucleotide sequence is present at a concentration of about 200 micromolar.

In some embodiments, the reaction mixture comprises a magnesium salt. In some embodiments, the magnesium salt is included in a sufficient quantity to allow the enzymes of the reaction (e.g., the reverse transcriptase enzyme) to function and to amplify targeted nucleic acids. In some embodiments, the magnesium salt is magnesium chloride. In some embodiments, the reaction mixture comprises a concentration of magnesium ions of about 0.1 mM to about 50 mM. In some embodiments, the concentration of magnesium ion is from about 1 mM to about 10 mM.

In some embodiments, the volume of said reaction mixture is from about 10 microliters to about 100 microliters. In some embodiments, the volume of said reaction mixture is from about 20 microliters to about 90 microliters, from about 30 microliters to about 80 microliters, or from about 40 microliters to about 60 microliters. In some embodiments, the volume of said reaction mixture is about 10, 20, 30, 40, 50, 60, 70, 80, 90, or 100 microliters.

Kits

Also described herein is a kit comprising an oligonucleotide primer pair described herein. In certain embodiments, is a kit comprising an oligonucleotide primer pair described herein and a synthetic nucleic acid according to this disclosure. The synthetic nucleic acid may be for an S1, N2 amplification. The kit may also contain reagents sufficient for amplification: such as buffers (provided at 10×, 5×, 2×, or 1×concentration) for reverse transcription, PCR amplification, and/or sequencing reactions, dNTPs, reverse transcriptase enzymes, PCR amplification enzymes (e.g., Taq polymerase and/or variants of the same). Theses components may be packaged in a vial or container singly or in combination as appropriate.

Also described herein is a kit for determining the presence or absence of a viral nucleic acid in a biological sample. In some embodiments, the kit comprises a synthetic nucleic acid provided herein and one or more enzymes or reagents sufficient to amplify the viral nucleic acid form the biological sample.

In some embodiments, the enzymes or reagents comprise a reverse transcriptase enzyme, dNTPs, a primer pair specific for said viral nucleotide sequence, a primer pair specific for a sample control nucleotide sequence, a magnesium salt, or combinations thereof.

In some embodiments, the kit comprises one or more enzymes which can be used to amplify the viral nucleic acid. In some embodiments, the enzyme is a reverse transcriptase. Non-limiting examples of reverse-transcriptase enzymes include Avian Myeloblastosis Virus (AMV) Reverse Transcriptase and Moloney Murine Leukemia Virus (M-MuLV, MMLV), and variants thereof.

In some embodiments, the kit comprises deoxynucleotide triphosphates (dNTPs). In some embodiments, the kit comprises a mixture of each of the dNTPs necessary for amplification of the viral nucleic acid, as well as any other desired nucleic acids (e.g., dATG, dCTP, dTTP, dGTP).

In some embodiments, the kit comprises a primer pair specific for the viral nucleotide sequence. The primer pair specific for the viral nucleotide sequence can be any of the primer pairs provided herein. said primer pair specific for said viral nucleotide sequence is specific for an influenza A nucleotide sequence, an influenza B nucleotide sequence and a coronavirus nucleotide sequence. In some embodiments, said primer pair specific for said viral nucleotide sequence is specific for a coronavirus S1 or N2 sequence.

In some embodiments, the kit comprises a primer pair specific for a sample control nucleotide sequence. In some embodiments, the primer pair specific for the sample control nucleotide sequence is specific for an endogenous nucleotide sequence expressed by the organism from which the biological sample is derived. In some embodiments, the primer pair specific for the sample control nucleotide is specific for a housekeeping gene. In some embodiments, the primer pair specific for the sample control nucleotide sequence is specific for GAPDH, RPP30, or ACTB. In some embodiments, the primer pair specific for the sample control nucleotide is specific for RPP30.

In some embodiments, the kit comprises a magnesium salt. In some embodiments, the magnesium salt is included in a sufficient quantity to allow the enzymes of the kit (e.g., the reverse transcriptase enzyme) to function. In some embodiments, the magnesium salt is magnesium chloride. The following embodiments recite nonlimiting permutations of combinations of features disclosed herein. Other permutations of combinations of features are also contemplated. In particular, each of these numbered embodiments is contemplated as depending from or relating to every previous or subsequent numbered embodiment, independent of their order as listed.

1. A method of diagnosing an individual with a pathogen infection, the method comprising: (a) providing a biological sample from said individual; (b) contacting said biological sample from said individual with a lysis agent, to obtain a lysed biological sample; (c) performing a polymerase chain reaction (PCR) on said lysed biological sample to obtain a PCR amplified lysed biological sample, wherein said PCR reaction on said lysed biological sample is performed with a first set of PCR primers, wherein said first set of PCR primers amplifies a pathogen nucleic acid sequence; (d) sequencing said PCR amplified lysed biological sample using next generation sequencing; and (e) providing a positive diagnosis for said pathogen infection if a pathogen sequence is detected by said PCR or by said sequencing or providing a negative diagnosis for said individual if a pathogen sequence is not detected by said PCR or by said sequencing. 2. The method of embodiment 1, wherein said individual is a human individual. 3. The method of embodiment 1 or 2, wherein said pathogen infection comprises a bacterial infection, a viral infection, or a fungal infection, and combinations thereof. 4. The method of any one of embodiments 1 to 3, wherein said lysis agent comprises water or PCR reaction buffer heated to at least 50 degrees Celsius. 5. The method of any one of embodiments 1 to 3, wherein said lysis agent comprises water or PCR reaction buffer heated to at least 90 degrees Celsius. 6. The method of any one of embodiments 1 to 5, wherein said bacterial infection is an infection by the genera *Streptococcus, Pseudomonas, Shigella, Campylobacter, Salmonella, Clostridium*, or *Escherichia*, and combinations thereof. 7. The method of any one of embodiments 1 to 5, wherein said fungal infection is an infection by *Candida, Blastomyces, Cryptococcus, Coccidoides, Histoplasma, Paracoccidioides, Sporothrix*, or *Pneumocystis*, and combinations thereof. 8. The method of any one of embodiments 1 to 5, wherein the viral infection is an infection by a DNA virus. 9. The method of embodiment 8, wherein said DNA virus comprises hepatitis B, Hepatitis C, papillomavirus, Epstein-Barr virus, varicella, or variola, and combinations thereof. 10. The method of any one of embodiments 1 to 5, wherein said viral infection is an infection by an RNA virus. 11. The method of embodiment 10, wherein said RNA virus comprises an influenza virus, a coronavirus, a polio virus, a measles virus, an Ebola virus, a retrovirus, or an Orthomyxovirus. 12. The method of embodiment 11, wherein said viral infection is a coronavirus infection. 13. The method of embodiment 12, wherein said coronavirus infection is SARS-COV-2 infection. 14. The method of any one of embodiments 1 to 13, wherein said biological sample from said individual is from a blood sample, a plasma sample, a serum sample, a cheek swab, a urine sample, a semen sample, a vaginal swab, a stool sample, a nasopharyngeal swab, mid-turbinate swab, or any combination thereof. 15. The method of embodiment 14, wherein said biological sample from said individual is from a nasopharyngeal swab, a mid-turbinate swab, or any combination thereof. 16. The method of any one of embodiments 1 to 15, comprising adding a synthetic nucleic acid to said lysis agent or said lysed biological sample. 17. The method of any one of embodiments 1 to 15, comprising adding a plurality of synthetic nucleic acids to said lysis agent or said lysed biological sample, the plurality comprising synthetic nucleic acids that have distinct sequences. 18. The method of embodiment 17, wherein the plurality comprises four. 19. The method of any one of embodiments 1 to 18, comprising adding a synthetic nucleic acid to said method. 20. The method of any one of embodiments 1 to 18, comprising adding a plurality of synthetic nucleic acids to said method, the plurality comprising synthetic nucleic acids that have distinct sequences. 21. The method of embodiment 20, wherein the plurality comprises four. 22. The method of embodiment 19, wherein said synthetic nucleic acid is an RNA. 23. The method of embodiment 19, wherein said synthetic nucleic acid is a DNA. 24. The method of any one of embodiments 19 or 23, wherein said synthetic nucleic acid comprises a set of sequences configured to be bound by said first set of PCR primers. 25. The method of any one of embodiments 19 to 24, wherein said first set of primers amplifies both said pathogen nucleic acid sequence and said synthetic nucleic acid. 26. The method of any one of embodiments 19 to 24, wherein said synthetic nucleic acid sequence comprises a nucleotide sequence that is not identical to said pathogen nucleic acid sequence. 27. The method of any one of embodiments 1 to 26, comprising performing a reverse transcription reaction on said lysed biological sample. 28. The method of embodiment 27, wherein said reverse transcription reaction is performed before said performing said polymerase chain reaction. 29. The method of any one of embodiments 1 to 26, wherein said reverse transcription reaction is performed without further purification of said lysed biological sample. 30. The method of any one of embodiments 1 to 26, wherein said reverse transcription reaction on said lysed biological sample produces viral cDNA. 31. The method of embodiment 30, wherein said viral cDNA is coronavirus cDNA. 32. The method of embodiment 31, wherein said coronavirus cDNA is SARS-COV-2 cDNA. 33. The method of any one of embodiments 1 to 31, wherein said reverse transcription reaction and said PCR is a single-step reaction. 34. The method of any one of embodiments 1 to 33, wherein said PCR is an end-point analysis. 35. The method of any one of embodiments 1 to 34, wherein said PCR is not a real-time PCR reaction. 36. The method of any one of embodiments 1 to 35, wherein said first set of PCR primers amplifies a coronavirus nucleic acid sequence. 37. The method of embodiment 36, wherein said coronavirus nucleic acid sequence is a SARS-COV-2 nucleic acid sequence. 38. The method of embodiment 37, wherein said SARS-COV-2 nucleic acid sequence comprises the N1 or S2 gene. 39. The method of any one of embodiments 1 to 38, comprising a second set of PCR primers wherein said second set of primers amplifies a nucleic acid sequence of said individual. 40. The method of embodiment 39, wherein said second set of PCR primers amplifies a human nucleic acid sequence. 41. The method of embodiment 40, wherein said second set of PCR primers amplifies a human nucleic acid sequence selected from GAPDH, ACTB, RPP30, and combinations thereof. 42. The method of embodiment 41, wherein said second set of PCR primers amplifies human RPP30. 43. The method of any one of embodiments 40 to 42, wherein the second set of PCR primer comprises a mixture of primers with sequencing adaptor sequences and primers without sequencing adaptor sequences. 44. The method of embodiment 43, wherein a ratio of primers with sequencing adaptor sequences to primers without sequencing adaptor sequences is about 1:1, about 1:2, about 1:3 or about 1:4. 45. The method of any one of embodiments 1 to 44, wherein said PCR comprises from 30 to 45 amplification cycles. 46. The method of embodiment 45, wherein said PCR comprises from 35 to 45 amplification cycles. 47. The method of embodiment 45, wherein said PCR comprises from 39 to 42 amplification cycles. 48. The method of any one of embodiments 1 to 47, wherein said first set of PCR primers, said second set of PCR primers, or both said first set of PCR primers and said second set of PCR primers comprises a nucleic acid sequence comprising a variable nucleotide sequence. 49. The method of embodiment 48, wherein said variable nucleotide sequence is a sample ID unique for said individual. 50. The method of any one of embodiments 1 to 49, wherein said first set of PCR primers, said second set of PCR primers, or both said first set of PCR primers and said second set of PCR primers comprises an adapter sequence for a next-generation sequencing reaction. 51. The method of any one of embodiments 39 to 50, comprising adding a second synthetic nucleic acid to said method. 52. The method of embodiment 51, wherein said second synthetic nucleic acid is an RNA. 53. The method of embodiment 51, wherein said second synthetic nucleic acid is a DNA. 54. The method of any one of embodiments 51 to 53, wherein said second synthetic nucleic acid comprises a set of sequences configured to be bound by said second set of PCR primers. 55. The method of any one of embodiments 51 to 54, wherein said second set of primers amplifies both said human nucleic acid sequence and said synthetic nucleic acid. 56. The method of any one of embodiments 51 to 54, wherein said synthetic nucleic acid sequence comprises a nucleotide sequence that is not identical to said human nucleic acid sequence. 57. The method of any one of embodiments 1 to 56, wherein said method can detect less than 10 copies of pathogen genome. 58. The method of any one of embodiments 1 to 56, wherein said method can detect less than 5 copies of pathogen genome. 59. The method of embodiment 57 or 58, wherein said pathogen genome is a coronavirus genome. 60. The method of embodiment 57 or 58, wherein said coronavirus genome is a SARS-COV-2 genome. 61. The method of any one of embodiments 1 to 60, wherein said positive diagnosis for coronavirus if a coronavirus sequence is detected by said PCR is a SARS-COV-2 diagnosis. 62. The method of any one of embodiments 1 to 61, wherein the method determines a strain of coronavirus. 63. The method of any one of embodiments 1 to 61, wherein the method determines a strain of COVD-19.

64. A method of diagnosing an individual with a pathogen infection, the method comprising amplifying nucleic acids from a biological sample from said individual using a first set of PCR primers thereby obtaining amplified nucleic acids, wherein said first set of PCR primers amplifies a pathogen nucleic acid sequence and a synthetic nucleic acid sequence from said biological sample, wherein said synthetic nucleic acid sequence differs from said pathogen nucleic acid sequence by at least one nucleotide. 65. The method of embodiment 64, wherein said individual is a human individual. 66. The method of embodiment 64 or 65, wherein said pathogen infection comprises a bacterial infection, a viral infection, or a fungal infection. 67. The method of any one of embodiments 64 to 66, wherein said bacterial infection is an infection by the genera *Streptococcus, Pseudomonas, Shigella, Campylobacter, Salmonella, Clostridium,* or *Escherichia*, and combinations thereof. 68. The method of any one of embodiments 64 to 66, wherein said fungal infection is an infection by *Candida, Blastomyces, Cryptococcus, Coccidoides, Histoplasma, Paracoccidioides, Sporothrix,* or *Pneumocystis*, and combinations thereof. 69. The method of any one of embodiments 64 to 66, wherein the viral infection is an infection by a DNA virus. 70. The method of embodiment 69, wherein said DNA virus comprises hepatitis B, Hepatitis C, papillomavirus, Epstein-Barr virus, varicella, variola, or any combination thereof. 71. The method of any one of embodiments 64 to 66, wherein said viral infection is an infection by an RNA virus. 72. The method of embodiment 71, wherein said RNA virus comprises an influenza virus, a coronavirus, a polio virus, a measles virus, an Ebola virus, a retrovirus, or an Orthomyxovirus. 73. The method of embodiment 71, wherein said viral infection is a coronavirus infection. 74.

The method of embodiment 73, wherein said coronavirus infection is SARS-COV-2 infection. 75. The method of any one of embodiments 64 to 74, wherein said biological sample from said individual is from a blood sample, a plasma sample, a serum sample, a cheek swab, a urine sample, a semen sample, a vaginal swab, a stool sample, a nasopharyngeal swab, mid-turbinate swab, or any combination thereof. 76. The method of embodiment 75, wherein said biological sample from said individual is from a nasopharyngeal swab, a mid-turbinate swab, or any combination thereof. 77. The method of any one of embodiments 64 to 76, wherein said synthetic nucleic acid is an RNA. 78. The method of any one of embodiments 64 to 76, wherein said synthetic nucleic acid is a DNA. 79. The method of any one of embodiments 64 to 78, wherein said synthetic nucleic acid comprises a set of sequences configured to be bound by said first set of PCR primers. 80. The method of any one of embodiments 64 to 79, wherein said synthetic nucleic acid sequence differs from said pathogen nucleic acid sequence by at least 5 nucleotides. 81. The method of any one of embodiments 64 to 79, wherein said pathogen infection is diagnosed based upon the ratio of synthetic nucleic acid sequence to pathogen nucleic acid sequence. 82. The method of any one of embodiments 64 to 81, comprising performing a reverse transcription reaction on said nucleic acids from said biological sample. 83. The method of any one of embodiments 64 to 81, wherein said reverse transcription reaction on said nucleic acids from said biological sample produces coronavirus cDNA. 84. The method of embodiment 83, wherein said coronavirus cDNA is SARS-COV-2 cDNA. 85. The method of any one of embodiments 64 to 84, wherein said amplifying nucleic acids comprises a PCR reaction. 86. The method of embodiment 85, wherein said PCR reaction is an end-point analysis. 87. The method of any one of embodiments 64 to 86, wherein said PCR reaction is not a real-time PCR reaction. 88. The method of any one of embodiments 64 to 87, wherein said first set of PCR primers amplifies a coronavirus nucleic acid sequence. 89. The method of embodiment 88, wherein said coronavirus nucleic acid sequence is a SARS-COV-2 nucleic acid sequence. 90. The method of embodiment 89, wherein said SARS-COV-2 nucleic acid sequence comprises the N1 or S2 gene. 91. The method of any one of embodiments 64 to 90, wherein said first set of PCR primers comprises a nucleic acid sequence comprising a variable nucleotide sequence. 92. The method of embodiment 91, wherein said variable nucleotide sequence is a sample ID unique for said individual. 93. The method of any one of embodiments 64 to 92, wherein said first set of PCR primers comprises an adapter sequence for a next-generation sequencing reaction. 94. The method of any one of embodiments 64 to 92, comprising amplifying nucleic acids from said biological sample using a second set of PCR primers, wherein said second set of PCR primers amplifies a human nucleic acid sequence. 95. The method of embodiment 94, wherein said second set of PCR primers amplifies a nucleic acid sequence selected from GAPDH, ACTB, RPP30, and combinations thereof. 96. The method of embodiment 95, wherein said second set of PCR primers amplifies human RPP30. 97. The method of any one of embodiments 94 to 96, wherein the second set of PCR primer comprises a mixture of primers with sequencing adaptor sequences and primers without sequencing adaptor sequences. 98. The method of embodiment 97, wherein a ratio of primers with sequencing adaptor sequences to primers without sequencing adaptor sequences is about 1:1, about 1:2, about 1:3 or about 1:4. 99. The method of any one of embodiments 64 to 98, wherein said PCR comprises from 30 to 45 amplification cycles. 100. The method of embodiment 99, wherein said PCR comprises from 35 to 45 amplification cycles. 101. The method of embodiment 99, wherein said PCR comprises from 39 to 42 amplification cycles. 102. The method of any one of embodiments 94 to 101, wherein said second set of PCR primers comprises a nucleic acid sequence comprising a variable nucleotide sequence. 103. The method of embodiment 102, wherein said variable nucleotide sequence is a sample ID unique for said individual. 104. The method of any one of embodiments 94 to 103, wherein said second set of PCR primers comprises an adapter sequence a next-generation sequencing reaction. 105. The method of any one of embodiments 64 to 104, comprising sequencing said amplified nucleic acids from said biological sample using a next-generation sequencing technology. 106. The method of any one of embodiments 64 to 105, wherein said method can detect less than 10 copies of pathogen genome. 107. The method of any one of embodiments 64 to 104, wherein said method can detect less than 5 copies of pathogen genome. 108. The method of embodiment 106 or 107, wherein said pathogen genome is coronavirus genome. 109. The method of embodiment 106 or 107, wherein said pathogen genome is SARS-COV-2 genome. 110. The method of any one of embodiments 64 to 109, wherein the method determines a strain of coronavirus. 111. The method of embodiment 110, wherein the method determines a strain of SARS-COV-2.

112. A synthetic nucleic acid comprising a 5' proximal region, a 3' proximal region and an intervening nucleic acid sequence. 113. The synthetic nucleic acid of embodiment 112, wherein said synthetic nucleic acid comprises RNA. 114. The synthetic nucleic acid of embodiment 112, wherein said synthetic nucleic acid comprises DNA. 115. The synthetic nucleic acid of any one of embodiments 112 to 114, wherein said 5' proximal region comprises a viral nucleic acid sequence. 116. The method of embodiment 115, wherein said viral nucleic acid sequence comprises a coronavirus sequence. 117. The method of embodiment 116, wherein said viral nucleic acid sequence comprises a SARS-COV-2 sequence. 118. The synthetic nucleic acid of any one of embodiments 112 to 114, wherein said 3' proximal region comprises a viral nucleic acid sequence. 119. The method of embodiment 118, wherein said viral nucleic acid sequence comprises a coronavirus sequence. 120. The method of embodiment 119, wherein said viral nucleic acid sequence comprises a SARS-COV-2 sequence. 121. The synthetic nucleic acid of any one of embodiments 112 to 120, wherein said 5' proximal region, said 3' proximal region, or both said 5' proximal region and said 3' proximal region are less than about 30 nucleotides in length. 122. The synthetic nucleic acid of any one of embodiments 112 to 120, wherein said 5' proximal region, said 3' proximal region, or both said 5' proximal region and said 3' proximal region are less than about 25 nucleotides in length. 123. The synthetic nucleic acid of any one of embodiments 112 to 120, wherein said 5' proximal region, said 3' proximal region, or both said 5' proximal region and said 3' proximal region are less than about 20 nucleotides in length. 124. The synthetic nucleic acid of any one of embodiments 112 to 123, wherein said 5' proximal region is at the 5' terminus of said synthetic nucleic acid. 125. The synthetic nucleic acid of any one of embodiments 112 to 123, wherein said 3' proximal region is at the 3' terminus of said synthetic nucleic acid. 126. The synthetic nucleic acid of any one of embodiments 112 to 125, wherein said intervening nucleic acid sequence is less than about 99%, 98%, 97%, 95%, 90%, 85%, 80%, or 75%, identical to a viral nucleic acid sequence. 127. The synthetic nucleic acid of embodiment 126, wherein said synthetic nucleic acid sequence is a coronavirus sequence. 128. The synthetic nucleic acid of embodiment 126, wherein said synthetic nucleic acid sequence is a SARS-COV-2 sequence. 129. Use of the synthetic nucleic acid of any one of embodiments 112 to 128 in a method to detect pathogen infection in said individual. 130. The use of embodiment 129, wherein said pathogen infection is a coronavirus infection. 131. The use of embodiment 130, wherein said viral infection is a SARS-COV-2 infection.

132. A method of nucleic acid processing for the detection of a viral infection, said method comprising: (a) providing a sample comprising a viral nucleic acid molecule and a host nucleic acid molecule; (b) generating a barcoded viral nucleic acid molecule by performing a nucleic acid extension reaction on said viral nucleic acid molecule using a first primer comprising a first barcode sequence; (c) generating a barcoded host nucleic acid molecule by performing a nucleic acid extension reaction on said host nucleic acid molecule using a second primer comprising a second barcode sequence; (d) sequencing said barcoded viral nucleic acid molecule and said barcoded host nucleic acid molecule to identify (i) said barcode sequence and (ii) a sequence corresponding to said viral nucleic acid molecule, or a derivative thereof, and said host nucleic acid molecule; and (e) providing a positive diagnosis for a viral infection if said sequence corresponding to said viral nucleic acid molecule is identified in (d). 133. The method of embodiment 132, wherein (b) and (c) are performed simultaneously. 134. The method of any one of embodiments 132 to 133, wherein said first primer further comprises one or more additional functional sequences selected from the group consisting of primer sequences, adapter sequences, primer annealing sequences, a unique molecular identifier sequence, and capture sequences. 135. The method of any one of embodiments 132 to 134, wherein said second primer further comprises one or more additional functional sequences selected from the group consisting of primer sequences, adapter sequences, primer annealing sequences, a unique molecular identifier sequence, and capture sequences. 136. The method of any one of embodiments 132 to 135, wherein (a) further comprises providing a synthetic nucleic acid molecule. 137. The method of embodiments 136, wherein the synthetic nucleic acid molecule comprises a synthetic sequence that is different from said viral nucleic acid molecule and said human nucleic acid molecule. 138. The method of embodiment 137, wherein (b) generating a barcoded synthetic nucleic acid molecule by performing said nucleic acid extension using said first primer. 139. The method of embodiment 137, wherein (c) generating a barcoded synthetic nucleic acid molecule by performing said nucleic acid extension using said second primer. 140. The method of any one of embodiments 132 to 139, wherein said nucleic acid extension reaction is a reverse transcription reaction. 141. The method of any one of embodiments 132 to 139, wherein said nucleic acid extension reaction is a polymerase chain reaction. 142. The method of any one of embodiments 132 to 139, wherein said nucleic acid extension reaction comprises a reverse transcriptase reaction, a polymerase chain reaction, or a combination thereof. 143. The method of embodiment 142, wherein (b), said nucleic acid extension reaction comprises: (i) hybridizing said first primer to said viral nucleic acid molecule; and (ii) using a reverse transcriptase enzyme to extend said primer. 144. The method of embodiment 142, wherein (b), said nucleic acid extension reaction comprises: (i) hybridizing said first primer to said viral nucleic acid molecule; and (ii) using a reverse transcriptase enzyme to extend said primer. 145. The method of embodiment 142, wherein (b), said nucleic acid extension reaction comprises: (i) hybridizing said first primer to said viral nucleic acid molecule; and (ii) using a polymerase enzyme to extend said primer. 146. The method of embodiment 142, wherein the polymerase chain reaction is an end-point polymer chain reaction. 147. The method of any one of embodiments 132 to 146, wherein the method further comprises, prior to (d), amplifying said barcoded viral nucleic acid molecule and said barcoded host nucleic acid molecule. 148. The method of any one of embodiments 132 to 147, wherein the method further comprises, prior to (d), subjecting said barcoded viral nucleic acid molecule and said barcoded host nucleic acid molecule to N cycles of a polymerase chain reaction. 149. The method of embodiment 148, wherein N is greater than 35 cycles. 150. The method of embodiment 148, wherein N is greater than 40 cycles. 151. The method of embodiment 148, wherein N is greater than 45 cycles. 152. The method of embodiment 148, wherein said polymerase chains reaction incorporates one or more additional sequences into one or both of said barcoded viral nucleic acid molecule and barcoded host nucleic acid molecule, selected from the group consisting of a sample index sequence, an adapter sequence, primer sequence, a primer binding sequence, a sequence configured to couple to the flow cell of a sequencer, and an additional barcode sequence. 153. The method of any one of embodiments 132 to 152, wherein subsequent to (b) and (c), said sample is combined with one or more samples after performing at least one nucleic acid extension reaction in (b) and (c). 154. The method of embodiment 153, wherein said sample is combined with one or more samples after performing a single round of said nucleic acid extension reaction in (b) and (c). 155. The method of any one of embodiments 132 to 154, wherein said sample comprises one or more cells. 156. The method of embodiment 155, further comprising prior to (b), releasing said viral nucleic acid molecule and said host nucleic acid molecule from said one or more cells. 157. The method of embodiment 155, further comprising prior to (b), subjecting said sample to conditions sufficient to release said viral nucleic acid molecule and said host nucleic acid molecule from said one or more cells. 158. The method of embodiment 157, wherein (b) and (c) are performed under said conditions sufficient to release said viral nucleic acid molecule and said host nucleic acid molecule from said one or more cells. 159. The method of embodiment 157, wherein said viral nucleic acid molecule and said host nucleic acid molecule is released is not purified from said sample prior to (b) and (c). 160. The method of any one of embodiments 132 to 159, further comprising in (d) using said barcode sequence to associate said viral nucleic acid molecule, or a derivative thereof, and said host nucleic acid molecule, or a derivative thereof, as being associated with said sample. 161. The method of any one of embodiments 132 to 160, further comprising in (e) using said barcode sequence of said barcoded viral nucleic acid molecule and said barcoded host nucleic acid molecule to identify said sample, wherein said sample corresponds to a subject being tested for said viral infection. 162. The method of any one of embodiments 132 to 161, wherein said sample is obtained from a subject. 163. The method of embodiment 162, wherein said subject is a human. 164. The method of embodiment 162, wherein said subject is an animal. 165. The method of embodiment 162, wherein said host nucleic acid molecule is part of a genome of said subject. 166. The method of embodiment 162, wherein said host nucleic acid molecule is part of a transcriptome of said subject. 167. The method of any one of embodiments 132 to 166, wherein said host nucleic acid molecule encodes an ubiquitously expressed protein. 168. The method of any one of embodiments 132 to 166, wherein said host nucleic acid molecule is a genomic DNA molecule. 169. The method of any one of embodiments 132 to 166, wherein said host nucleic acid molecule is an ubiquitously transcribed RNA molecule. 170. The method of any one of embodiments 132 to 169, wherein said host nucleic acid is GAPDH, ACTB, RPP30, and combinations thereof. 171. The method of any one of embodiments 132 to 170, wherein said viral nucleic acid molecule is part of a genome of a virus. 172. The method of embodiment 171, wherein said virus is a coronavirus. 173. The method of embodiment 172, wherein said coronavirus is selected from the group consisting of severe acute respiratory syndrome coronavirus 2 (SARS-COV-2), severe acute respiratory syndrome coronavirus (SARS-COV), and Middle East respiratory syndrome coronavirus (MERS-COV). 174. The method of embodiment 173, wherein said coronavirus is SARS-COV-2. 175. The method of embodiment 174, wherein said virus is an RNA virus. 176. The method of embodiment 175, wherein said RNA virus comprises a double-stranded RNA genome. 177. The method of embodiment 175, wherein said RNA virus comprises a single-stranded RNA genome. 178. The method of embodiment 175, wherein said RNA virus is selected from the group consisting of coronavirus, influenza, human immunodeficiency virus, and Ebola virus. 179. The method of embodiment 170, wherein said virus is a DNA virus. 180. The method of any one of embodiments 34 to 169, further comprising, prior to (a), partitioning said sample. 181. The method of embodiment 180, wherein said partition is a well. 182. The method of embodiment 180, wherein said partition is a well among a plurality of wells. 183. The method of embodiment 182, wherein said barcode sequence is unique to said well among said plurality of wells. 184. The method of any one of embodiments 132 to 183, wherein (b) and (c) are performed concurrently. 185. The method of any one of embodiments 132 to 184, wherein the viral infection is SARS-COV-2. 186. The method of any one of embodiments 132 to 183, wherein the sample is obtained from a subject via a nasopharyngeal or mid-turbinate swab.

187. A composition, comprising a synthetic nucleic acid molecule comprising a first nucleic acid sequence and a second nucleic acid sequence, wherein (1) the first nucleic acid sequence is identical to a sequence from a pathogen nucleic acid molecule, and (2) the second nucleic acid sequence is not identical to a sequence the pathogen nucleic acid molecule. 188. The composition of embodiment 187, wherein the first nucleic acid sequence is located to the 3' the second nucleic acid sequence. 189. The composition of any one of embodiments 187 to 188, wherein the synthetic nucleic acid molecule further comprises a third nucleic acid sequence, wherein the third nucleic acid sequence is identical to a second sequence from the pathogen nucleic acid molecule. 190. The composition of embodiment 176, wherein the third nucleic acid sequence is 5' to the second nucleic acid sequence. 191. The composition of any one of embodiments 187 to 190, wherein the first nucleic acid sequence or the third nucleic acid sequence is less than 5, 10, 15, 20, 25, or 30 nucleotides. 192. The composition of any one of embodiments 187 to 191, wherein the second nucleic acid sequence comprises a total number of nucleotides less than 25, 50, 100, 150, 200, or 500 nucleotides. 193. The composition of any one of embodiments 187 to 191, wherein the second nucleic acid sequence comprises a total number of nucleotides greater than 25, 50, 100, 150, 200, or 500 nucleotides. 194. The composition of any one of embodiments 187 to 193, wherein the synthetic nucleic acid molecule is a ribonucleic acid (RNA) molecule, a deoxyribonucleic acid (DNA) molecule, or an RNA-DNA hybrid molecule. 195. The composition of any one of embodiments 187 to 194, wherein the first nucleic acid sequence, the third nucleic acid sequence, or both the first nucleic acid sequence and the third nucleic acid sequence comprise a primer binding site. 196. The composition of any one of embodiments 187 to 194, wherein the composition further comprises the pathogen nucleic acid molecule. 197. The composition of embodiment 196, wherein the pathogen nucleic molecule is from a pathogen, wherein the pathogen comprises a bacterium, a virus, a fungus, or combinations thereof. 198. The composition of embodiment 197, wherein the bacterium is from the genera *Streptococcus, Pseudomonas, Shigella, Campylobacter, Salmonella, Clostridium*, or *Escherichia*, and combinations thereof. 199. The composition of embodiment 197, wherein the fungus is *Candida, Blastomyces, Cryptococcus, Coccidoides, Histoplasma, Paracoccidioides, Sporothrix*, or *Pneumocystis*, and combinations thereof. 200. The composition of embodiment 197, wherein the virus is a DNA virus. 201. The composition of embodiment 200, wherein the DNA virus comprises hepatitis B, Hepatitis C, papillomavirus, Epstein-Barr virus, varicella, or variola, and combinations thereof. 202. The composition of embodiment 197, wherein the virus is an RNA virus. 203. The composition of embodiment 202, wherein the RNA virus comprises an influenza virus, a coronavirus, a polio virus, a measles virus, an Ebola virus, a retrovirus, or an Orthomyxovirus. 204. The composition of embodiment 189, wherein the virus is a coronavirus. 205. The composition of embodiment 190, wherein the coronavirus is a SARS-COV-2 virus. 206. The composition of any one of embodiments 196 to 205, wherein the composition further comprises a plurality of primers, wherein a primer of the plurality of primers is configured to hybridize to a sequence of the synthetic nucleic acid molecule or a sequence of the pathogen nucleic acid molecule. 207. The composition of embodiment 206, wherein a sequence of the synthetic nucleic acid molecule and the sequence the pathogen nucleic acid molecule are identical. 208. The composition of any one of embodiments 187 to 207, wherein the synthetic nucleic acid molecule is amplified with the same efficiency as the pathogen nucleic acid molecule. 209. The composition of any one of embodiments 187 to 207, wherein the synthetic nucleic acid molecule is configured to create an amplification produce the same size or within 10 base pairs in size as an amplification product of the pathogen nucleic acid molecule.

210. A method of diagnosing an individual with a pathogen infection, the method comprising: (a) providing a biological sample from said individual; (c) performing a polymerase chain reaction (PCR) on said biological sample to obtain a PCR amplified biological sample, wherein said PCR reaction on said biological sample is performed with a first set of PCR primers, wherein said first set of PCR primers amplifies a pathogen nucleic acid sequence; (d) sequencing said PCR amplified lysed biological sample using next generation sequencing; and (e) providing a positive diagnosis for said pathogen infection if a pathogen sequence is detected by said PCR or by said sequencing or providing a negative diagnosis for said individual if a pathogen sequence is not detected by said PCR or by said sequencing. 211. The method of embodiment 210, wherein said individual is a human individual. 212. The method of embodiment 210 or 211, wherein said pathogen infection comprises a bacterial infection, a viral infection, or a fungal infection, and combinations thereof. 213. The method of any one of embodiments 210 to 212, wherein said bacterial infection is an infection by the genera *Streptococcus, Pseudomonas, Shigella, Campylobacter, Salmonella, Clostridium,* or *Escherichia,* and combinations thereof. 214. The method of any one of embodiments 210 to 212, wherein said fungal infection is an infection by *Candida, Blastomyces, Cryptococcus, Coccidoides, Histoplasma, Paracoccidioides, Sporothrix,* or *Pneumocystis,* and combinations thereof. 215. The method of any one of embodiments 210 to 212, wherein the viral infection is an infection by a DNA virus. 216. The method of embodiment 215, wherein said DNA virus comprises hepatitis B, Hepatitis C, papillomavirus, Epstein-Barr virus, varicella, or variola, and combinations thereof. 217. The method of any one of embodiments 210 to 216, wherein said viral infection is an infection by an RNA virus. 218. The method of embodiment 217, wherein said RNA virus comprises an influenza virus, a coronavirus, a polio virus, a measles virus, an Ebola virus, a retrovirus, or an Orthomyxovirus. 219. The method of embodiment 218, wherein said viral infection is a coronavirus infection. 220. The method of embodiment 219, wherein said coronavirus infection is SARS-COV-2 infection. 221. The method of any one of embodiments 210 to 220, wherein said biological sample from said individual is from a blood sample, a plasma sample, a serum sample, a cheek swab, a urine sample, a semen sample, a vaginal swab, a stool sample, a nasopharyngeal swab, mid-turbinate swab, or any combination thereof. 222. The method of embodiment 221, wherein said biological sample from said individual is from a nasopharyngeal swab, a mid-turbinate swab, or any combination thereof. 223. The method of any one of embodiments 210 to 222, comprising adding a synthetic nucleic acid to said lysis agent or said lysed biological sample. 224. The method of any one of embodiments 210 to 222, comprising adding a synthetic nucleic acid to said method. 225. The method of embodiment 224, wherein said synthetic nucleic acid is an RNA. 226. The method of embodiment 224, wherein said synthetic nucleic acid is a DNA. 227. The method of any one of embodiments 224 to 226, wherein said synthetic nucleic acid comprises a set of sequences configured to be bound by said first set of PCR primers. 228. The method of any one of embodiments 224 to 227, wherein said first set of primers amplifies both said pathogen nucleic acid sequence and said synthetic nucleic acid. 229. The method of any one of embodiments 224 to 228, wherein said synthetic nucleic acid sequence comprises a nucleotide sequence that is not identical to said pathogen nucleic acid sequence. 230. The method of any one of embodiments 210 to 229, comprising performing a reverse transcription reaction on said lysed biological sample. 231. The method of embodiment 230, wherein said reverse transcription reaction is performed before said performing said polymerase chain reaction. 232. The method of any one of embodiments 210 to 231, wherein said reverse transcription reaction is performed without further purification of said lysed biological sample. 233. The method of any one of embodiments 210 to 231, wherein said reverse transcription reaction on said lysed biological sample produces viral cDNA. 234. The method of embodiment 233, wherein said viral cDNA is coronavirus cDNA. 235. The method of embodiment 233, wherein said coronavirus cDNA is SARS-COV-2 cDNA. 236. The method of any one of embodiments 210 to 235, wherein said reverse transcription reaction and said PCR is a single-step reaction. 237. The method of any one of embodiments 210 to 236, wherein said PCR is an end-point analysis. 238. The method of any one of embodiments 210 to 237, wherein said PCR is not a real-time PCR reaction. 239. The method of any one of embodiments 210 to 238, wherein said first set of PCR primers amplifies a coronavirus nucleic acid sequence. 240. The method of embodiment 239, wherein said coronavirus nucleic acid sequence is a SARS-COV-2 nucleic acid sequence. 241. The method of embodiment 240, wherein said SARS-COV-2 nucleic acid sequence comprises the N1 or S2 gene. 242. The method of any one of embodiments 210 to 241, comprising a second set of PCR primers wherein said second set of primers amplifies a nucleic acid sequence of said individual. 243. The method of embodiment 242, wherein said second set of PCR primers amplifies a human nucleic acid sequence. 244. The method of embodiment 243, wherein said second set of PCR primers amplifies a human nucleic acid sequence selected from GAPDH, ACTB, RPP30, and combinations thereof. 245. The method of embodiment 244, wherein said second set of PCR primers amplifies human RPP30. 246. The method of any one of embodiments 242 to 245, wherein the second set of PCR primer comprises a mixture of primers with sequencing adaptor sequences and primers without sequencing adaptor sequences. 247. The method of embodiment 246, wherein a ratio of primers with sequencing adaptor sequences to primers without sequencing adaptor sequences is about 1:1, about 1:2, about 1:3 or about 1:4. 248. The method of any one of embodiments 210 to 247, wherein said PCR comprises from 30 to 45 amplification cycles. 249. The method of embodiment 248, wherein said PCR comprises from 35 to 45 amplification cycles. 250. The method of embodiment 248, wherein said PCR comprises from 39 to 42 amplification cycles. 251. The method of any one of embodiments 210 to 250, wherein said first set of PCR primers, said second set of PCR primers, or both said first set of PCR primers and said second set of PCR primers comprises a nucleic acid sequence comprising a variable nucleotide sequence. 252. The method of embodiment 251, wherein said variable nucleotide sequence is a sample ID unique for said individual. 253. The method of any one of embodiments 210 to 252, wherein said first set of PCR primers, said second set of PCR primers, or both said first set of PCR primers and said second set of PCR primers comprises an adapter sequence for a next-generation sequencing reaction. 254. The method of any one of embodiments 210 to 253, wherein said method can detect less than 10 copies of pathogen genome. 255. The method of any one of embodiments 210 to 253, wherein said method can detect less than 5 copies of pathogen genome. 256. The method of embodiment 254 or 255, wherein said pathogen genome is a coronavirus genome. 257. The method of embodiment 254 or 255, wherein said coronavirus genome is a SARS-COV-2 genome. 258. The method of any one of embodiments 210 to 257, wherein said positive diagnosis for coronavirus if a coronavirus sequence is detected by said PCR is a SARS-COV-2 diagnosis. 259. The method of any one of embodiments 210 to 258, wherein the method determines a strain of coronavirus. 260. The method of any one of embodiments 210 to 258, wherein the method determines a strain of COVD-19.

261. A composition comprising a plurality of synthetic nucleic acids with a distinct nucleic acid sequence, said plurality of synthetic nucleic acids with a distinct nucleic acid sequence composing a common 5' sequence identical to a pathogen nucleic acid sequence, a common 3' sequence identical to a pathogen nucleic acid sequence, and an intervening sequence that differs among the plurality of sequences. 262. The composition of embodiment 261, wherein said plurality of synthetic nucleic acids with a distinct nucleic acid sequence are single-stranded. 263. The composition of embodiment 261, wherein said plurality of synthetic nucleic acids with a distinct nucleic acid sequence are double-stranded. 264. The composition of any one of embodiments 261 to 263, wherein said plurality of synthetic nucleic acids with a distinct nucleic acid sequences consist of or comprise RNA. 265. The composition of any one of embodiments 261 to 263, wherein said plurality of synthetic nucleic acids with a distinct nucleic acid sequences consist of or comprise DNA. 266. The composition of any one of embodiments 261 to 265, wherein said common 5' sequence identical to a pathogen nucleic acid sequence is 30 nucleotides or less. 267. The composition of any one of embodiments 261 to 266, wherein said common 3' sequence identical to a pathogen nucleic acid sequence is 30 nucleotides or less. 268. The composition of any one of embodiments 261 to 267, wherein said intervening sequence is 50 nucleotides or less. 269. The composition of embodiment 268, wherein said intervening sequence is 30 nucleotides or less. 270. The composition of any one of embodiments 261 to 269, wherein the pathogen nucleic acid sequence is from a bacterial pathogen, a fungal pathogen, or a viral pathogen. 271. The composition of embodiment 270, wherein said bacterial pathogen is of the genera *Streptococcus, Pseudomonas, Shigella, Campylobacter, Salmonella, Clostridium*, or *Escherichia*, and combinations thereof. 272. The composition of embodiment 270, wherein said fungal pathogen is *Candida, Blastomyces, Cryptococcus, Coccidoides, Histoplasma, Paracoccidioides, Sporothrix*, or *Pneumocystis*, and combinations thereof. 273. The composition of embodiment 270, wherein said viral pathogen is a DNA virus. 274. The composition of embodiment 273, wherein said DNA virus comprises hepatitis B, Hepatitis C, papillomavirus, Epstein-Barr virus, varicella, or variola, and combinations thereof. 275. The composition of any one of embodiments 1 to 3, wherein said viral pathogen is an RNA virus. 276. The composition of embodiment 270, wherein said RNA virus comprises an influenza virus, a coronavirus, a polio virus, a measles virus, an Ebola virus, a retrovirus, an Orthomyxovirus, or combinations thereof. 277. The composition of embodiment 276, wherein said viral pathogen is a coronavirus. 278. The composition of embodiment 277, wherein said coronavirus is SARS-COV-2. 279. The composition of embodiments 277 or 278, wherein said pathogen nucleic acid sequence is a nucleic acid sequence that encodes a coronavirus spike protein. 280. The composition of any one of embodiments 277 to 279, wherein said plurality of synthetic nucleic acids with a distinct nucleic acid sequence comprise or consist of a sequence selected from any one or more of S2_001, S2_002, S2_003, and S2_004. 281. The composition of any one of embodiments 261 to 280, for use in a method of diagnosing or detecting infection with a pathogen. 282. The composition of any one of embodiments 261 to 280, for use in a method of normalizing pathogen next-generation sequence reads.

EXAMPLES

The following illustrative examples are representative of embodiments of compositions and methods described herein and are not meant to be limiting in any way.

Example 1—SwabSeq Diagnosis of Viral Infection

FIG. 1 shows an example workflow for collecting and processing samples. Samples can be obtained from human subjects using swaps (e.g. saliva, nasopharyngeal or mid-turbinate) as exemplified in 102. Swabs can be directly placed into the conditions sufficient to lyse the cells within the sample as exemplified in 106. No RNA isolation is needed thus (1) reducing the time it takes to perform the assay, (2) increasing sensitivity, and (3) reducing the cost of materials for the assay. Samples can optionally be stored in a buffer (e.g. TE buffer) and lysed at a later time within days of obtaining the sample as in steps 126, 128. To facilitate accurate and sensitive identification of a viral nucleic acid, the lysed sample can be spiked with a synthetic nucleic acid that can benchmark subsequent nucleic acid processing and the resulting sequence information (exemplified in 108). The synthetic nucleic acid comprises sequences able to be amplified by virus specific primers, but has a known sequence that can be readily identified in the sequence output as different from the viral target. The samples are partitioned and processed in microtiter plates that enable scales between 1 and 32 384-well plates, enabling testing of at least 384-12, 288 samples.

Nucleic acid processing and library prep is then performed by reverse transcription and PCR, as exemplified in 110, within the partition/well. The primers used for detection comprises sequences complementary to (a) the target of interest (a small region from coronavirus or influenza for instance); (b) a human target (controls to make sure there is some human sequence there; e.g., RPP30 (RNaseP), which is used by the CDC in their standard qPCR based tests; and (c) an internal synthetic RNA molecule (as noted above) to ensure that the target assay amplifies, and to quantify the target, allowing for example normalization of reads from the pathogen sequences. Amplification by PCR is performed to endpoint and followed by sequencing. Endpoint PCR and the synthetic template add a level of normalization to avoid expensive normalization steps. The design of primers used for target amplification allows for the addition of indices that allow sample deconvolution and the identification of which sample comprised a positive sequencing read for a viral sequence.

The samples are subsequently sequenced to identify barcoded sequences and the presence of viral target reads. Reads are bioinformatically processed to gauge sequencing data positive or negative for a viral vector and viral load. It is possible to further develop the assay to sequence polymorphic regions and determine pathogen strain. This can be achieved by comparing the ratio of target pathogen amplicons, to human target amplicon, to spike in amplicon.

Example 2—Detection of SARS-COV RNA in a Sample

Figure 2A:
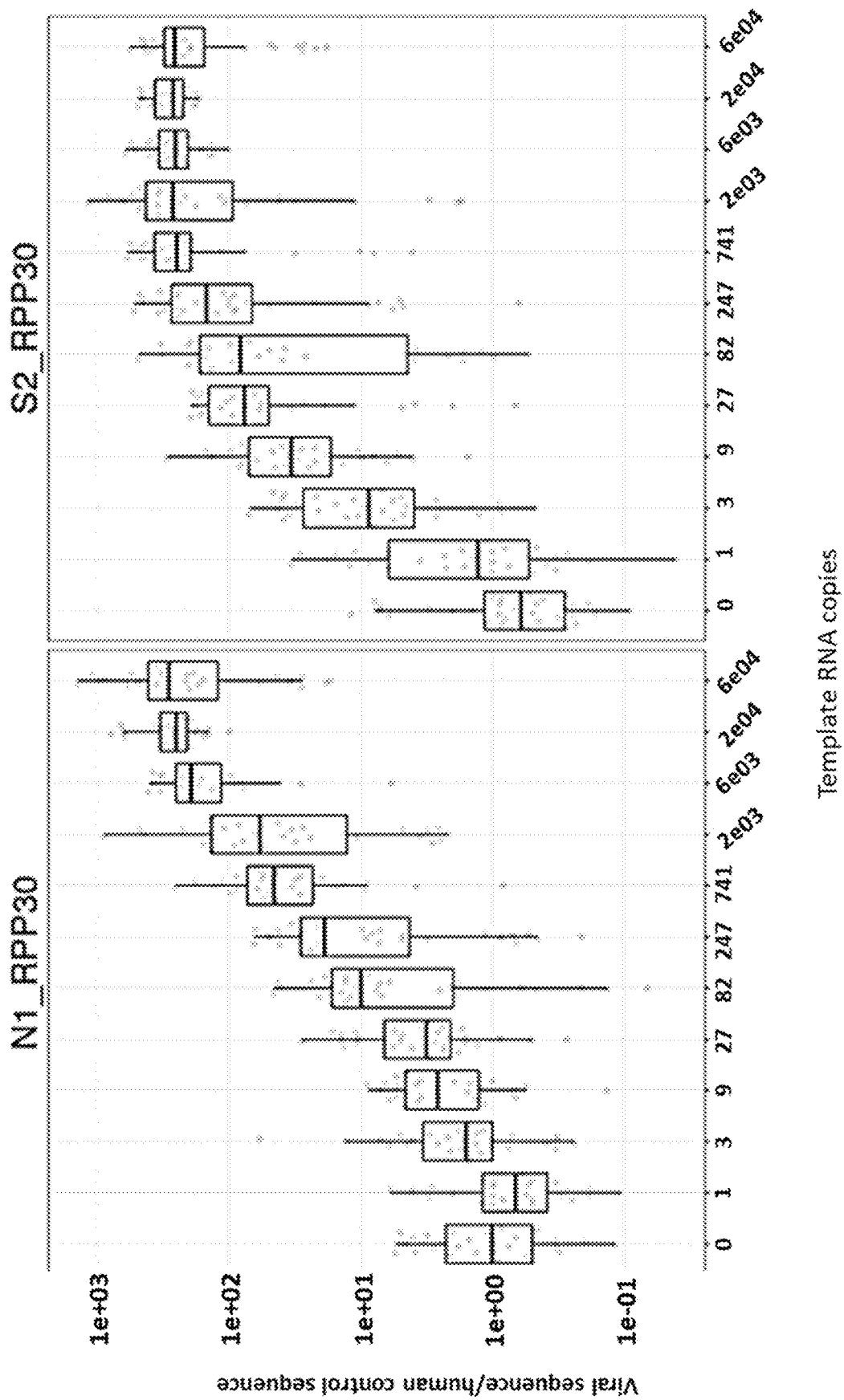
FIGS. 2A and 2B illustrates data demonstrating the detection of SARS-COV-2 nucleic acids in a sample.
Figure 2B:
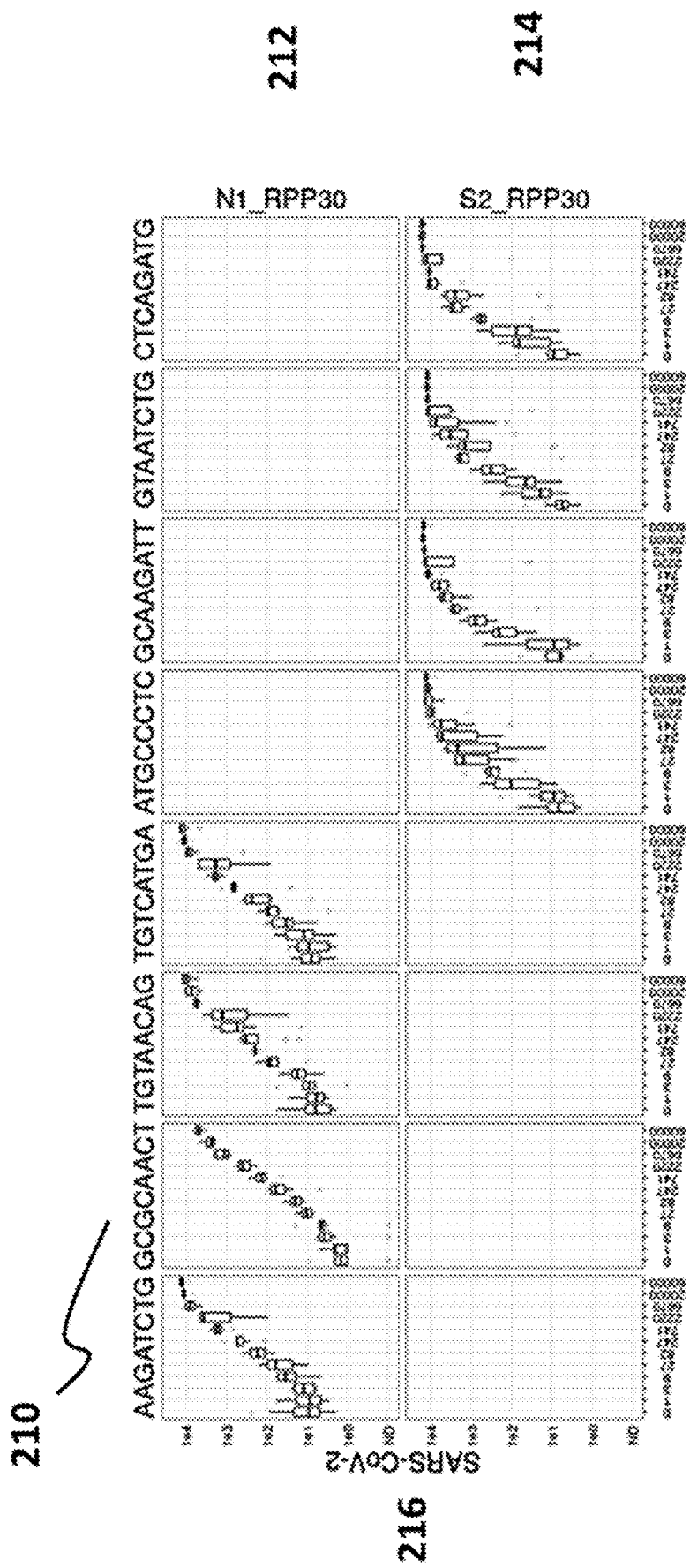

Samples comprising SARS-COV-2 RNA were analyzed using the methods disclosed herein. Samples comprised a defined copy number of a SARS-COV-2 RNA molecule. Primers targeting the N1 region (nucleocapsid) and subunit S2 region were used for detecting the SARS-CoV-2 RNA molecule. Resulting sequencing products were compared against human RRP30 RNA. SARS-COV: RRP30 as a function of copy number was analyzed for reach target region 206, 216 (FIG. 2A-B). Surprisingly, targeting subunit S2 resulted in distinguishable detection within samples comprising 3 copies of the SARS-COV-2 RNA molecule. Targeting N1 demonstrated distinguishable detection at copy numbers 2-5 times higher than that of S2, but with acceptable sensitivity. FIG. 2B demonstrates the analysis of different primer sequences 210 complementary to the N1 locus and S2 locus. Detection was dependent on primer sequences for both N1 and S2 targets. Across all primers tested, targeting S2 demonstrated distinguishable detection at copy numbers 2-5 times fewer than that of N1, conferring that targeting S2 provides higher resolution analysis for the detection of SARS-COV RNA in a sample.

Example 3—Viral Diagnosis by Amplification and Sequencing

Described herein is one example of an amplification and sequencing protocol for use with the methods described herein. Samples in lysis buffer may be heated before addition of QRT-PCR reaction (e.g., 75° C. for 10 minutes).

QRT-PCR Reaction Setup with Individual Reactions run in 20 μL total volume; 7 μL of sample lysate; 10 μL Luna® Universal One-Step Reaction Mix; 1 μL Enzyme Mix; 400 nM viral nucleic acid target primers; housekeeping primers (e.g., RPP3 100 nM no adaptor, 50 nM with adaptor); 100 copies of synthetic nucleic acid (same priming regions as the viral target). By reducing the concentration of RPP3 primers with sequencing adaptors while keeping overall RPP3 primer concentration high, low amounts of RPP3 are still detected while limiting the number of sequencing reads dedicated to host RNA. Additionally, this also attenuated primer dimer formation.

Cycling protocol 55° C. for 30 min (reverse transcription reaction); 95C° For 1 min, followed by 40 cycles of {95° C. for 10 seconds and 60° for 30 seconds).

Pool 5 μL of each well for sequencing and purify using the [AxyPrep PCR Clean-up Kit](www.fishersci.com/shop/products/axygen-axyprep-mag-pcr-clean-up-kits/14223152). Quantify libraries with the [deNovix dsDNA High Sensitivity Fluorescent Assay Kit](www.denovix.com/denovix-dsdna-assays/). Can add up to 50% PhiX control library DNA. Sequence the libraries using Illumina dual-indexed single-read sequencing on a NextSeq and MiSeq.

Below is a table (Table 1) describing primer pairs that can be used in the methods of detecting viral infection described herein. Primer pairs are disclosed as pairs, for example, 0325_octN1_F and 0326_octN1_R describe a primer pair designed to produce amplification of viral nucleic acid. Sequences described below may also comprise sequencing adaptor and or index sequences.

TABLE 1

| SEQUENCE ID NO. | name | seq |
| --- | --- | --- |
| SEQ ID NO: 100 | o258_o258 SARS-CoV-2 N1 luc index 1 primer | tggggtcTTACACGGCGATCTTGCC |
| SEQ ID NO: 101 | o259_o259 SARS-CoV-2 N1 oct index 1 primer | gggtcAACGTGTCGGCATGGATTCT |
| SEQ ID NO: 102 | o260_o260 SARS-CoV-2 N1 luc read 1 | AGTTACATTCACGCCAGTTGTGtctggt |
| SEQ ID NO: 103 | o261_o261 SARS-CoV-2 N2 luc read 1 | AGTTACATTCACGCCAGTTGTGgcg |
| SEQ ID NO: 104 | o262_o262 SARS-CoV-2 N2 luc index 1 primer | gtttgtaaTTACACGGCGATCTTGCC |
| SEQ ID NO: 105 | o263_o263 RP luc index 1 primer | GTCCAAATCTTTACACGGCGATCTTGCC |
| SEQ ID NO: 106 | o264_o264 RP luc read 1 | AGTTACATTCACGCCAGTTGTGGAGC |
| SEQ ID NO: 107 | o265_o265 T7prom-SARS-CoV-2 N | TAATACGACTCACTATAGggtctgataatggacc ccaaaatca |
| SEQ ID NO: 108 | o266_o266_SARS-CoV-2 N R | ttaggcctgagttgagtcagc |
| SEQ ID NO: 109 | o267_index A01 N1_F | CAAGCAGAAGACGGCATACGAGAT GTTCTATC GACCCCAAAATCAGCGAAAT |
| SEQ ID NO: 110 | o268_index plate 1 N1_R | AATGATACGGCGACCACCGAGATCTACAC AAGATCTG TCTGGTTACTGCCAGTTGAATCTG |
| SEQ ID NO: 111 | o269_index A01 N2_F | CAAGCAGAAGACGGCATACGAGAT GTTCTATC TTACAAACATTGGCCGCAAA |
| SEQ ID NO: 112 | o270_index plate 1 N2_R | AATGATACGGCGACCACCGAGATCTACAC AAGATCTG GCGCGACATTCCGAAGAA |
| SEQ ID NO: 113 | o271_index A01 RP_F | CAAGCAGAAGACGGCATACGAGAT GTTCTATC AGATTTGGACCTGCGAGCG |
| SEQ ID NO: 114 | o272_index plate 1 RP_R | AATGATACGGCGACCACCGAGATCTACAC AAGATCTG GAGCGGCTGTCTCCACAAGT |
| SEQ ID NO: 115 | o273_index A01 HKU_N_F | CAAGCAGAAGACGGCATACGAGAT GTTCTATC TAATCAGACAAGGAACTGATTA |
| SEQ ID NO: 116 | o274_index plate 1 HKU_N_R | AATGATACGGCGACCACCGAGATCTACAC AAGATCTG CGAAGGTGTGACTTCCATG |

TABLE 1-continued

| SEQUENCE ID NO. | name | seq |
|---|---|---|
| SEQ ID NO: 117 | o275_index A01 octN1_F | AATGATACGGCGACCACCGAGATCTACAC AAGATCTGGATCAAAACAACGTCGGCCC |
| SEQ ID NO: 118 | o276_index plate 1 octN1_R | CAAGCAGAAGACGGCATACGAGAT GTTCTATCCCATGTTGAGTGAGAGCGGT |
| SEQ ID NO: 119 | o277_index A01 octN2_F | AATGATACGGCGACCACCGAGATCTACAC AAGATCTGTGGACCCCAAAATCAGCGAA |
| SEQ ID NO: 120 | o278_index plate 1 octN2_R | CAAGCAGAAGACGGCATACGAGAT GTTCTATCACTGCGTTCTCCATTCTGGTT |
| SEQ ID NO: 121 | o279_index A01 octN3_F | AATGATACGGCGACCACCGAGATCTACAC AAGATCTGCAGCGTTCTTCGGAATGTCG |
| SEQ ID NO: 122 | o280_index plate 1 octN3_R | CAAGCAGAAGACGGCATACGAGAT GTTCTATCGCACCTGTGTAGGTCAACCA |
| SEQ ID NO: 123 | o281_index A01 octN4_F | AATGATACGGCGACCACCGAGATCTACAC AAGATCTGGAAATGCACCCCGCATTACG |
| SEQ ID NO: 124 | o282_index plate 1 octN4_R | CAAGCAGAAGACGGCATACGAGAT GTTCTATCCCCACTGCGTTCTCCATTCT |
| SEQ ID NO: 125 | o283_index A01 octN5_F | AATGATACGGCGACCACCGAGATCTACAC AAGATCTGGTCTTGGTTCACCGCTCTCA |
| SEQ ID NO: 126 | o284_index plate 1 octN5_R | CAAGCAGAAGACGGCATACGAGAT GTTCTATCTTGGAACGCCTTGTCCTCG |
| SEQ ID NO: 127 | o285_index A01 octN6_F | AATGATACGGCGACCACCGAGATCTACAC AAGATCTGGCAGTCAAGCCTCTTCTCGT |
| SEQ ID NO: 128 | o286_index plate 1 octN6_R | CAAGCAGAAGACGGCATACGAGAT GTTCTATCGAAGTTCCCCTACTGCTGCC |
| SEQ ID NO: 129 | o287_index A01 octN7_F | AATGATACGGCGACCACCGAGATCTACAC AAGATCTGCGTTTGGTGGACCCTCAGAT |
| SEQ ID NO: 130 | o288_index plate 1 octN7_R | CAAGCAGAAGACGGCATACGAGAT GTTCTATCGACGTTGTTTTGATCGCGCC |
| SEQ ID NO: 131 | o289_index A01 octN8_F | AATGATACGGCGACCACCGAGATCTACAC AAGATCTGAAGGCCAACAACAACAAGGC |
| SEQ ID NO: 132 | o290_index plate 1 octN8_R | CAAGCAGAAGACGGCATACGAGAT GTTCTATCGGCAGTACGTTTTTGCCGAG |
| SEQ ID NO: 133 | o291_index A01 octN9_F | AATGATACGGCGACCACCGAGATCTACAC AAGATCTGACCAGAATGGAGAACGCAGT |
| SEQ ID NO: 134 | o292_index plate 1 octN9_R | CAAGCAGAAGACGGCATACGAGAT GTTCTATCCGGTGAACCAAGACGCAGTA |
| SEQ ID NO: 135 | o293_index A01 octN10_F | AATGATACGGCGACCACCGAGATCTACAC AAGATCTGCCGCATTACGTTTGGTGGAC |
| SEQ ID NO: 136 | o294_index plate 1 octN10_R | CAAGCAGAAGACGGCATACGAGAT GTTCTATCGGCCGACGTTGTTTTGATCG |
| SEQ ID NO: 137 | o295_index A01 octN11_F | AATGATACGGCGACCACCGAGATCTACAC AAGATCTGGCCTCGGCAAAAACGTACTG |
| SEQ ID NO: 138 | o296_index plate 1 octN11_R | CAAGCAGAAGACGGCATACGAGAT GTTCTATCTTGTTCTGGACCACGTCTGC |
| SEQ ID NO: 139 | o297_index A01 octN12_F | AATGATACGGCGACCACCGAGATCTACAC AAGATCTGAATTCCCTCGAGGACAAGGC |
| SEQ ID NO: 140 | o298_index plate 1 octN12_R | CAAGCAGAAGACGGCATACGAGAT GTTCTATCTCGTCTGGTAGCTCTTCGGT |
| SEQ ID NO: 141 | o299_index A01 octN13_F | AATGATACGGCGACCACCGAGATCTACAC AAGATCTGGCTTCAGCGTTCTTCGGAAT |

TABLE 1-continued

| SEQUENCE ID NO. | name | seq |
|---|---|---|
| SEQ ID NO: 142 | o300_index plate 1 octN13_R | CAAGCAGAAGACGGCATACGAGAT GTTCTATCTGGCACCTGTGTAGGTCAAC |
| SEQ ID NO: 143 | o301_SARS-CoV-2_IBS_RdRP2_F | AATGATACGGCGACCACCGAGATCTACAC AAGATCTGAGAATAGAGCTCGCACCGTA |
| SEQ ID NO: 144 | o302_SARS-CoV-2_IBS_RdRP2_R | CAAGCAGAAGACGGCATACGAGAT GTTCTATC CTCCTCTAGTGGCGGCTATT |
| SEQ ID NO: 145 | o303_SARS-CoV-2_IBS_s2_F | AATGATACGGCGACCACCGAGATCTACAC AAGATCTG GCTGGTGCTGCAGCTTATTA |
| SEQ ID NO: 146 | o304_SARS-CoV-2_IBS_s2_R | CAAGCAGAAGACGGCATACGAGAT GTTCTATC AGGGTCAAGTGCACAGTCTA |
| SEQ ID NO: 147 | o305_SARS-CoV-2_IBS_E2_F | AATGATACGGCGACCACCGAGATCTACAC AAGATCTG TTCGGAAGAGACAGGTACGTTA |
| SEQ ID NO: 148 | o306_SARS-CoV-2_IBS_E2_R | CAAGCAGAAGACGGCATACGAGAT GTTCTATC AGCAGTACGCACACAATCG |
| SEQ ID NO: 149 | o307_SARS-CoV-2_IBS_N1_F | AATGATACGGCGACCACCGAGATCTACAC AAGATCTG CAATGCTGCAATCGTGCTAC |
| SEQ ID NO: 150 | o308_SARS-CoV-2_IBS_N1_R | CAAGCAGAAGACGGCATACGAGAT GTTCTATC GTTGCGACTACGTGATGAGG |
| SEQ ID NO: 151 | o309_RNAse P Forward Primer | AGATTTGGACCTGCGAGCG |
| SEQ ID NO: 152 | o310_RNAse P Reverse Primer | GAGCGGCTGTCTCCACAAGT |
| SEQ ID NO: 153 | o311_SARS-CoV-2_IBS_RdRP2_F | AGAATAGAGCTCGCACCGTA |
| SEQ ID NO: 154 | o312_SARS-CoV-2_IBS_RdRP2_R | CTCCTCTAGTGGCGGCTATT |
| SEQ ID NO: 155 | o313_SARS-CoV-2_IBS_s2_F | GCTGGTGCTGCAGCTTATTA |
| SEQ ID NO: 156 | o314_SARS-CoV-2_IBS_s2_R | AGGGTCAAGTGCACAGTCTA |
| SEQ ID NO: 157 | o315_SARS-CoV-2_IBS_E2_F | TTCGGAAGAGACAGGTACGTTA |
| SEQ ID NO: 158 | o316_SARS-CoV-2_IBS_E2_R | AGCAGTACGCACACAATCG |
| SEQ ID NO: 159 | o317_SARS-CoV-2_IBS_N1_F | CAATGCTGCAATCGTGCTAC |
| SEQ ID NO: 160 | o318_SARS-CoV-2_IBS_N1_R | GTTGCGACTACGTGATGAGG |
| SEQ ID NO: 161 | o319_2019-nCoV_N1 Forward Primer | GACCCCAAAATCAGCGAAAT |
| SEQ ID NO: 162 | o320_2019-nCoV_N1 Reverse Primer | TCTGGTTACTGCCAGTTGAATCTG |
| SEQ ID NO: 163 | o321_2019-nCoV_N2 Forward Primer | TTACAAACATTGGCCGCAAA |
| SEQ ID NO: 164 | o322_2019-nCoV_N2 Reverse Primer | GCGCGACATTCCGAAGAA |
| SEQ ID NO: 165 | o323_HKU-NF | TAATCAGACAAGGAACTGATTA |
| SEQ ID NO: 166 | o324_HKU-NR | CGAAGGTGTGACTTCCATG |
| SEQ ID NO: 167 | o325_octN1_F | GATCAAAACAACGTCGGCCC |
| SEQ ID NO: 168 | o326_octN1_R | CCATGTTGAGTGAGAGCGGT |
| SEQ ID NO: 169 | o327_octN2_F | TGGACCCCAAAATCAGCGAA |
| SEQ ID NO: 170 | o328_octN2_R | ACTGCGTTCTCCATTCTGGTT |
| SEQ ID NO: 171 | o329_octN3_F | CAGCGTTCTTCGGAATGTCG |

TABLE 1-continued

| SEQUENCE ID NO. | name | seq |
|---|---|---|
| SEQ ID NO: 172 | o330_octN3_R | GCACCTGTGTAGGTCAACCA |
| SEQ ID NO: 173 | o331_octN4_F | GAAATGCACCCCGCATTACG |
| SEQ ID NO: 174 | o332_octN4_R | CCCACTGCGTTCTCCATTCT |
| SEQ ID NO: 175 | o333_octN5_F | GTCTTGGTTCACCGCTCTCA |
| SEQ ID NO: 176 | o334_octN5_R | TTGGAACGCCTTGTCCTCG |
| SEQ ID NO: 177 | o335_octN6_F | GCAGTCAAGCCTCTTCTCGT |
| SEQ ID NO: 178 | o336_octN6_R | GAAGTTCCCCTACTGCTGCC |
| SEQ ID NO: 179 | o337_octN7_F | CGTTTGGTGGACCCTCAGAT |
| SEQ ID NO: 180 | o338_octN7_R | GACGTTGTTTTGATCGCGCC |
| SEQ ID NO: 181 | o339_octN8_F | AAGGCCAACAACAACAAGGC |
| SEQ ID NO: 182 | o340_octN8_R | GGCAGTACGTTTTTGCCGAG |
| SEQ ID NO: 183 | o341_octN9_F | ACCAGAATGGAGAACGCAGT |
| SEQ ID NO: 184 | o342_octN9_R | CGGTGAACCAAGACGCAGTA |
| SEQ ID NO: 185 | o343_octN10_F | CCGCATTACGTTTGGTGGAC |
| SEQ ID NO: 186 | o344_octN10_R | GGCCGACGTTGTTTTGATCG |
| SEQ ID NO: 187 | o345_octN11_F | GCCTCGGCAAAAACGTACTG |
| SEQ ID NO: 188 | o346_octN11_R | TTGTTCTGGACCACGTCTGC |
| SEQ ID NO: 189 | o347_octN12_F | AATTCCCTCGAGGACAAGGC |
| SEQ ID NO: 190 | o348_octN12_R | TCGTCTGGTAGCTCTTCGGT |
| SEQ ID NO: 191 | o349_octN13_F | GCTTCAGCGTTCTTCGGAAT |
| SEQ ID NO: 192 | o350_octN13_R | TGGCACCTGTGTAGGTCAAC |
| SEQ ID NO: 193 | o351_skpp15-1-F_RPP30 | GGGTCACGCGTAGGA GTTCTATC AGATTTGGACCTGCGAGCG |
| SEQ ID NO: 194 | o352_skpp15-1-R_RPP30 | GTTCCGCAGCCACAC AAGATCTG GAGCGGCTGTCTCCACAAGT |
| SEQ ID NO: 195 | o353_skpp15-2-F_RPP30 | CGCGTCGAGTAGGGT GTTCTATC AGATTTGGACCTGCGAGCG |
| SEQ ID NO: 196 | o354_skpp15-2-R_RPP30 | GCCGTGTGAAGCTGG AAGATCTG GAGCGGCTGTCTCCACAAGT |
| SEQ ID NO: 197 | o355_skpp15-3-F_RPP30 | CGATCGCCCTTGGTG GTTCTATC AGATTTGGACCTGCGAGCG |
| SEQ ID NO: 198 | o356_skpp15-3-R_RPP30 | GGTTTAGCCGGCGTG AAGATCTG GAGCGGCTGTCTCCACAAGT |
| SEQ ID NO: 199 | o357_skpp15-4-F_RPP30 | GGTCGAGCCGGAACT GTTCTATC AGATTTGGACCTGCGAGCG |
| SEQ ID NO: 200 | o358_skpp15-4-R_RPP30 | GGATGCGCACCCAGA AAGATCTG GAGCGGCTGTCTCCACAAGT |
| SEQ ID NO: 201 | o359_skpp15-5-F_RPP30 | TCCCGGCGTTGTCCT GTTCTATC AGATTTGGACCTGCGAGCG |
| SEQ ID NO: 202 | o360_skpp15-5-R_RPP30 | GCTCCGTCACTGCCCAAGATCTG GAGCGGCTGTCTCCACAAGT |
| SEQ ID NO: 203 | o361_skpp15-6-F_RPP30 | CGCAGGGTCCAGAGTGTTCTATC AGATTTGGACCTGCGAGCG |

TABLE 1-continued

| SEQUENCE ID NO. | name | seq |
|---|---|---|
| SEQ ID NO: 204 | o362_skpp15-6-R_RPP30 | GTTCGCGCGAAGGAA AAGATCTG GAGCGGCTGTCTCCACAAGT |
| SEQ ID NO: 205 | o363_skpp-1-F s_RPP30 | ATATAGATGCCGTCCTAGCG GTTCTATC AGATTTGGACCTGCGAGCG |
| SEQ ID NO: 206 | o364_skpp-1-R s_RPP30 | AAGTATCTTTCCTGTGCCCA AAGATCTG GAGCGGCTGTCTCCACAAGT |
| SEQ ID NO: 207 | o365_skpp-2-F s_RPP30 | CCCTTTAATCAGATGCGTCG GTTCTATC AGATTTGGACCTGCGAGCG |
| SEQ ID NO: 208 | o366_skpp-2-R s_RPP30 | TGGTAGTAATAAGGGCGACC AAGATCTG GAGCGGCTGTCTCCACAAGT |
| SEQ ID NO: 209 | o367_skpp-3-F s_RPP30 | TTGGTCATGTGCTTTTCGTT GTTCTATC AGATTTGGACCTGCGAGCG |
| SEQ ID NO: 210 | o368_skpp-3-R s_RPP30 | AGGGGTATCGGATACTCAGA AAGATCTG GAGCGGCTGTCTCCACAAGT |
| SEQ ID NO: 211 | o369_skpp-4-F s_RPP30 | GGGTGGGTAAATGGTAATGC GTTCTATC AGATTTGGACCTGCGAGCG |
| SEQ ID NO: 212 | o370_skpp-4-R s_RPP30 | ATCGATTCCCCGGATATAGC AAGATCTG GAGCGGCTGTCTCCACAAGT |
| SEQ ID NO: 213 | o371_skpp-5-F s_RPP30 | TCCGACGGGGAGTATATACT GTTCTATC AGATTTGGACCTGCGAGCG |
| SEQ ID NO: 214 | o372_skpp-5-R s_RPP30 | TACTAACTGCTTCAGGCCAA AAGATCTG GAGCGGCTGTCTCCACAAGT |
| SEQ ID NO: 215 | o373_skpp-6-F s_RPP30 | CATGTTTAGGAACGCTACCG GTTCTATC AGATTTGGACCTGCGAGCG |
| SEQ ID NO: 216 | o374_skpp-6-R s_RPP30 | AATAATCTCCGTTCCCTCCC AAGATCTG GAGCGGCTGTCTCCACAAGT |
| SEQ ID NO: 217 | o375_T7prom o267_o268 spike_F | TAATACGACTCACTATAGggaccccaaaatcagc gaaatgcaccccgcattacgAAACCAggaccctc agattcaactg |
| SEQ ID NO: 218 | o376_T7prom o267_o268 spike_R | cgcagtattattgggtaaacct |
| SEQ ID NO: 219 | o377_T7prom o303_o304 spike_F | TAATACGACTCACTATAGggctggtgctgcagct tattatgtgggtATAGAAcaacctaggacttttc tattaa |
| SEQ ID NO: 220 | o378_T7prom o303_o304 spike_R | aacgtacactttgtttctgagagagg |
| SEQ ID NO: 221 | o379_A1_N1_F | CAAGCAGAAGACGGCATACGAGATGAGTCTTCGA CCCCAAAATCAGCGAAAT |
| SEQ ID NO: 222 | o380_A2_N1_F | CAAGCAGAAGACGGCATACGAGATGTTCTATCGA CCCCAAAATCAGCGAAAT |
| SEQ ID NO: 223 | o381_A3_N1_F | CAAGCAGAAGACGGCATACGAGATTGGGCCAAGA CCCCAAAATCAGCGAAAT |
| SEQ ID NO: 224 | o382_A4_N1_F | CAAGCAGAAGACGGCATACGAGATATTGTTGGGA CCCCAAAATCAGCGAAAT |
| SEQ ID NO: 225 | o383_A5_N1_F | CAAGCAGAAGACGGCATACGAGATTCCCGTTGGA CCCCAAAATCAGCGAAAT |
| SEQ ID NO: 226 | o384_A6_N1_F | CAAGCAGAAGACGGCATACGAGATACACACTTGA CCCCAAAATCAGCGAAAT |
| SEQ ID NO: 227 | o385_A7_N1_F | CAAGCAGAAGACGGCATACGAGATCCATTCCAGA CCCCAAAATCAGCGAAAT |
| SEQ ID NO: 228 | o386_A8_N1_F | CAAGCAGAAGACGGCATACGAGATCTAACGGGGA CCCCAAAATCAGCGAAAT |

TABLE 1-continued

| SEQUENCE ID NO. | name | seq |
| --- | --- | --- |
| SEQ ID NO: 229 | o387_A9_N1_F | CAAGCAGAAGACGGCATACGAGATCCATAGGAGA CCCCAAAATCAGCGAAAT |
| SEQ ID NO: 230 | o388_A10_N1_F | CAAGCAGAAGACGGCATACGAGATCAGTGTAGGA CCCCAAAATCAGCGAAAT |
| SEQ ID NO: 231 | o389_A11_N1_F | CAAGCAGAAGACGGCATACGAGATGATTCTCAGA CCCCAAAATCAGCGAAAT |
| SEQ ID NO: 232 | o390_A1_N1_F | CAAGCAGAAGACGGCATACGAGATCCTTCTTAGA CCCCAAAATCAGCGAAAT |
| SEQ ID NO: 233 | o391_B1_N1_F | CAAGCAGAAGACGGCATACGAGATTCTAAGACGA CCCCAAAATCAGCGAAAT |
| SEQ ID NO: 234 | o392_B2_N1_F | CAAGCAGAAGACGGCATACGAGATGCGGCATAGA CCCCAAAATCAGCGAAAT |
| SEQ ID NO: 235 | o393_B3_N1_F | CAAGCAGAAGACGGCATACGAGATATTGACGAGA CCCCAAAATCAGCGAAAT |
| SEQ ID NO: 236 | o394_B4_N1_F | CAAGCAGAAGACGGCATACGAGATGCTCCTGAGA CAAGCAGAAGACGGCATACGAGATGCAATCCTGA |
| SEQ ID NO: 237 | o395_B5_N1_F | CCCCAAAATCAGCGAAATS CCCCAAAATCAGCGAAAT |
| SEQ ID NO: 238 | o396_B6_N1_F | CAAGCAGAAGACGGCATACGAGATATGTCGTTGA CCCCAAAATCAGCGAAAT |
| SEQ ID NO: 239 | o397_B7_N1_F | CAAGCAGAAGACGGCATACGAGATTTCTCGGCGA CCCCAAAATCAGCGAAAT |
| SEQ ID NO: 240 | o398_B8_N1_F | CAAGCAGAAGACGGCATACGAGATCAGGGCTAGA CCCCAAAATCAGCGAAAT |
| SEQ ID NO: 241 | o399_B9_N1_F | CAAGCAGAAGACGGCATACGAGATAGCCAAGCGA CCCCAAAATCAGCGAAAT |
| SEQ ID NO: 242 | o400_B10_N1_F | CAAGCAGAAGACGGCATACGAGATAAGCCTGAGA CCCCAAAATCAGCGAAAT |
| SEQ ID NO: 243 | o401_B11_N1_F | CAAGCAGAAGACGGCATACGAGATCTACAGAGGA CCCCAAAATCAGCGAAAT |
| SEQ ID NO: 244 | o402_B12_N1_F | CAAGCAGAAGACGGCATACGAGATCGTAGTCGGA CCCCAAAATCAGCGAAAT |
| SEQ ID NO: 245 | o403_C1_N1_F | CAAGCAGAAGACGGCATACGAGATTTCTGCTCGA CCCCAAAATCAGCGAAAT |
| SEQ ID NO: 246 | o404_C2_N1_F | CAAGCAGAAGACGGCATACGAGATGTGCACACGA CCCCAAAATCAGCGAAAT |
| SEQ ID NO: 247 | o405_C3_N1_F | CAAGCAGAAGACGGCATACGAGATAAAGCTCAGA CCCCAAAATCAGCGAAAT |
| SEQ ID NO: 248 | o406_C4_N1_F | CAAGCAGAAGACGGCATACGAGATGACCTCAGGA CCCCAAAATCAGCGAAAT |
| SEQ ID NO: 249 | o407_C5_N1_F | CAAGCAGAAGACGGCATACGAGATCTTTCCAAGA CCCCAAAATCAGCGAAAT |
| SEQ ID NO: 250 | o408_C6_N1_F | CAAGCAGAAGACGGCATACGAGATTCTTGGCTGA CCCCAAAATCAGCGAAAT |
| SEQ ID NO: 251 | o409_C7_N1_F | CAAGCAGAAGACGGCATACGAGATCGCGTCTAGA CCCCAAAATCAGCGAAAT |
| SEQ ID NO: 252 | o410_C8_N1_F | CAAGCAGAAGACGGCATACGAGATTCGCGCTAGA CCCCAAAATCAGCGAAAT |
| SEQ ID NO: 253 | o411_C9_N1_F | CAAGCAGAAGACGGCATACGAGATATCCATTCGA CCCCAAAATCAGCGAAAT |

TABLE 1-continued

| SEQUENCE ID NO. | name | seq |
|---|---|---|
| SEQ ID NO: 254 | o412_C10_N1_F | CAAGCAGAAGACGGCATACGAGATGCCCAGTAGACCCCAAAATCAGCGAAAT |
| SEQ ID NO: 255 | o413_C11_N1_F | CAAGCAGAAGACGGCATACGAGATTACCGACGGACCCCAAAATCAGCGAAAT |
| SEQ ID NO: 256 | o414_C12_N1_F | CAAGCAGAAGACGGCATACGAGATTCCATACGGACCCCAAAATCAGCGAAAT |
| SEQ ID NO: 257 | o415_D1_N1_F | CAAGCAGAAGACGGCATACGAGATAACATGTCGACCCCAAAATCAGCGAAAT |
| SEQ ID NO: 258 | o416_D2_N1_F | CAAGCAGAAGACGGCATACGAGATCGACTATAGACCCCAAAATCAGCGAAAT |
| SEQ ID NO: 259 | o417_D3_N1_F | CAAGCAGAAGACGGCATACGAGATACCCAAGGACCCCAAAATCAGCGAAAT |
| SEQ ID NO: 260 | o418_D4_N1_F | CAAGCAGAAGACGGCATACGAGATATCGATCGACCCCAAAATCAGCGAAAT |
| SEQ ID NO: 261 | o419_D5_N1_F | CAAGCAGAAGACGGCATACGAGATGTTGGATGGACCCCAAAATCAGCGAAAT |
| SEQ ID NO: 262 | o420_D6_N1_F | CAAGCAGAAGACGGCATACGAGATCTATGTGAGACCCCAAAATCAGCGAAAT |
| SEQ ID NO: 263 | o421_D7_N1_F | CAAGCAGAAGACGGCATACGAGATTATTTCGCGACCCCAAAATCAGCGAAAT |
| SEQ ID NO: 264 | o422_D8_N1_F | CAAGCAGAAGACGGCATACGAGATCCATGTATGACCCCAAAATCAGCGAAAT |
| SEQ ID NO: 265 | o423_D9_N1_F | CAAGCAGAAGACGGCATACGAGATGCCACGTTGACCCCAAAATCAGCGAAAT |
| SEQ ID NO: 266 | o424_D10_N1_F | CAAGCAGAAGACGGCATACGAGATGTCGTGTAGACCCCAAAATCAGCGAAAT |
| SEQ ID NO: 267 | o425_D11_N1_F | CAAGCAGAAGACGGCATACGAGATTAAAGTCGGACCCCAAAATCAGCGAAAT |
| SEQ ID NO: 268 | o426_D12_N1_F | CAAGCAGAAGACGGCATACGAGATCTTCGGACGACCCCAAAATCAGCGAAAT |
| SEQ ID NO: 269 | o427_E1_N1_F | CAAGCAGAAGACGGCATACGAGATGCACTCTCGACCCCAAAATCAGCGAAAT |
| SEQ ID NO: 270 | o428_E2_N1_F | CAAGCAGAAGACGGCATACGAGATTCAGATACGACCCCAAAATCAGCGAAAT |
| SEQ ID NO: 271 | o429_E3_N1_F | CAAGCAGAAGACGGCATACGAGATCAGTCCCTGACCCCAAAATCAGCGAAAT |
| SEQ ID NO: 272 | o430_E4_N1_F | CAAGCAGAAGACGGCATACGAGATGCCCTAACGACCCCAAAATCAGCGAAAT |
| SEQ ID NO: 273 | o431_E5_N1_F | CAAGCAGAAGACGGCATACGAGATCTGCATCAGACCCCAAAATCAGCGAAAT |
| SEQ ID NO: 274 | o432_E6_N1_F | CAAGCAGAAGACGGCATACGAGATCGGTATCGGACCCCAAAATCAGCGAAAT |
| SEQ ID NO: 275 | o433_E7_N1_F | CAAGCAGAAGACGGCATACGAGATAAGTATGGGACCCCAAAATCAGCGAAAT |
| SEQ ID NO: 276 | o434_E8_N1_F | CAAGCAGAAGACGGCATACGAGATATTCGCGCGACCCCAAAATCAGCGAAAT |
| SEQ ID NO: 277 | o435_E9_N1_F | CAAGCAGAAGACGGCATACGAGATATCAAGGTGACCCCAAAATCAGCGAAAT |
| SEQ ID NO: 278 | o436_E10_N1_F | CAAGCAGAAGACGGCATACGAGATTTGTGCATGACCCCAAAATCAGCGAAAT |

TABLE 1-continued

| SEQUENCE ID NO. | name | seq |
|---|---|---|
| SEQ ID NO: 279 | o437_E11_N1_F | CAAGCAGAAGACGGCATACGAGATCTGTGCTGGACCCCAAAATCAGCGAAAT |
| SEQ ID NO: 280 | o438_E12_N1_F | CAAGCAGAAGACGGCATACGAGATGTCCGTAGGACCCCAAAATCAGCGAAAT |
| SEQ ID NO: 281 | o439_F1_N1_F | CAAGCAGAAGACGGCATACGAGATGTTCAAGAGACCCCAAAATCAGCGAAAT |
| SEQ ID NO: 282 | o440_F2_N1_F | CAAGCAGAAGACGGCATACGAGATCACCGTTCGACCCCAAAATCAGCGAAAT |
| SEQ ID NO: 283 | o441_F3_N1_F | CAAGCAGAAGACGGCATACGAGATCGAGTTGAGACCCCAAAATCAGCGAAAT |
| SEQ ID NO: 284 | o442_F4_N1_F | CAAGCAGAAGACGGCATACGAGATGAGCACGAGACCCCAAAATCAGCGAAAT |
| SEQ ID NO: 285 | o443_F5_N1_F | CAAGCAGAAGACGGCATACGAGATAGTTCGTGGACCCCAAAATCAGCGAAAT |
| SEQ ID NO: 286 | o444_F6_N1_F | CAAGCAGAAGACGGCATACGAGATCATCAACTGACCCCAAAATCAGCGAAAT |
| SEQ ID NO: 287 | o445_F7_N1_F | CAAGCAGAAGACGGCATACGAGATCGAGATCTGACCCCAAAATCAGCGAAAT |
| SEQ ID NO: 288 | o446_F8_N1_F | CAAGCAGAAGACGGCATACGAGATTGGCCAGAGACCCCAAAATCAGCGAAAT |
| SEQ ID NO: 289 | o447_F9_N1_F | CAAGCAGAAGACGGCATACGAGATTTCACCATGACCCCAAAATCAGCGAAAT |
| SEQ ID NO: 290 | o448_F10_N1_F | CAAGCAGAAGACGGCATACGAGATGAATGCATGACCCCAAAATCAGCGAAAT |
| SEQ ID NO: 291 | o449_F11_N1_F | CAAGCAGAAGACGGCATACGAGATTGGACCCTGACCCCAAAATCAGCGAAAT |
| SEQ ID NO: 292 | o450_F12_N1_F | CAAGCAGAAGACGGCATACGAGATGATAGCACGACCCCAAAATCAGCGAAAT |
| SEQ ID NO: 293 | o451_G1_N1_F | CAAGCAGAAGACGGCATACGAGATACGACGACGACCCCAAAATCAGCGAAAT |
| SEQ ID NO: 294 | o452_G2_N1_F | CAAGCAGAAGACGGCATACGAGATCTCAGTATGACCCCAAAATCAGCGAAAT |
| SEQ ID NO: 295 | o453_G3_N1_F | CAAGCAGAAGACGGCATACGAGATCTTAGCTAGACCCCAAAATCAGCGAAAT |
| SEQ ID NO: 296 | o454_G4_N1_F | CAAGCAGAAGACGGCATACGAGATCTGTTTACGACCCCAAAATCAGCGAAAT |
| SEQ ID NO: 297 | o455_G5_N1_F | CAAGCAGAAGACGGCATACGAGATTGTCCCACGACCCCAAAATCAGCGAAAT |
| SEQ ID NO: 298 | o456_G6_N1_F | CAAGCAGAAGACGGCATACGAGATTCCTGAGGGACCCCAAAATCAGCGAAAT |
| SEQ ID NO: 299 | o457_G7_N1_F | CAAGCAGAAGACGGCATACGAGATTAGTCCAGACCCCAAAATCAGCGAAAT |
| SEQ ID NO: 300 | o458_G8_N1_F | CAAGCAGAAGACGGCATACGAGATCATGACTCGACCCCAAAATCAGCGAAAT |
| SEQ ID NO: 301 | o459_G9_N1_F | CAAGCAGAAGACGGCATACGAGATGTAAGCGCGACCCCAAAATCAGCGAAAT |
| SEQ ID NO: 302 | o460_G10_N1_F | CAAGCAGAAGACGGCATACGAGATAACCCAGTGACCCCAAAATCAGCGAAAT |
| SEQ ID NO: 303 | o461_G11_N1_F | CAAGCAGAAGACGGCATACGAGATTTTGAGGGGACCCCAAAATCAGCGAAAT |

TABLE 1-continued

| SEQUENCE ID NO. | name | seq |
| --- | --- | --- |
| SEQ ID NO: 304 | o462_G12_N1_F | CAAGCAGAAGACGGCATACGAGATAGCCGACAGACCCCAAAATCAGCGAAAT |
| SEQ ID NO: 305 | o463_H1_N1_F | CAAGCAGAAGACGGCATACGAGATAAACCCGCGACCCCAAAATCAGCGAAAT |
| SEQ ID NO: 306 | o464_H2_N1_F | CAAGCAGAAGACGGCATACGAGATGTAGGGCTGACCCCAAAATCAGCGAAAT |
| SEQ ID NO: 307 | o465_H3_N1_F | CAAGCAGAAGACGGCATACGAGATAGACGATTGACCCCAAAATCAGCGAAAT |
| SEQ ID NO: 308 | o466_H4_N1_F | CAAGCAGAAGACGGCATACGAGATAGGATGATGACCCCAAAATCAGCGAAAT |
| SEQ ID NO: 309 | o467_H5_N1_F | CAAGCAGAAGACGGCATACGAGATATAATGGCGACCCCAAAATCAGCGAAAT |
| SEQ ID NO: 310 | o468_H6_N1_F | CAAGCAGAAGACGGCATACGAGATCTTGGCGTGACCCCAAAATCAGCGAAAT |
| SEQ ID NO: 311 | o469_H7_N1_F | CAAGCAGAAGACGGCATACGAGATAGCTGTGCGACCCCAAAATCAGCGAAAT |
| SEQ ID NO: 312 | o470_H8_N1_F | CAAGCAGAAGACGGCATACGAGATGAGTCCAAGACCCCAAAATCAGCGAAAT |
| SEQ ID NO: 313 | o471_H9_N1_F | CAAGCAGAAGACGGCATACGAGATGAATACCAGACCCCAAAATCAGCGAAAT |
| SEQ ID NO: 314 | o472_H10_N1_F | CAAGCAGAAGACGGCATACGAGATAGGAGCTTGACCCCAAAATCAGCGAAAT |
| SEQ ID NO: 315 | o473_H11_N1_F | CAAGCAGAAGACGGCATACGAGATGTGACTTAGACCCCAAAATCAGCGAAAT |
| SEQ ID NO: 316 | o474_H12_N1_F | CAAGCAGAAGACGGCATACGAGATTTTGGAACGACCCCAAAATCAGCGAAAT |
| SEQ ID NO: 317 | o475_A1_S2_R | CAAGCAGAAGACGGCATACGAGATGAGTCTTCAGGGTCAAGTGCACAGTCTA |
| SEQ ID NO: 318 | o476_A2_S2_R | CAAGCAGAAGACGGCATACGAGATGTTCTATCAGGGTCAAGTGCACAGTCTA |
| SEQ ID NO: 319 | o477_A3_S2_R | CAAGCAGAAGACGGCATACGAGATTGGGCCAAAGGGTCAAGTGCACAGTCTA |
| SEQ ID NO: 320 | o478_A4_S2_R | CAAGCAGAAGACGGCATACGAGATATTGTTGGAGGGTCAAGTGCACAGTCTA |
| SEQ ID NO: 321 | o479_A5_S2_R | CAAGCAGAAGACGGCATACGAGATTCCCGTTGAGGGTCAAGTGCACAGTCTA |
| SEQ ID NO: 322 | o480_A6_S2_R | CAAGCAGAAGACGGCATACGAGATACACACTTAGGGTCAAGTGCACAGTCTA |
| SEQ ID NO: 323 | o481_A7_S2_R | CAAGCAGAAGACGGCATACGAGATCCATTCCAAGGGTCAAGTGCACAGTCTA |
| SEQ ID NO: 324 | o482_A8_S2_R | CAAGCAGAAGACGGCATACGAGATCTAACGGGAGGGTCAAGTGCACAGTCTA |
| SEQ ID NO: 325 | o483_A9_S2_R | CAAGCAGAAGACGGCATACGAGATCCATAGGAAGGGTCAAGTGCACAGTCTA |
| SEQ ID NO: 326 | o484_A10_S2_R | CAAGCAGAAGACGGCATACGAGATCAGTGTAGAGGGTCAAGTGCACAGTCTA |
| SEQ ID NO: 327 | o485_A11_S2_R | CAAGCAGAAGACGGCATACGAGATGATTCTCAAGGGTCAAGTGCACAGTCTA |
| SEQ ID NO: 328 | o486_A12_S2_R | CAAGCAGAAGACGGCATACGAGATCCTTCTTAAGGGTCAAGTGCACAGTCTA |

TABLE 1-continued

| SEQUENCE ID NO. | name | seq |
|---|---|---|
| SEQ ID NO: 329 | o487_B1_S2_R | CAAGCAGAAGACGGCATACGAGATTCTAAGACAGGGTCAAGTGCACAGTCTA |
| SEQ ID NO: 330 | o488_B2_S2_R | CAAGCAGAAGACGGCATACGAGATGCGGCATAAGGGTCAAGTGCACAGTCTA |
| SEQ ID NO: 331 | o489_B3_S2_R | CAAGCAGAAGACGGCATACGAGATATTGACGAAGGGTCAAGTGCACAGTCTA |
| SEQ ID NO: 332 | o490_B4_S2_R | CAAGCAGAAGACGGCATACGAGATGCTCCTGAAGGGTCAAGTGCACAGTCTA |
| SEQ ID NO: 333 | o491_B5_S2_R | CAAGCAGAAGACGGCATACGAGATGCAATCCTAGGGTCAAGTGCACAGTCTA |
| SEQ ID NO: 334 | o492_B6_S2_R | CAAGCAGAAGACGGCATACGAGATATGTCGTTAGGGTCAAGTGCACAGTCTA |
| SEQ ID NO: 335 | o493_B7_S2_R | CAAGCAGAAGACGGCATACGAGATTTCTCGGCAGGGTCAAGTGCACAGTCTA |
| SEQ ID NO: 336 | o494_B8_S2_R | CAAGCAGAAGACGGCATACGAGATCAGGGCTAAGGGTCAAGTGCACAGTCTA |
| SEQ ID NO: 337 | o495_B9_S2_R | CAAGCAGAAGACGGCATACGAGATAGCCAAGCAGGGTCAAGTGCACAGTCTA |
| SEQ ID NO: 338 | o496_B10_S2_R | CAAGCAGAAGACGGCATACGAGATAAGCCTGAAGGGTCAAGTGCACAGTCTA |
| SEQ ID NO: 339 | o497_B11_S2_R | CAAGCAGAAGACGGCATACGAGATCTACAGAGAGGGTCAAGTGCACAGTCTA |
| SEQ ID NO: 340 | o498_B12_S2_R | CAAGCAGAAGACGGCATACGAGATCGTAGTCGAGGGTCAAGTGCACAGTCTA |
| SEQ ID NO: 341 | o499_C1_S2_R | CAAGCAGAAGACGGCATACGAGATTTCTGCTCAGGGTCAAGTGCACAGTCTA |
| SEQ ID NO: 342 | o500_C2_S2_R | CAAGCAGAAGACGGCATACGAGATGTGCACACAGGGTCAAGTGCACAGTCTA |
| SEQ ID NO: 343 | o501_C3_S2_R | CAAGCAGAAGACGGCATACGAGATAAAGCTCAAGGGTCAAGTGCACAGTCTA |
| SEQ ID NO: 344 | o502_C4_S2_R | CAAGCAGAAGACGGCATACGAGATGACCTCAGAGGGTCAAGTGCACAGTCTA |
| SEQ ID NO: 345 | o503_C5_S2_R | CAAGCAGAAGACGGCATACGAGATCTTTCCAAAGGGTCAAGTGCACAGTCTA |
| SEQ ID NO: 346 | o504_C6_S2_R | CAAGCAGAAGACGGCATACGAGATTCTTGGCTAGGGTCAAGTGCACAGTCTA |
| SEQ ID NO: 347 | o505_C7_S2_R | CAAGCAGAAGACGGCATACGAGATCGCGTCTAAGGGTCAAGTGCACAGTCTA |
| SEQ ID NO: 348 | o506_C8_S2_R | CAAGCAGAAGACGGCATACGAGATTCGCGCTAAGGGTCAAGTGCACAGTCTA |
| SEQ ID NO: 349 | o507_C9_S2_R | CAAGCAGAAGACGGCATACGAGATATCCATTCAGGGTCAAGTGCACAGTCTA |
| SEQ ID NO: 350 | o508_C10_S2_R | CAAGCAGAAGACGGCATACGAGATGCCCAGTAAGGGTCAAGTGCACAGTCTA |
| SEQ ID NO: 351 | o509_C11_S2_R | CAAGCAGAAGACGGCATACGAGATTACCGACGAGGGTCAAGTGCACAGTCTA |
| SEQ ID NO: 352 | o510_C12_S2_R | CAAGCAGAAGACGGCATACGAGATTCCATACGAGGGTCAAGTGCACAGTCTA |
| SEQ ID NO: 353 | o511_D1_S2_R | CAAGCAGAAGACGGCATACGAGATAACATGTCAGGGTCAAGTGCACAGTCTA |

TABLE 1-continued

| SEQUENCE ID NO. | name | seq |
|---|---|---|
| SEQ ID NO: 354 | o512_D2_S2_R | CAAGCAGAAGACGGCATACGAGATCGACTATAAGGGTCAAGTGCACAGTCTA |
| SEQ ID NO: 355 | o513_D3_S2_R | CAAGCAGAAGACGGCATACGAGATACCCAAAGAGGGTCAAGTGCACAGTCTA |
| SEQ ID NO: 356 | o514_D4_S2_R | CAAGCAGAAGACGGCATACGAGATATCGATCGAGGGTCAAGTGCACAGTCTA |
| SEQ ID NO: 357 | o515_D5_S2_R | CAAGCAGAAGACGGCATACGAGATGTTGGATGAGGGTCAAGTGCACAGTCTA |
| SEQ ID NO: 358 | o516_D6_S2_R | CAAGCAGAAGACGGCATACGAGATCTATGTGAAGGGTCAAGTGCACAGTCTA |
| SEQ ID NO: 359 | o517_D7_S2_R | CAAGCAGAAGACGGCATACGAGATTATTTCGCAGGGTCAAGTGCACAGTCTA |
| SEQ ID NO: 360 | o518_D8_S2_R | CAAGCAGAAGACGGCATACGAGATCCATGTATAGGGTCAAGTGCACAGTCTA |
| SEQ ID NO: 361 | o519_D9_S2_R | CAAGCAGAAGACGGCATACGAGATGCCACGTTAGGGTCAAGTGCACAGTCTA |
| SEQ ID NO: 362 | o520_D10_S2_R | CAAGCAGAAGACGGCATACGAGATGTCGTGTAAGGGTCAAGTGCACAGTCTA |
| SEQ ID NO: 363 | o521_D11_S2_R | CAAGCAGAAGACGGCATACGAGATTAAAGTCGAGGGTCAAGTGCACAGTCTA |
| SEQ ID NO: 364 | o522_D12_S2_R | CAAGCAGAAGACGGCATACGAGATCTTCGGACAGGGTCAAGTGCACAGTCTA |
| SEQ ID NO: 365 | o523_E1_s2_R | CAAGCAGAAGACGGCATACGAGATGCACTCTCAGGGTCAAGTGCACAGTCTA |
| SEQ ID NO: 366 | o524_E2_S2_R | CAAGCAGAAGACGGCATACGAGATTCAGATACAGGGTCAAGTGCACAGTCTA |
| SEQ ID NO: 367 | o525_E3_S2_R | CAAGCAGAAGACGGCATACGAGATCAGTCCCTAGGGTCAAGTGCACAGTCTA |
| SEQ ID NO: 368 | o526_E4_S2_R | CAAGCAGAAGACGGCATACGAGATGCCCTAACAGGGTCAAGTGCACAGTCTA |
| SEQ ID NO: 369 | o527_E5_S2_R | CAAGCAGAAGACGGCATACGAGATCTGCATCAAGGGTCAAGTGCACAGTCTA |
| SEQ ID NO: 370 | o528_E6_S2_R | CAAGCAGAAGACGGCATACGAGATCGGTATCGAGGGTCAAGTGCACAGTCTA |
| SEQ ID NO: 371 | o529_E7_s2_R | CAAGCAGAAGACGGCATACGAGATAAGTATGGAGGGTCAAGTGCACAGTCTA |
| SEQ ID NO: 372 | o530_E8_S2_R | CAAGCAGAAGACGGCATACGAGATATTCGCGCAGGGTCAAGTGCACAGTCTA |
| SEQ ID NO: 373 | o531_E9_S2_R | CAAGCAGAAGACGGCATACGAGATATCAAGGTAGGGTCAAGTGCACAGTCTA |
| SEQ ID NO: 374 | o532_E10_S2_R | CAAGCAGAAGACGGCATACGAGATTTGTGCATAGGGTCAAGTGCACAGTCTA |
| SEQ ID NO: 375 | o533_E11_s2_R | CAAGCAGAAGACGGCATACGAGATCTGTGCTGAGGGTCAAGTGCACAGTCTA |
| SEQ ID NO: 376 | o534_E12_S2_R | CAAGCAGAAGACGGCATACGAGATGTCCGTAGAGGGTCAAGTGCACAGTCTA |
| SEQ ID NO: 377 | o535_F1_s2_R | CAAGCAGAAGACGGCATACGAGATGTTCAAGAAGGGTCAAGTGCACAGTCTA |
| SEQ ID NO: 378 | o536_F2_S2_R | CAAGCAGAAGACGGCATACGAGATCACCGTTCAGGGTCAAGTGCACAGTCTA |

TABLE 1-continued

| SEQUENCE ID NO. | name | seq |
| --- | --- | --- |
| SEQ ID NO: 379 | o537_F3_S2_R | CAAGCAGAAGACGGCATACGAGATCGAGTTGAAGGGTCAAGTGCACAGTCTA |
| SEQ ID NO: 380 | o538_F4_S2_R | CAAGCAGAAGACGGCATACGAGATGAGCACGAAGGGTCAAGTGCACAGTCTA |
| SEQ ID NO: 381 | o539_F5_s2_R | CAAGCAGAAGACGGCATACGAGATAGTTCGTGAGGGTCAAGTGCACAGTCTA |
| SEQ ID NO: 382 | o540_F6_S2_R | CAAGCAGAAGACGGCATACGAGATCATCAACTAGGGTCAAGTGCACAGTCTA |
| SEQ ID NO: 383 | o541_F7_S2_R | CAAGCAGAAGACGGCATACGAGATCGAGATCTAGGGTCAAGTGCACAGTCTA |
| SEQ ID NO: 384 | o542_F8_S2_R | CAAGCAGAAGACGGCATACGAGATTGGCCAGAAGGGTCAAGTGCACAGTCTA |
| SEQ ID NO: 385 | o543_F9_S2_R | CAAGCAGAAGACGGCATACGAGATTTCACCATAGGGTCAAGTGCACAGTCTA |
| SEQ ID NO: 386 | o544_F10_S2_R | CAAGCAGAAGACGGCATACGAGATGAATGCATAGGGTCAAGTGCACAGTCTA |
| SEQ ID NO: 387 | o545_F11_S2_R | CAAGCAGAAGACGGCATACGAGATTGGACCCTAGGGTCAAGTGCACAGTCTA |
| SEQ ID NO: 388 | o546_F12_S2_R | CAAGCAGAAGACGGCATACGAGATGATAGCACAGGGTCAAGTGCACAGTCTA |
| SEQ ID NO: 389 | o547_G1_S2_R | CAAGCAGAAGACGGCATACGAGATACGACGACAGGGTCAAGTGCACAGTCTA |
| SEQ ID NO: 390 | o548_G2_S2_R | CAAGCAGAAGACGGCATACGAGATCTCAGTATAGGGTCAAGTGCACAGTCTA |
| SEQ ID NO: 391 | o549_G3_S2_R | CAAGCAGAAGACGGCATACGAGATCTTAGCTAAGGGTCAAGTGCACAGTCTA |
| SEQ ID NO: 392 | o550_G4_S2_R | CAAGCAGAAGACGGCATACGAGATCTGTTTACAGGGTCAAGTGCACAGTCTA |
| SEQ ID NO: 393 | o551_G5_S2_R | CAAGCAGAAGACGGCATACGAGATTGTCCCACAGGGTCAAGTGCACAGTCTA |
| SEQ ID NO: 394 | o552_G6_S2_R | CAAGCAGAAGACGGCATACGAGATTCCTGAGGAGGGTCAAGTGCACAGTCTA |
| SEQ ID NO: 395 | o553_G7_S2_R | CAAGCAGAAGACGGCATACGAGATTAGTTCCAAGGGTCAAGTGCACAGTCTA |
| SEQ ID NO: 396 | o554_G8_S2_R | CAAGCAGAAGACGGCATACGAGATCATGACTCAGGGTCAAGTGCACAGTCTA |
| SEQ ID NO: 397 | o555_G9_s2_R | CAAGCAGAAGACGGCATACGAGATGTAAGCGCAGGGTCAAGTGCACAGTCTA |
| SEQ ID NO: 398 | o556_G10_S2_R | CAAGCAGAAGACGGCATACGAGATAACCCAGTAGGGTCAAGTGCACAGTCTA |
| SEQ ID NO: 399 | o557_G11_s2_R | CAAGCAGAAGACGGCATACGAGATTTTGAGGGAGGGTCAAGTGCACAGTCTA |
| SEQ ID NO: 400 | o558_G12_S2_R | CAAGCAGAAGACGGCATACGAGATAGCCGACAAGGGTCAAGTGCACAGTCTA |
| SEQ ID NO: 401 | o559_H1_S2_R | CAAGCAGAAGACGGCATACGAGATAAACCCGCAGGGTCAAGTGCACAGTCTA |
| SEQ ID NO: 402 | o560_H2_S2_R | CAAGCAGAAGACGGCATACGAGATGTAGGGCTAGGGTCAAGTGCACAGTCTA |
| SEQ ID NO: 403 | o561_H3_S2_R | CAAGCAGAAGACGGCATACGAGATAGACGATTAGGGTCAAGTGCACAGTCTA |

TABLE 1-continued

| SEQUENCE ID NO. | name | seq |
|---|---|---|
| SEQ ID NO: 404 | o562_H4_S2_R | CAAGCAGAAGACGGCATACGAGATAGGATGATAGGGTCAAGTGCACAGTCTA |
| SEQ ID NO: 405 | o563_H5_s2_R | CAAGCAGAAGACGGCATACGAGATATAATGGCAGGGTCAAGTGCACAGTCTA |
| SEQ ID NO: 406 | o564_H6_S2_R | CAAGCAGAAGACGGCATACGAGATCTTGGCGTAGGGTCAAGTGCACAGTCTA |
| SEQ ID NO: 407 | o565_H7_s2_R | CAAGCAGAAGACGGCATACGAGATAGCTGTGCAGGGTCAAGTGCACAGTCTA |
| SEQ ID NO: 408 | o566_H8_S2_R | CAAGCAGAAGACGGCATACGAGATGAGTCCAAGGGTCAAGTGCACAGTCTA |
| SEQ ID NO: 409 | o567_H9_S2_R | CAAGCAGAAGACGGCATACGAGATGAATACCAAGGGTCAAGTGCACAGTCTA |
| SEQ ID NO: 410 | o568_H10_S2_R | CAAGCAGAAGACGGCATACGAGATAGGAGCTTAGGGTCAAGTGCACAGTCTA |
| SEQ ID NO: 411 | o569_H11_S2_R | CAAGCAGAAGACGGCATACGAGATGTGACTTAAGGGTCAAGTGCACAGTCTA |
| SEQ ID NO: 412 | o570_H12_S2_R | CAAGCAGAAGACGGCATACGAGATTTTGGAACAGGGTCAAGTGCACAGTCTA |
| SEQ ID NO: 413 | o571_plate1_N1_R | AATGATACGGCGACCACCGAGATCTACACAAGATCTGTCTGGTTACTGCCAGTTGAATCTG |
| SEQ ID NO: 414 | o572_plate2_N1_R | AATGATACGGCGACCACCGAGATCTACACTGTCATGATCTGGTTACTGCCAGTTGAATCTG |
| SEQ ID NO: 415 | o573_plate3_N1_R | AATGATACGGCGACCACCGAGATCTACACTGTAACAGTCTGGTTACTGCCAGTTGAATCTG |
| SEQ ID NO: 416 | o574_plate4_N1_R | AATGATACGGCGACCACCGAGATCTACACGCGCAACTTCTGGTTACTGCCAGTTGAATCTG |
| SEQ ID NO: 417 | o575_plate1_N1_R_shortP5 | AATGATACGGCGACCACCGATCGATGGCTCTGGTTACTGCCAGTTGAATCTG |
| SEQ ID NO: 418 | o576_plate2_N1_R_shortP5 | AATGATACGGCGACCACCGACATGGTTTTCTGGTTACTGCCAGTTGAATCTG |
| SEQ ID NO: 419 | o577_plate3_N1_R_shortP5 | AATGATACGGCGACCACCGAACGAAAGCTCTGGTTACTGCCAGTTGAATCTG |
| SEQ ID NO: 420 | o578_plate4_N1_R_shortP5 | AATGATACGGCGACCACCGAGCTCTGATTCTGGTTACTGCCAGTTGAATCTG |
| SEQ ID NO: 421 | o579_plate1_S2_F | AATGATACGGCGACCACCGAGATCTACACATGCCCTCGCTGGTGCTGCAGCTTATTA |
| SEQ ID NO: 422 | o580_plate2_S2_F | AATGATACGGCGACCACCGAGATCTACACCTCAGATGGCTGGTGCTGCAGCTTATTA |
| SEQ ID NO: 423 | o581_plate3_S2_F | AATGATACGGCGACCACCGAGATCTACACGTAATCTGGCTGGTGCTGCAGCTTATTA |
| SEQ ID NO: 424 | o582_plate4_S2_F | AATGATACGGCGACCACCGAGATCTACACGCAAGATTGCTGGTGCTGCAGCTTATTA |
| SEQ ID NO: 425 | o583_plate1_S2_F_shortP5 | AATGATACGGCGACCACCGAATACGCCAGCTGGTGCTGCAGCTTATTA |
| SEQ ID NO: 426 | o584_plate2_S2_F_shortP5 | AATGATACGGCGACCACCGAACCAGTCGGCTGGTGCTGCAGCTTATTA |
| SEQ ID NO: 427 | o585_plate3_S2_F_shortP5 | AATGATACGGCGACCACCGAAACACGGAGCTGGTGCTGCAGCTTATTA |
| SEQ ID NO: 428 | o586_plate4_S2_F_shortP5 | AATGATACGGCGACCACCGACTGCCTAGGCTGGTGCTGCAGCTTATTA |

TABLE 1-continued

| SEQUENCE ID NO. | name | seq |
|---|---|---|
| SEQ ID NO: 429 | o587_N1_read1 | tctggttactgccagttgaatctgagggtcc |
| SEQ ID NO: 430 | o588_N1_i7 | ggtgcatttcgctgattttggggtc |
| SEQ ID NO: 431 | o589_N1_i5 | ggaccctcagattcaactggcagtaaccaga |
| SEQ ID NO: 432 | o590_S2_read1 | gctggtgctgcagcttattatgtgggt |
| SEQ ID NO: 433 | o591_S2_i7 | agatgctgtagactgtgcacttgaccct |
| SEQ ID NO: 434 | o592_S2_i5 | acccacataataagctgcagcaccagc |
| SEQ ID NO: 435 | o593_RP_read1 | gagcggctgtctccacaagtccg |
| SEQ ID NO: 436 | o594_RP_i7 | acccgctcgcaggtccaaatctg |
| SEQ ID NO: 437 | o595_RP_i5 | cggacttgtggagacagccgctc |
| SEQ ID NO: 438 | o596_A1_RP_F | CAAGCAGAAGACGGCATACGAGATGAGTCTTCAGATTTGGACCTGCGAGCG |
| SEQ ID NO: 439 | o597_A2_RP_F | CAAGCAGAAGACGGCATACGAGATGTTCTATCAGATTTGGACCTGCGAGCG |
| SEQ ID NO: 440 | o598_A3_RP_F | CAAGCAGAAGACGGCATACGAGATTGGGCCAAGATTTGGACCTGCGAGCG |
| SEQ ID NO: 441 | o599_A4_RP_F | CAAGCAGAAGACGGCATACGAGATATTGTTGGAGATTTGGACCTGCGAGCG |
| SEQ ID NO: 442 | o600_A5_RP_F | CAAGCAGAAGACGGCATACGAGATTCCCGTTGAGATTTGGACCTGCGAGCG |
| SEQ ID NO: 443 | o601_A6_RP_F | CAAGCAGAAGACGGCATACGAGATACACACTTAGATTTGGACCTGCGAGCG |
| SEQ ID NO: 444 | o602_A7_RP_F | CAAGCAGAAGACGGCATACGAGATCCATTCCAAGATTTGGACCTGCGAGCG |
| SEQ ID NO: 445 | o603_A8_RP_F | CAAGCAGAAGACGGCATACGAGATCTAACGGGAGATTTGGACCTGCGAGCG |
| SEQ ID NO: 446 | o604_A9_RP_F | CAAGCAGAAGACGGCATACGAGATCCATAGGAAGATTTGGACCTGCGAGCG |
| SEQ ID NO: 447 | o605_A10_RP_F | CAAGCAGAAGACGGCATACGAGATCAGTGTAGAGATTTGGACCTGCGAGCG |
| SEQ ID NO: 448 | o606_A11_RP_F | CAAGCAGAAGACGGCATACGAGATGATTCTCAAGATTTGGACCTGCGAGCG |
| SEQ ID NO: 449 | o607_A12_RP_F | CAAGCAGAAGACGGCATACGAGATCCTTCTTAAGATTTGGACCTGCGAGCG |
| SEQ ID NO: 450 | o608_B1_RP_F | CAAGCAGAAGACGGCATACGAGATTCTAAGACAGATTTGGACCTGCGAGCG |
| SEQ ID NO: 451 | o609_B2_RP_F | CAAGCAGAAGACGGCATACGAGATGCGGCATAAGATTTGGACCTGCGAGCG |
| SEQ ID NO: 452 | o610_B3_RP_F | CAAGCAGAAGACGGCATACGAGATATTGACGAAGATTTGGACCTGCGAGCG |
| SEQ ID NO: 453 | o611_B4_RP_F | CAAGCAGAAGACGGCATACGAGATGCTCCTGAAGATTTGGACCTGCGAGCG |
| SEQ ID NO: 454 | o612_B5_RP_F | CAAGCAGAAGACGGCATACGAGATGCAATCCTAGATTTGGACCTGCGAGCG |
| SEQ ID NO: 455 | o613_B6_RP_F | CAAGCAGAAGACGGCATACGAGATATGTCGTTAGATTTGGACCTGCGAGCG |
| SEQ ID NO: 456 | o614_B7_RP_F | CAAGCAGAAGACGGCATACGAGATTTCTCGGCAGATTTGGACCTGCGAGCG |

TABLE 1-continued

| SEQUENCE ID NO. | name | seq |
|---|---|---|
| SEQ ID NO: 457 | o615_B8_RP_F | CAAGCAGAAGACGGCATACGAGATCAGGGCTAAGATTTGGACCTGCGAGCG |
| SEQ ID NO: 458 | o616_B9_RP_F | CAAGCAGAAGACGGCATACGAGATAGCCAAGCAGATTTGGACCTGCGAGCG |
| SEQ ID NO: 459 | o617_B10_RP_F | CAAGCAGAAGACGGCATACGAGATAAGCCTGAAGATTTGGACCTGCGAGCG |
| SEQ ID NO: 460 | o618_B11_RP_F | CAAGCAGAAGACGGCATACGAGATCTACAGAGAGATTTGGACCTGCGAGCG |
| SEQ ID NO: 461 | o619_B12_RP_F | CAAGCAGAAGACGGCATACGAGATCGTAGTCGAGATTTGGACCTGCGAGCG |
| SEQ ID NO: 462 | o620_C1_RP_F | CAAGCAGAAGACGGCATACGAGATTTCTGCTCAGATTTGGACCTGCGAGCG |
| SEQ ID NO: 463 | o621_C2_RP_F | CAAGCAGAAGACGGCATACGAGATGTGCACACAGATTTGGACCTGCGAGCG |
| SEQ ID NO: 464 | o622_C3_RP_F | CAAGCAGAAGACGGCATACGAGATAAAGCTCAAGATTTGGACCTGCGAGCG |
| SEQ ID NO: 465 | o623_C4_RP_F | CAAGCAGAAGACGGCATACGAGATGACCTCAGAGATTTGGACCTGCGAGCG |
| SEQ ID NO: 466 | o624_C5_RP_F | CAAGCAGAAGACGGCATACGAGATCTTTCCAAAGATTTGGACCTGCGAGCG |
| SEQ ID NO: 467 | o625_C6_RP_F | CAAGCAGAAGACGGCATACGAGATTCTTGGCTAGATTTGGACCTGCGAGCG |
| SEQ ID NO: 468 | o626_C7_RP_F | CAAGCAGAAGACGGCATACGAGATCGCGTCTAAGATTTGGACCTGCGAGCG |
| SEQ ID NO: 469 | o627_C8_RP_F | CAAGCAGAAGACGGCATACGAGATTCGCGCTAAGATTTGGACCTGCGAGCG |
| SEQ ID NO: 470 | o628_C9_RP_F | CAAGCAGAAGACGGCATACGAGATATCCATTCAGATTTGGACCTGCGAGCG |
| SEQ ID NO: 471 | o629_C10_RP_F | CAAGCAGAAGACGGCATACGAGATGCCCAGTAAGATTTGGACCTGCGAGCG |
| SEQ ID NO: 472 | o630_C11_RP_F | CAAGCAGAAGACGGCATACGAGATTACCGACGAGATTTGGACCTGCGAGCG |
| SEQ ID NO: 473 | o631_C12_RP_F | CAAGCAGAAGACGGCATACGAGATTCCATACGAGATTTGGACCTGCGAGCG |
| SEQ ID NO: 474 | o632_D1_RP_F | CAAGCAGAAGACGGCATACGAGATAACATGTCAGATTTGGACCTGCGAGCG |
| SEQ ID NO: 475 | o633_D2_RP_F | CAAGCAGAAGACGGCATACGAGATCGACTATAAGATTTGGACCTGCGAGCG |
| SEQ ID NO: 476 | o634_D3_RP_F | CAAGCAGAAGACGGCATACGAGATACCCAAAGAGATTTGGACCTGCGAGCG |
| SEQ ID NO: 477 | o635_D4_RP_F | CAAGCAGAAGACGGCATACGAGATATCGATCGAGATTTGGACCTGCGAGCG |
| SEQ ID NO: 478 | o636_D5_RP_F | CAAGCAGAAGACGGCATACGAGATGTTGGATGAGATTTGGACCTGCGAGCG |
| SEQ ID NO: 479 | o637_D6_RP_F | CAAGCAGAAGACGGCATACGAGATCTATGTGAAGATTTGGACCTGCGAGCG |
| SEQ ID NO: 480 | o638_D7_RP_F | CAAGCAGAAGACGGCATACGAGATTATTTCGCAGATTTGGACCTGCGAGCG |
| SEQ ID NO: 481 | o639_D8_RP_F | CAAGCAGAAGACGGCATACGAGATCCATGTATAGATTTGGACCTGCGAGCG |

TABLE 1-continued

| SEQUENCE ID NO. | name | seq |
| --- | --- | --- |
| SEQ ID NO: 482 | o640_D9_RP_F | CAAGCAGAAGACGGCATACGAGATGCCACGTTAGATTTGGACCTGCGAGCG |
| SEQ ID NO: 483 | o641_D10_RP_F | CAAGCAGAAGACGGCATACGAGATGTCGTGTAAGATTTGGACCTGCGAGCG |
| SEQ ID NO: 484 | o642D11_RP_F | CAAGCAGAAGACGGCATACGAGATTAAAGTCGAGATTTGGACCTGCGAGCG |
| SEQ ID NO: 485 | o643_D12_RP_F | CAAGCAGAAGACGGCATACGAGATCTTCGGACAGATTTGGACCTGCGAGCG |
| SEQ ID NO: 486 | o644_E1_RP_F | CAAGCAGAAGACGGCATACGAGATGCACTCTCAGATTTGGACCTGCGAGCG |
| SEQ ID NO: 487 | o645_E2_RP_F | CAAGCAGAAGACGGCATACGAGATTCAGATACAGATTTGGACCTGCGAGCG |
| SEQ ID NO: 488 | o646_E3_RP_F | CAAGCAGAAGACGGCATACGAGATCAGTCCCTAGATTTGGACCTGCGAGCG |
| SEQ ID NO: 489 | o647_E4_RP_F | CAAGCAGAAGACGGCATACGAGATGCCCTAACAGATTTGGACCTGCGAGCG |
| SEQ ID NO: 490 | o648_E5_RP_F | CAAGCAGAAGACGGCATACGAGATCTGCATCAAGATTTGGACCTGCGAGCG |
| SEQ ID NO: 491 | o649_E6_RP_F | CAAGCAGAAGACGGCATACGAGATCGGTATCGAGATTTGGACCTGCGAGCG |
| SEQ ID NO: 492 | o650_E7_RP_F | CAAGCAGAAGACGGCATACGAGATAAGTATGGAGATTTGGACCTGCGAGCG |
| SEQ ID NO: 493 | o651_E8_RP_F | CAAGCAGAAGACGGCATACGAGATATTCGCGCAGATTTGGACCTGCGAGCG |
| SEQ ID NO: 494 | o652_E9_RP_F | CAAGCAGAAGACGGCATACGAGATATCAAGGTAGATTTGGACCTGCGAGCG |
| SEQ ID NO: 495 | o653_E10_RP_F | CAAGCAGAAGACGGCATACGAGATTTGTGCATAGATTTGGACCTGCGAGCG |
| SEQ ID NO: 496 | o654_E11_RP_F | CAAGCAGAAGACGGCATACGAGATCTGTGCTGAGATTTGGACCTGCGAGCG |
| SEQ ID NO: 497 | o655_E12_RP_F | CAAGCAGAAGACGGCATACGAGATGTCCGTAGAGATTTGGACCTGCGAGCG |
| SEQ ID NO: 498 | o656_F1_RP_F | CAAGCAGAAGACGGCATACGAGATGTTCAAGAAGATTTGGACCTGCGAGCG |
| SEQ ID NO: 499 | o657_F2_RP_F | CAAGCAGAAGACGGCATACGAGATCACCGTTCAGATTTGGACCTGCGAGCG |
| SEQ ID NO: 500 | o658_F3_RP_F | CAAGCAGAAGACGGCATACGAGATCGAGTTGAAGATTTGGACCTGCGAGCG |
| SEQ ID NO: 501 | o659_F4_RP_F | CAAGCAGAAGACGGCATACGAGATGAGCACGAAGATTTGGACCTGCGAGCG |
| SEQ ID NO: 502 | o660_F5_RP_F | CAAGCAGAAGACGGCATACGAGATAGTTCGTGAGATTTGGACCTGCGAGCG |
| SEQ ID NO: 503 | o661_F6_RP_F | CAAGCAGAAGACGGCATACGAGATCATCAACTAGATTTGGACCTGCGAGCG |
| SEQ ID NO: 504 | o662_F7_RP_F | CAAGCAGAAGACGGCATACGAGATCGAGATCTAGATTTGGACCTGCGAGCG |
| SEQ ID NO: 505 | o663_F8_RP_F | CAAGCAGAAGACGGCATACGAGATTGGCCAGAAGATTTGGACCTGCGAGCG |

TABLE 1-continued

| SEQUENCE ID NO. | name | seq |
|---|---|---|
| SEQ ID NO: 506 | o664_F9_RP_F | CAAGCAGAAGACGGCATACGAGATTTCACCATAGATTTGGACCTGCGAGCG |
| SEQ ID NO: 507 | o665_F10_RP_F | CAAGCAGAAGACGGCATACGAGATGAATGCATAGATTTGGACCTGCGAGCG |
| SEQ ID NO: 508 | o666_F11_RP_F | CAAGCAGAAGACGGCATACGAGATTGGACCCTAGATTTGGACCTGCGAGCG |
| SEQ ID NO: 509 | o667_F12_RP_F | CAAGCAGAAGACGGCATACGAGATGATAGCACAGATTTGGACCTGCGAGCG |
| SEQ ID NO: 510 | o668_G1_RP_F | CAAGCAGAAGACGGCATACGAGATACGACGACAGATTTGGACCTGCGAGCG |
| SEQ ID NO: 511 | o669_G2_RP_F | CAAGCAGAAGACGGCATACGAGATCTCAGTATAGATTTGGACCTGCGAGCG |
| SEQ ID NO: 512 | o670_G3_RP_F | CAAGCAGAAGACGGCATACGAGATCTTAGCTAAGATTTGGACCTGCGAGCG |
| SEQ ID NO: 513 | o671_G4_RP_F | CAAGCAGAAGACGGCATACGAGATCTGTTTACAGATTTGGACCTGCGAGCG |
| SEQ ID NO: 514 | o672_G5_RP_F | CAAGCAGAAGACGGCATACGAGATTGTCCCACAGATTTGGACCTGCGAGCG |
| SEQ ID NO: 515 | o673_G6_RP_F | CAAGCAGAAGACGGCATACGAGATTCCTGAGGAGATTTGGACCTGCGAGCG |
| SEQ ID NO: 516 | o674_G7_RP_F | CAAGCAGAAGACGGCATACGAGATTAGTTCCAAGATTTGGACCTGCGAGCG |
| SEQ ID NO: 517 | o675_G8_RP_F | CAAGCAGAAGACGGCATACGAGATCATGACTCAGATTTGGACCTGCGAGCG |
| SEQ ID NO: 518 | o676_G9_RP_F | CAAGCAGAAGACGGCATACGAGATGTAAGCGCAGATTTGGACCTGCGAGCG |
| SEQ ID NO: 519 | o677_G10_RP_F | CAAGCAGAAGACGGCATACGAGATAACCCAGTAGATTTGGACCTGCGAGCG |
| SEQ ID NO: 520 | o678_G11_RP_F | CAAGCAGAAGACGGCATACGAGATTTTGAGGGAGATTTGGACCTGCGAGCG |
| SEQ ID NO: 521 | o679_G12_RP_F | CAAGCAGAAGACGGCATACGAGATAGCCGACAAGATTTGGACCTGCGAGCG |
| SEQ ID NO: 522 | o680_H1_RP_F | CAAGCAGAAGACGGCATACGAGATAAACCCGCAGATTTGGACCTGCGAGCG |
| SEQ ID NO: 523 | o681_H2_RP_F | CAAGCAGAAGACGGCATACGAGATGTAGGGCTAGATTTGGACCTGCGAGCG |
| SEQ ID NO: 524 | o682_H3_RP_F | CAAGCAGAAGACGGCATACGAGATAGACGATTAGATTTGGACCTGCGAGCG |
| SEQ ID NO: 525 | o683_H4_RP_F | CAAGCAGAAGACGGCATACGAGATAGGATGATAGATTTGGACCTGCGAGCG |
| SEQ ID NO: 526 | o684_H5_RP_F | CAAGCAGAAGACGGCATACGAGATATAATGGCAGATTTGGACCTGCGAGCG |
| SEQ ID NO: 527 | o685_H6_RP_F | CAAGCAGAAGACGGCATACGAGATCTTGGCGTAGATTTGGACCTGCGAGCG |
| SEQ ID NO: 528 | o686_H7_RP_F | CAAGCAGAAGACGGCATACGAGATAGCTGTGCAGATTTGGACCTGCGAGCG |
| SEQ ID NO: 529 | o687_H8_RP_F | CAAGCAGAAGACGGCATACGAGATGAGTCCAAGATTTGGACCTGCGAGCG |
| SEQ ID NO: 530 | o688_H_RP_F | CAAGCAGAAGACGGCATACGAGATGAATACCAAGATTTGGACCTGCGAGCG |

TABLE 1-continued

| SEQUENCE ID NO. | name | seq |
|---|---|---|
| SEQ ID NO: 531 | o689_H10_RP_F | CAAGCAGAAGACGGCATACGAGATAGGAGCTTAGATTTGGACCTGCGAGCG |
| SEQ ID NO: 532 | o690_H11_RP_F | CAAGCAGAAGACGGCATACGAGATGTGACTTAAGATTTGGACCTGCGAGCG |
| SEQ ID NO: 533 | o691_H12_RP_F | CAAGCAGAAGACGGCATACGAGATTTTGGAACAGATTTGGACCTGCGAGCG |
| SEQ ID NO: 534 | o692_plate1_RP_R | AATGATACGGCGACCACCGAGATCTACACCTCTCTATGAGCGGCTGTCTCCACAAGT |
| SEQ ID NO: 535 | o693_plate2_RP_R | AATGATACGGCGACCACCGAGATCTACACTATCCTCTGAGCGGCTGTCTCCACAAGT |
| SEQ ID NO: 536 | o694_plate3_RP_R | AATGATACGGCGACCACCGAGATCTACACGTAAGGAGGAGCGGCTGTCTCCACAAGT |
| SEQ ID NO: 537 | o695_plate4_RP_R | AATGATACGGCGACCACCGAGATCTACACACTGCATAGAGCGGCTGTCTCCACAAGT |
| SEQ ID NO: 538 | o696_plate1_RP_R_shortP5 | AATGATACGGCGACCACCGAAAGGAGTAGAGCGGCTGTCTCCACAAGT |
| SEQ ID NO: 539 | o697_plate2_RP_R_shortP5 | AATGATACGGCGACCACCGACTAAGCCTGAGCGGCTGTCTCCACAAGT |
| SEQ ID NO: 540 | o698_plate3_RP_R_shortP5 | AATGATACGGCGACCACCGACGTCTAATGAGCGGCTGTCTCCACAAGT |
| SEQ ID NO: 541 | o699_plate4_RP_R_shortP5 | AATGATACGGCGACCACCGATCTCTCCGGAGCGGCTGTCTCCACAAGT |
| SEQ ID NO: 542 | o700_plate1_RP_R | AATGATACGGCGACCACCGAGATCTACACAAGATCTGGAGCGGCTGTCTCCACAAGT |
| SEQ ID NO: 543 | o701_plate2_RP_R | AATGATACGGCGACCACCGAGATCTACACTGTCATGAGAGCGGCTGTCTCCACAAGT |
| SEQ ID NO: 544 | o702_plate3_RP_R | AATGATACGGCGACCACCGAGATCTACACTGTAACAGGAGCGGCTGTCTCCACAAGT |
| SEQ ID NO: 545 | o703_plate4_RP_R | AATGATACGGCGACCACCGAGATCTACACGCGCAACTGAGCGGCTGTCTCCACAAGT |
| SEQ ID NO: 546 | o704_plate1_RP_R_shortP5 | AATGATACGGCGACCACCGATCGATGGCGAGCGGCTGTCTCCACAAGT |
| SEQ ID NO: 547 | o705_plate2_RP_R_shortP5 | AATGATACGGCGACCACCGACATGGTTTGAGCGGCTGTCTCCACAAGT |
| SEQ ID NO: 548 | o706_plate3_RP_R_shortP5 | AATGATACGGCGACCACCGAACGAAAGCGAGCGGCTGTCTCCACAAGT |
| SEQ ID NO: 549 | o707_plate4_RP_R_shortP5 | AATGATACGGCGACCACCGAGCTCTGATGAGCGGCTGTCTCCACAAGT |
| SEQ ID NO: 550 | o708_plate1_RP_R | AATGATACGGCGACCACCGAGATCTACACATGCCCTCGAGCGGCTGTCTCCACAAGT |
| SEQ ID NO: 551 | o709_plate2_RP_R | AATGATACGGCGACCACCGAGATCTACACCTCAGATGGAGCGGCTGTCTCCACAAGT |
| SEQ ID NO: 552 | o710_plate3_RP_R | AATGATACGGCGACCACCGAGATCTACACGTAATCTGGAGCGGCTGTCTCCACAAGT |
| SEQ ID NO: 553 | o711_plate4_RP_R | AATGATACGGCGACCACCGAGATCTACACGCAAGATTGAGCGGCTGTCTCCACAAGT |
| SEQ ID NO: 554 | o712_plate1_RP_R_shortP5 | AATGATACGGCGACCACCGAATACGCCAGAGCGGCTGTCTCCACAAGT |
| SEQ ID NO: 555 | o713_plate2_RP_R_shortP5 | AATGATACGGCGACCACCGAACCAGTCGGAGCGGCTGTCTCCACAAGT |

TABLE 1-continued

| SEQUENCE ID NO. | name | seq |
|---|---|---|
| SEQ ID NO: 556 | o714_plate3_RP_R_shortP5 | AATGATACGGCGACCACCGAAACACGGAGAGCGGCTGTCTCCACAAGT |
| SEQ ID NO: 557 | o715_plate4_RP_R_shortP5 | AATGATACGGCGACCACCGACTGCCTAGGAGCGGCTGTCTCCACAAGT |
| SEQ ID NO: 558 | o716_skpp15-1-F_N1 | GGGTCACGCGTAGGAGTTCTATCGACCCCAAAATCAGCGAAAT |
| SEQ ID NO: 559 | o717_skpp15-1-R_N1 | GTTCCGCAGCCACACAAGATCTGTCTGGTTACTGCCAGTTGAATCTG |
| SEQ ID NO: 560 | o718_skpp15-2-F_N1 | CGCGTCGAGTAGGGTGTTCTATCGACCCCAAAATCAGCGAAAT |
| SEQ ID NO: 561 | o719_skpp15-2-R_N1 | GCCGTGTGAAGCTGGAAGATCTGTCTGGTTACTGCCAGTTGAATCTG |
| SEQ ID NO: 562 | o720_skpp15-3-F_N1 | CGATCGCCCTTGGTGGTTCTATCGACCCCAAAATCAGCGAAAT |
| SEQ ID NO: 563 | o721_skpp15-3-R_N1 | GGTTTAGCCGGCGTGAAGATCTGTCTGGTTACTGCCAGTTGAATCTG |
| SEQ ID NO: 564 | o722_skpp15-4-F_N1 | GGTCGAGCCGGAACTGTTCTATCGACCCCAAAATCAGCGAAAT |
| SEQ ID NO: 565 | o723_skpp15-4-R_N1 | GGATGCGCACCCAGAAAGATCTGTCTGGTTACTGCCAGTTGAATCTG |
| SEQ ID NO: 566 | o724_skpp15-5-F_N1 | TCCCGGCGTTGTCCTGTTCTATCGACCCCAAAATCAGCGAAAT |
| SEQ ID NO: 567 | o725_skpp15-5-R_N1 | GCTCCGTCACTGCCCAAGATCTGTCTGGTTACTGCCAGTTGAATCTG |
| SEQ ID NO: 568 | o726_skpp15-6-F_N1 | CGCAGGGTCCAGAGTGTTCTATCGACCCCAAAATCAGCGAAAT |
| SEQ ID NO: 569 | o727_skpp15-6-R_N1 | GTTCGCGCGAAGGAAAAGATCTGTCTGGTTACTGCCAGTTGAATCTG |
| SEQ ID NO: 570 | o728_skpp-1-F_N1 | ATATAGATGCCGTCCTAGCGGTTCTATCGACCCCAAAATCAGCGAAAT |
| SEQ ID NO: 571 | o729_skpp-1-R_N1 | AAGTATCTTTCCTGTGCCCAAAGATCTGTCTGGTTACTGCCAGTTGAATCTG |
| SEQ ID NO: 572 | o730_skpp-2-F_N1 | CCCTTTAATCAGATGCGTCGGTTCTATCGACCCCAAAATCAGCGAAAT |
| SEQ ID NO: 573 | o731_skpp-2-R_N1 | TGGTAGTAATAAGGGCGACCAAGATCTGTCTGGTTACTGCCAGTTGAATCTG |
| SEQ ID NO: 574 | o732_skpp-3-F_N1 | TTGGTCATGTGCTTTTCGTTGTTCTATCGACCCCAAAATCAGCGAAAT |
| SEQ ID NO: 575 | o733_skpp-3-R_N1 | AGGGGTATCGGATACTCAGAAAGATCTGTCTGGTTACTGCCAGTTGAATCTG |
| SEQ ID NO: 576 | o734_skpp-4-F_N1 | GGGTGGGTAAATGGTAATGCGTTCTATCGACCCCAAAATCAGCGAAAT |
| SEQ ID NO: 577 | o735_skpp-4-R_N1 | ATCGATTCCCCGGATATAGCAAGATCTGTCTGGTTACTGCCAGTTGAATCTG |
| SEQ ID NO: 578 | o736_skpp-5-F_N1 | TCCGACGGGGAGTATATACTGTTCTATCGACCCCAAAATCAGCGAAAT |
| SEQ ID NO: 579 | o737_skpp-5-R_N1 | TACTAACTGCTTCAGGCCAAAAGATCTGTCTGGTTACTGCCAGTTGAATCTG |
| SEQ ID NO: 580 | o738_skpp-6-F_N1 | CATGTTTAGGAACGCTACCGGTTCTATCGACCCCAAAATCAGCGAAAT |

TABLE 1-continued

| SEQUENCE ID NO. | name | seq |
|---|---|---|
| SEQ ID NO: 581 | o739_skpp-6-R_N1 | AATAATCTCCGTTCCCTCCC AAGATCTGTCTGGTTACTGCCAGTTGAATCTG |
| SEQ ID NO: 582 | o740_skpp15-1-F_S2 | GGGTCACGCGTAGGA GTTCTATCGCTGGTGCTGCAGCTTATTA |
| SEQ ID NO: 583 | o741_skpp15-1-R_S2 | GTTCCGCAGCCACAC AAGATCTGAGGGTCAAGTGCACAGTCTA |
| SEQ ID NO: 584 | o742_skpp15-2-F_S2 | CGCGTCGAGTAGGGT GTTCTATCGCTGGTGCTGCAGCTTATTA |
| SEQ ID NO: 585 | o743_skpp15-2-R_S2 | GCCGTGTGAAGCTGG AAGATCTGAGGGTCAAGTGCACAGTCTA |
| SEQ ID NO: 586 | o744_skpp15-3-F_S2 | CGATCGCCCTTGGTG GTTCTATCGCTGGTGCTGCAGCTTATTA |
| SEQ ID NO: 587 | o745_skpp15-3-R_S2 | GGTTTAGCCGGCGTG AAGATCTGAGGGTCAAGTGCACAGTCTA |
| SEQ ID NO: 588 | o746_skpp15-4-F_S2 | GGTCGAGCCGGAACT GTTCTATCGCTGGTGCTGCAGCTTATTA |
| SEQ ID NO: 589 | o747_skpp15-4-R_S2 | GGATGCGCACCCAGA AAGATCTGAGGGTCAAGTGCACAGTCTA |
| SEQ ID NO: 590 | o748_skpp15-5-F_S2 | TCCCGGCGTTGTCCT GTTCTATCGCTGGTGCTGCAGCTTATTA |
| SEQ ID NO: 591 | o749_skpp15-5-R_S2 | GCTCCGTCACTGCCC AAGATCTGAGGGTCAAGTGCACAGTCTA |
| SEQ ID NO: 592 | o750_skpp15-6-F_S2 | CGCAGGGTCCAGAGT GTTCTATCGCTGGTGCTGCAGCTTATTA |
| SEQ ID NO: 593 | o751_skpp15-6-R_S2 | GTTCGCGCGAAGGAA AAGATCTGAGGGTCAAGTGCACAGTCTA |
| SEQ ID NO: 594 | o752_skpp-1-F s_S2 | ATATAGATGCCGTCCTAGCG GTTCTATCGCTGGTGCTGCAGCTTATTA |
| SEQ ID NO: 595 | o753_skpp-1-R s_S2 | AAGTATCTTTCCTGTGCCCA AAGATCTGAGGGTCAAGTGCACAGTCTA |
| SEQ ID NO: 596 | o754_skpp-2-F s_S2 | CCCTTTAATCAGATGCGTCG GTTCTATCGCTGGTGCTGCAGCTTATTA |
| SEQ ID NO: 597 | o755_skpp-2-R s_S2 | TGGTAGTAATAAGGGCGACC AAGATCTGAGGGTCAAGTGCACAGTCTA |
| SEQ ID NO: 598 | o756_skpp-3-F s_S2 | TTGGTCATGTGCTTTTCGTT GTTCTATCGCTGGTGCTGCAGCTTATTA |
| SEQ ID NO: 599 | o757_skpp-3-R s_S2 | AGGGGTATCGGATACTCAGA AAGATCTGAGGGTCAAGTGCACAGTCTA |
| SEQ ID NO: 600 | o758_skpp-4-F s_S2 | GGGTGGGTAAATGGTAATGC GTTCTATCGCTGGTGCTGCAGCTTATTA |
| SEQ ID NO: 601 | o759_skpp-4-R s_S2 | ATCGATTCCCCGGATATAGC AAGATCTGAGGGTCAAGTGCACAGTCTA |
| SEQ ID NO: 602 | o760_skpp-5-F s_S2 | TCCGACGGGGAGTATATACT GTTCTATCGCTGGTGCTGCAGCTTATTA |
| SEQ ID NO: 603 | o761_skpp-5-R s_S2 | TACTAACTGCTTCAGGCCAA AAGATCTGAGGGTCAAGTGCACAGTCTA |
| SEQ ID NO: 604 | o762_skpp-6-F s_S2 | CATGTTTAGGAACGCTACCG GTTCTATCGCTGGTGCTGCAGCTTATTA |
| SEQ ID NO: 605 | o763_skpp-6-R s_S2 | AATAATCTCCGTTCCCTCCC AAGATCTGAGGGTCAAGTGCACAGTCTA |

Example 4—SwabSeq: A High-Throughput Platform for Massively Scaled Up SARS-COV-2 Testing In the absence of an effective vaccine, public health strategies remain the only tools for controlling the spread of SARS-COV-2, the cause of COVID-19. In contrast to SARS-COV-1, for which infectivity is associated with symptoms, infectivity of SARS-COV-2 is high during the asymptomatic/presymptomatic phase. As a consequence, containing transmission based solely on symptoms is impossible, which makes screening for SARS-COV-2 essential for pandemic control.

As regional lockdowns have been lifted and people have returned to work and resumed other activities, rates of infection have started to rise again. In many parts of the United States, the rise in cases has overwhelmed the capacity of quantitative RT-PCR tests that make up the majority of FDA-approved tests for COVID-19. Even in those parts of the country that have expanded testing capacity, the cost of each test, at approximately $100, prohibits the deployment of clinical testing for population screening. Furthermore, the long delays in returning results are due to the insufficient testing capacity and not due to the few hours of assay time, which renders testing useless in preventing viral transmission and suppressing local outbreaks. Frequent, inexpensive mass testing, combined with contact tracing and isolation of infected individuals, offers the best chance of stopping the spread of virus. Described herein is SwabSeq, a SARS-COV-2 testing platform that leverages next-generation sequencing to massively scale up testing capacity.

SwabSeq improves on one-step reverse transcription and polymerase chain reaction (RT-PCR) approaches in several key areas. SwabSeq uses molecular barcodes that are embedded in the RT and PCR primers to uniquely label each sample. After the RT-PCR step, the barcoded samples are combined into a single sequencing library, which enables multiplexing of up to hundreds of thousands of samples on an Illumina sequencer. The readout of the test is not fluorescence (thus obviating the need for expensive qPCR machines) but the count of viral sequencing reads. A short read length (26 base pairs) is sufficient to identify the target sequence and keeps total sequencing time down to approximately 5 hours.

The key to SwabSeqs robust capability to identify SARS-COV-2 is the inclusion of an internal in vitro RNA standard that allows normalization of viral read counts within each well. This internal standard turns a count-based assay into a ratiometric one. This is important, as it allows for the ability to accurately call positive and negative samples despite heterogeneity in RT- and PCR-inhibition in clinical samples. Reliance on sequencing as the readout, along with the in vitro RNA standard, allows SwabSeq to use amplification performed for up to 50 cycles until primers are consumed. This endpoint PCR overcomes enzyme inhibition present in extraction-free samples, enabling further streamlining of the workflow with minimal loss of analytical sensitivity. These features enable testing at much higher throughput than the current RT-quantitativePCR (RT-qPCR) diagnostic tests, which require RNA purification and RT-qPCR-costly, labor- and reagent-intensive steps that are constrained by the availability of the necessary instrumentation. In contrast, SwabSeq relies only on readily available and underutilized thermocyclers and DNA sequencers. SwabSeq can be performed at the scale of tens of thousands of samples per day without the extensive automation that is typically required for scale beyond hundreds of samples per day.

As demonstrated herein, SwabSeq has extremely high sensitivity and specificity for the detection of viral RNA in purified samples. The disclosure and examples herein further demonstrate a low limit of detection in extraction-free lysates from mid-nasal swabs and oral fluids. These results demonstrate the potential of SwabSeq to be used for SARS-COV-2 testing on an unprecedented scale.

Results

SwabSeq is a simple and scalable protocol, consisting of 5 steps (FIG. 4, panel A): (1) sample collection, (2) reverse transcription and PCR using primers that contain unique molecular indices at the i7 and i5 positions (FIG. 4, panel B, FIG. 6), (3) pooling of the uniquely barcoded samples for library preparation, (4) sequencing of the pooled library, and (5) computational assignment of barcoded sequencing reads to each sample for counting and viral detection.

The assay consists of two primers sets that amplify two genes: the S2 gene of SARS-CoV-2 and the human Ribonuclease P/MRP Subunit P30 (RPP30). The assay includes a synthetic in vitro transcribed control RNA that is identical to the viral sequence targeted for amplification, except for a short-altered stretch (FIG. 4, panel C) that allows distinguishing of sequencing reads corresponding to the synthetic control from those corresponding to the native sequence. The primers amplify both the native and the synthetic sequences with equal efficiency (FIG. 7).

Figure 4:
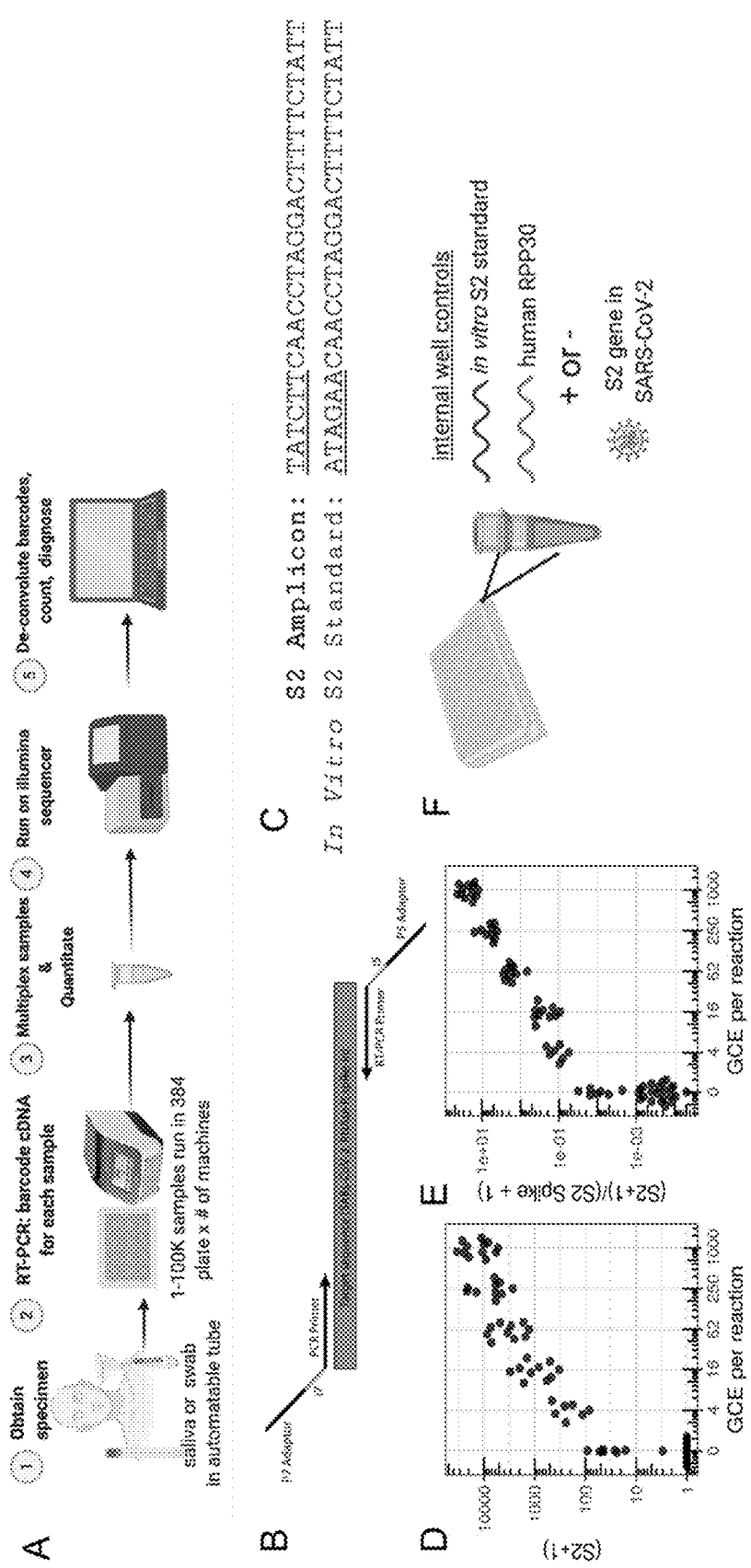
FIG. 4 illustrates the SwabSeq Diagnostic Testing Platform for COVID19.

The S2 internal control serves two purposes. First, inhibitors of PCR and reverse transcription, as well as other sources of well-to-well variation, are likely to affect the amplification of both the control and the sample in the same way. The ratio of the number of native reads to the number of control reads provides a more accurate and quantitative measure of viral load than native read counts alone (FIG. 4, panels E and D). Second, the internal control allows the retention of linearity over a large range of viral input despite the use of endpoint PCR (FIG. 8). With this approach, the final amount of DNA in each well is largely defined by the total primer concentration rather than by the viral load—a negative sample is expected to have a similar total number of S2 reads as a positive one. The difference is that in a negative sample all S2 amplicon reads map to the control synthetic sequence. In addition to viral S2, the assay/method comprises reverse-transcribing and amplifying a human housekeeping gene to control for specimen quality and collection efficiency (FIG. 4 panel F).

After RT-PCR samples are combined at equal volumes, purified, and used to generate one sequencing library. Both the Illumina MiSeq and/or the Illumina NextSeq can be used to sequence these libraries (FIG. 9). Instrument sequencing time is minnized by only sequencing 26 base pairs of the amplicons (Methods). Each read is classified as deriving from native or control S2 or RPP30 based on its sequence, and assigned to a sample based on the associated index sequences (barcodes). To maximize specificity and avoid false-positive signals arising from incorrect classification or assignment, conservative edit distance thresholds are used for this matching operation (Methods and Supplemental Results). A sequencing read is discarded if it does not match one of the expected sequences. Counts for native and control S2 and RPP30 reads are obtained for each sample and used for downstream analyses (Methods, below).

It was observed that a few thousand reads are sufficient to detect and quantify the presence of viral RNA in a sample (10,000 conservatively). This translates to 1,500 samples per run on a MiSeq v3 flow cell, 20,000 samples per run on a NextSeq, and up to 150,000 samples per run on a NovaSeq S2 flow cell. Computational analysis takes only minutes per run. SwabSeq is a streamlined and scalable protocol for COVID-19 testing. The SwabSeq protocol was further optimized by identifying and eliminating multiple sources of noise (FIG. 21, panels A, B, C, and D).

Validation of SwabSeq as a Diagnostic Platform

SwabSeq was first validated on purified RNA samples that were previously tested by the UCLA Clinical Laboratory with a standard RT-qPCR assay. To determine the analytical limit of detection, inactivated virus was diluted with pooled, remnant clinical nasopharyngeal swab specimens. The remnant samples were all confirmed to be negative for SARS-COV-2. In these remnant samples, a serial, 2-fold dilution of heat-inactivated SARS-COV-2 (ATCC® VR-1986HK) was performed, in the range from 8000 to 125 genome copy equivalents (GCE) per mL. SARS-COV-2 in all samples down to 250 GCE per mL were detected, and in most samples to 125 GCE per mL (FIG. 2A). These results established that SwabSeq is highly sensitive, with an analytical limit of detection (LOD) of 250 GCE per mL. This limit of detection is lower than many currently approved and highly sensitive RT-qPCR assays. This comparison demonstrates that SwabSeq can be highly effective as a clinical diagnostic test.

SwabSeq detects virus with high sensitivity and specificity. Confirmed positive (n=31) and negative (n=33) samples from the UCLA Clinical Microbiology Laboratory were retested. 100% agreement with RT-qPCR results for all samples (FIG. 5) was observed. The libraries were sequenced on both a MiSeq and a NextSeq550 (FIG. 9), with 100% concordance between the different sequencing instruments.

One of the major bottlenecks in scaling up RT-qPCR diagnostic tests is the RNA purification step. RNA extraction is challenging to automate, and supply chains have not been able to keep up with the demand for necessary reagents during the course of the pandemic. The ability of SwabSeq to detect SARS-COV-2 directly from a variety of extraction-free sample types was explored as a way to circumvent the bottleneck of RNA purification.

Figure 5:
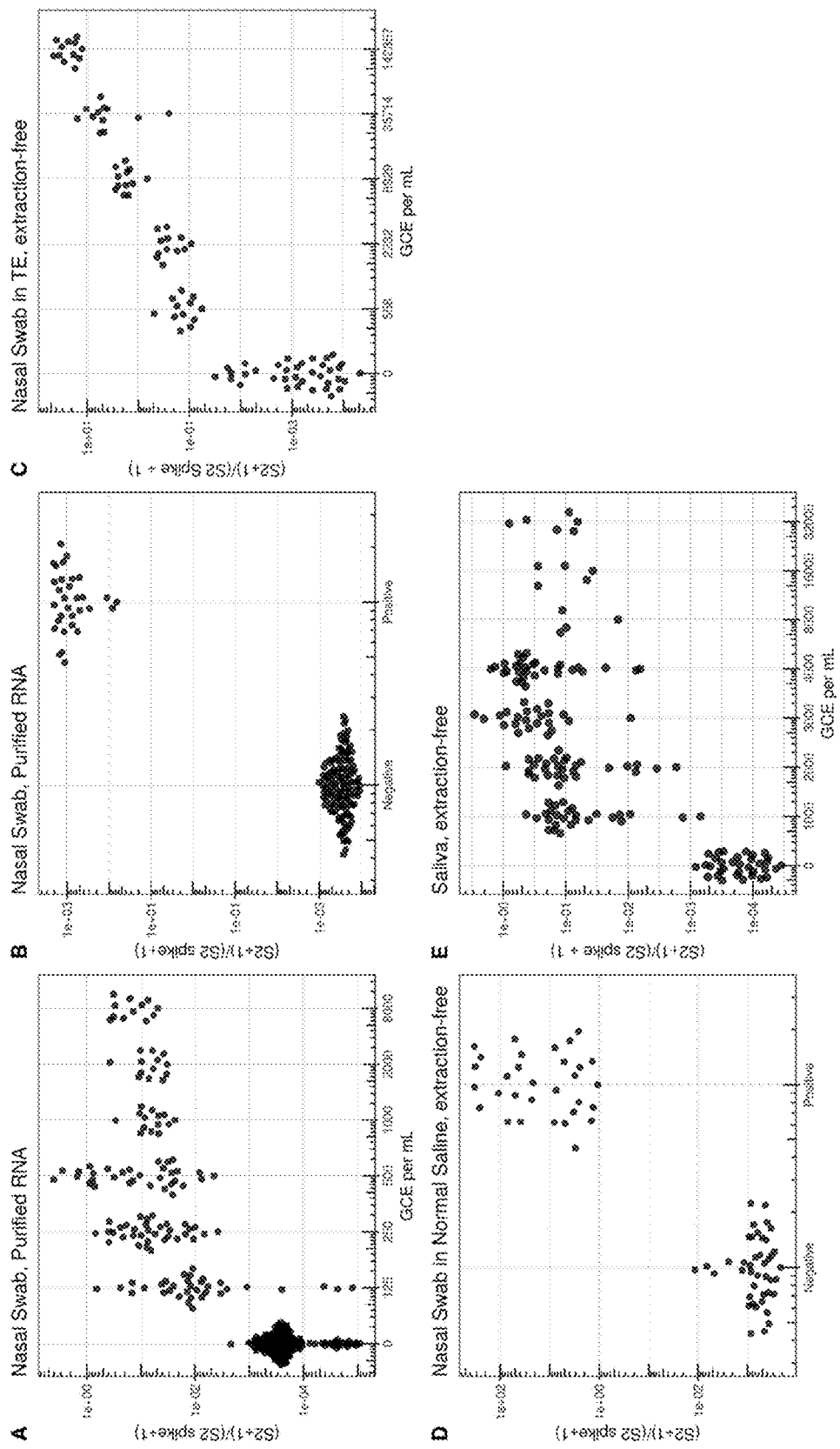
FIG. 5 shows validation in clinical specimens and demonstrates a limit of detection equivalent to sensitive RT-qPCR reactions.

There are several types of media that are recommended by the CDC for nasal swab collection: viral transport medium (VTM), Amies transport medium, and normal saline. A main technical challenge arises from RT or PCR inhibition by ingredients in the collection buffers. Dilution of specimens with water overcame the RT and PCR inhibition and allowed for the ability to detect viral RNA in contrived and positive clinical patient samples (FIG. 11). Nasal swabs that had been collected directly into the Tris-EDTA (TE) buffer, diluted 1:1 with water were tested. This approach yielded a limit of detection of 558 GCE/mL (FIG. 5, panel C). A comparison between the extraction free-protocol for nasopharyngeal samples collected into normal saline and RT-qPCR conducted by the UCLA Clinical Microbiology Lab showed 100% agreement for all samples (FIG. 2D).

Extraction-free saliva protocols in which saliva is collected directly into a matrix tube using a funnel-like collection device were also tested (FIG. 12). The main technical challenge has been preventing the various components in saliva from degrading viral RNA and ensuring accurate pipetting of this heterogeneous and viscous sample type. Heating the saliva samples to 95° C. for 30 minutes reduced PCR inhibition and improved detection of the S2 amplicon as compared to no preheating (FIG. 13). After the heat step, samples were diluted at a 1:1 volume of 2×TBE with 0.1% Tween-20. Using this method, a LoD of 2000 GCE/mL was obtained (FIG. 5, panel E).

DISCUSSION

Swabseq has the potential to alleviate existing bottlenecks in diagnostic clinical testing. Further, SwabSeq has even greater potential to enable testing on a scale necessary for pandemic suppression via population surveillance. The technology represents a novel use of massively parallel next-generation sequencing for infectious disease surveillance and diagnostics. SwabSeq can detect SARS-COV-2 RNA in clinical specimens from both purified RNA and extraction-free lysates, and maintain high clinical and analytical sensitivity and specificity comparable to RT-qPCR performed in a clinical diagnostic laboratory. SwabSeq was also further optimized to prioritize scale and low cost, as these are the key factors that are missing from current COVID-19 diagnostic tests.

SwabSeq should be evaluated as a tool for surveillance testing, rather than for clinical testing. Clinical testing informs clinical decision making, and thus requires high sensitivity and specificity, while for surveillance testing the most important factors are the breadth and frequency of testing and the turn-around-time. Sufficiently broad and frequent testing with rapid return of results can effectively suppress viral outbreaks by selective quarantine of infectious individuals rather than blanket stay-at-home orders. Epidemiological modeling of surveillance testing on university campuses has shown that even diagnostic tests with 70% sensitivity, but performed frequently with a short turn-around time, can suppress transmission. Major challenges for practical implementation of frequent testing include the cost of testing and the logistics of collecting and processing hundreds and thousands of samples per day.

The use of Illumina sequencing in diagnostic testing has garnered concern with regards to turn-around-time and cost. SwabSeq uses short sequencing runs that read out the molecular indexes and 26 base pairs of the target sequence in 5 hours, followed by computational analysis that can be performed on a desktop computer in 5 minutes. The cost of sequencing reagents when 1,000 samples are analyzed in one MiSeq run is less than $1 per sample. Running 10,000 samples on a NextSeq550, which generates 13 times more reads per flow cell, can reduce this cost approximately 10-fold. Further optimization to decrease reaction volumes and to use less expensive RT-PCR reagents can further decrease the total cost per test.

Finally, scaling up testing for SARS-COV-2 requires high throughput sample collection and processing workflows. Manual processes, common in most academic clinical laboratories, are not easily compatible with simple automation. The current protocols with nasopharyngeal swabs into VTM, Amies or NS are collection methods that date back to the pre-molecular-genetics era, when live viral culture was used to identify cytopathic effects on cell lines, and when testing was performed manually with low throughput. A fresh perspective on collection methods that scale would be enormously beneficial to the testing community.

Several groups, have piloted "lightweight" sample collection approaches, which push sample registration and patient information collection directly onto the individual tested via a smartphone app. Much of the labor of sample requisition is due to a lack of interoperability between electronic health systems, with laboratory professionals manually entering information for every sample by hand. By developing a HIPAA-compliant registration process, labor-intensive sample requisition can be streamlined. To promote scalability, sample collection protocols that use smaller-volume tubes that are compatible with simple automation, such as automated capper-decapper and 96-head liquid handlers can be used. These approaches decrease the amount of hands-on work required in the laboratory to process and perform testing.

The SwabSeq diagnostic platform complements traditional clinical diagnostics tests, as well as the growing arsenal of point-of-care rapid diagnostic platforms emerging for COVID-19, by increasing test capacity to meet the needs of both diagnostic and widespread surveillance testing. Looking forward, SwabSeq is easily extensible to accommodate additional pathogens and viral targets. This could further increase the usefulness of the test, particularly during the winter cold and flu season, when multiple respiratory pathogens circulate in the populations and cannot be easily differentiated based on symptoms alone. Surveillance testing is likely to become a part of the new normal as society aims to safely reopen the educational, business and recreational sectors of society.

Methods

Sample Collection: All patient samples used in the study were deidentified. All samples were obtained with UCLA IRB Approval. Nasopharyngeal samples were collected by health care providers in patients with suspicion of COVID19.

Creation of Contrived Specimens: For the clinical limit of detection experiments, confirmed COVID-19 negative remnant nasopharyngeal swab specimens collected by the UCLA Clinical Microbiology Laboratory were pooled. Pooled clinical samples were then spiked with ATCC Inactivated Virus (ATCC 1986-HK) at specified concentrations and extracted as described below. For the clinical purified RNA samples, they were collected as nasopharyngeal swabs and purified using the KingFisherFlex (Thermofisher Scientific) instrument using the MagMax bead extraction. All extractions were performed according to manufacturer's protocols. For Extraction free samples, samples were first contrived at specified concentrations into pooled, confirmed negative clinical samples and performed diluted samples in TE buffer or water prior to adding to the RT-PCR master mix.

Processing of Extraction-Free Saliva Specimens: Direct Saliva is collected into a matrix tube using a small funnel (part number from Amazon). The saliva samples were collected into a matrix tube and heated to 95C for 30 minutes. Samples were then either frozen or processed by dilution with 2X TBE with 1% Tween-20, for final concentration of 1× TBE and 0.5% Tween-2. 1× Tween with Qiagen Protease and RNA Secure (ThermoFisher) was tested, which also works but resulted in more sample-to-sample variability and required additional incubation steps.

Processing of Extraction-Free Nasal Swab Lysates: All extraction free lysates were inactivated using a heat inactivation at 56C for 30 minutes. Samples were then diluted with water at a ratio of 1:4 and then directly added to mastermix. Dilution amounts varied depending on the liquid media that was used. Of the CDC recommended media, normal saline performed the most robustly. Viral Transport Media and Amies Buffer showed significant PCR inhibition that was difficult to overcome, even with dilution in water. In an embodiment, the swab is placed directly into the diluted TE buffer, which has no effects on PCR inhibition.

Barcode Primer Design: Barcode primers were chosen from a set of 1,536 unique 10 bp i5 barcodes and a set of 1,536 unique 10 bp i7 barcodes. These 10 bp barcodes satisfy the criteria that there is a minimum levenshtein distance of 3 between any two indices (within the i5 and i7 sets) and that the barcodes contain no homopolymer repeats greater than 2 nucleotides. Additionally, barcodes were chosen to minimize homo- and hetero-dimerization using helper functions in the python API to Primer3.

Construction of S2 and RPP30 Synthetic Spike: RT-PCR was performed using primers in Table 2 on gRNA of SARS-COV-2 (Twist BioSciences, #1) for construction of a S2 spike-in DNA template. RT PCR (FP_1, R) and a second round of PCR (FP_2, R) was performed on HEK293T lysate for construction of a RPP30 spike-in DNA template. Products were run on a gel to identify specific products at ~150 bp. DNA was purified using Ampure beads (Axygen) using a ratio of 1.8 ratio of beads:sample volume. Mixture was vortexed and incubated for 5 minutes at room temperature. A magnet was used to bind beads for 1 minute, washed twice with 70% EtOH, beads were air-dried for 5 minutes, and then removed from the magnet and eluted in 100 μL of IDTE Buffer. Bead solution was placed back on the magnet and the eluate was removed after 1 minute. DNA was quantified by nanodrop (Denovix).

This prepared DNA template was used for standard HiScribe T7 in vitro transcription (NEB). IVT reactions prepared according to manufacturer's instructions using 300 ng of template DNA per 20 μL reaction with a 16 hour incubation at 37 degrees. IVT reactions were treated with DNAseI according to the manufacturer's instructions. RNA was purified with an RNA Clean & Concentrator-25 kit (Zymo Research) according to the manufacturer's instructions and eluted into water. RNA spike-in was quantified both by nanodrop and with a RNA screen tape kit for the TapeStation according to the manufacturer's instructions (Agilent) to verify the RNA was the correct size (~133 nt).

TABLE 2

| | |
|---|---|
| SEQ ID NO:S2_FP 13 | TAATACGACTCACTATAGGGCTGGTGCTGCAGCTTATTATGTGG GTATAGAACAACCTAGGACTTTTCTATTAA |
| SEQ ID NO:S2_RP 14 | AACGTACACTTTGTTTCTGAGAGAGG |
| SEQ ID NO:RPP30_FP_1 15 | CTGACCTGAAGGCTGACGCCGGACTTGTGGAGACAGC |
| SEQ ID NO:RPP30_FP2 16 | TAATACGACTCACTATAGGGAGATTTGGACCTGCGAGCGGGTTC TGACCTGAAGGCTGA |
| SEQ ID NO:RPP30_R 17 | GGTTTTTCAATTTCCTGTTTCTTTTCCTTAAAGTCAACG |

One-Step RT-PCR: RT-PCR were performed using either the Luna® Universal One-Step RT-qPCR Kit (New England BioSciences E3005) or the TaqPath™ 1-Step RT-qPCR Master Mix (Thermofisher Scientific, A15300) with a reaction volume of 20 μL. Both kits were used according to the manufacturer's protocol. The final concentration of primers in the mastermix was 50 nM for RPP30 F and R primers and 400 nM for S2 F and R primers. Synthetic S2 RNA was added directly to mastermix at a copy number of 500 copies per reaction. Sample was loaded into a 20 μL reaction. All reactions were run on a 96- or 384-well format and thermocycler conditions were run according to the manufacturer's protocol. For purified RNA samples 40 cycles of PCR was performed. For unpurified samples, endpoint PCR for 50 cycles was performed.

Multiplex Library Preparation: After the RT-PCR reaction, samples were pooled using multichannel pipet or Integra Viaflow Benchtop liquid handler. 6 μL from each well was combined into a sterile reservoir and the entire volume was transferred into a 15 mL conical tube and vortexed. 100 μL of the total volume was transferred to a 1.7 mL eppendorf tube for a double-sided SPRI cleanup. Briefly, 50 μL of AmpureXP beads (A63880) were added to 100 μL of the pooled PCR volume and vortexed. After 5 minutes, a magnet was used to collect beads for 1 minute and supernatant transferred to a new eppendorf tube. An additional 130 μL of Ampure XP beads were added to the 150 μL of supernatant and vortexed. After an additional 5 minutes, the magnet was used to collect beads for 1 minute and the beads were washed twice with fresh 70% EtOH. DNA was eluted off the beads in 40 μL of qiagen EB buffer. The magnet was used to collect beads for 1 minute and 33 μL of supernatant was transferred to a new tube.

Sequencing Protocol: Libraries were sequenced on either an Illumina MiSeq (2012) or Nextseq550. Prior to each MiSeq run, a bleach wash was performed using a sodium hypochlorite solution (Sigma Aldrich, 239305) according to Illumina protocols. The pooled and quantitated library was diluted to a concentration of 6 nM (based on Qubit 4 Fluorometer and Illumina's formula for conversion between ng/ul and nM) and was loaded on the sequencer at either 25 pM (MiSeq) or 1.5 pM (NextSeq). PhiX Control v3 (Illumina, FC-110-3001) was spiked into the library at an estimated 30-40% of the library. PhiX provides additional sequence diversity to Read 1, which assists with template registration and improves run and base quality.

For this application, the MiSeq requires 2 custom sequencing primer mixes, the Read1 primer mix and the i7 primer mix. Both mixes have a final concentration of 20 uM of primers (10 uM of each amplicon's sequencing primer). The NextSeq requires an additional sequencing primer mix, the i5 primer mix, which also has a final concentration of 20 uM. The MiSeq Reagent Kit v3 (150-cycle; MS-102-3001) is loaded with 30 μL of Read1 sequencing primer mix into reservoir 12 and 30 μL of the i7 sequencing primer primer mix into reservoir 13. The NextSeq 500/550 Mid Output Kit is loaded with 52 ul of Read1 sequencing primer mix into reservoir 20, 85 ul of i7 sequencing primer mix into reservoir 22, and 85 ul of i5 sequencing primer mix into reservoir 22. Index 1 and 2 are each 10 bp, and Read 1 is 26 bp.

Analysis: The bioinformatic analysis consists of standard conversion of BCL files into FASTQ sequencing files using Illumina's bcl2fastq software (v2.20.0.422). Demultiplexing and read counts per sample are performed using the custom software. Here read1 is matched to one of the three expected amplicons allowing for the possibility of a single nucleotide error in the amplicon sequence. The hamming distance is the number of positions at which the corresponding sequences are different from each other and is a commonly used measure of distance between sequences. Samples are demultiplexed using the two index reads in order to identify which sample the read originated from. Observed index reads are matched to the expected index sequences allowing for the possibility of a single nucleotide error in one or both of the index sequences. The set of three reads are discarded if both index 1 and index2 have hamming distances greater than 1 from the expected index sequences. The count of reads for each amplicon and each sample is calculated. In this analysis a few custom scripts were written in R that rely on the ShortRead and stringdist packages for processing fastq files and calculating hamming distances between observed and expected amplicons and indices. This approach is very conservative and gave very low-level control of the sequencing analysis. However, continued development of the kallisto and bustools SwabSeq analysis tools can provide a more user-friendly and computationally efficient solution for other groups implementing SwabSeq.

Criteria for Classification of Purified Patient Samples: For the analytic pipeline, QC metrics for each type of specimen were developed. For purified RNA, each sample required that there are at least 10 reads are detected for RPP30 and that the sum of S2 and S2 synthetic spike-in reads exceeds 2,000 reads. If these conditions are not met, the sample is rerun one time and if there is a second fail a resample is requested. To determine if SARS-COV-2 is present the ratio of S2 to S2 spike exceeds 0.003 is calculated. (adding 1 count to both S2 and S2 spike before calculating this ratio facilitates plotting the results on a logarithmic scale.) If the ratio is greater than 0.003 it is concluded that SARS-COV-2 is detected for that sample and if it is less than or equal to 0.003 it is concluded that SARS-COV-2 is not detected (FIG. 10, panels A, B, and C).

The same pair of primers will amplify both the S and S spike amplicons. Because the run is an endpoint assay, the primers will be the limiting reagent to continued amplification. In developing this assay, observed was that as S2 counts increase for a sample, the S2 spike counts will decrease (FIG. 8). At the very high viral loads, S2 spike read counts decreased to less than 1000 reads. Therefore, considering S2 and S2 spike together allowed the QC to call SARS-COV-2 even at extremely high viral titers. Thus, accounting for the scenario where S2 spike counts are low because S2 amplicon counts are very high and the sample contains large amounts of SARS-COV-2 RNA is also important (FIG. 8).

Therefore, since the S2 and S2 spike are derived from the same primer pair, it was required in the QC that the sum of S2 and S2 spike counts together exceeds 2000. For example, detection greater than 2000 S2 counts and 0 S2 spike counts this would certainly be a SARS-COV-2 positive sample and would result: SARS-COV-2 detected.

Analysis of index mis-assignment: Unique dual indices and amplicon specific indices were used to study index mis-assignment. In this scheme, each sample was assigned two unique indices for the S or Spike amplicon and two unique indices for the RPP30 amplicon for a total of four unique indices per sample. A count matrix with all possible pairwise combinations of each index pair (one i7 and one i5) was used to generate a matching matrix. The counts on the diagonal of the matching matrix correspond to real samples and counts off of the diagonal correspond to index swapping events. The extent of index mis-assignment for the i7 and i5 index was determined by taking the row and column sum, respectively, of the off-diagonal elements of the matching matrix. The observed rate of index swapping to wells with a known zero amount of viral RNA was computed by taking the mean of the viral S counts to spike ratio for those wells.

Supplemental Results

Improving Limit of Detection Requires Minimizing Sources of Noise: One of the major challenges in running a highly sensitive molecular diagnostic assay is that even a single contaminant or source of noise can decrease the test's analytical sensitivity. In the process of developing SwabSeq, S2 reads from control samples in which no SARS-COV-2 RNA was present was observed (FIG. 4, panel D). These reads are referred to as "no template control" (NTC) reads. A key part of SwabSeq optimization has been understanding and minimizing the sources of NTC reads in order to improve the limit of detection (LoD) of the assay. Two sources of NTC reads: molecular contamination and mis-assignment sequencing reads were identified.

To minimize molecular contamination, protocols and procedures that are commonly used in molecular genetic diagnostic laboratories were followed. To limit molecular contamination, a dedicated hood for making dilutions of the synthetic RNA controls and master mix was used. At the start of each new run, the pipettes were sterilized, dilution solutions, and PCR plates with 10% bleach, followed by UV-light treatment for 15 minutes.

To prevent post-PCR products that are high concentration contaminating the pre-PCR processes, pre- and post-PCR steps were physically separated into two separate rooms, where any amplified plates were never opened within the pre-PCR laboratory space. To further protect from post-PCR contamination, RT-PCR mastermixes with or without Uracil-N-glycosylase (UNG) were compared. The presence of UNG in the TaqPath™ 1-Step RT-qPCR Master Mix (Thermofisher Scientific) showed a significant improvement reducing post-PCR contamination of S2 reads present in the negative patient samples as compared with the LunaR One Step RT-PCR Mix (New England Biosciences) (FIG. 14). The RT-PCR mastermix contains a mix of dTTP and dUTP such that post-PCR amplicons are uracil containing DNA. These post-PCR that are remnants of previously run Swab-Seq experiments therefore can be selectively eliminated by UNG.

A third source of molecular contamination was carryover contamination on the sequencer template line of the Illumina MiSeq. Without a bleach maintenance wash, indices that were run on the previous sequencing run were identified in an experiment where those indices were not included. While the number of reads for some indices were present at a number of S2 reads, the presence of carryover contamination affects the sensitivity and specificity of the assay. After an extra maintenance and bleach wash, the amount of carryover reads present to less than 10 reads was substantially reduced (FIG. 15).

Another source of NTC reads is mis-assignment of amplicons. Mis-assignment of amplicons occurs when sequencing (and perhaps at a lower rate, oligo synthesis) errors result in an amplicon sequence that originates from the S2 spike but is mistakenly assigned to the S2 sequence within a given sample. Only 6 bp distinguishes S2 from S2 spike at the beginning of read 1. Sequencing errors can result in S2 spike reads being misclassified as S2 reads as error rates appear to be higher in the beginning of the read (FIG. 16, panel A). If computational error correction of the amplicon reads is too tolerant, these reads may be inadvertently counted to the wrong category. To reduce this source of S2 read misassignment, a more conservative thresholding on edit distance was used (FIG. 16, panel B). Future redesigns or extensions to additional viral amplicons should consider engineering longer regions of sequence diversity here.

An additional source of NTC reads is when S2 amplicon reads are mis-assigned to the wrong sample based on the indexing strategy. In the assay, individual samples are identified by pairs of index reads (FIG. 4, panel B). Mis-assignment of samples to the wrong index could occur due to contamination of index primer sequences, synthesis errors in the index sequence, sequencing errors in the index sequences or "index hopping".

Multiple indexing strategies in the development of Swab Seq were leveraged, from fully combinatorial indexing (where each possible combination of i5 and i7 indices are used to tag samples in the assay) to unique-dual indexing (UDI) where each sample has distinct and unrelated i7 and i5 indices (FIG. 17). However, the ability to scale can be limited due to the substantial upfront cost of developing that many unique primers. Fully combinatorial indexing approaches significantly expand the number of unique primer combinations. A compromise strategy between fully combinatorial indexing and UDI where sets of indices are only shared between small subsets of samples can also be used. Such designs reduce the effect of sample mis-assignment and facilitates scaling to tens of thousands of patient samples (FIG. 17). With a fully combinatorial indexing (FIG. 17) NTC read depth was correlated with the total number of S2 reads summed across all samples that shared the same i7 sequence (FIG. 18, panel A). This is consistent with the effect of indexing hopping from samples with high S2 viral reads to samples that shared the same indices. When positive samples are randomized across indices it is possible to computationally correct for this effect, for example using a linear mixed model.

Finally, the challenges associated with combinatorial and semi-combinatorial indexing strategies can be mitigated by using unique dual indexing (UDI), which is a strategy to reduce the number of index-hopped reads by two orders of magnitude. Consistently lower S2 viral reads for negative control samples UDI was observed. It also enables quantification of index mis-assignment by counting reads for index combinations that should not occur in the assay (FIG. 21, panels A and B). The number of index hopping events is correlated with the total number of S2+S2 spike reads (FIG. 21, panels C and D), indicating that hopped reads are more likely to come from wells where the expected index has strong viral signal. The overall rate of hopping as 1-2% was quantified on a MiSeq and is known to be higher on patterned flow cell instruments.

There are many sources of noise in amplicon-based sequencing, from environmental contamination in the RT-PCR and sequencing steps to misassignment of reads based on computational correction and "index-hopping" on the Illumina flow cells. Preventing and correcting these sources of error drastically improves the limit of detection of the SwabSeq assay.

Example 5—Effect of Primer Concentration on SARS-COV-2 Testing

The effect of lowered primer concentrations was tested for the S2 and N1 amplicon. The concentration of primers was lowered from 400 nM to 100 nM in a 20 μL reaction using either saliva (diluted 1:1) or nasal swabs. The RPP30 amplicon primer concentration was the same at 50 nM. Lowering the primer concentration allows retention of quantitative ability. The lower primer concentrations also lead to less primer dimers and non-specific amplification products that take up sequencing reads. In the gels shown in FIG. 22 this primer dimer band was at ~120 bp in the no template control (NTC) lanes. Each gel was loaded with the same amount of DNA. In the gel showing the RT-PCR done with 400 nM primer, it can see that this primer dimer band at 120 bp in the NTC lane is much brighter than in the gel showing the RT-PCR done with 100 nM primer. Using a 200 nM concentration for primers in the amplification reaction also showed marked improvement and reduction of primer dimers and non-specific products.

Example 6—Diversified Synthetic Sequences

The methods described herein are improved by the presence of a synthetic nucleic acid sequence, that acts as an internal control sequence that is co-extracted, transcribed, and amplified with a sample.

S2 Synthetic Nucleic Acid Sequences

Four synthetic RNA S2 oligos were designed to increase nucleotide base diversity during sequencing which enables sufficient base diversity to ensure robust base calling during sequencing without the need for PhiX. The synthetic RNA oligos were pooled together in an equimolar fashion and spiked into the RT-PCR mastermix at a total concentration of 250 copies of RNA per reaction. Several combinations, but found that set #1 worked best. These sequences were derived from the wildtype S2 sequence with specific base-pair changes to equally represent each of the four bases at each position (targeting 25% A, 25% T, 25% G, 25% C). Achieving equal distribution of nucleotides required sequence randomization, leading to final diversified S2 spike sequences that do not resemble the original template in the 26-bp read region. The sequences were optimized to reduce secondary structure and all have a similar melting temperature. The flanking sequences share homology with S2 amplicon. The LoD using this spike was as good, sequences shown in FIG. 23. Primers used for this analysis were forward GCTGGTGCTGCAGCTTATTATGTGGGT (SEQ ID NO: 18) and reverse AGGGTCAAGTGCACAGTCTA (SEQ ID NO: 19).

N1 Synthetic Nucleic Acid Sequences

This was also apparent when using diversified synthetic sequences that could be amplified using N1 specific primers. These N1 sequences were amplified with 2019-nCOV_N1-F; GACCCCAAAATCAGCGAAAT (SEQ ID NO: 20) and 2019-nCOV_N1-R; TCTGGTTACTGCCAGTTGAATCTG (SEQ ID NO: 21).

Figure 25:
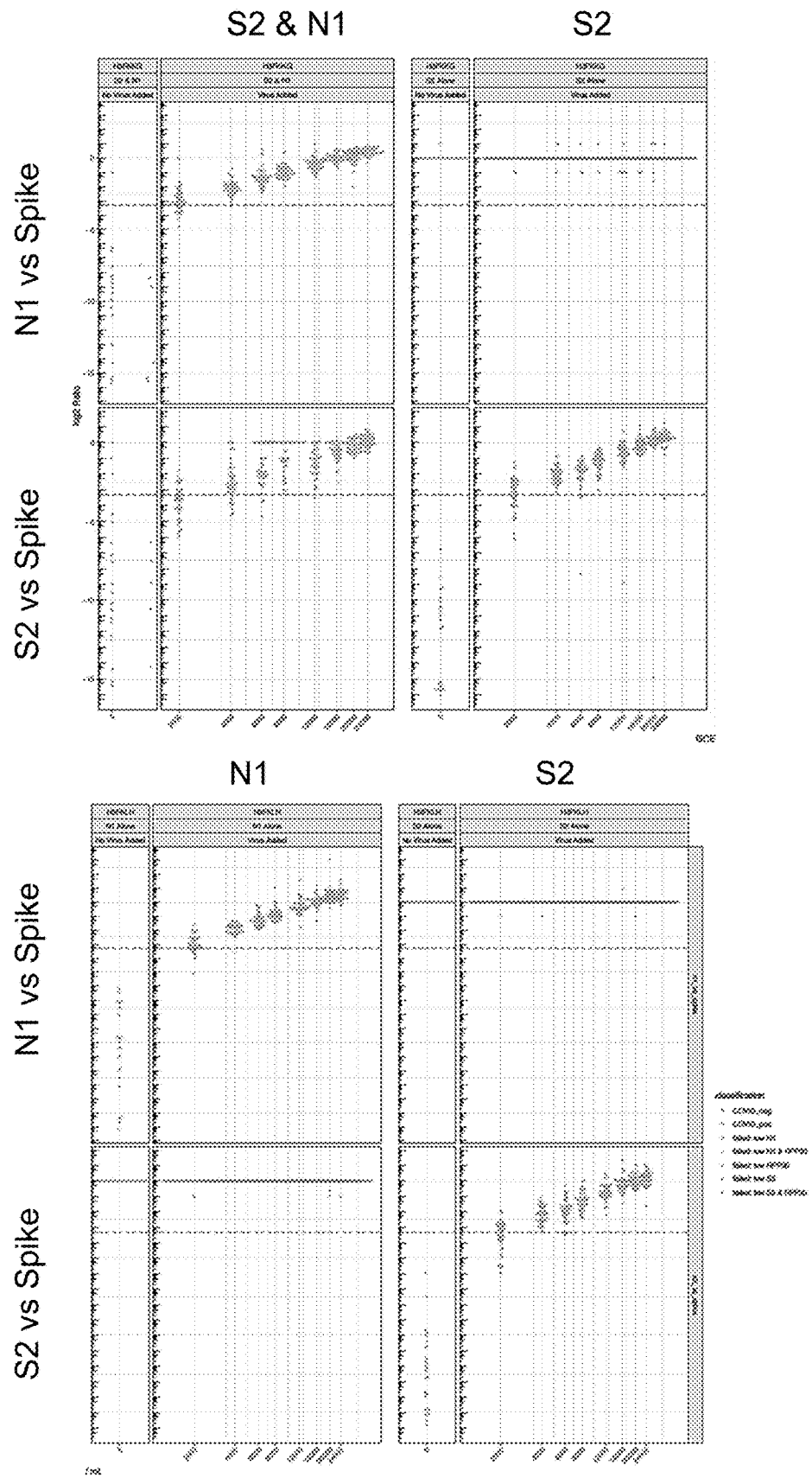
FIG. 25 shows that combining N1 and S2 can increase sensitivity and of SARS-COV2-detection compared to either individually.

Preliminary limit of detection experiments were done with contrived samples (using ATCC heat inactivated SARS-COV-2 standard) spiked into negative saliva and diluted serially. This was done using three primer conditions: both N1 and S2, just N1, and just S2. RPP30 was present at final reaction concentration of 50 nM, S2 at 100 nM, and N1 at 100 nM. The sensitivity of our assay with just S2 was determined to be 8000 GCE/mL. A preliminary LoD of N1 from this experiment is 6000 GCE/mL, and a preliminary LoD of N1+S2 is 4000 GCE/mL, indicating adding N1 improves the sensitivity of the SwabSEQ assay, as shown in FIG. 25.

The inclusion of the diversified synthetic sequences allowed for improvements in sensitivity and accuracy of the SwabSEQ test while reducing the reliance on PhiX during the sequencing process. Exemplary synthetic sequences are shown in table 3 below.

TABLE 3

| Sequences for COVID 19 S2 and N1 synthetic spike sequences | |
| --- | --- |
| S2_001 | GCTGGTGCTGCAGCTTATTATGTGGGTGTGTATCTCACGAAGCGACCCTTTGGA AAATATAATGAAAATGGAACCATTACAGATGCTGTAGACTGTGCACTTGACCCT |
| S2_002 | GCTGGTGCTGCAGCTTATTATGTGGGTCCTCGCTAGGACGTCGCTATgacgccAAA ATATAATGAAAATGGAACCATTACAGATGCTGTAGACTGTGCACTTGACCCT |
| S2_003 | GCTGGTGCTGCAGCTTATTATGTGGGTAGCACGACTTGATCTAACTgacactaAAAA TATAATGAAAATGGAACCATTACAGATGCTGTAGACTGTGCACTTGACCCT |
| S2_004 | GCTGGTGCTGCAGCTTATTATGTGGGTTAAGTAGGACTTCGATTggaTggaatAAAA TATAATGAAAATGGAACCATTACAGATGCTGTAGACTGTGCACTTGACCCT |
| N1_001 | TCTGGTTACTGCCAGTTGAATCTGAGGGTCCGGACGGATATCGCACTAAGTGTA CCTGGTGCATTTCGCTGATTTTGGGGTC |
| N1_002 | TCTGGTTACTGCCAGTTGAATCTGAGGGTCCCATGACCATGTCACTGGCTACAC TGAGGTGCATTTCGCTGATTTTGGGGTC |
| N1_003 | TCTGGTTACTGCCAGTTGAATCTGAGGGTCCTTGACATGGCATGTGACTCCACT GTCGGTGCATTTCGCTGATTTTGGGGTC |
| N1_004 | TCTGGTTACTGCCAGTTGAATCTGAGGGTCCACCTTTGCCAGATGACTGAGTGG AAGGGTGCATTTCGCTGATTTTGGGGTC |
| N1_005 | TCTGGTTACTGCCAGTTGAATCTGAGGGTCCAGCTTGAAGCGTTCGCGACAAGT GTCGGTGCATTTCGCTGATTTTGGGGTC |
| N1_006 | TCTGGTTACTGCCAGTTGAATCTGAGGGTCCTCACGTCCTGAGATCAACTGCTA CATGGTGCATTTCGCTGATTTTGGGGTC |
| N1_007 | TCTGGTTACTGCCAGTTGAATCTGAGGGTCCGTTGACTGATCACATGCTGCTCC ACGGGTGCATTTCGCTGATTTTGGGGTC |
| N1_008 | TCTGGTTACTGCCAGTTGAATCTGAGGGTCCCAGACAGTCATCGGATTGATGAG TGAGGTGCATTTCGCTGATTTTGGGGTC |

Example 7—SwabSeq can Detect Multiple Different SARS-COV-2 Amplicons

Figure 24:
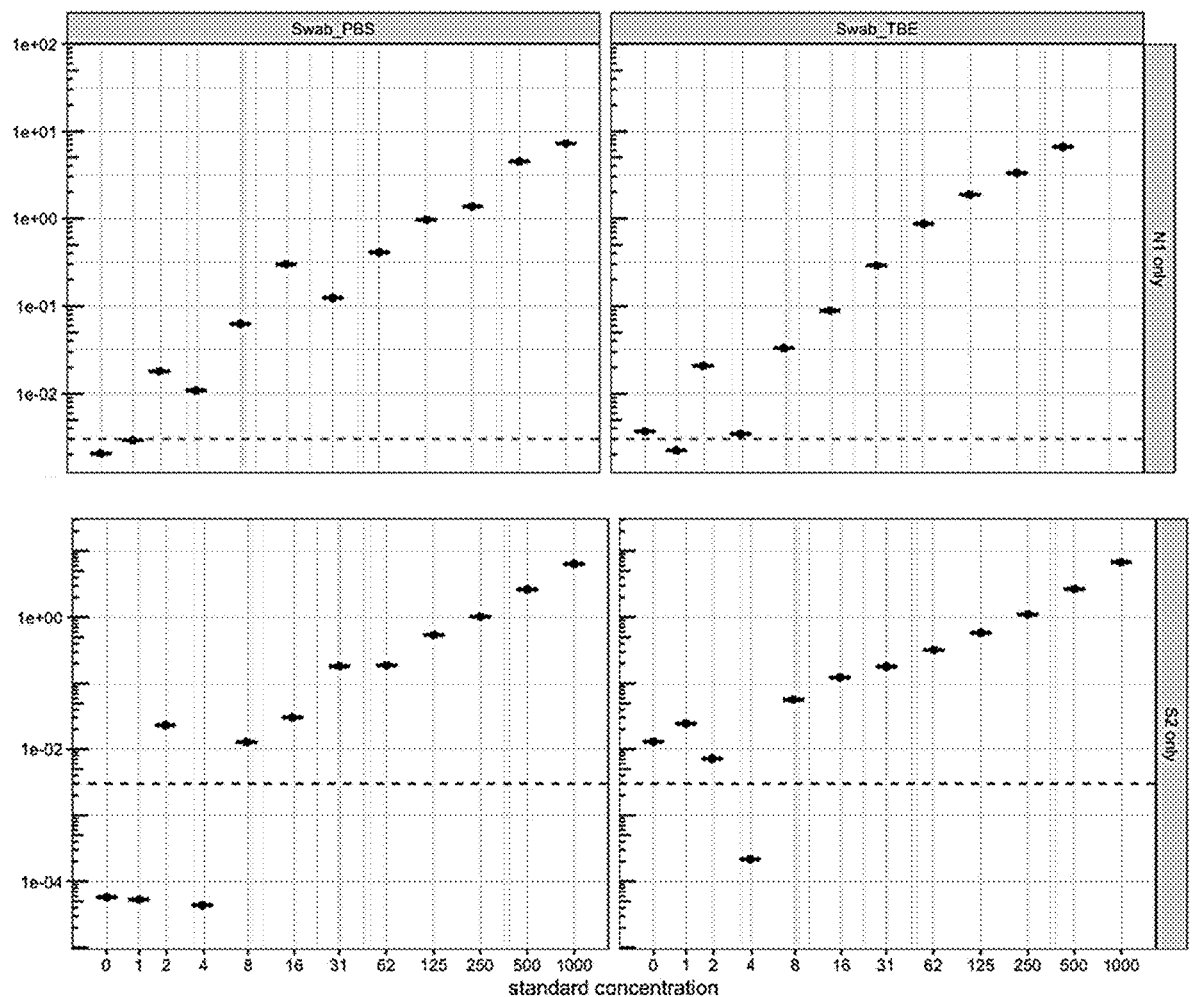
FIG. 24 shows data obtained with N1 spike in (top) or S2 spike in (bottom) and detection of different amplicons N1 (top) or (S2) bottom.

SwabSeq is able to detect two SARS-COV-2 genes: N1 and S2 and synthetic N1 and S2 controls, increasing the ability to call positive samples. Data for each amplicon is shown in FIG. 24.

N1 F:
(SEQ ID NO: 22)
CAAGCAGAAGACGGCATACGAGAT XXXXXXXXXX ACCCCAAAATCAGC

GAAAT;

N1 R:
(SEQ ID NO: 23)
AATGATACGGCGACCACCGAGATCTACAC XXXXXXXXXX TCTGGTTAC

TGCCAGTTGAATCTG;
X is representative of the unique dual index (UDI) for each primer.

Example 8—SwabSeq Performance with Different Samples

Figure 26:
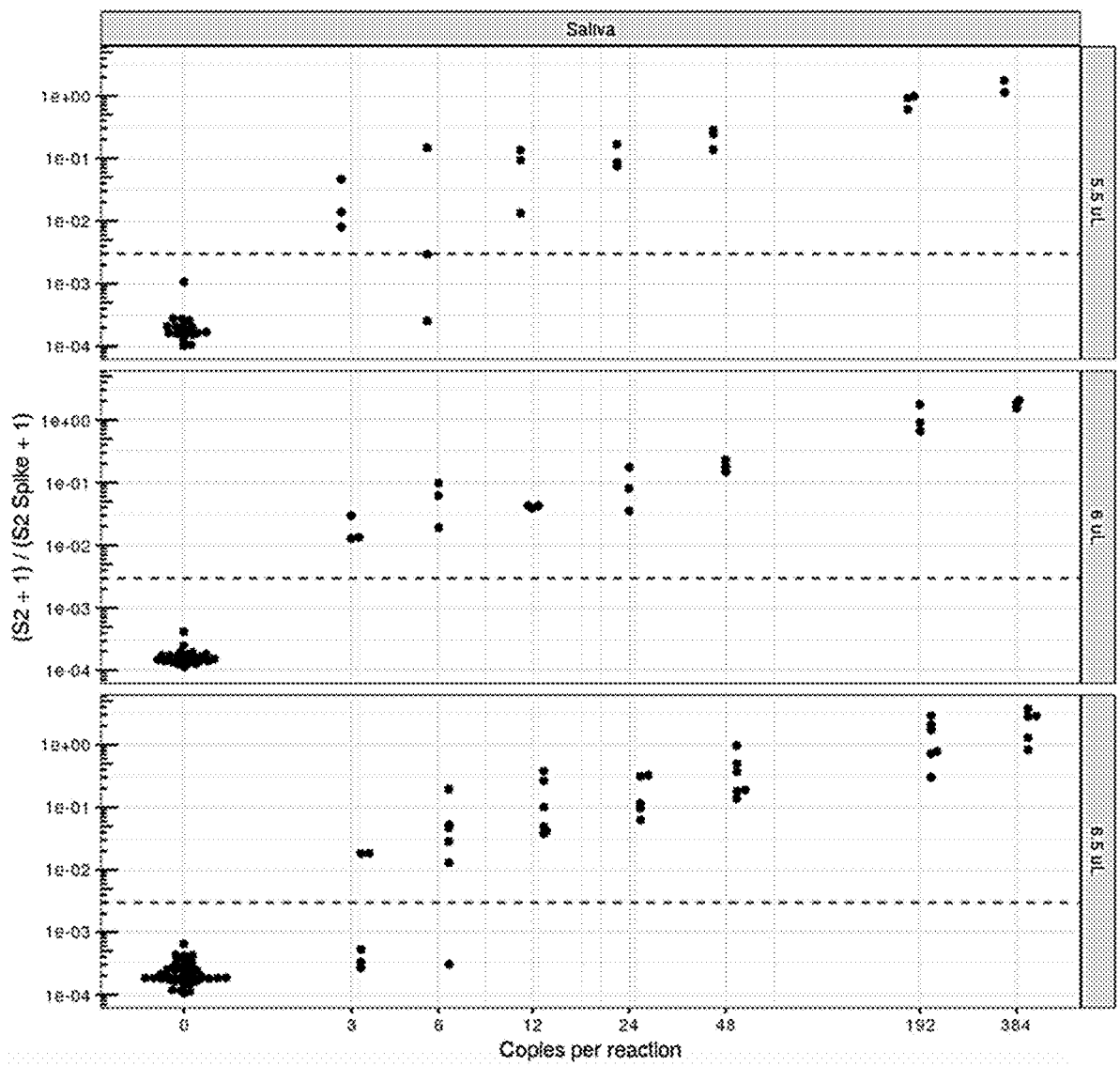
FIG. 26 shows results for detection using different volumes of saliva sample.
Figure 27:
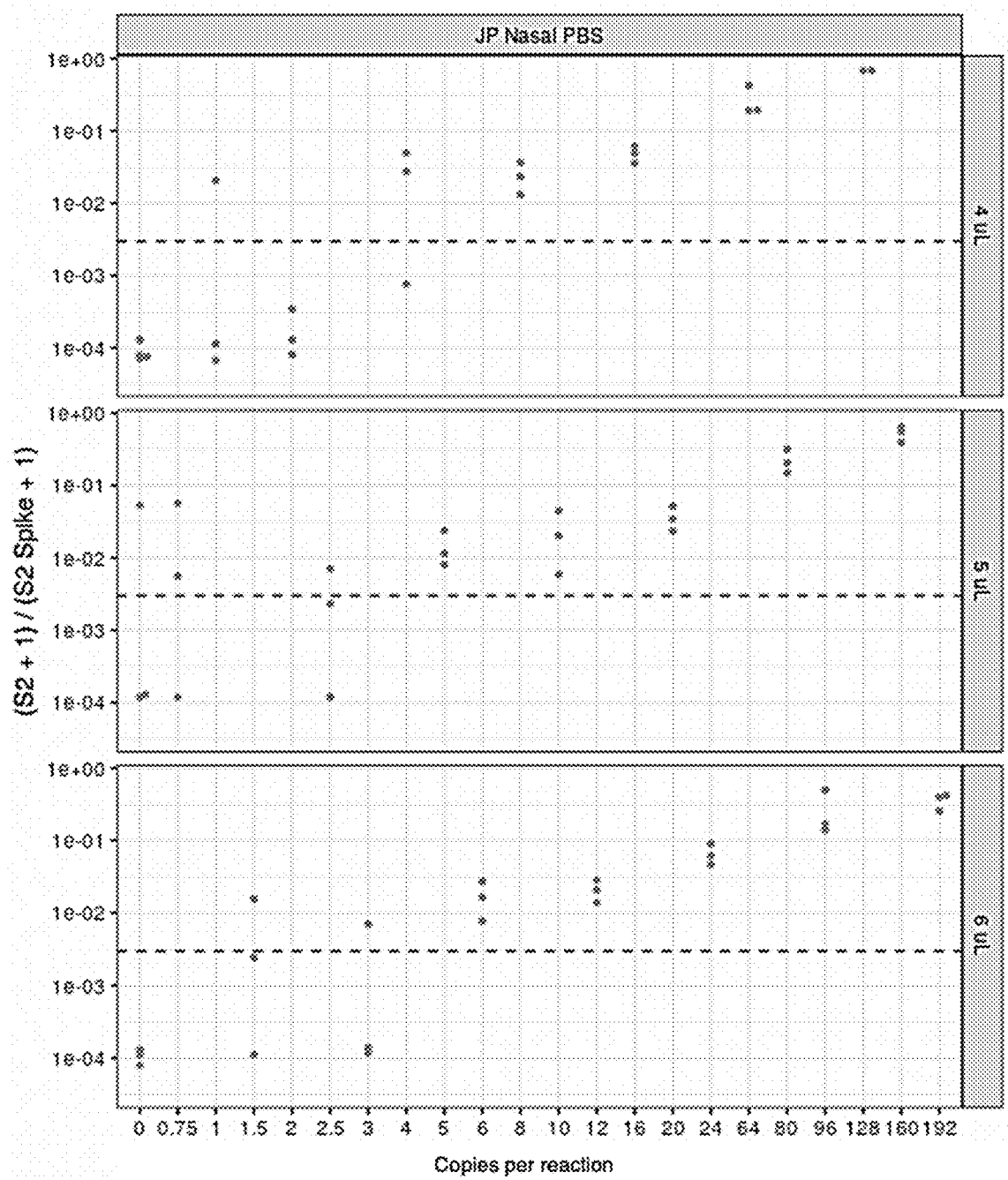
FIG. 27 shows results for detection using different volumes of nasal swab sample.

The ability to work from minimal or small samples is important for testing, especially if less invasive saliva samples can be used. FIG. 26 shows that up to 10 μL of saliva sample can be used during library preparation without inhibiting RT or PCR, and FIG. 27 shows that up to 6 μL of nasal swab sample (nasal swab inoculated into 1 mL of 1×PBS) can be used during library preparation without inhibiting RT or PCR.

Example 9—SwabSeq can be Used to Detect Both Influenza Virus and SARS-COV-2 Virus Sequencing and detection systems and platforms that can detect multiple viruses simultaneously are advantageous. Experiments for codetection of SARS-COV-2 and Influenza A and Influenza B were conducted.

Figure 28:
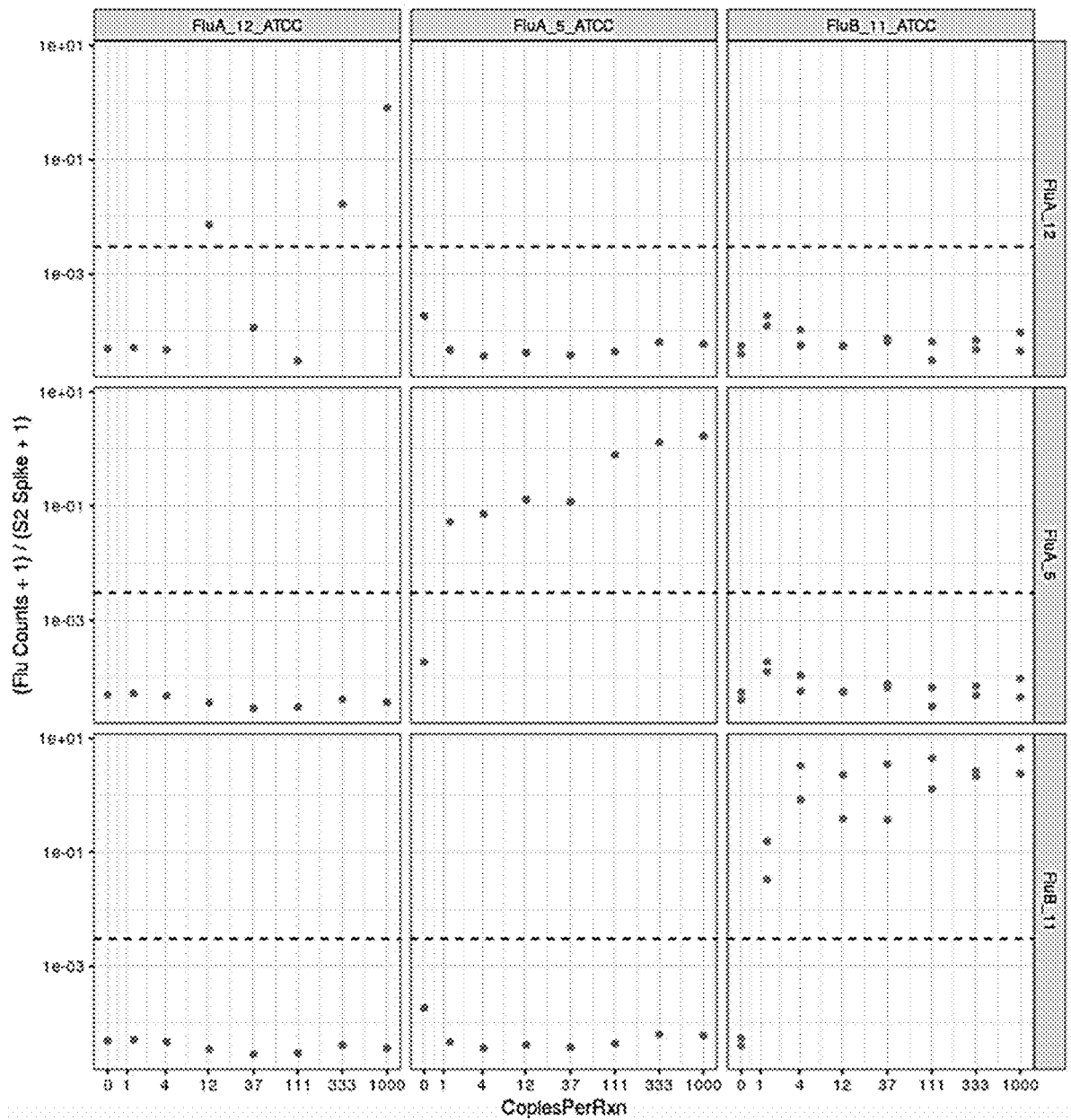
FIG. 28 shows that SwabSeq can detect Influenza A or Influenza B.

Specifically, the ability of SwabSeq to identify target amplicons for FluA MP, FluA NS and FluB NS. genome sequences were downloaded from the NCBI Influenza Database. Preliminary primers were then aligned to these sequences and the target amplification regions of each of these genomes were extracted. This information was then used to further optimize the primers to target as many of these amplicons as possible. All unique amplification regions were then exported and added to the target list. Results shown in FIG. 28 indicates that SwabSeq can detect influenza A or B in contrived samples.

To implement Swabseq for other respiratory pathogens, universal Influenza A and Influenza B Swabseq primers were designed. For Influenza A, 2 primer pairs targeting Influenza A were tested Ml (FluA_5_f1 GACCAATCYTGT-CACCTCTGAC (SEQ ID NO: 24), FluA_5_f2 GAC-CAATYCTGTCACCTYTGAC (SEQ ID NO: 25), FluA_5_r AGGGCATTTTGGAYAAAGCGTCTA (SEQ ID NO: 26))0 and NS1 (FluA_12_f TTGGGGTCCTCATCGGAG (SEQ ID NO: 27), FluA_12_r TTCTC-CAAGCGAATCTCTGTA, (SEQ ID NO: 28)) genes.

For Influenza B, a primer pair specific for the NS1 (FluB_11_f AAGATGGCCATCGGATCC, (SEQ ID NO: 29) FluB_11_r GTCTCCCTCTTCTGGTGATAATC, (SEQ ID NO: 30)) gene. Synthetic Nucleic Acid Spike sequences are shown below:

FluA_5_spike_004
(SEQ ID NO: 31)
GACCGATCCTGTCACCTCTGACTAAGGGTGGCACAACGCAGTGTGTTGAG

CTCCCTTAGTAGGGTGACTAGCACCGGCAGCGTAGACGCTTTGTCCAAAA

TGCCCT

FluA_12_spike_002
(SEQ ID NO: 32)
TTGGGGTCCTCATCGGAGGACGCTTAAATAATAGTAGGAACGTTCGAGTC

TCTAAAAATATACAGAGATTCGCTTGGAGAA

FluB_11_spike_004
(SEQ ID NO: 33)
AAGATGGCCATCGGATCCTCAACTCACTCCTGTAATGAGTCGTAGACAAG

GATAAGAGGCCCGATCGGCAGTATTTCGCCCTTTCTAAAAATAATGTGAC

CTGGGACGCACTGCACCGATTATCACCAGAAGAGGGAGAC

Example 10—Inclusivity and Cross Reactivity of S2 Primers

Given the high rate of mutation of SARS-COV-2 it is important that primers utilized in sequencing tests be able to amplify many different variants. In silico analysis of the S2 primer sets and S2 amplicon sequence were performed to evaluate the inclusivity of the SwabSeq test. For the primer analysis, SARS-COV-2 sequences available on GISAID were evaluated. We first filtered out low quality genomes, which we defined as having greater than or equal to 1% unidentified nucleotides (N's). A BLASTn (NCBI) analysis was performed on the remaining 324,355 high quality genomes to quantify the level of primer homology across these sequences by querying each of the two SARS-COV-2 primer sequences against the downloaded SARS-COV-2 sequences. The analysis showed that 91.24% of all analyzed strains have 100% homology to both primer sequences and 28,398 strains (or 8.76%) of the 324,355 complete genomes have less than 100% homology to a primer. For the forward S2 primers, 303,840 (93.67%) GISAID genomes have 100% homology. For the reverse S2 primers, 305,019 (94.04%) GISAID genomes have 100% homology. The S2 amplicon is 26 base pairs and 303,934 (93.70%)GISAID genomes have 100% homology.

In silico analysis was performed to evaluate the cross-reactivity of the SwabSeq primers with representative common respiratory pathogens. For the primer analysis, 38 non-SARS-COV-2 consensus genomes were downloaded from NCBI as the negative sample cohort. A BLASTn (NCBI) analysis was then performed to quantify the number of primer pairs with more than 80% homology with each of the genomes in the cohort. None of the pathogens exhibit greater than 80% homology with any of the primers.

Example 11—Analysis of Sequencing Data

Presented herein is an example of an analysis platform the determination of infection with a pathogen, that can be combined with the extraction, amplification, and sequencing steps of SwabSeq.

First, all single nucleotide substitutions, deletions, and insertions for all targeted amplicons and barcode indices are generated. These are then used to as keys in a nested data structure that contains the original sequence, name of target, and type of match (exact match, mismatch, deletion, insertion). Since the keys in this data structure are indexed, exact string matching can be performed on sequencing data and the target information retrieved quickly within predetermined matching tolerances (single base substitutions, deletions, and insertions). All duplicated sequences are removed, and the match type of the remaining unique sequence is re-classified to "undetermined."

The sequencing data are then extracted from the FASTQ files and matched with their corresponding dictionaries (index 1, index 2, or amplicons). Prior to matching, the instrument and kit information is read in to determine which sequences need to be reverse-complimented prior to matching.

The matching function returns either the original target sequence (used for the indices) or the name of the target (used for amplicons). This is a key step since many targets, including the diversified spikes and Influenza targets have several sequences that require aggregation together. Other data such as match type can be returned as well.

Matched sequences are then aggregated by their indices and amplicon target and a table of total reads per index pair is returned. This information is used downstream for quality control (can be used to determine carryover contamination, index hopping, failed amplification, etc.) as well as presence or absence of COVID-19 and Influenza A/B.

This information is returned as an automatically generated PDF that contains quality control plots as well as tables with information about each sample such as QC pass/fail, COVID-19 positive/negative, Influenza A/B positive/negative.

Dictionary-based exact matching of amplicons and barcodes enables fast analysis without depending on existing bioinformatics analysis libraries while accounting for all single base deletions, insertions and mismatches.

Figure 29:
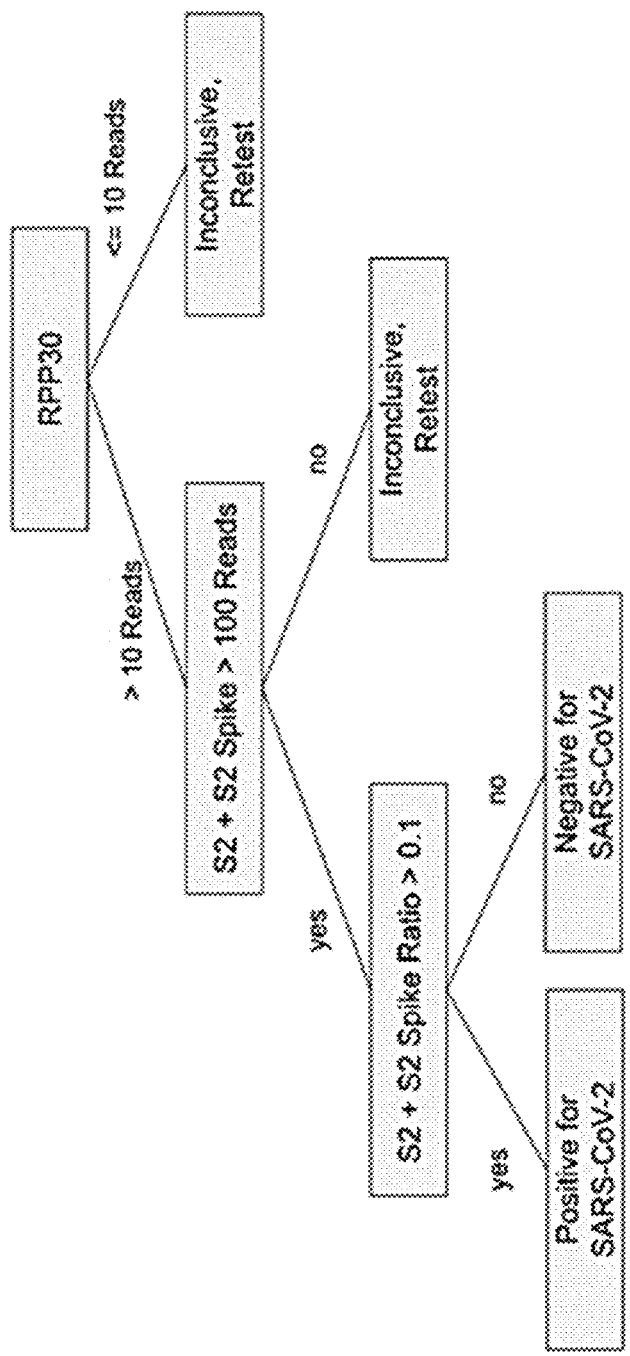
FIG. 29 shows an exemplary algorithm for calling positive and negative samples.

An example of an algorithm for calling positive samples when using the S2 primers, S2 synthetic nucleic acid and RPP30 primers is shown in table 4 below and FIG. 29 and requires an absolute number of reads of RPP30 amplicon, an absolute number of S2+S2 spike, and a ratio of S2/S2 spike greater than 0.1.

series. Eleven extraction replicates were performed per concentration. The preliminary LoD was defined as the lowest concentration with 11 of 11 replicates that test positive. The LoD determination was carried out independently for the Luna® Probe One-Step RT-qPCR 4X Mix with UDG and the TaqPath™ 1-Step RT-qPCR Master Mix. For both RT-qPCR mastermixes, the preliminary LoD was determined to be 8,000 GCE/ml. See results in table 5 below.

TABLE 5

Preliminary LoD Determination Results

| Viral Concentration (GCE/ml) | Detection Rate (%) Luna ® | Detection Rate (%) TaqPath ™ |
|---|---|---|
| 24,000 | 11/11 (100%) | 11/11 (100%) |
| 20,000 | 11/11 (100%) | 11/11 (100%) |
| 16,000 | 11/11 (100%) | 11/11 (100%) |
| 12,000 | 11/11 (100%) | 11/11 (100%) |
| 8,000 | 11/11 (100%) | 11/11 (100%) |
| 6,000 | 11/11 (100%) | 10/11 (90.9%) |
| 4,000 | 6/11 (54.5%) | 6/11 (54.5%) |
| 2,000 | 1/11 (9.1%) | 1/11 (9.1%) |

A limit of detection confirmation study for both the LunaR Probe One-Step RT-qPCR 4X Mix with UDG and the TaqPath™ 1-Step RT-qPCR Master Mix was performed by spiking in heat-inactivated SARS-COV-2 virus (ATCC, VR-1986) in negative saliva specimens at a final concentration of 12,000 GCE/mL and 8,000 GCE/mL, corresponding to 1.5X and 1X the determined limit of detection. Ten (10) extraction replicates were performed for each concentration. The LoD confirmation at these two concentrations was carried out independently for the Luna Probe One-Step RT-qPCR 4X Mix with UDG and the TaqPath™ 1-Step RT-qPCR Master Mix. The minimal LoD in both RT-qPCR mastermixes was confirmed to be 8,000 GCE/mL for both Luna® Probe One-Step RT-qPCR 4X Mix with UDG and the TaqPath™ 1-Step RT-qPCR Master Mix.

TABLE 4

| Well-controls | | | Results | | |
|---|---|---|---|---|---|
| Total S2 + S2 Spike | RPP30 read count | S2/S2 spike ratio | Result | Interpretation | Action |
| >100 | >10 | >0.1 | SARS-CoV-2 Detected | Positive for SARS-CoV-2 for the Sample ID. | Report results to physician, patient, and appropriate public health authorities. |
| >100 | >10 | <0.1 | SARS-CoV-2 Not Detected | Negative for SARS-CoV-2 for the Sample ID. | Report results to physician, patient, and appropriate public health authorities. |
| <100 | >10 | — | Inconclusive | Invalid for the Sample ID. | Quality control for the Sample ID is FAIL. Repeat sample or Recollect sample |
| <100 | <10 | — | Inconclusive | Invalid for the Sample ID. | Quality control for the Sample ID is FAIL. Repeat sample or Recollect sample |

Example 12—Limit of Detection

A limit of detection (LoD) study was performed by spiking in heat inactivated SARS-CoV-2 virus (ATCC, VR-1986) in negative saliva specimens using a dilution Example 13—Clinical Evaluation A study was performed to evaluate the performance of SwabSeq comparing saliva clinical samples that had previously been analyzed and confirmed as positive or negative using a laboratory-developed test (LDT).

Saliva samples were collected and run through using the MiniSeq Illumina sequencer. Results using the Luna® Probe One-Step RT-qPCR 4× Mix with UDG are summarized in Table 6. Using Luna® Probe One-Step RT-qPCR 4× Mix with UDG, the positive agreement (25/25) was 100% and negative agreement (93/93) was 100%. Results using TaqPath™ 1-Step RT-qPCR Master Mix are summarized in Table 7. The positive agreement (25/25) was 100% and negative agreement (93/93) was 100%.

TABLE 6

Evaluation with Clinical Specimens Using Luna® Probe One-Step RT-qPCR 4X Mix with UDG

|  |  | LDT Comparator Assay | | |
|---|---|---|---|---|
|  |  | Positive | Negative | Total |
| Ginkgo SARS-CoV-2 NGS Test (Octant v1) - Luna® | Positive | 25 | 0 | 25 |
|  | Negative | 0 | 93 | 93 |
|  | Inconclusive | 0 | 0 | 0 |
|  | Total | 25 | 93 | 118 |
| Positive Agreement |  | 100% (25/25); 82.4%-100%[1] | | |
| Negative Agreement |  | 100% (93/93); 96.1%-100%[1] | | |
| Overall Agreement |  | 100% (118/118); 96.9%-100%[1] | | |

[1]Two-sided 95% score confidence intervals

TABLE 7

Evaluation with Clinical Specimens Using TaqPath™ 1-Step RT-qPCR Master Mix

|  |  | LDT Comparator Assay | | |
|---|---|---|---|---|
|  |  | Positive | Negative | Total |
| Ginkgo SARS-CoV-2 NGS Test (Octant v1) - TaqPath™ | Positive | 25 | 0 | 25 |
|  | Negative | 0 | 93 | 93 |
|  | Inconclusive | 0 | 0 | 0 |
|  | Total | 25 | 93 | 118 |
| Positive Agreement |  | 100% (25/25); 82.4%-100%[1] | | |
| Negative Agreement |  | 100% (93/93); 96.1%-100%[1] | | |
| Overall Agreement |  | 100% (118/118); 96.9%-100%[1] | | |

[1]Two-sided 95% score confidence intervals

An intermediate precision study was performed on a second day using the same clinical samples to evaluate the reliability of SwabSeq. The person performing the test and instruments used in the test (Viaflo-96, manual pipette set, MiniSeq Sequencer, Thermal Cycler) used on the second day were all different than the first. Saliva clinical samples were then compared that had previously been analyzed and confirmed as positive or negative using a laboratory-developed test (LDT).

Results using SwabSeq are summarized in Table 8 and Table 9. Clinical samples analyzed using the Luna® Probe One-Step RT-qPCR 4× Mix with UDG are summarized in Table 8. The positive agreement (25/25) was 100% and negative agreement (93/93) was 100%, and the concordance across the two intermediate precision runs was 100%. Clinical samples analyzed using Taqpath™ 1-Step RT-qPCR Master Mix are summarized in Table 9. The positive agreement (25/25) was 100% and negative agreement (93/93) was 100%, and the concordance across the two intermediate precision runs was 100%.

TABLE 8

Evaluation with Clinical Specimens Using Luna® Probe One-Step RT-qPCR 4X Mix with UDG

|  |  | LDT Comparator Assay | | |
|---|---|---|---|---|
|  |  | Positive | Negative | Total |
| Ginkgo SARS-CoV-2 NGS Test (Octant v1) - Luna® | Positive | 25 | 0 | 25 |
|  | Negative | 0 | 93 | 93 |
|  | Inconclusive | 0 | 0 | 0 |
|  | Total | 25 | 93 | 118 |
| Positive Agreement |  | 100% (25/25); 82.4%-100%[1] | | |
| Negative Agreement |  | 100% (93/93); 96.1%-100%[1] | | |
| Overall Agreement |  | 100% (118/118); 96.9%-100%[1] | | |

[1]Two-sided 95% score confidence intervals

TABLE 9

Evaluation with Clinical Specimens Using TaqPath™ 1-Step RT-qPCR Master Mix

|  |  | LDT Comparator Assay | | |
|---|---|---|---|---|
|  |  | Positive | Negative | Total |
| Ginkgo SARS-CoV-2 NGS Test (Octant v1) - TaqPath™ | Positive | 25 | 0 | 25 |
|  | Negative | 0 | 93 | 93 |
|  | Inconclusive | 0 | 0 | 0 |
|  | Total | 25 | 93 | 118 |
| Positive Agreement |  | 100% (25/25); 82.4%-100%[1] | | |
| Negative Agreement |  | 100% (93/93); 96.1%-100%[1] | | |
| Overall Agreement |  | 100% (118/118); 96.9%-100%[1] | | |

[1]Two-sided 95% score confidence intervals

The two intermediate precision runs performed using SwabSeq comparing saliva clinical samples that had previously been analyzed and confirmed as positive or negative show a 100% concordance.

Example 14—Precision

To assess within run and between run precision, replicates at two contrived concentrations of virus/mL: 12,000 copies/mL and 24,000 copies/mL across 3 runs on the MiniSeq Sequencers were run. This was repeated so that both the Luna® Probe One-Step RT-qPCR 4X Mix with UDG (Table 10) and TaqPath™ 1-Step RT-qPCR Master Mix (Table 11) were used. These concentrations represent 1.5X and 3X the limit of detection of our assay. It was observed that the agreement of our third precision run using the Taqpath™ mastermix was not 100% (see Table 11). It was sometimes observed that contrived samples consisting of a viral RNA SARS-COV-2 standard spiked into negative control saliva can degrade if not processed quickly enough. A fourth precision run for both Luna® and Taqpath™ where run with contrived samples did not sit for so long at room temperature and found that there was 100% agreement in the fourth run.

TABLE 10

Precision of Contrived Samples Using Luna ® Probe One-Step RT-qPCR 4X Mix with UDG

| copies/mL | Detection rate % Luna ® | | | | Between-run Concordance |
|---|---|---|---|---|---|
| | Run1 | Run2 | Run3 | Run4 | |
| 12,000 | 6/6 (100%) | 6/6 (100%) | 6/6 (100%) | 6/6 (100%) | 24/24 (100%) |
| 24,000 | 6/6 (100%) | 6/6 (100%) | 6/6 (100%) | 6/6 (100%) | 24/24 (100%) |
| In-run Concordance | 12/12 (100%) | 12/12 (100%) | 12/12 (100%) | 12/12 (100%) | |

TABLE 11

Precision of Contrived Samples Using TaqPath™ 1-Step RT-qPCR Master Mix

| copies/mL | Detection rate % TaqPath™ | | | | Between Run Concordance |
|---|---|---|---|---|---|
| | Run1 | Run2 | Run3 | Run4 | |
| 12,000 | 6/6 (100%) | 6/6 (100%) | 5/6 (83.3%) | 6/6 (100%) | 23/24 (95.8%) |
| 24,000 | 6/6 (100%) | 6/6 (100%) | 4/6 (66.6%) | 6/6 (100%) | 22/24 (91.6%) |
| In-run Concordance | 12/12 (100%) | 12/12 (100%) | 9/12 (75%) | 12/12 (100%) | |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A method of detecting a Coronavirus infection in an individual, the method comprising:
   (a) providing a sample, wherein said sample comprises a biological sample from said individual and a Coronavirus synthetic RNA, wherein a nucleic acid sequence of said Coronavirus synthetic RNA differs from a naturally occurring Coronavirus nucleic acid sequence;
   (b) lysing said sample, thereby producing a lysed sample;
   (c) performing a reverse transcription reaction on said lysed sample to obtain a lysed, reverse transcribed sample, wherein RNA from said lysed sample is not purified before performing said reverse transcription reaction;
   (d) performing an amplification reaction on said lysed, reverse transcribed sample to obtain an amplified biological sample, wherein said amplification reaction on said lysed, reverse transcribed sample is performed with a set of Coronavirus primers specific for a Coronavirus nucleic acid sequence, wherein said set of Coronavirus primers amplify said Coronavirus nucleic acid sequence and said Coronavirus synthetic RNA; and
   (e) sequencing said amplified sample.

2. The method of claim 1, further comprising providing a positive diagnosis for Coronavirus infection if sequence reads from said Coronavirus nucleic acid sequence are detected.

3. The method of claim 1, wherein said Coronavirus infection is a SARS-Cov-2 infection.

4. The method of claim 2, wherein said positive diagnosis for said Coronavirus infection or SARS-Cov-2 infection is provided when a ratio or a mathematical equivalent thereof of said sequence reads from said Coronavirus nucleic acid sequence to sequence reads of said Coronavirus synthetic RNA exceed about 0.1.

5. The method of claim 2, wherein said positive diagnosis for Coronavirus infection is provided when said sequence reads from said Coronavirus nucleic acid sequence and said sequence reads of Coronavirus synthetic RNA exceed about 100 total sequence reads.

6. The method of claim 1, wherein the method further comprises detecting an Influenza A infection, an Influenza B infection, or a combination thereof.

7. The method of claim 1, wherein lysing said sample comprises thermal lysis.

8. The method of claim 7, wherein said thermal lysis comprises heating said sample to a temperature of at least about 50° C.

9. The method of claim 1, wherein said sample from said individual comprises a plurality of Coronavirus synthetic RNA sequences, wherein said plurality of Coronavirus synthetic RNA sequences comprise at least two distinct synthetic Coronavirus RNA sequences.

10. The method of claim 9, wherein said plurality of synthetic Coronavirus RNA sequences comprise at least four distinct synthetic Coronavirus RNA nucleic acid sequences.

11. The method of claim 9, wherein the Coronavirus synthetic RNA or the plurality of Coronavirus synthetic RNA sequences comprises an amount of guanine nucleotide that is from about 20% to about 30%, an amount of adenine nucleotide that is from about 20% to about 30%, an amount of cytosine nucleotide that is from about 20% to about 30%, an amount of uracil nucleotide that is from about 20% to about 30%.

12. The method of claim 1, wherein said amplification reaction on said lysed sample is further performed with a set of influenza A primers specific for an influenza A nucleic acid sequence and/or a set of influenza B primers specific for an influenza B nucleic acid sequence.

13. The method of claim 1, wherein said Coronavirus synthetic RNA is present at a concentration from about 10 copies per/reaction to about 500 copies per reaction.

14. The method of claim 1, wherein sequencing said amplified sample comprises single molecule real-time sequencing, sequencing-by-synthesis, or ion semiconductor sequencing.

15. The method of claim 1, wherein sequencing of said amplified sample is not Sanger sequencing.

16. The method of claim 1, wherein sequencing said amplified sample generates at least 1 million sequence reads.

* * * * *

SEQUENCE LISTING

```
<160> NUMBER OF SEQ ID NOS: 632

<210> SEQ ID NO 1
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
gcuggugcug cagcuuauua ugugggugug uaucucacga agcgacccuu uggaaaauau      60
aaugaaaaug gaaccauuac agaugcugua gacugugcac uugacccu                   108

<210> SEQ ID NO 2
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
gcuggugcug cagcuuauua ugugggúccu cgcuaggacg ucgcuaugac gccaaaauau      60
aaugaaaaug gaaccauuac agaugcugua gacugugcac uugacccu                   108

<210> SEQ ID NO 3
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
```

```
gcuggugcug cagcuuauua ugugggua gc acgacuugau cuaacugaca cuaaaaauau    60
aaugaaaaug gaaccauuac agaugcugua gacugugcac uugacccu                 108

<210> SEQ ID NO 4
<211> LENGTH: 108
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
gcuggugcug cagcuuauua uguggguuaa guaggacuuc gauuggaugg aauaaaauau    60
aaugaaaaug gaaccauuac agaugcugua gacugugcac uugacccu                 108

<210> SEQ ID NO 5
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ucugguuacu gccaguugaa ucugaggguc cggacggaua ucgcacuaag uguaccuggu    60
gcauuucgcu gauuuugggg uc                                             82

<210> SEQ ID NO 6
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ucugguuacu gccaguugaa ucugagdgguc ccaugaccau gucacuggcu acacugaggu   60
gcauuucgcu gauuuugggg uc                                             82

<210> SEQ ID NO 7
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
ucugguuacu gccaguugaa ucugagdgguc cuugacaugg caugugacuc cacugucggu   60
gcauuucgcu gauuuugggg uc                                             82

<210> SEQ ID NO 8
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 8
ucugguuacu gccaguugaa ucugagggguc caccuuugcc agaugacuga guggaaggu    60 gcauuucgcu gauuuggggg uc    82

<210> SEQ ID NO 9
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ucugguuacu gccaguugaa ucugagggguc cagcuugaag cguucgcgac aagugucggu    60
gcauuucgcu gauuuggggg uc    82

<210> SEQ ID NO 10
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
ucugguuacu gccaguugaa ucugagggguc cucacguccu gagaucaacu gcuacauggu    60
gcauuucgcu gauuuggggg uc    82

<210> SEQ ID NO 11
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
ucugguuacu gccaguugaa ucugagggguc cguugacuga ucacaugcug cuccacgggu    60
gcauuucgcu gauuuggggg uc    82

<210> SEQ ID NO 12
<211> LENGTH: 82
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
ucugguuacu gccaguugaa ucugagggguc ccagacaguc aucggauuga ugagugaggu    60
gcauuucgcu gauuuggggg uc    82

<210> SEQ ID NO 13
<211> LENGTH: 74
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 13
taatacgact cactataggg ctggtgctgc agcttattat gtgggtatag aacaacctag    60
gacttttcta ttaa                                                     74

<210> SEQ ID NO 14
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
aacgtacact ttgtttctga gagagg                                        26

<210> SEQ ID NO 15
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ctgacctgaa ggctgacgcc ggacttgtgg agacagc                            37

<210> SEQ ID NO 16
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
taatacgact cactataggg agatttggac ctgcgagcgg gttctgacct gaaggctga    59

<210> SEQ ID NO 17
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17 ggttttcaa tttcctgttt cttttcctta aagtcaacg                           39

<210> SEQ ID NO 18
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
gctggtgctg cagcttatta tgtgggt                                       27

<210> SEQ ID NO 19
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
agggtcaagt gcacagtcta                                                 20

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
gaccccaaaa tcagcgaaat                                                 20

<210> SEQ ID NO 21
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
tctggttact gccagttgaa tctg                                            24

<210> SEQ ID NO 22
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (25)..(34)
<223> OTHER INFORMATION: a, c, t, g, unknown or other

<400> SEQUENCE: 22
caagcagaag acggcatacg agatnnnnnn nnnnacccca aaatcagcga aat             53

<210> SEQ ID NO 23
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (30)..(39)
<223> OTHER INFORMATION: a, c, t, g, unknown or other

<400> SEQUENCE: 23
aatgatacgg cgaccaccga gatctacacn nnnnnnnnnt ctggttactg ccagttgaat     60
ctg                                                                   63
```

```
<210> SEQ ID NO 24
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
gaccaatcyt gtcacctctg ac                                              22

<210> SEQ ID NO 25
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
gaccaatyct gtcacctytg ac                                              22

<210> SEQ ID NO 26
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
agggcatttt ggayaaagcg tcta                                            24

<210> SEQ ID NO 27
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
ttggggtcct catcggag                                                   18

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ttctccaagc gaatctctgt a                                               21

<210> SEQ ID NO 29
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 29
aagatggcca tcggatcc                                                   18

<210> SEQ ID NO 30
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
gtctccctct tctggtgata atc                                             23

<210> SEQ ID NO 31
<211> LENGTH: 106
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
gaccgatcct gtcacctctg actaagggtg gcacaacgca gtgtgttgag ctcccttagt     60
agggtgacta gcaccggcag cgtagacgct ttgtccaaaa tgccct                   106

<210> SEQ ID NO 32
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
ttggggtcct catcggagga cgcttaaata atagtaggaa cgttcgagtc tctaaaata     60 tacagagatt cgcttggaga a                                               81

<210> SEQ ID NO 33
<211> LENGTH: 140
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
aagatggcca tcggatcctc aactcactcc tgtaatgagt cgtagacaag gataagaggc     60
ccgatcggca gtatttcgcc ctttctaaaa ataatgtgac ctgggacgca ctgcaccgat    120
tatcaccaga agagggagac                                                140

<210> SEQ ID NO 34

<400> SEQUENCE: 34

000

<210> SEQ ID NO 35

<400> SEQUENCE: 35
```

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

```
<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80
```

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

-continued

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
tggggtctta cacggcgatc ttgcc                                25

<210> SEQ ID NO 101
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
gggtcaacgt gtcggcatgg attct                                    25

<210> SEQ ID NO 102
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
agttacattc acgccagttg tgtctggt                                 28

<210> SEQ ID NO 103
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
agttacattc acgccagttg tggcg                                    25

<210> SEQ ID NO 104
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
gtttgtaatt acacggcgat cttgcc                                   26

<210> SEQ ID NO 105
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
gtccaaatct ttacacggcg atcttgcc                                 28

<210> SEQ ID NO 106
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
agttacattc acgccagttg tggagc                                   26

<210> SEQ ID NO 107
<211> LENGTH: 43
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
taatacgact cactataggg tctgataatg gaccccaaaa tca                      43

<210> SEQ ID NO 108
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
ttaggcctga gttgagtcag c                                             21

<210> SEQ ID NO 109
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
caagcagaag acggcatacg agatgttcta tcgaccccaa aatcagcgaa at            52

<210> SEQ ID NO 110
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
aatgatacgg cgaccaccga gatctacaca agatctgtct ggttactgcc agttgaatct   60
g                                                                   61

<210> SEQ ID NO 111
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
caagcagaag acggcatacg agatgttcta tcttacaaac attggccgca aa            52

<210> SEQ ID NO 112
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
```
aatgatacgg cgaccaccga gatctacaca agatctggcg cgacattccg aagaa    55

<210> SEQ ID NO 113
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
caagcagaag acggcatacg agatgttcta tcagatttgg acctgcgagc g    51

<210> SEQ ID NO 114
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
aatgatacgg cgaccaccga gatctacaca agatctggag cggctgtctc cacaagt    57

<210> SEQ ID NO 115
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
caagcagaag acggcatacg agatgttcta tctaatcaga caaggaactg atta    54

<210> SEQ ID NO 116
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
aatgatacgg cgaccaccga gatctacaca agatctgcga aggtgtgact tccatg    56

<210> SEQ ID NO 117
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
aatgatacgg cgaccaccga gatctacaca agatctggat caaaacaacg tcggccc    57

<210> SEQ ID NO 118
<211> LENGTH: 52
<212> TYPE: DNA
<213> ORGANISM: Artificial Sequence
<220> FEATURE:

<220> FEATURE:
<221> NAME/KEY: source
<223> OTHER INFORMATION: /note="Description of Artificial Sequence:
      Synthetic oligonucleotide"

<400> SEQUENCE: 118
caagcagaag acggcatacg agatgttcta tcccatgttg agtgagagcg gt            52

<210> SEQ ID NO 119
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
aatgatacgg cgaccaccga gatctacaca agatctgtgg accccaaaat cagcgaa      57

<210> SEQ ID NO 120
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
caagcagaag acggcatacg agatgttcta tcactgcgtt ctccattctg gtt           53

<210> SEQ ID NO 121
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
aatgatacgg cgaccaccga gatctacaca agatctgcag cgttcttcgg aatgtcg      57

<210> SEQ ID NO 122
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
caagcagaag acggcatacg agatgttcta tcgcacctgt gtaggtcaac ca            52

<210> SEQ ID NO 123
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
aatgatacgg cgaccaccga gatctacaca agatctggaa atgcaccccg cattacg      57

```
<210> SEQ ID NO 124
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
caagcagaag acggcatacg agatgttcta tccccactgc gttctccatt ct           52

<210> SEQ ID NO 125
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
aatgatacgg cgaccaccga gatctacaca agatctggtc ttggttcacc gctctca      57

<210> SEQ ID NO 126
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
caagcagaag acggcatacg agatgttcta tcttggaacg ccttgtcctc g            51

<210> SEQ ID NO 127
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
aatgatacgg cgaccaccga gatctacaca agatctggca gtcaagcctc ttctcgt      57

<210> SEQ ID NO 128
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
caagcagaag acggcatacg agatgttcta tcgaagttcc cctactgctg cc           52

<210> SEQ ID NO 129
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 129
aatgatacgg cgaccaccga gatctacaca agatctgcgt ttggtggacc ctcagat    57

<210> SEQ ID NO 130
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
caagcagaag acggcatacg agatgttcta tcgacgttgt tttgatcgcg cc    52

<210> SEQ ID NO 131
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
aatgatacgg cgaccaccga gatctacaca agatctgaag gccaacaaca acaaggc    57

<210> SEQ ID NO 132
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
caagcagaag acggcatacg agatgttcta tcggcagtac gttttttgccg ag    52

<210> SEQ ID NO 133
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
aatgatacgg cgaccaccga gatctacaca agatctgacc agaatggaga acgcagt    57

<210> SEQ ID NO 134
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
caagcagaag acggcatacg agatgttcta tccggtgaac caagacgcag ta    52

<210> SEQ ID NO 135
<211> LENGTH: 57
<212> TYPE: DNA
<213> ORGANISM: Artificial Sequence

```
-continued

<220> FEATURE:
<221> NAME/KEY: source
<223> OTHER INFORMATION: /note="Description of Artificial Sequence:
      Synthetic oligonucleotide"

<400> SEQUENCE: 135
aatgatacgg cgaccaccga gatctacaca agatctgccg cattacgttt ggtggac      57

<210> SEQ ID NO 136
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
caagcagaag acggcatacg agatgttcta tcggccgacg ttgttttgat cg           52

<210> SEQ ID NO 137
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
aatgatacgg cgaccaccga gatctacaca agatctggcc tcggcaaaaa cgtactg      57

<210> SEQ ID NO 138
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
caagcagaag acggcatacg agatgttcta tcttgttctg gaccacgtct gc           52

<210> SEQ ID NO 139
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
aatgatacgg cgaccaccga gatctacaca agatctgaat ccctcgagg acaaggc       57

<210> SEQ ID NO 140
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
caagcagaag acggcatacg agatgttcta tctcgtctgg tagctcttcg gt           52
```

<210> SEQ ID NO 141
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
aatgatacgg cgaccaccga gatctacaca agatctggct tcagcgttct tcggaat       57

<210> SEQ ID NO 142
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
caagcagaag acggcatacg agatgttcta tctggcacct gtgtaggtca ac            52

<210> SEQ ID NO 143
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
aatgatacgg cgaccaccga gatctacaca agatctgaga atagagctcg caccgta       57

<210> SEQ ID NO 144
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
caagcagaag acggcatacg agatgttcta tcctcctcta gtggcggcta tt            52

<210> SEQ ID NO 145
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
aatgatacgg cgaccaccga gatctacaca agatctggct ggtgctgcag cttatta       57

<210> SEQ ID NO 146
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
caagcagaag acggcatacg agatgttcta tcagggtcaa gtgcacagtc ta    52

<210> SEQ ID NO 147
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
aatgatacgg cgaccaccga gatctacaca agatctgttc ggaagagaca ggtacgtta    59

<210> SEQ ID NO 148
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
caagcagaag acggcatacg agatgttcta tcagcagtac gcacacaatc g    51

<210> SEQ ID NO 149
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
aatgatacgg cgaccaccga gatctacaca agatctgcaa tgctgcaatc gtgctac    57

<210> SEQ ID NO 150
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
caagcagaag acggcatacg agatgttcta tcgttgcgac tacgtgatga gg    52

<210> SEQ ID NO 151
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
agatttggac ctgcgagcg    19

<210> SEQ ID NO 152
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
gagcggctgt ctccacaagt                                              20

<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
agaatagagc tcgcaccgta                                              20

<210> SEQ ID NO 154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
ctcctctagt ggcggctatt                                              20

<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
gctggtgctg cagcttatta                                              20

<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
agggtcaagt gcacagtcta                                              20

<210> SEQ ID NO 157
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
ttcggaagag acaggtacgt ta                                           22
```

```
<210> SEQ ID NO 158
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
agcagtacgc acacaatcg                                                    19

<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
caatgctgca atcgtgctac                                                   20

<210> SEQ ID NO 160
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
gttgcgacta cgtgatgagg                                                   20

<210> SEQ ID NO 161
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
gaccccaaaa tcagcgaaat                                                   20

<210> SEQ ID NO 162
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
tctggttact gccagttgaa tctg                                              24

<210> SEQ ID NO 163
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 163
ttacaaacat tggccgcaaa                                                   20

<210> SEQ ID NO 164
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
gcgcgacatt ccgaagaa                                                     18

<210> SEQ ID NO 165
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
taatcagaca aggaactgat ta                                                22

<210> SEQ ID NO 166
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
cgaaggtgtg acttccatg                                                    19

<210> SEQ ID NO 167
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
gatcaaaaca acgtcggccc                                                   20

<210> SEQ ID NO 168
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
ccatgttgag tgagagcggt                                                   20

<210> SEQ ID NO 169
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
tggaccccaa aatcagcgaa                                              20

<210> SEQ ID NO 170
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
actgcgttct ccattctggt t                                            21

<210> SEQ ID NO 171
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
cagcgttctt cggaatgtcg                                              20

<210> SEQ ID NO 172
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
gcacctgtgt aggtcaacca                                              20

<210> SEQ ID NO 173
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
gaaatgcacc ccgcattacg                                              20

<210> SEQ ID NO 174
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
```

```
cccactgcgt tctccattct                                               20

<210> SEQ ID NO 175
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gtcttggttc accgctctca                                               20

<210> SEQ ID NO 176
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
ttggaacgcc ttgtcctcg                                                19

<210> SEQ ID NO 177
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
gcagtcaagc ctcttctcgt                                               20

<210> SEQ ID NO 178
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gaagttcccc tactgctgcc                                               20

<210> SEQ ID NO 179
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
cgtttggtgg accctcagat                                               20

<210> SEQ ID NO 180
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 180
gacgttgttt tgatcgcgcc                                              20

<210> SEQ ID NO 181
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
aaggccaaca acaacaaggc                                              20

<210> SEQ ID NO 182
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
ggcagtacgt ttttgccgag                                              20

<210> SEQ ID NO 183
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
accagaatgg agaacgcagt                                              20

<210> SEQ ID NO 184
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
cggtgaacca agacgcagta                                              20

<210> SEQ ID NO 185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
ccgcattacg tttggtggac                                              20

<210> SEQ ID NO 186
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
ggccgacgtt gttttgatcg                                                 20

<210> SEQ ID NO 187
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
gcctcggcaa aaacgtactg                                                 20

<210> SEQ ID NO 188
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
ttgttctgga ccacgtctgc                                                 20

<210> SEQ ID NO 189
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
aattccctcg aggacaaggc                                                 20

<210> SEQ ID NO 190
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
tcgtctggta gctcttcggt                                                 20

<210> SEQ ID NO 191
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
```

```
gcttcagcgt tcttcggaat                                               20
```

<210> SEQ ID NO 192
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192

```
tggcacctgt gtaggtcaac                                               20
```

<210> SEQ ID NO 193
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193

```
gggtcacgcg taggagttct atcagatttg gacctgcgag cg                      42
```

<210> SEQ ID NO 194
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194

```
gttccgcagc cacacaagat ctggagcggc tgtctccaca agt                     43
```

<210> SEQ ID NO 195
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195

```
cgcgtcgagt agggtgttct atcagatttg gacctgcgag cg                      42
```

<210> SEQ ID NO 196
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196

```
gccgtgtgaa gctggaagat ctggagcggc tgtctccaca agt                     43
```

<210> SEQ ID NO 197
<211> LENGTH: 42
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 197
cgatcgccct tggtggttct atcagatttg gacctgcgag cg                            42

<210> SEQ ID NO 198
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
ggtttagccg gcgtgaagat ctggagcggc tgtctccaca agt                           43

<210> SEQ ID NO 199
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
ggtcgagccg gaactgttct atcagatttg gacctgcgag cg                            42

<210> SEQ ID NO 200
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
ggatgcgcac ccagaaagat ctggagcggc tgtctccaca agt                           43

<210> SEQ ID NO 201
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
tcccggcgtt gtcctgttct atcagatttg gacctgcgag cg                            42

<210> SEQ ID NO 202
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
gctccgtcac tgcccaagat ctggagcggc tgtctccaca agt                           43
```

```
<210> SEQ ID NO 203
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
cgcagggtcc agagtgttct atcagatttg gacctgcgag cg                         42

<210> SEQ ID NO 204
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
gttcgcgcga aggaaaagat ctggagcggc tgtctccaca agt                        43

<210> SEQ ID NO 205
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
atatagatgc cgtcctagcg gttctatcag atttggacct gcgagcg                    47

<210> SEQ ID NO 206
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
aagtatcttt cctgtgccca aagatctgga gcggctgtct ccacaagt                   48

<210> SEQ ID NO 207
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
ccctttaatc agatgcgtcg gttctatcag atttggacct gcgagcg                    47

<210> SEQ ID NO 208
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 208
tggtagtaat aagggcgacc aagatctgga gcggctgtct ccacaagt          48

<210> SEQ ID NO 209
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
ttggtcatgt gcttttcgtt gttctatcag atttggacct gcgagcg           47

<210> SEQ ID NO 210
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
aggggtatcg gatactcaga aagatctgga gcggctgtct ccacaagt          48

<210> SEQ ID NO 211
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
gggtgggtaa atggtaatgc gttctatcag atttggacct gcgagcg           47

<210> SEQ ID NO 212
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
atcgattccc cggatatagc aagatctgga gcggctgtct ccacaagt          48

<210> SEQ ID NO 213
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
tccgacgggg agtatatact gttctatcag atttggacct gcgagcg           47

<210> SEQ ID NO 214
<211> LENGTH: 48
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 214
tactaactgc ttcaggccaa aagatctgga gcggctgtct ccacaagt            48

<210> SEQ ID NO 215
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
catgtttagg aacgctaccg gttctatcag atttggacct gcgagcg             47

<210> SEQ ID NO 216
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
aataatctcc gttccctccc aagatctgga gcggctgtct ccacaagt            48

<210> SEQ ID NO 217
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
taatacgact cactataggg accccaaaat cagcgaaatg cacccgcat tacgaaacca   60 ggaccctcag attcaactg                                              79

<210> SEQ ID NO 218
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
cgcagtatta ttgggtaaac ct                                        22

<210> SEQ ID NO 219
<211> LENGTH: 74
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
```

```
taatacgact cactataggg ctggtgctgc agcttattat gtgggtatag aacaacctag    60
gacttttcta ttaa                                                     74
```

<210> SEQ ID NO 220
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220

```
aacgtacact ttgtttctga gagagg                                        26
```

<210> SEQ ID NO 221
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221

```
caagcagaag acggcatacg agatgagtct tcgaccccaa aatcagcgaa at           52
```

<210> SEQ ID NO 222
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222

```
caagcagaag acggcatacg agatgttcta tcgaccccaa aatcagcgaa at           52
```

<210> SEQ ID NO 223
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223

```
caagcagaag acggcatacg agattgggcc aagaccccaa aatcagcgaa at           52
```

<210> SEQ ID NO 224
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224

```
caagcagaag acggcatacg agatattgtt gggaccccaa aatcagcgaa at           52
```

<210> SEQ ID NO 225
<211> LENGTH: 52
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 225
caagcagaag acggcatacg agattcccgt tggacccccaa aatcagcgaa at            52

<210> SEQ ID NO 226
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
caagcagaag acggcatacg agatacacac ttgaccccaa aatcagcgaa at            52

<210> SEQ ID NO 227
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
caagcagaag acggcatacg agatccattc cagaccccaa aatcagcgaa at            52

<210> SEQ ID NO 228
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
caagcagaag acggcatacg agatctaacg gggaccccaa aatcagcgaa at            52

<210> SEQ ID NO 229
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
caagcagaag acggcatacg agatccatag gagaccccaa aatcagcgaa at            52

<210> SEQ ID NO 230
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
caagcagaag acggcatacg agatcagtgt aggaccccaa aatcagcgaa at            52
```

<210> SEQ ID NO 231
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
caagcagaag acggcatacg agatgattct cagacccaa aatcagcgaa at           52

<210> SEQ ID NO 232
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
caagcagaag acggcatacg agatccttct tagacccaa aatcagcgaa at           52

<210> SEQ ID NO 233
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
caagcagaag acggcatacg agattctaag acgacccaa aatcagcgaa at           52

<210> SEQ ID NO 234
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
caagcagaag acggcatacg agatgcggca tagacccaa aatcagcgaa at           52

<210> SEQ ID NO 235
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
caagcagaag acggcatacg agatattgac gagacccaa aatcagcgaa at           52

<210> SEQ ID NO 236
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
caagcagaag acggcatacg agatgctcct gagaccccaa aatcagcgaa at        52

<210> SEQ ID NO 237
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
caagcagaag acggcatacg agatgcaatc ctgaccccaa aatcagcgaa at        52

<210> SEQ ID NO 238
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
caagcagaag acggcatacg agatatgtcg ttgaccccaa aatcagcgaa at        52

<210> SEQ ID NO 239
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
caagcagaag acggcatacg agatttctcg gcgaccccaa aatcagcgaa at        52

<210> SEQ ID NO 240
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
caagcagaag acggcatacg agatcagggc tagaccccaa aatcagcgaa at        52

<210> SEQ ID NO 241
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
caagcagaag acggcatacg agatagccaa gcgaccccaa aatcagcgaa at        52

<210> SEQ ID NO 242
<211> LENGTH: 52
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
caagcagaag acggcatacg agataagcct gagaccccaa aatcagcgaa at         52

<210> SEQ ID NO 243
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
caagcagaag acggcatacg agatctacag aggaccccaa aatcagcgaa at         52

<210> SEQ ID NO 244
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
caagcagaag acggcatacg agatcgtagt cggaccccaa aatcagcgaa at         52

<210> SEQ ID NO 245
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
caagcagaag acggcatacg agatttctgc tcgaccccaa aatcagcgaa at         52

<210> SEQ ID NO 246
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
caagcagaag acggcatacg agatgtgcac acgaccccaa aatcagcgaa at         52

<210> SEQ ID NO 247
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
caagcagaag acggcatacg agataaagct cagaccccaa aatcagcgaa at         52
```

```
<210> SEQ ID NO 248
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
caagcagaag acggcatacg agatgacctc aggaccccaa aatcagcgaa at         52

<210> SEQ ID NO 249
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
caagcagaag acggcatacg agatctttcc aagaccccaa aatcagcgaa at         52

<210> SEQ ID NO 250
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
caagcagaag acggcatacg agattcttgg ctgaccccaa aatcagcgaa at         52

<210> SEQ ID NO 251
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
caagcagaag acggcatacg agatcgcgtc tagaccccaa aatcagcgaa at         52

<210> SEQ ID NO 252
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
caagcagaag acggcatacg agattcgcgc tagaccccaa aatcagcgaa at         52

<210> SEQ ID NO 253
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 253
caagcagaag acggcatacg agatatccat tcgaccccaa aatcagcgaa at    52

<210> SEQ ID NO 254
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
caagcagaag acggcatacg agatgcccag tagaccccaa aatcagcgaa at    52

<210> SEQ ID NO 255
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
caagcagaag acggcatacg agattaccga cggaccccaa aatcagcgaa at    52

<210> SEQ ID NO 256
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
caagcagaag acggcatacg agattccata cggaccccaa aatcagcgaa at    52

<210> SEQ ID NO 257
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
caagcagaag acggcatacg agataacatg tcgaccccaa aatcagcgaa at    52

<210> SEQ ID NO 258
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
caagcagaag acggcatacg agatcgacta tagaccccaa aatcagcgaa at    52

<210> SEQ ID NO 259
<211> LENGTH: 52

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
caagcagaag acggcatacg agatacccaa aggaccccaa aatcagcgaa at            52

<210> SEQ ID NO 260
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
caagcagaag acggcatacg agatatcgat cggaccccaa aatcagcgaa at            52

<210> SEQ ID NO 261
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
caagcagaag acggcatacg agatgttgga tggaccccaa aatcagcgaa at            52

<210> SEQ ID NO 262
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
caagcagaag acggcatacg agatctatgt gagaccccaa aatcagcgaa at            52

<210> SEQ ID NO 263
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
caagcagaag acggcatacg agattatttc gcgaccccaa aatcagcgaa at            52

<210> SEQ ID NO 264
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
```
caagcagaag acggcatacg agatccatgt atgaccccaa aatcagcgaa at                    52

<210> SEQ ID NO 265
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
caagcagaag acggcatacg agatgccacg ttgaccccaa aatcagcgaa at                    52

<210> SEQ ID NO 266
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
caagcagaag acggcatacg agatgtcgtg tagaccccaa aatcagcgaa at                    52

<210> SEQ ID NO 267
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
caagcagaag acggcatacg agattaaagt cggaccccaa aatcagcgaa at                    52

<210> SEQ ID NO 268
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
caagcagaag acggcatacg agatcttcgg acgaccccaa aatcagcgaa at                    52

<210> SEQ ID NO 269
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
caagcagaag acggcatacg agatgcactc tcgaccccaa aatcagcgaa at                    52

<210> SEQ ID NO 270
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 270
caagcagaag acggcatacg agattcagat acgaccccaa aatcagcgaa at    52

<210> SEQ ID NO 271
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 271
caagcagaag acggcatacg agatcagtcc ctgaccccaa aatcagcgaa at    52

<210> SEQ ID NO 272
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 272
caagcagaag acggcatacg agatgcccta acgaccccaa aatcagcgaa at    52

<210> SEQ ID NO 273
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 273
caagcagaag acggcatacg agatctgcat cagaccccaa aatcagcgaa at    52

<210> SEQ ID NO 274
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 274
caagcagaag acggcatacg agatcggtat cggaccccaa aatcagcgaa at    52

<210> SEQ ID NO 275
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 275
caagcagaag acggcatacg agataagtat gggaccccaa aatcagcgaa at    52

<210> SEQ ID NO 276

```
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
caagcagaag acggcatacg agatattcgc gcgaccccaa aatcagcgaa at            52

<210> SEQ ID NO 277
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
caagcagaag acggcatacg agatatcaag gtgaccccaa aatcagcgaa at            52

<210> SEQ ID NO 278
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
caagcagaag acggcatacg agatttgtgc atgaccccaa aatcagcgaa at            52

<210> SEQ ID NO 279
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
caagcagaag acggcatacg agatctgtgc tggaccccaa aatcagcgaa at            52

<210> SEQ ID NO 280
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
caagcagaag acggcatacg agatgtccgt aggaccccaa aatcagcgaa at            52

<210> SEQ ID NO 281
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
```
caagcagaag acggcatacg agatgttcaa gagaccccaa aatcagcgaa at            52

<210> SEQ ID NO 282
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
caagcagaag acggcatacg agatcaccgt tcgaccccaa aatcagcgaa at            52

<210> SEQ ID NO 283
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
caagcagaag acggcatacg agatcgagtt gagaccccaa aatcagcgaa at            52

<210> SEQ ID NO 284
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
caagcagaag acggcatacg agatgagcac gagaccccaa aatcagcgaa at            52

<210> SEQ ID NO 285
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
caagcagaag acggcatacg agatagttcg tggaccccaa aatcagcgaa at            52

<210> SEQ ID NO 286
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
caagcagaag acggcatacg agatcatcaa ctgaccccaa aatcagcgaa at            52

<210> SEQ ID NO 287
<211> LENGTH: 52
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 287
caagcagaag acggcatacg agatcgagat ctgaccccaa aatcagcgaa at            52

<210> SEQ ID NO 288
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
caagcagaag acggcatacg agattggcca gagaccccaa aatcagcgaa at            52

<210> SEQ ID NO 289
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
caagcagaag acggcatacg agatttcacc atgaccccaa aatcagcgaa at            52

<210> SEQ ID NO 290
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
caagcagaag acggcatacg agatgaatgc atgaccccaa aatcagcgaa at            52

<210> SEQ ID NO 291
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
caagcagaag acggcatacg agattggacc ctgaccccaa aatcagcgaa at            52

<210> SEQ ID NO 292
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
caagcagaag acggcatacg agatgatagc acgaccccaa aatcagcgaa at            52
```

```
<210> SEQ ID NO 293
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
caagcagaag acggcatacg agatacgacg acgaccccaa aatcagcgaa at          52

<210> SEQ ID NO 294
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
caagcagaag acggcatacg agatctcagt atgaccccaa aatcagcgaa at          52

<210> SEQ ID NO 295
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
caagcagaag acggcatacg agatcttagc tagaccccaa aatcagcgaa at          52

<210> SEQ ID NO 296
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
caagcagaag acggcatacg agatctgttt acgaccccaa aatcagcgaa at          52

<210> SEQ ID NO 297
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
caagcagaag acggcatacg agattgtccc acgaccccaa aatcagcgaa at          52

<210> SEQ ID NO 298
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 298
caagcagaag acggcatacg agattcctga gggaccccaa aatcagcgaa at    52

<210> SEQ ID NO 299
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
caagcagaag acggcatacg agattagttc cagaccccaa aatcagcgaa at    52

<210> SEQ ID NO 300
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
caagcagaag acggcatacg agatcatgac tcgaccccaa aatcagcgaa at    52

<210> SEQ ID NO 301
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
caagcagaag acggcatacg agatgtaagc gcgaccccaa aatcagcgaa at    52

<210> SEQ ID NO 302
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
caagcagaag acggcatacg agataaccca gtgaccccaa aatcagcgaa at    52

<210> SEQ ID NO 303
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
caagcagaag acggcatacg agattttgag gggaccccaa aatcagcgaa at    52

<210> SEQ ID NO 304
<211> LENGTH: 52
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 304
caagcagaag acggcatacg agatagccga cagaccccaa aatcagcgaa at          52

<210> SEQ ID NO 305
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
caagcagaag acggcatacg agataaaccc gcgaccccaa aatcagcgaa at          52

<210> SEQ ID NO 306
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
caagcagaag acggcatacg agatgtaggg ctgaccccaa aatcagcgaa at          52

<210> SEQ ID NO 307
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
caagcagaag acggcatacg agatagacga ttgaccccaa aatcagcgaa at          52

<210> SEQ ID NO 308
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
caagcagaag acggcatacg agataggatg atgaccccaa aatcagcgaa at          52

<210> SEQ ID NO 309
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
caagcagaag acggcatacg agatataatg gcgaccccaa aatcagcgaa at          52
```

<210> SEQ ID NO 310
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 310
caagcagaag acggcatacg agatcttggc gtgaccccaa aatcagcgaa at        52

<210> SEQ ID NO 311
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 311
caagcagaag acggcatacg agatagctgt gcgaccccaa aatcagcgaa at        52

<210> SEQ ID NO 312
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 312
caagcagaag acggcatacg agatgagtcc aagaccccaa aatcagcgaa at        52

<210> SEQ ID NO 313
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 313
caagcagaag acggcatacg agatgaatac cagaccccaa aatcagcgaa at        52

<210> SEQ ID NO 314
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 314
caagcagaag acggcatacg agataggagc ttgaccccaa aatcagcgaa at        52

<210> SEQ ID NO 315
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 315
caagcagaag acggcatacg agatgtgact tagaccccaa aatcagcgaa at          52

<210> SEQ ID NO 316
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
caagcagaag acggcatacg agattttgga acgaccccaa aatcagcgaa at          52

<210> SEQ ID NO 317
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
caagcagaag acggcatacg agatgagtct tcagggtcaa gtgcacagtc ta          52

<210> SEQ ID NO 318
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
caagcagaag acggcatacg agatgttcta tcagggtcaa gtgcacagtc ta          52

<210> SEQ ID NO 319
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
caagcagaag acggcatacg agattgggcc aaagggtcaa gtgcacagtc ta          52

<210> SEQ ID NO 320
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
caagcagaag acggcatacg agatattgtt ggagggtcaa gtgcacagtc ta          52

<210> SEQ ID NO 321
<211> LENGTH: 52
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
caagcagaag acggcatacg agattcccgt tgagggtcaa gtgcacagtc ta          52

<210> SEQ ID NO 322
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
caagcagaag acggcatacg agatacacac ttagggtcaa gtgcacagtc ta          52

<210> SEQ ID NO 323
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
caagcagaag acggcatacg agatccattc caagggtcaa gtgcacagtc ta          52

<210> SEQ ID NO 324
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
caagcagaag acggcatacg agatctaacg ggagggtcaa gtgcacagtc ta          52

<210> SEQ ID NO 325
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
caagcagaag acggcatacg agatccatag gaagggtcaa gtgcacagtc ta          52

<210> SEQ ID NO 326
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
caagcagaag acggcatacg agatcagtgt agagggtcaa gtgcacagtc ta          52
```

<210> SEQ ID NO 327
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
caagcagaag acggcatacg agatgattct caagggtcaa gtgcacagtc ta         52

<210> SEQ ID NO 328
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
caagcagaag acggcatacg agatccttct taagggtcaa gtgcacagtc ta         52

<210> SEQ ID NO 329
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
caagcagaag acggcatacg agattctaag acagggtcaa gtgcacagtc ta         52

<210> SEQ ID NO 330
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
caagcagaag acggcatacg agatgcggca taagggtcaa gtgcacagtc ta         52

<210> SEQ ID NO 331
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
caagcagaag acggcatacg agatattgac gaagggtcaa gtgcacagtc ta         52

<210> SEQ ID NO 332
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 332
caagcagaag acggcatacg agatgctcct gaagggtcaa gtgcacagtc ta    52

<210> SEQ ID NO 333
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
caagcagaag acggcatacg agatgcaatc ctagggtcaa gtgcacagtc ta    52

<210> SEQ ID NO 334
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
caagcagaag acggcatacg agatatgtcg ttagggtcaa gtgcacagtc ta    52

<210> SEQ ID NO 335
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
caagcagaag acggcatacg agatttctcg gcagggtcaa gtgcacagtc ta    52

<210> SEQ ID NO 336
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
caagcagaag acggcatacg agatcagggc taagggtcaa gtgcacagtc ta    52

<210> SEQ ID NO 337
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
caagcagaag acggcatacg agatagccaa gcagggtcaa gtgcacagtc ta    52

<210> SEQ ID NO 338
<211> LENGTH: 52

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
caagcagaag acggcatacg agataagcct gaagggtcaa gtgcacagtc ta         52

<210> SEQ ID NO 339
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
caagcagaag acggcatacg agatctacag agagggtcaa gtgcacagtc ta         52

<210> SEQ ID NO 340
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
caagcagaag acggcatacg agatcgtagt cgagggtcaa gtgcacagtc ta         52

<210> SEQ ID NO 341
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
caagcagaag acggcatacg agatttctgc tcagggtcaa gtgcacagtc ta         52

<210> SEQ ID NO 342
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
caagcagaag acggcatacg agatgtgcac acagggtcaa gtgcacagtc ta         52

<210> SEQ ID NO 343
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
```
caagcagaag acggcatacg agataaagct caagggtcaa gtgcacagtc ta                52

<210> SEQ ID NO 344
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
caagcagaag acggcatacg agatgacctc agagggtcaa gtgcacagtc ta                52

<210> SEQ ID NO 345
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
caagcagaag acggcatacg agatctttcc aaagggtcaa gtgcacagtc ta                52

<210> SEQ ID NO 346
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
caagcagaag acggcatacg agattcttgg ctagggtcaa gtgcacagtc ta                52

<210> SEQ ID NO 347
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
caagcagaag acggcatacg agatcgcgtc taagggtcaa gtgcacagtc ta                52

<210> SEQ ID NO 348
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
caagcagaag acggcatacg agattcgcgc taagggtcaa gtgcacagtc ta                52

<210> SEQ ID NO 349
<211> LENGTH: 52
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 349
caagcagaag acggcatacg agatatccat tcagggtcaa gtgcacagtc ta            52

<210> SEQ ID NO 350
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
caagcagaag acggcatacg agatgcccag taagggtcaa gtgcacagtc ta            52

<210> SEQ ID NO 351
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
caagcagaag acggcatacg agattaccga cgagggtcaa gtgcacagtc ta            52

<210> SEQ ID NO 352
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
caagcagaag acggcatacg agattccata cgagggtcaa gtgcacagtc ta            52

<210> SEQ ID NO 353
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
caagcagaag acggcatacg agataacatg tcagggtcaa gtgcacagtc ta            52

<210> SEQ ID NO 354
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
caagcagaag acggcatacg agatcgacta taagggtcaa gtgcacagtc ta            52

<210> SEQ ID NO 355
```

<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
caagcagaag acggcatacg agatacccaa agagggtcaa gtgcacagtc ta      52

<210> SEQ ID NO 356
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
caagcagaag acggcatacg agatatcgat cgagggtcaa gtgcacagtc ta      52

<210> SEQ ID NO 357
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
caagcagaag acggcatacg agatgttgga tgagggtcaa gtgcacagtc ta      52

<210> SEQ ID NO 358
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
caagcagaag acggcatacg agatctatgt gaagggtcaa gtgcacagtc ta      52

<210> SEQ ID NO 359
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
caagcagaag acggcatacg agattatttc gcagggtcaa gtgcacagtc ta      52

<210> SEQ ID NO 360
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360

-continued caagcagaag acggcatacg agatccatgt atagggtcaa gtgcacagtc ta    52

<210> SEQ ID NO 361
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
caagcagaag acggcatacg agatgccacg ttagggtcaa gtgcacagtc ta    52

<210> SEQ ID NO 362
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
caagcagaag acggcatacg agatgtcgtg taagggtcaa gtgcacagtc ta    52

<210> SEQ ID NO 363
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
caagcagaag acggcatacg agattaaagt cgagggtcaa gtgcacagtc ta    52

<210> SEQ ID NO 364
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
caagcagaag acggcatacg agatcttcgg acagggtcaa gtgcacagtc ta    52

<210> SEQ ID NO 365
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
caagcagaag acggcatacg agatgcactc tcagggtcaa gtgcacagtc ta    52

<210> SEQ ID NO 366
<211> LENGTH: 52
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 366
caagcagaag acggcatacg agattcagat acagggtcaa gtgcacagtc ta         52

<210> SEQ ID NO 367
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
caagcagaag acggcatacg agatcagtcc ctagggtcaa gtgcacagtc ta         52

<210> SEQ ID NO 368
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
caagcagaag acggcatacg agatgcccta acagggtcaa gtgcacagtc ta         52

<210> SEQ ID NO 369
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
caagcagaag acggcatacg agatctgcat caagggtcaa gtgcacagtc ta         52

<210> SEQ ID NO 370
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
caagcagaag acggcatacg agatcggtat cgagggtcaa gtgcacagtc ta         52

<210> SEQ ID NO 371
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
caagcagaag acggcatacg agataagtat ggagggtcaa gtgcacagtc ta         52
```

<210> SEQ ID NO 372
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 372
caagcagaag acggcatacg agatattcgc gcagggtcaa gtgcacagtc ta          52

<210> SEQ ID NO 373
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 373
caagcagaag acggcatacg agatatcaag gtagggtcaa gtgcacagtc ta          52

<210> SEQ ID NO 374
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 374
caagcagaag acggcatacg agatttgtgc atagggtcaa gtgcacagtc ta          52

<210> SEQ ID NO 375
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 375
caagcagaag acggcatacg agatctgtgc tgagggtcaa gtgcacagtc ta          52

<210> SEQ ID NO 376
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 376
caagcagaag acggcatacg agatgtccgt agagggtcaa gtgcacagtc ta          52

<210> SEQ ID NO 377
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 377
caagcagaag acggcatacg agatgttcaa gaagggtcaa gtgcacagtc ta    52

<210> SEQ ID NO 378
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
caagcagaag acggcatacg agatcaccgt tcagggtcaa gtgcacagtc ta    52

<210> SEQ ID NO 379
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
caagcagaag acggcatacg agatcgagtt gaagggtcaa gtgcacagtc ta    52

<210> SEQ ID NO 380
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
caagcagaag acggcatacg agatgagcac gaagggtcaa gtgcacagtc ta    52

<210> SEQ ID NO 381
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
caagcagaag acggcatacg agatagttcg tgagggtcaa gtgcacagtc ta    52

<210> SEQ ID NO 382
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
caagcagaag acggcatacg agatcatcaa ctagggtcaa gtgcacagtc ta    52

<210> SEQ ID NO 383
<211> LENGTH: 52
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 383
caagcagaag acggcatacg agatcgagat ctagggtcaa gtgcacagtc ta            52

<210> SEQ ID NO 384
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
caagcagaag acggcatacg agattggcca gaagggtcaa gtgcacagtc ta            52

<210> SEQ ID NO 385
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
caagcagaag acggcatacg agatttcacc atagggtcaa gtgcacagtc ta            52

<210> SEQ ID NO 386
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
caagcagaag acggcatacg agatgaatgc atagggtcaa gtgcacagtc ta            52

<210> SEQ ID NO 387
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
caagcagaag acggcatacg agattggacc ctagggtcaa gtgcacagtc ta            52

<210> SEQ ID NO 388
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
caagcagaag acggcatacg agatgatagc acagggtcaa gtgcacagtc ta            52
```

<210> SEQ ID NO 389
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 389
caagcagaag acggcatacg agatacgacg acagggtcaa gtgcacagtc ta           52

<210> SEQ ID NO 390
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 390
caagcagaag acggcatacg agatctcagt atagggtcaa gtgcacagtc ta           52

<210> SEQ ID NO 391
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 391
caagcagaag acggcatacg agatcttagc taagggtcaa gtgcacagtc ta           52

<210> SEQ ID NO 392
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 392
caagcagaag acggcatacg agatctgttt acagggtcaa gtgcacagtc ta           52

<210> SEQ ID NO 393
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 393
caagcagaag acggcatacg agattgtccc acagggtcaa gtgcacagtc ta           52

<210> SEQ ID NO 394
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 394
caagcagaag acggcatacg agattcctga ggagggtcaa gtgcacagtc ta        52

<210> SEQ ID NO 395
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
caagcagaag acggcatacg agattagttc caagggtcaa gtgcacagtc ta        52

<210> SEQ ID NO 396
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
caagcagaag acggcatacg agatcatgac tcagggtcaa gtgcacagtc ta        52

<210> SEQ ID NO 397
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
caagcagaag acggcatacg agatgtaagc gcagggtcaa gtgcacagtc ta        52

<210> SEQ ID NO 398
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
caagcagaag acggcatacg agataaccca gtagggtcaa gtgcacagtc ta        52

<210> SEQ ID NO 399
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
caagcagaag acggcatacg agattttgag ggagggtcaa gtgcacagtc ta        52

<210> SEQ ID NO 400
<211> LENGTH: 52
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
caagcagaag acggcatacg agatagccga caagggtcaa gtgcacagtc ta          52

<210> SEQ ID NO 401
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
caagcagaag acggcatacg agataaaccc gcagggtcaa gtgcacagtc ta          52

<210> SEQ ID NO 402
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
caagcagaag acggcatacg agatgtaggg ctagggtcaa gtgcacagtc ta          52

<210> SEQ ID NO 403
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
caagcagaag acggcatacg agatagacga ttagggtcaa gtgcacagtc ta          52

<210> SEQ ID NO 404
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
caagcagaag acggcatacg agataggatg atagggtcaa gtgcacagtc ta          52

<210> SEQ ID NO 405
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
caagcagaag acggcatacg agatataatg gcagggtcaa gtgcacagtc ta          52
```

<210> SEQ ID NO 406
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
caagcagaag acggcatacg agatcttggc gtagggtcaa gtgcacagtc ta        52

<210> SEQ ID NO 407
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
caagcagaag acggcatacg agatagctgt gcagggtcaa gtgcacagtc ta        52

<210> SEQ ID NO 408
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
caagcagaag acggcatacg agatgagtcc aaagggtcaa gtgcacagtc ta        52

<210> SEQ ID NO 409
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
caagcagaag acggcatacg agatgaatac caagggtcaa gtgcacagtc ta        52

<210> SEQ ID NO 410
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
caagcagaag acggcatacg agataggagc ttagggtcaa gtgcacagtc ta        52

<210> SEQ ID NO 411
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 411
caagcagaag acggcatacg agatgtgact taagggtcaa gtgcacagtc ta          52

<210> SEQ ID NO 412
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
caagcagaag acggcatacg agattttgga acagggtcaa gtgcacagtc ta          52

<210> SEQ ID NO 413
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
aatgatacgg cgaccaccga gatctacaca agatctgtct ggttactgcc agttgaatct  60
g                                                                  61

<210> SEQ ID NO 414
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
aatgatacgg cgaccaccga gatctacact gtcatgatct ggttactgcc agttgaatct  60
g                                                                  61

<210> SEQ ID NO 415
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
aatgatacgg cgaccaccga gatctacact gtaacagtct ggttactgcc agttgaatct  60
g                                                                  61

<210> SEQ ID NO 416
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416

```
aatgatacgg cgaccaccga gatctacacg cgcaacttct ggttactgcc agttgaatct    60
g                                                                    61
```

<210> SEQ ID NO 417
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417

```
aatgatacgg cgaccaccga tcgatggctc tggttactgc cagttgaatc tg            52
```

<210> SEQ ID NO 418
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418

```
aatgatacgg cgaccaccga catggttttc tggttactgc cagttgaatc tg            52
```

<210> SEQ ID NO 419
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419

```
aatgatacgg cgaccaccga acgaaagctc tggttactgc cagttgaatc tg            52
```

<210> SEQ ID NO 420
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420

```
aatgatacgg cgaccaccga gctctgattc tggttactgc cagttgaatc tg            52
```

<210> SEQ ID NO 421
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421

```
aatgatacgg cgaccaccga gatctacaca tgccctcgct ggtgctgcag cttatta       57
```

<210> SEQ ID NO 422
<211> LENGTH: 57
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
aatgatacgg cgaccaccga gatctacacc tcagatggct ggtgctgcag cttatta        57

<210> SEQ ID NO 423
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
aatgatacgg cgaccaccga gatctacacg taatctggct ggtgctgcag cttatta        57

<210> SEQ ID NO 424
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
aatgatacgg cgaccaccga gatctacacg caagattgct ggtgctgcag cttatta        57

<210> SEQ ID NO 425
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
aatgatacgg cgaccaccga atacgccagc tggtgctgca gcttatta        48

<210> SEQ ID NO 426
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
aatgatacgg cgaccaccga accagtcggc tggtgctgca gcttatta        48

<210> SEQ ID NO 427
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
aatgatacgg cgaccaccga aacacggagc tggtgctgca gcttatta        48
```

<210> SEQ ID NO 428
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
aatgatacgg cgaccaccga ctgcctaggc tggtgctgca gcttatta                    48

<210> SEQ ID NO 429
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
tctggttact gccagttgaa tctgagggtc c                                     31

<210> SEQ ID NO 430
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
ggtgcatttc gctgattttg gggtc                                            25

<210> SEQ ID NO 431
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
ggaccctcag attcaactgg cagtaaccag a                                     31

<210> SEQ ID NO 432
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
gctggtgctg cagcttatta tgtgggt                                          27

<210> SEQ ID NO 433
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 433
agatgctgta gactgtgcac ttgaccct                                    28

<210> SEQ ID NO 434
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
acccacataa taagctgcag caccagc                                     27

<210> SEQ ID NO 435
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
gagcggctgt ctccacaagt ccg                                         23

<210> SEQ ID NO 436
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
acccgctcgc aggtccaaat ctg                                         23

<210> SEQ ID NO 437
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
cggacttgtg gagacagccg ctc                                         23

<210> SEQ ID NO 438
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
caagcagaag acggcatacg agatgagtct tcagatttgg acctgcgagc g          51

<210> SEQ ID NO 439
<211> LENGTH: 51

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
caagcagaag acggcatacg agatgttcta tcagatttgg acctgcgagc g            51

<210> SEQ ID NO 440
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
caagcagaag acggcatacg agattgggcc aaagatttgg acctgcgagc g            51

<210> SEQ ID NO 441
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
caagcagaag acggcatacg agatattgtt ggagatttgg acctgcgagc g            51

<210> SEQ ID NO 442
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
caagcagaag acggcatacg agattcccgt tgagatttgg acctgcgagc g            51

<210> SEQ ID NO 443
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
caagcagaag acggcatacg agatacacac ttagatttgg acctgcgagc g            51

<210> SEQ ID NO 444
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
```
caagcagaag acggcatacg agatccattc caagatttgg acctgcgagc g    51

<210> SEQ ID NO 445
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
caagcagaag acggcatacg agatctaacg ggagatttgg acctgcgagc g    51

<210> SEQ ID NO 446
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
caagcagaag acggcatacg agatccatag gaagatttgg acctgcgagc g    51

<210> SEQ ID NO 447
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
caagcagaag acggcatacg agatcagtgt agagatttgg acctgcgagc g    51

<210> SEQ ID NO 448
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
caagcagaag acggcatacg agatgattct caagatttgg acctgcgagc g    51

<210> SEQ ID NO 449
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
caagcagaag acggcatacg agatccttct taagatttgg acctgcgagc g    51

<210> SEQ ID NO 450
<211> LENGTH: 51
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 450
caagcagaag acggcatacg agattctaag acagatttgg acctgcgagc g          51

<210> SEQ ID NO 451
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
caagcagaag acggcatacg agatgcggca taagatttgg acctgcgagc g          51

<210> SEQ ID NO 452
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
caagcagaag acggcatacg agatattgac gaagatttgg acctgcgagc g          51

<210> SEQ ID NO 453
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
caagcagaag acggcatacg agatgctcct gaagatttgg acctgcgagc g          51

<210> SEQ ID NO 454
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
caagcagaag acggcatacg agatgcaatc ctagatttgg acctgcgagc g          51

<210> SEQ ID NO 455
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
caagcagaag acggcatacg agatatgtcg ttagatttgg acctgcgagc g          51

<210> SEQ ID NO 456
```

-continued

```
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
caagcagaag acggcatacg agatttctcg gcagatttgg acctgcgagc g         51

<210> SEQ ID NO 457
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
caagcagaag acggcatacg agatcagggc taagatttgg acctgcgagc g         51

<210> SEQ ID NO 458
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
caagcagaag acggcatacg agatagccaa gcagatttgg acctgcgagc g         51

<210> SEQ ID NO 459
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
caagcagaag acggcatacg agataagcct gaagatttgg acctgcgagc g         51

<210> SEQ ID NO 460
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
caagcagaag acggcatacg agatctacag agagatttgg acctgcgagc g         51

<210> SEQ ID NO 461
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
```
caagcagaag acggcatacg agatcgtagt cgagatttgg acctgcgagc g          51

<210> SEQ ID NO 462
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
caagcagaag acggcatacg agatttctgc tcagatttgg acctgcgagc g          51

<210> SEQ ID NO 463
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
caagcagaag acggcatacg agatgtgcac acagatttgg acctgcgagc g          51

<210> SEQ ID NO 464
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
caagcagaag acggcatacg agataaagct caagatttgg acctgcgagc g          51

<210> SEQ ID NO 465
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
caagcagaag acggcatacg agatgacctc agagatttgg acctgcgagc g          51

<210> SEQ ID NO 466
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
caagcagaag acggcatacg agatctttcc aaagatttgg acctgcgagc g          51

<210> SEQ ID NO 467
<211> LENGTH: 51
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 467
caagcagaag acggcatacg agattcttgg ctagatttgg acctgcgagc g          51

<210> SEQ ID NO 468
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
caagcagaag acggcatacg agatcgcgtc taagatttgg acctgcgagc g          51

<210> SEQ ID NO 469
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
caagcagaag acggcatacg agattcgcgc taagatttgg acctgcgagc g          51

<210> SEQ ID NO 470
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
caagcagaag acggcatacg agatatccat tcagatttgg acctgcgagc g          51

<210> SEQ ID NO 471
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
caagcagaag acggcatacg agatgcccag taagatttgg acctgcgagc g          51

<210> SEQ ID NO 472
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
caagcagaag acggcatacg agattaccga cgagatttgg acctgcgagc g          51
```

```
<210> SEQ ID NO 473
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
caagcagaag acggcatacg agattccata cgagatttgg acctgcgagc g       51

<210> SEQ ID NO 474
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
caagcagaag acggcatacg agataacatg tcagatttgg acctgcgagc g       51

<210> SEQ ID NO 475
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
caagcagaag acggcatacg agatcgacta taagatttgg acctgcgagc g       51

<210> SEQ ID NO 476
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
caagcagaag acggcatacg agatacccaa agagatttgg acctgcgagc g       51

<210> SEQ ID NO 477
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
caagcagaag acggcatacg agatatcgat cgagatttgg acctgcgagc g       51

<210> SEQ ID NO 478
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 478
caagcagaag acggcatacg agatgttgga tgagatttgg acctgcgagc g     51

<210> SEQ ID NO 479
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
caagcagaag acggcatacg agatctatgt gaagatttgg acctgcgagc g     51

<210> SEQ ID NO 480
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
caagcagaag acggcatacg agattatttc gcagatttgg acctgcgagc g     51

<210> SEQ ID NO 481
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
caagcagaag acggcatacg agatccatgt atagatttgg acctgcgagc g     51

<210> SEQ ID NO 482
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
caagcagaag acggcatacg agatgccacg ttagatttgg acctgcgagc g     51

<210> SEQ ID NO 483
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
caagcagaag acggcatacg agatgtcgtg taagatttgg acctgcgagc g     51

<210> SEQ ID NO 484
<211> LENGTH: 51
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 484
caagcagaag acggcatacg agattaaagt cgagatttgg acctgcgagc g          51

<210> SEQ ID NO 485
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
caagcagaag acggcatacg agatcttcgg acagatttgg acctgcgagc g          51

<210> SEQ ID NO 486
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
caagcagaag acggcatacg agatgcactc tcagatttgg acctgcgagc g          51

<210> SEQ ID NO 487
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
caagcagaag acggcatacg agattcagat acagatttgg acctgcgagc g          51

<210> SEQ ID NO 488
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
caagcagaag acggcatacg agatcagtcc ctagatttgg acctgcgagc g          51

<210> SEQ ID NO 489
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
caagcagaag acggcatacg agatgcccta acagatttgg acctgcgagc g          51
```

```
<210> SEQ ID NO 490
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
caagcagaag acggcatacg agatctgcat caagatttgg acctgcgagc g            51

<210> SEQ ID NO 491
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
caagcagaag acggcatacg agatcggtat cgagatttgg acctgcgagc g            51

<210> SEQ ID NO 492
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
caagcagaag acggcatacg agataagtat ggagatttgg acctgcgagc g            51

<210> SEQ ID NO 493
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
caagcagaag acggcatacg agatattcgc gcagatttgg acctgcgagc g            51

<210> SEQ ID NO 494
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
caagcagaag acggcatacg agatatcaag gtagatttgg acctgcgagc g            51

<210> SEQ ID NO 495
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 495
caagcagaag acggcatacg agatttgtgc atagatttgg acctgcgagc g    51

<210> SEQ ID NO 496
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
caagcagaag acggcatacg agatctgtgc tgagatttgg acctgcgagc g    51

<210> SEQ ID NO 497
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
caagcagaag acggcatacg agatgtccgt agagatttgg acctgcgagc g    51

<210> SEQ ID NO 498
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
caagcagaag acggcatacg agatgttcaa gaagatttgg acctgcgagc g    51

<210> SEQ ID NO 499
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
caagcagaag acggcatacg agatcaccgt tcagatttgg acctgcgagc g    51

<210> SEQ ID NO 500
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
caagcagaag acggcatacg agatcgagtt gaagatttgg acctgcgagc g    51

<210> SEQ ID NO 501
<211> LENGTH: 51
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
caagcagaag acggcatacg agatgagcac gaagatttgg acctgcgagc g          51

<210> SEQ ID NO 502
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
caagcagaag acggcatacg agatagttcg tgagatttgg acctgcgagc g          51

<210> SEQ ID NO 503
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
caagcagaag acggcatacg agatcatcaa ctagatttgg acctgcgagc g          51

<210> SEQ ID NO 504
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
caagcagaag acggcatacg agatcgagat ctagatttgg acctgcgagc g          51

<210> SEQ ID NO 505
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
caagcagaag acggcatacg agattggcca gaagatttgg acctgcgagc g          51

<210> SEQ ID NO 506
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
caagcagaag acggcatacg agatttcacc atagatttgg acctgcgagc g          51
```

<210> SEQ ID NO 507
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
caagcagaag acggcatacg agatgaatgc atagatttgg acctgcgagc g                51

<210> SEQ ID NO 508
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
caagcagaag acggcatacg agattggacc ctagatttgg acctgcgagc g                51

<210> SEQ ID NO 509
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
caagcagaag acggcatacg agatgatagc acagatttgg acctgcgagc g                51

<210> SEQ ID NO 510
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
caagcagaag acggcatacg agatacgacg acagatttgg acctgcgagc g                51

<210> SEQ ID NO 511
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
caagcagaag acggcatacg agatctcagt atagatttgg acctgcgagc g                51

<210> SEQ ID NO 512
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 512
caagcagaag acggcatacg agatcttagc taagatttgg acctgcgagc g    51

<210> SEQ ID NO 513
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
caagcagaag acggcatacg agatctgttt acagatttgg acctgcgagc g    51

<210> SEQ ID NO 514
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
caagcagaag acggcatacg agattgtccc acagatttgg acctgcgagc g    51

<210> SEQ ID NO 515
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
caagcagaag acggcatacg agattcctga ggagatttgg acctgcgagc g    51

<210> SEQ ID NO 516
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
caagcagaag acggcatacg agattagttc caagatttgg acctgcgagc g    51

<210> SEQ ID NO 517
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
caagcagaag acggcatacg agatcatgac tcagatttgg acctgcgagc g    51

<210> SEQ ID NO 518
<211> LENGTH: 51

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
caagcagaag acggcatacg agatgtaagc gcagatttgg acctgcgagc g          51

<210> SEQ ID NO 519
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
caagcagaag acggcatacg agataaccca gtagatttgg acctgcgagc g          51

<210> SEQ ID NO 520
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
caagcagaag acggcatacg agattttgag ggagatttgg acctgcgagc g          51

<210> SEQ ID NO 521
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
caagcagaag acggcatacg agatagccga caagatttgg acctgcgagc g          51

<210> SEQ ID NO 522
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
caagcagaag acggcatacg agataaaccc gcagatttgg acctgcgagc g          51

<210> SEQ ID NO 523
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
```
caagcagaag acggcatacg agatgtaggg ctagatttgg acctgcgagc g    51

<210> SEQ ID NO 524
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
caagcagaag acggcatacg agatagacga ttagatttgg acctgcgagc g    51

<210> SEQ ID NO 525
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
caagcagaag acggcatacg agataggatg atagatttgg acctgcgagc g    51

<210> SEQ ID NO 526
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
caagcagaag acggcatacg agatataatg gcagatttgg acctgcgagc g    51

<210> SEQ ID NO 527
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
caagcagaag acggcatacg agatcttggc gtagatttgg acctgcgagc g    51

<210> SEQ ID NO 528
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
caagcagaag acggcatacg agatagctgt gcagatttgg acctgcgagc g    51

<210> SEQ ID NO 529
<211> LENGTH: 51
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 529
caagcagaag acggcatacg agatgagtcc aaagatttgg acctgcgagc g          51

<210> SEQ ID NO 530
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
caagcagaag acggcatacg agatgaatac caagatttgg acctgcgagc g          51

<210> SEQ ID NO 531
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
caagcagaag acggcatacg agataggagc ttagatttgg acctgcgagc g          51

<210> SEQ ID NO 532
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
caagcagaag acggcatacg agatgtgact taagatttgg acctgcgagc g          51

<210> SEQ ID NO 533
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
caagcagaag acggcatacg agattttgga acagatttgg acctgcgagc g          51

<210> SEQ ID NO 534
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
aatgatacgg cgaccaccga gatctacacc tctctatgag cggctgtctc cacaagt    57

<210> SEQ ID NO 535
```

<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
aatgatacgg cgaccaccga gatctacact atcctctgag cggctgtctc cacaagt    57

<210> SEQ ID NO 536
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
aatgatacgg cgaccaccga gatctacacg taaggaggag cggctgtctc cacaagt    57

<210> SEQ ID NO 537
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
aatgatacgg cgaccaccga gatctacaca ctgcatagag cggctgtctc cacaagt    57

<210> SEQ ID NO 538
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
aatgatacgg cgaccaccga aaggagtaga gcggctgtct ccacaagt    48

<210> SEQ ID NO 539
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
aatgatacgg cgaccaccga ctaagcctga gcggctgtct ccacaagt    48

<210> SEQ ID NO 540
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540

-continued

```
aatgatacgg cgaccaccga cgtctaatga gcggctgtct ccacaagt                48
```

<210> SEQ ID NO 541
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541

```
aatgatacgg cgaccaccga tctctccgga gcggctgtct ccacaagt                48
```

<210> SEQ ID NO 542
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542

```
aatgatacgg cgaccaccga gatctacaca agatctggag cggctgtctc cacaagt      57
```

<210> SEQ ID NO 543
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543

```
aatgatacgg cgaccaccga gatctacact gtcatgagag cggctgtctc cacaagt      57
```

<210> SEQ ID NO 544
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544

```
aatgatacgg cgaccaccga gatctacact gtaacaggag cggctgtctc cacaagt      57
```

<210> SEQ ID NO 545
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545

```
aatgatacgg cgaccaccga gatctacacg cgcaactgag cggctgtctc cacaagt      57
```

<210> SEQ ID NO 546
<211> LENGTH: 48
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 546
aatgatacgg cgaccaccga tcgatggcga gcggctgtct ccacaagt        48

<210> SEQ ID NO 547
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
aatgatacgg cgaccaccga catggtttga gcggctgtct ccacaagt        48

<210> SEQ ID NO 548
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
aatgatacgg cgaccaccga acgaaagcga gcggctgtct ccacaagt        48

<210> SEQ ID NO 549
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
aatgatacgg cgaccaccga gctctgatga gcggctgtct ccacaagt        48

<210> SEQ ID NO 550
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
aatgatacgg cgaccaccga gatctacaca tgccctcgag cggctgtctc cacaagt        57

<210> SEQ ID NO 551
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
aatgatacgg cgaccaccga gatctacacc tcagatggag cggctgtctc cacaagt        57
```

```
<210> SEQ ID NO 552
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
aatgatacgg cgaccaccga gatctacacg taatctggag cggctgtctc cacaagt      57

<210> SEQ ID NO 553
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
aatgatacgg cgaccaccga gatctacacg caagattgag cggctgtctc cacaagt      57

<210> SEQ ID NO 554
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
aatgatacgg cgaccaccga atacgccaga gcggctgtct ccacaagt      48

<210> SEQ ID NO 555
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
aatgatacgg cgaccaccga accagtcgga gcggctgtct ccacaagt      48

<210> SEQ ID NO 556
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
aatgatacgg cgaccaccga aacacggaga gcggctgtct ccacaagt      48

<210> SEQ ID NO 557
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 557
aatgatacgg cgaccaccga ctgcctagga gcggctgtct ccacaagt        48

<210> SEQ ID NO 558
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
gggtcacgcg taggagttct atcgacccca aaatcagcga aat             43

<210> SEQ ID NO 559
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
gttccgcagc cacacaagat ctgtctggtt actgccagtt gaatctg         47

<210> SEQ ID NO 560
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
cgcgtcgagt agggtgttct atcgacccca aaatcagcga aat             43

<210> SEQ ID NO 561
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
gccgtgtgaa gctggaagat ctgtctggtt actgccagtt gaatctg         47

<210> SEQ ID NO 562
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
cgatcgccct tggtggttct atcgacccca aaatcagcga aat             43

<210> SEQ ID NO 563
<211> LENGTH: 47
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 563
ggtttagccg gcgtgaagat ctgtctggtt actgccagtt gaatctg             47

<210> SEQ ID NO 564
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
ggtcgagccg gaactgttct atcgacccca aaatcagcga aat                 43

<210> SEQ ID NO 565
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
ggatgcgcac ccagaaagat ctgtctggtt actgccagtt gaatctg             47

<210> SEQ ID NO 566
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
tcccggcgtt gtcctgttct atcgacccca aaatcagcga aat                 43

<210> SEQ ID NO 567
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
gctccgtcac tgcccaagat ctgtctggtt actgccagtt gaatctg             47

<210> SEQ ID NO 568
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
cgcagggtcc agagtgttct atcgacccca aaatcagcga aat                 43
```

<210> SEQ ID NO 569
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
gttcgcgcga aggaaaagat ctgtctggtt actgccagtt gaatctg                47

<210> SEQ ID NO 570
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
atatagatgc cgtcctagcg gttctatcga ccccaaaatc agcgaaat              48

<210> SEQ ID NO 571
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
aagtatcttt cctgtgccca aagatctgtc tggttactgc cagttgaatc tg         52

<210> SEQ ID NO 572
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
ccctttaatc agatgcgtcg gttctatcga ccccaaaatc agcgaaat              48

<210> SEQ ID NO 573
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
tggtagtaat aagggcgacc aagatctgtc tggttactgc cagttgaatc tg         52

<210> SEQ ID NO 574
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 574
ttggtcatgt gcttttcgtt gttctatcga ccccaaaatc agcgaaat          48

<210> SEQ ID NO 575
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
aggggtatcg gatactcaga aagatctgtc tggttactgc cagttgaatc tg        52

<210> SEQ ID NO 576
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
gggtgggtaa atggtaatgc gttctatcga ccccaaaatc agcgaaat          48

<210> SEQ ID NO 577
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
atcgattccc cggatatagc aagatctgtc tggttactgc cagttgaatc tg        52

<210> SEQ ID NO 578
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
tccgacgggg agtatatact gttctatcga ccccaaaatc agcgaaat          48

<210> SEQ ID NO 579
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
tactaactgc ttcaggccaa aagatctgtc tggttactgc cagttgaatc tg        52

<210> SEQ ID NO 580
<211> LENGTH: 48
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
catgtttagg aacgctaccg gttctatcga ccccaaaatc agcgaaat          48

<210> SEQ ID NO 581
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
aataatctcc gttccctccc aagatctgtc tggttactgc cagttgaatc tg       52

<210> SEQ ID NO 582
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
gggtcacgcg taggagttct atcgctggtg ctgcagctta tta                43

<210> SEQ ID NO 583
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
gttccgcagc cacacaagat ctgagggtca agtgcacagt cta                43

<210> SEQ ID NO 584
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
cgcgtcgagt agggtgttct atcgctggtg ctgcagctta tta                43

<210> SEQ ID NO 585
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
gccgtgtgaa gctggaagat ctgagggtca agtgcacagt cta                43
```

<210> SEQ ID NO 586
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
cgatcgccct tggtggttct atcgctggtg ctgcagctta tta                43

<210> SEQ ID NO 587
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
ggtttagccg gcgtgaagat ctgagggtca agtgcacagt cta                43

<210> SEQ ID NO 588
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
ggtcgagccg gaactgttct atcgctggtg ctgcagctta tta                43

<210> SEQ ID NO 589
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
ggatgcgcac ccagaaagat ctgagggtca agtgcacagt cta                43

<210> SEQ ID NO 590
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
tcccggcgtt gtcctgttct atcgctggtg ctgcagctta tta                43

<210> SEQ ID NO 591
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 591
gctccgtcac tgcccaagat ctgagggtca agtgcacagt cta        43

<210> SEQ ID NO 592
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
cgcagggtcc agagtgttct atcgctggtg ctgcagctta tta        43

<210> SEQ ID NO 593
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
gttcgcgcga aggaaaagat ctgagggtca agtgcacagt cta        43

<210> SEQ ID NO 594
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
atatagatgc cgtcctagcg gttctatcgc tggtgctgca gcttatta        48

<210> SEQ ID NO 595
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
aagtatcttt cctgtgccca aagatctgag ggtcaagtgc acagtcta        48

<210> SEQ ID NO 596
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596 cccttttaatc agatgcgtcg gttctatcgc tggtgctgca gcttatta        48

<210> SEQ ID NO 597
<211> LENGTH: 48

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
tggtagtaat aagggcgacc aagatctgag ggtcaagtgc acagtcta        48

<210> SEQ ID NO 598
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
ttggtcatgt gcttttcgtt gttctatcgc tggtgctgca gcttatta        48

<210> SEQ ID NO 599
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
aggggtatcg gatactcaga aagatctgag ggtcaagtgc acagtcta        48

<210> SEQ ID NO 600
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
gggtgggtaa atggtaatgc gttctatcgc tggtgctgca gcttatta        48

<210> SEQ ID NO 601
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
atcgattccc cggatatagc aagatctgag ggtcaagtgc acagtcta        48

<210> SEQ ID NO 602
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
```
tccgacgggg agtatatact gttctatcgc tggtgctgca gcttatta            48

<210> SEQ ID NO 603
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
tactaactgc ttcaggccaa aagatctgag ggtcaagtgc acagtcta            48

<210> SEQ ID NO 604
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
catgtttagg aacgctaccg gttctatcgc tggtgctgca gcttatta            48

<210> SEQ ID NO 605
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
aataatctcc gttccctccc aagatctgag ggtcaagtgc acagtcta            48

<210> SEQ ID NO 606
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 606
gctggtgctg cagcttatta tgtgggtgtg tatctcacga agcgaccctt tggaaaatat    60
aatgaaaatg gaaccattac agatgctgta gactgtgcac ttgaccct               108

<210> SEQ ID NO 607
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 607
gctggtgctg cagcttatta tgtgggtcct cgctaggacg tcgctatgac gccaaaatat    60
aatgaaaatg gaaccattac agatgctgta gactgtgcac ttgaccct               108

<210> SEQ ID NO 608
<211> LENGTH: 108

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 608
gctggtgctg cagcttatta tgtgggtagc acgacttgat ctaactgaca ctaaaaatat    60
aatgaaaatg gaaccattac agatgctgta gactgtgcac ttgaccct              108

<210> SEQ ID NO 609
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 609
gctggtgctg cagcttatta tgtgggttaa gtaggacttc gattggatgg aataaaatat    60
aatgaaaatg gaaccattac agatgctgta gactgtgcac ttgaccct              108

<210> SEQ ID NO 610
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
tctggttact gccagttgaa tctgagggtc cggacggata tcgcactaag tgtacctggt    60
gcatttcgct gattttgggg tc                                           82

<210> SEQ ID NO 611
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
tctggttact gccagttgaa tctgagggtc ccatgaccat gtcactggct acactgaggt    60
gcatttcgct gattttgggg tc                                           82

<210> SEQ ID NO 612
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
tctggttact gccagttgaa tctgagggtc cttgacatgg catgtgactc cactgtcggt    60
gcatttcgct gattttgggg tc                                           82

<210> SEQ ID NO 613
```

```
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
tctggttact gccagttgaa tctgagggtc cacctttgcc agatgactga gtggaagggt      60
gcatttcgct gattttgggg tc                                              82

<210> SEQ ID NO 614
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
tctggttact gccagttgaa tctgagggtc cagcttgaag cgttcgcgac aagtgtcggt      60
gcatttcgct gattttgggg tc                                              82

<210> SEQ ID NO 615
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
tctggttact gccagttgaa tctgagggtc ctcacgtcct gagatcaact gctacatggt      60
gcatttcgct gattttgggg tc                                              82

<210> SEQ ID NO 616
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
tctggttact gccagttgaa tctgagggtc cgttgactga tcacatgctg ctccacgggt      60
gcatttcgct gattttgggg tc                                              82

<210> SEQ ID NO 617
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
tctggttact gccagttgaa tctgagggtc ccagacagtc atcggattga tgagtgaggt      60
gcatttcgct gattttgggg tc                                              82
```

```
<210> SEQ ID NO 618
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
tatcttcaac ctaggacttt tctatt                                           26

<210> SEQ ID NO 619
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
atagaacaac ctaggacttt tctatt                                           26

<210> SEQ ID NO 620
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (30)..(39)
<223> OTHER INFORMATION: a, c, t, g, unknown or other
<220> FEATURE:
<221> NAME/KEY: variation
<222> LOCATION: (67)..(72)
<223> OTHER INFORMATION: /replace="atagaa"
<220> FEATURE:
<221> NAME/KEY: misc_feature
<222> LOCATION: (1)..(92)
<223> OTHER INFORMATION: /note="Variant positions given in the sequence
      have no preference with respect to those in the annotations
      for variant positions"

<400> SEQUENCE: 620
aatgatacgg cgaccaccga gatctacacn nnnnnnnnng ctggtgctgc agcttattat      60
gtgggttatc ttcaacctag gacttttcta tt                                   92

<210> SEQ ID NO 621
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (29)..(38)
<223> OTHER INFORMATION: a, c, t, g, unknown or other

<400> SEQUENCE: 621
agatgctgta gactgtgcac ttgaccctnn nnnnnnnnat ctcgtatgcc gtcttctgct      60
tg                                                                    62

<210> SEQ ID NO 622
```

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 622
agatgctgta gactgtgcac ttgaccct                                            28

<210> SEQ ID NO 623
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 623
acccacataa taagctgcag caccagc                                             27

<210> SEQ ID NO 624
<211> LENGTH: 138
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (30)..(39)
<223> OTHER INFORMATION: a, c, t, g, unknown or other
<220> FEATURE:
<221> NAME/KEY: variation
<222> LOCATION: (63)..(67)
<223> OTHER INFORMATION: /replace="gcgtc"
<220> FEATURE:
<221> NAME/KEY: modified_base
<222> LOCATION: (105)..(114)
<223> OTHER INFORMATION: a, c, t, g, unknown or other
<220> FEATURE:
<221> NAME/KEY: misc_feature
<222> LOCATION: (1)..(138)
<223> OTHER INFORMATION: /note="Variant positions given in the sequence
      have no preference with respect to those in the annotations
      for variant positions"

<400> SEQUENCE: 624
aatgatacgg cgaccaccga gatctacacn nnnnnnnnng agcggctgtc tccacaagtc         60
cgcgcagagc cttcaggtca gaacccgctc gcaggtccaa atctnnnnnn nnnnatctcg        120
tatgccgtct tctgcttg                                                     138

<210> SEQ ID NO 625
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 625
gagcggctgt ctccacaagt ccg                                                 23

<210> SEQ ID NO 626
<211> LENGTH: 22
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 626
acccgctcgc aggtccaaat ct                                           22

<210> SEQ ID NO 627
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 627
cggacttgtg gagacagccg ctc                                          23

<210> SEQ ID NO 628
<211> LENGTH: 108
<212> TYPE: DNA
<213> ORGANISM: Severe acute respiratory syndrome coronavirus 2

<400> SEQUENCE: 628
gctggtgctg cagcttatta tgtgggttat cttcaaccta ggacttttct attaaaatat     60
aatgaaaatg gaaccattac agatgctgta gactgtgcac ttgaccct               108

<210> SEQ ID NO 629
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 629
gctggtgctg cagcttatta tgtgggtata gaacaaccta ggacttttct attaaaatat     60
aatgaaaatg gaaccattac agatgctgta gactgtgcac ttgaccct               108

<210> SEQ ID NO 630
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 630
gctggtgctg cagcttatta tgtgggttgg actacctagg actgcgcgac taaaaatat     60 aatgaaaatg gaaccattac agatgctgta gactgtgcac ttgaccct               108

<210> SEQ ID NO 631
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

```
<400> SEQUENCE: 631
gctggtgctg cagcttatta tgtgggtcac ctcgtaggac ttctgaaata gccaaaatat      60
aatgaaaatg gaaccattac agatgctgta gactgtgcac ttgaccct                 108

<210> SEQ ID NO 632
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 632
gctggtgctg cagcttatta tgtgggtgct tggtggatct cagaacgcgg cggaaaatat     60
aatgaaaatg gaaccattac agatgctgta gactgtgcac ttgaccct                 108
```